United States Patent
Caldwell et al.

[11] Patent Number: 6,136,827
[45] Date of Patent: Oct. 24, 2000

[54] CYCLIC AMINE MODULATIONS OF CHEMOKINE RECEPTOR ACTIVITY

[75] Inventors: Charles G. Caldwell, Scotch Plains; Paul E. Finke, Milltown; Malcolm Maccoss, Freehold; Laura C. Meurer; Sander G. Mills, both of Scotch Plains; Bryan Oates, Wayne, all of N.J.

[73] Assignee: Merck & Co., Inc., Rahway, N.J.

[21] Appl. No.: 09/120,010

[22] Filed: Jul. 21, 1998

Related U.S. Application Data

[60] Provisional application No. 60/053,754, Jul. 25, 1997.

[51] Int. Cl.[7] ............ A61K 31/445; C07D 211/56
[52] U.S. Cl. ............ 514/329; 544/188; 544/193; 544/194; 544/199; 544/201; 544/207; 544/208; 544/209; 544/214; 544/217; 544/221; 544/223; 544/225; 544/228; 544/229; 544/231; 544/234; 544/331; 544/336; 544/405; 544/408; 544/409; 514/252; 514/255; 514/318; 514/319; 514/322; 514/323; 514/324; 514/327; 514/330; 514/331
[58] Field of Search .................... 546/188, 193, 546/194, 199, 201, 207, 208, 209, 214, 217, 221, 223, 225, 228, 229, 231, 234, 331; 514/252, 255, 318, 319, 322, 323, 324, 327, 329, 330, 331; 544/336, 405, 408, 409

[56] References Cited

U.S. PATENT DOCUMENTS

| | | | |
|---|---|---|---|
| 5,434,158 | 7/1995 | Shah | 514/278 |
| 5,489,599 | 2/1996 | Carter et al. | 514/317 |
| 5,576,333 | 11/1996 | Miller | 514/316 |
| 5,789,422 | 8/1998 | Reichard et al. | 514/327 |

FOREIGN PATENT DOCUMENTS

| | | |
|---|---|---|
| 2145000 | 3/1995 | Canada . |
| WO 96/24582 | 8/1996 | WIPO . |
| WO 98/25604 | 6/1998 | WIPO . |
| WO 98/25605 | 6/1998 | WIPO . |
| WO 98/25617 | 6/1998 | WIPO . |

OTHER PUBLICATIONS

Rogers, et al., *Cell. Mol. Basics Cholinergic Func.*, pp. 333–337, 1987.
Carter, et al., *Chem. Abs.*, vol. 117:191696, 1992.
Glennon, et al., *Chem. Abs.*, vol. 122:205210, 1991.
Glennon, *Chem. Abs.*, vol. 115:182801, 1991.
Wiederman, et al., *Chem. Abs.*, vol. 111, No. 17, 1989.
Yao, et al., *Chem. Abs.*, vol. 127, No. 1, p. 606, 1997.
Hirschmann, *Book of Abstracts, 213th ACS National Meeting*, San Francisco, Apr. 13–17, 1997, Abs. No. 001, 1997.
Rogers et al., "The most interesting members of the AH5183 family of drugs" CA 108:68302, 1987.

*Primary Examiner*—Ceila Chang
*Attorney, Agent, or Firm*—J. Eric Thies; David L. Rose

[57] ABSTRACT

The present invention is directed to cyclic amines of the formula I:

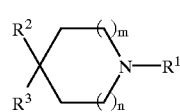

I (wherein $R^1$, $R^2$, $R^3$, m and n are defined herein) which are useful as modulators of chemokine receptor activity. In particular, these compounds are useful as modulators of the chemokine receptors CCR-1, CCR-2, CCR-2A, CCR-2B, CCR-3, CCR-4, CCR-5, CXCR-3, and/or CXCR-4.

20 Claims, No Drawings

CYCLIC AMINE MODULATIONS OF CHEMOKINE RECEPTOR ACTIVITY

This application claims benefit of provisional application 60/053,754, filed Jul. 25, 1997.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., *J. Biol. Chem.*, 270 22123–22128 (1995); Beote, et al, *Cell*, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma and allergic diseases, as well as autoimmune pathologies such as rheumatoid arthritis and atherosclerosis. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 gyycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro apper to be unusually resistant to HIV-1 infection and are not immunocompromised by the presence of this genetic variant (*Nature*, 382, 722–725 (1996)). Absence of CCR-5 appears to confer protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1$\alpha$, MIP-1$\beta$, MCP-1, and MCP-3 are known to bind to chemokine receptors. As noted above, the inhibitors of HIV-1 replication present in supernatants of CD8+ T cells have been characterized as the $\beta$-chemokines RANTES, MIP-1$\alpha$ and MIP-1$\beta$. PCT Patent Publication WO 97/10211 and EPO Patent Publication EP 0,673,928 disclose certain piperidines as tachykinin antagonists.

SUMMARY OF THE INVENTION

The present invention is directed to compounds which are modulators of chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of formula I:

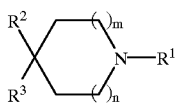

I wherein:
$R^1$ is selected from a group consisting of:
  linear or branched $C_{1-8}$ alkyl, linear or branched $C_{2-8}$ alkenyl,
    wherein the $C_{1-8}$ alkyl or $C_{2-8}$ alkenyl is optionally mono, di, tri or tetra substituted, where the substituents are independently selected from:
    (a) hydroxy,
    (b) oxo,
    (c) cyano,
    (d) halogen which is selected from F, Cl, Br, and I,
    (e) trifluoromethyl,
    (f) phenyl
    (g) mono, di or tri-substituted phenyl, where the substituents are independently selected from:
      (1') phenyl,
      (2') hydroxy,
      (3') $C_{1-3}$alkyl,
      (4') cyano,
      (5') halogen,
      (6') trifluoromethyl,
      (7') —NR$^6$COR$^7$,
      (8') —NR$^6$CO$_2$R$^7$,
      (9') —NR$^6$CONHR$^7$,
      (10') —NR$^6$S(O)$_j$R$^7$, wherein j is 1 or 2,
      (11') —CONR$^6$R$^7$,
      (12') —COR$^6$,
      (13') —CO$_2$R$^6$,
      (14') —OR$^6$,
      (15') —S(O)$_k$R$^6$, wherein k is 0, 1 or 2,
    (h) $C_{1-6}$ alkyl, unsubstituted or substituted with hydroxy,
    (i) —NR$^6$R$^7$,
    (j) —NR$^6$COR$^7$,
    (k) —NR$^6$CO$_2$R$^7$,
    (l) —NR$^6$CONHR$^7$,
    (m) —NR$^6$S(O)$_j$—R$^7$,
    (n) —CONR$^6$R$^7$,
    (o) —COR$^6$,
    (p) —CO$_2$R$^6$,
    (q) —OCOR$^6$,
    (r) —CN,
    (s) —OR$^6$,
    (t) —S(O)$_k$R$^6$,
    (u) —NR$^6$CO-heteroaryl,
    (v) —NR$^6$S(O)j-heteroaryl, and
    (w) heteroaryl, wherein heteroaryl is selected from the group consisting of:
      (1') benzimidazolyl,
      (2') benzofuranyl,
      (3') benzoxazolyl,
      (4') furanyl,
      (5') imidazolyl,
      (6') indolyl,
      (7') isooxazolyl,
      (8') isothiazolyl,
      (9') oxadiazolyl,
      (10') oxazolyl,
      (11') pyrazinyl,
      (12') pyrazolyl,
      (13') pyridyl,
      (14') pyrimidyl,
      (15') pyrrolyl,
      (16') quinolyl,
      (17') tetrazolyl,
      (18') thiadiazolyl,
      (19') thiazolyl,
      (20') thienyl, and
      (21') triazolyl,
      wherein the heteroaryl is unsubstituted or mono di or tri-substituted, where the substituents are independently selected from:
        (a") phenyl,
        (b") hydroxy,
        (c") oxo,
        (d") cyano,
        (e") halogen, and
        (f") trifluoromethyl;
$R^2$ is selected from the group consisting of:
  (1) hydrogen,
  (2) hydroxy,
  (3) $C_{1-6}$ alkyl,
  (4) substituted $C_{1-6}$ alkyl, where the substituents are independently selected from:
    (a) phenyl,
    (b) hydroxy,
    (c) oxo,
    (d) halogen,
    (e) trifluoromethyl,
    (f) —N(R$^4$)(R$^5$), wherein R$^4$ and R$^5$ are independently selected from hydrogen, $C_{1-10}$ linear or branched alkyl, and $C_{0-6}$ alkyl substituted with $C_{3-8}$ cycloalkyl,
    (g) —N(R$^4$)—CO—O—(R$^5$), and
    (h) —N(R$^{4'}$)—CO—N(R$^4$)(R$^5$), wherein R$^{4'}$ is selected from the definitions of R$^4$, (5) —O—$C_{1-6}$ alkyl, and
(6) phenyl;
$R^3$ is selected from the group consisting of:
(1) Ar,
(2) —N($R^4$)—CO—O—($C_{1-6}$ alkyl)—Ar,
(3) —N($R^4$)—CO—O—$R^7$,
(4) —($C_{1-6}$ alkyl)—Ar,
(5) —($C_{1-6}$ alkyl)—O—($C_{1-6}$ alkyl)—Ar, and
(6) —($C_{1-6}$ alkyl)—O—($C_{1-6}$ alkyl)—Ar;
Ar is selected from the group consisting of:
(1) phenyl,
(2) pyridyl,
(3) pyrimidyl,
(4) naphthyl,
(5) furyl,
(6) pyrryl,
(7) thienyl,
(8) isothiazolyl,
(9) imidazolyl,
(10) benzimidazolyl,
(11) tetrazolyl,
(12) pyrazinyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) isoxazolyl,
(23) thiazolyl,
(24) oxazolyl,
(25) triazinyl, and
(26) benzthiazolyl,
(27) benzoxazolyl,
(28) imidazopyrazinyl,
(29) triazolopyrazinyl,
(30) naphthyridinyl,
(31) furopyridinyl,
(32) thiopyranopyrimidyl and the 5-oxide and 5-dioxide thereof,
(33) pyridazinyl,
(34) quinazolinyl,
(35) pteridinyl,
(36) triazolopyrimidyl,
(37) triazolopyrazinyl,
(38) thiapurinyl,
(39) oxapurinyl, and
(40) deazapurinyl,
wherein Ar items (1) to (40) are unsubstituted or mono or di-substituted,
where the substituents are independently selected from:
(a) $C_{1-3}$ alkyl, unsubstituted or substituted with a substituent selected from:
(1') oxo,
(2') hydroxy,
(3') —$OR^7$,
(4') phenyl,
(5') trifluoromethyl, and
(6') phenyl or mono, di or tri-substituted phenyl, where the substituents are independently selected from: hydroxy, cyano, halogen, and trifluoromethyl,
(b) halogen,
(c) —$OC_{1-6}$ alkyl,
(d) trifluoromethyl,
(e) hydroxy,
(f) —$NO_2$,
(g) —$(CH_2)_p S(O)_k$—($C_{1-6}$ alkyl), wherein p is 0, 1 or 2,
(h) —$(CH_2)_p S(O)_j$—$NH_2$,
(i) —$(CH_2)_p S(O)_j$—$NH(C_{1-6}$ alkyl),
(j) —$(CH_2)_p S(O)_j$—$NHR^6$,
(k) —$(CH_2)_p S(O)_j$—$NR^6$—($C_{1-6}$ alkyl),
(l) —$(CH_2)_p CONH_2$,
(m) —$(CH_2)_p CONH$—($C_{1-6}$ alkyl),
(n) —$(CH_2)_p CONHR^6$,
(o) —$(CH_2)_p CONR^6 R^7$,
(p) —$(CH_2)_p CO_2 H$,
(q) —$(CH_2)_p CO_2$—($C_{1-6}$ alkyl),
(r) —$(CH_2)_p NR^6 R^7$,
(s) —$(CH_2)_p NH$—C(O)—$C_{1-6}$alkyl,
(t) —$(CH_2)_p NH$—C(O)—$NH_2$,
(u) —$(CH_2)_p NH$—C(O)—$NHC_{1-6}$alkyl,
(v) —$(CH_2)_p NH$—C(O)—$N(C_{1-6}$ alkyl$)_2$,
(w) —$(CH_2)_p NH$—$S(O)_k$—$C_{1-6}$alkyl,
(x) —$(CH_2)_p N(C_{1-3}$alkyl)—C(O)—N(di$C_{1-6}$ alkyl),
(y) —$(CH_2)_p$—heteroaryl, —C(O)—heteroaryl or —$(CH_2)_p$—O—heteroaryl, wherein the heteroaryl is selected from the group consisting of:
(1') benzimidazolyl,
(2') benzofuranyl,
(3') benzoxazolyl,
(4') furanyl,
(5') imidazolyl,
(6') indolyl,
(7') isooxazolyl,
(8') isothiazolyl,
(9') oxadiazolyl,
(10') oxazolyl,
(11') pyrazinyl,
(12') pyrazolyl,
(13') pyridyl or oxopyridyl,
(14') pyrimidyl,
(15') pyrrolyl,
(16') quinolyl,
(17') tetrazolyl,
(18') thiadiazolyl,
(19') thiazolyl,
(20') thienyl, and
(21') triazolyl,
wherein the heteroaryl group of items (1') to (21') is unsubstituted, or mono, di or tri-substituted, where the substituents are selected from:
(a') hydrogen,
(b') $C_{1-6}$ alkyl, branched or unbranched, unsubstituted or mono or di-substituted, where the substituents are selected from: hydrogen and hydroxy,
(c') hydroxy,
(d') oxo,
(e') —$OR^6$,
(f') halogen, (g') trifluoromethyl,
(h') nitro,
(i') cyano,
(j') —NHR$^6$,
(k') —NR$^6$R$^7$,
(l') —NHCOR$^6$,
(m') —NR$^6$COR$^7$,
(n') —NHCOR$^6$,
(o') —NR$^6$CO$_2$R$^7$,
(p') —NHS(O)$_j$R$^6$,
(q') —NR$_6$S(O)$_j$R$^7$,
(r') —CONR$^6$R$^7$,
(s') —COR$^6$,
(t') —CO$_2$R$^6$, and
(u') —S(O)$_j$R$^6$;

R$^6$ is selected from the group consisting of:
(1) hydrogen,
(2) C$_{1-6}$ alkyl,
(3) substituted C$_{1-6}$ alkyl, where the substituents are independently selected from:
  (a) phenyl,
  (b) hydroxy,
  (c) oxo,
  (d) cyano,
  (e) halogen,
  (f) trifluoromethyl, and
  (g) C$_{5-8}$ cycloalkyl,
(4) phenyl,
(5) mono, di or tri-substituted phenyl, where the substituents are independently selected from:
  (a) hydroxy,
  (b) C$_{1-3}$alkyl,
  (c) cyano,
  (d) halogen, and
  (e) trifluoromethyl;

R$^7$ is selected from the group consisting of:
(1) hydrogen,
(2) C$_{1-6}$ alkyl or C$_{5-8}$ cycloalkyl,
(3) substituted C$_{1-6}$ alkyl or C$_{5-8}$ cycloalkyl, where the substituents are independently selected from:
  (a) phenyl,
  (b) mono, di or tri-substituted phenyl, where the substituent is independently selected from:
    (1') hydroxy,
    (2') C$_{1-3}$alkyl,
    (3') cyano,
    (4') halogen,
    (5') trifluoromethyl, and
    (6') C$_{1-3}$alkyloxy,
  (b) hydroxy,
  (c) oxo,
  (d) cyano,
  (e) halogen, and
  (f) trifluoromethyl,
(4) phenyl,
(5) mono, di or tri-substituted phenyl, where the substituents are independently selected from:
  (a) hydroxy,
  (b) C$_{1-3}$alkyl,
  (c) cyano,
  (d) halogen, and
  (e) trifluoromethyl;
or R$^6$ and R$^7$ may be joined together to form a 5-, 6-, or 7-membered monocyclic saturated ring containing 1 or 2 heteroatoms independently selected from nitrogen, oxygen, and sulfur, and in which the ring is unsubstituted or mono or di-substituted, the substituents independently selected from:
(1) hydroxy,
(2) oxo,
(3) cyano,
(4) halogen,
(5) trifluoromethyl, m is an integer selected from 0, 1 and 2, n is an integer selected from 0, 1 and 2, and pharmaceutically acceptable salts thereof.

Preferred compounds of the present invention include those of formula Ia:

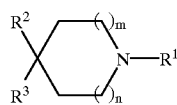

wherein:
R$^1$ is selected from a group consisting of:
C$_3$, C$_4$, C$_5$, C$_6$, C$_7$, or C$_8$ linear or branched alkyl, which is unsubstituted or mono, di or tri-substituted, where the substituents are independently selected from:
  (a) hydroxy,
  (b) Cl or F,
  (c) phenyl,
  (d) mono, di or tri-substituted phenyl, where the substituents are independently selected from:
    (1') phenyl,
    (2') hydroxy,
    (3') C$_{1-3}$alkyl,
    (4') cyano,
    (5') halogen, and
    (6') trifluoromethyl,
  (e) C$_{1-6}$ alkyl, unsubstituted or substituted with hydroxy,
  (f) —NR$^6$CO—R$^7$, wherein R$^6$ is hydrogen or C$_{1-3}$ alkyl, unsubstituted or substituted with C$_{5-8}$ cycloalkyl, and R$^7$ is C$_{1-6}$ alkyl, benzyl or phenyl which is unsubsituted or substituted with halo, CF$_3$, C$_{1-3}$alkyl, or C$_{1-3}$alkoxy,
  (g) —COR$^6$,
  (h) —OR$^6$,
  (i) —NR$^6$S(O)$_j$—R$^7$, where j is 1 or 2,
  (j) —NR$^6$S(O)$_j$—heteroaryl, wherein heteroaryl is selected from the group consisting of:
    (1') benzimidazolyl,
    (2') benzofuranyl,
    (3') benzoxazolyl,
    (4') furanyl,
    (5') imidazolyl,
    (6') indolyl,
    (7') isooxazolyl,
    (8') isothiazolyl,
    (9') oxadiazolyl,
    (10') oxazolyl,
    (11') pyrazinyl,
    (12') pyrazolyl,
    (13') pyridyl,
    (14') pyrimidyl,
    (15') pyrrolyl,
    (16') quinolyl,
    (17') tetrazolyl,
    (18') thiadiazolyl, (19') thiazolyl,
(20') thienyl, and
(21') triazolyl,
wherein the heteroaryl is unsubstituted or mono di or tri-substituted, where the substituents are independently selected from:
(a') phenyl,
(b') hydroxy,
(c') oxo,
(d') cyano,
(e') halogen, and
(f) trifluoromethyl;
$R^2$ is selected from the group consisting of:
(1) hydrogen,
(2) hydroxy,
(3) $C_{1-6}$ alkyl,
(4) —O—$C_{1-6}$ alkyl,
(5) phenyl,
(6) —N(CH$_3$)—CO—N(H)(CH$_3$),
(7) —N(H)—CO—O—CH$_3$, and
(8) —CO—CH$_3$;
$R^3$ is selected from the group consisting of:
(1) Ar,
(2) —($C_{1-6}$ alkyl)—Ar,
(3) —($C_{1-6}$ alkyl)—O—($C_{1-6}$ alkyl)—Ar, and
(4) —N($R^4$)—CO—O—($C_{1-6}$ alkyl)—Ar, wherein $R^4$ is selected from hydrogen, $C_{1-10}$ linear or branched alkyl, and $C_{0-6}$ alkyl substituted with $C_{3-8}$ cycloalkyl,
(5) —N($R^4$)—CO—O—$R^7$;
Ar is selected from the group consisting of:
(1) phenyl,
(2) pyrazinyl,
(3) pyrazolyl,
(4) pyridyl,
(5) pyrimidyl, and
(6) thienyl,
wherein the Ar is unsubstituted or mono or di-substituted, and the substituents are independently selected from:
(a) $C_{1-3}$ alkyl, unsubstituted or substituted with
(1') oxo,
(2') hydroxy,
(3') —O$R^7$,
(4') phenyl, and
(5') trifluoromethyl,
(b) halogen,
(c) —O$C_{1-6}$ alkyl,
(d) trifluoromethyl,
(e) —NO$_2$,
(f) CONR$^6$—($C_{1-2}$ alkyl),
(g) CO$_2$H,
(h) CO$_2$—($C_{1-2}$ alkyl),
(i) CH$_2$NR$^6$—($C_{1-2}$ alkyl),
(j) CH$_2$NH—C(O)—$C_{1-3}$alkyl,
(k) CH$_2$NH—C(O)NH$_2$,
(l) CH$_2$NH—C(O)NHC$_{1-3}$alkyl,
(m) CH$_2$NH—C(O)N—di$C_{-3}$ alkyl),
(n) CH$_2$NH—S(O)$_j$—$C_{1-3}$alkyl,
(o) CH$_2$—heteroaryl, with the heteroaryl is selected from the group consisting of:
(1') imidazolyl,
(2') oxazolyl,
(3') pyridyl,
(4') tetrazolyl,
(5') triazolyl,
and the heteroaryl is unsubstituted, mono, di or tri-substituted, where the substituents selected from:
(a') hydrogen,
(b') $C_{1-6}$ alkyl, branched or unbranched, unsubstituted or mono or di-substituted, the substituents being selected from hydrogen and hydroxy;
m is an integer selected from 0, 1 and 2,
n is an integer selected from 0, 1 and 2, with the proviso that the sum of m+n is 2;
and pharmaceutically acceptable salts thereof.

More preferred compounds of the present invention include those of formula Ib:

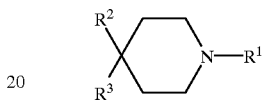

Ib wherein:
$R^1$, $R^2$ and $R^3$ are as defined herein; and pharmaceutically acceptable salts thereof.
In the present invention it is preferred that
$R^1$ is selected from the group consisting of:
$C_3$, $C_4$, $C_5$, $C_6$, $C_7$, or $C_8$ linear or branched alkyl, which is unsubstituted or mono, di or tri-substituted, where the substituents are independently selected from:
(a) hydroxy,
(b) Cl or F,
(c) phenyl,
(d) mono, di or tri-substituted phenyl, where the substituents are independently selected from:
(1') phenyl,
(2') hydroxy,
(3') $C_{1-3}$alkyl,
(4') cyano,
(5') halogen, and
(6') trifluoromethyl,
(e) $C_{1-6}$ alkyl, unsubstituted or substituted with hydroxy,
(f) —NR$^6$CO—R$^7$, wherein $R^6$ is hydrogen or $C_{1-3}$ alkyl, unsubstituted or substituted with $C_{5-8}$ cycloalkyl, and $R^7$ is $C_{1-6}$ alkyl, benzyl or phenyl which is unsubsituted or substituted with halo, CF$_3$, $C_{1-3}$alkyl, or $C_{1-3}$alkoxy,
(g) —COR$^6$,
(h) —OR$^6$,
(i) —NR$^6$S(O)$_j$—R$^7$, where j is 1 or 2,
(j) —NR$^6$S(O)$_j$—heteroaryl, wherein heteroaryl is selected from the group consisting of:
(1') benzimidazolyl,
(2') benzofuranyl,
(3') benzoxazolyl,
(4') furanyl,
(5') imidazolyl,
(6') indolyl,
(7') isooxazolyl,
(8') isothiazolyl,
(9') oxadiazolyl,
(10') oxazolyl,
(11') pyrazinyl,
(12') pyrazolyl,
(13') pyridyl,
(14') pyrimidyl, (15') pyrrolyl,
(16') quinolyl,
(17') tetrazolyl,
(18') thiadiazolyl,
(19') thiazolyl,
(20') thienyl, and
(21') triazolyl,
wherein the heteroaryl is unsubstituted or mono di or tri-substituted, where the substituents are independently selected from:
(a') phenyl,
(b') hydroxy,
(c') oxo,
(d') cyano,
(e') halogen, and
(f') trifluoromethyl.

In the present invention it is preferred that if $R^3$ is Ar, m is 1, n is 1, and $R^1$ is $C_5$ alkyl which bears a group selected from: $-NR^6R^7$, $-NR^6COR^7$, $-NR^6CO_2R^7$, or $-NR^6CONHR^7$, then $R^1$ does not bear a substituent which is 2,3-dichlorophenyl.

In the present invention it is preferred that $R^1$ bears at least one substituent which is selected from:
(a) $-NR^6CO-R^7$, wherein $R^6$ is $C_{1-3}$ alkyl, unsubstituted or substituted with cyclohexyl, and $R^7$ is $C_{1-6}$ alkyl, benzyl or phenyl which is unsubstituted or substituted with halo, $CF_3$, $C_{1-3}$alkyl, or $C_{1-3}$alkoxy, and
(b) $-NR^6S(O)_j-R^7$, where j is 1 or 2.

In the present invention it is more preferred that $R^1$ is selected from the group consisting of:
$C_4$, $C_5$, $C_6$, $C_7$ or $C_8$ linear or branched alkyl, which is mono, di- or tri-substituted, where the substituents are independently selected from:
(a) hydroxy,
(b) Cl or F,
(c) phenyl,
(d) mono, di or tri-substituted phenyl, where the substituents are independently selected from:
(1') hydroxy,
(2') methyl or ethyl,
(3') Cl or F, and
(4') trifluoromethyl,
(e) $C_{1-6}$ alkyl, unsubstituted or substituted with hydroxy,
(f) $-NR^6CO-R^7$, wherein $R^6$ is $C_{1-3}$ alkyl, unsubstituted or substituted with cyclohexyl, and $R^7$ is $C_{1-6}$ alkyl, benzyl or phenyl which is unsubsituted or substituted with halo, $CF_3$, $C_{1-3}$alkyl, or $C_{1-3}$alkoxy,
(g) $-NR^6S(O)_j-R^7$, where j is 1 or 2.

In the present invention it is still more preferred that $R^1$ is selected from the group consisting of:
$C_4$, $C_5$, or $C_6$ linear alkyl, which is substituted, where the substituents are independently selected from:
(a) phenyl,
(b) mono, di or tri-substituted phenyl, where the substituents are independently selected from:
(1') hydroxy,
(2') methyl or ethyl,
(3') Cl or F, and
(4') trifluoromethyl,
(c) $C_{1-6}$ alkyl, unsubstituted or substituted with hydroxy,
(d) $-NR^6CO-R^7$, wherein $R^6$ is methyl, unsubstituted or substituted with cyclohexyl, and $R^7$ is phenyl which is unsubstituted or substituted with Cl, F, $CF_3$, $C_{1-3}$alkyl or $C_{1-3}$alkoxy, and
(e) $-NR^6S(O)_j-R^7$, where j is 1 or 2.

In the present invention it is still more preferred that $R^1$ is $C_4$ linear alkyl, which is substituted, where the substituents are independently selected from:
(a) phenyl,
(b) mono, di or tri-substituted phenyl, where the substituents are independently selected from:
(1') hydroxy,
(2') methyl or ethyl,
(3') Cl or F, and
(4') trifluoromethyl,
(c) $C_{1-6}$ alkyl, unsubstituted or substituted with hydroxy, and
(d) $-NR^6S(O)_j-R^7$, where $R^6$ is methyl, unsubstituted or substituted with cyclohexyl, and $R^7$ is phenyl which is unsubstituted or substituted with Cl, F, $CF_3$, $C_{1-3}$alkyl or $C_{1-3}$alkoxy, and j is 1 or 2.

In the present invention it is even more preferred that $R^1$ is:

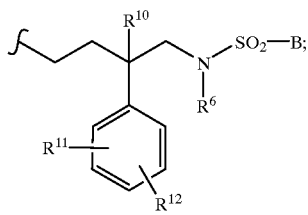

wherein:

B is selected from the group consisting of:
(a) phenyl, and
(b) di or tri-substituted phenyl, wherein the substituents on phenyl are independently selected from: chloro, methyl, phenyl, $C_{1-3}$alkoxy, and $CF_3$;

$R^6$ is $C_{1-3}$ alkyl, unsubstituted or substituted with cyclohexyl;

$R^{10}$ is selected from the group consisting of:
(1) hydrogen, and
(2) $C_{1-6}$ alkyl, unsubstituted or substituted with hydroxy;

$R^{11}$ and $R^{12}$ are independently selected from the group consisting of:
(1) hydrogen,
(2) hydroxy,
(3) methyl or ethyl,
(4) Cl or F, and
(5) trifluoromethyl.

In the present invention it is highly preferred that $R^1$ is selected from the group consisting of:

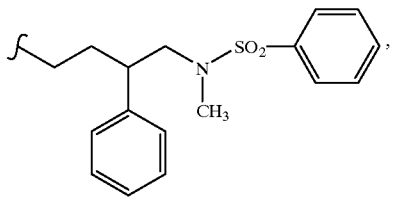

-continued

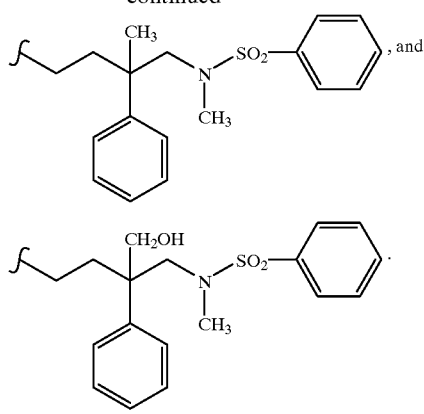

In the present invention it is most preferred that $R^1$ is selected from the group consisting of:

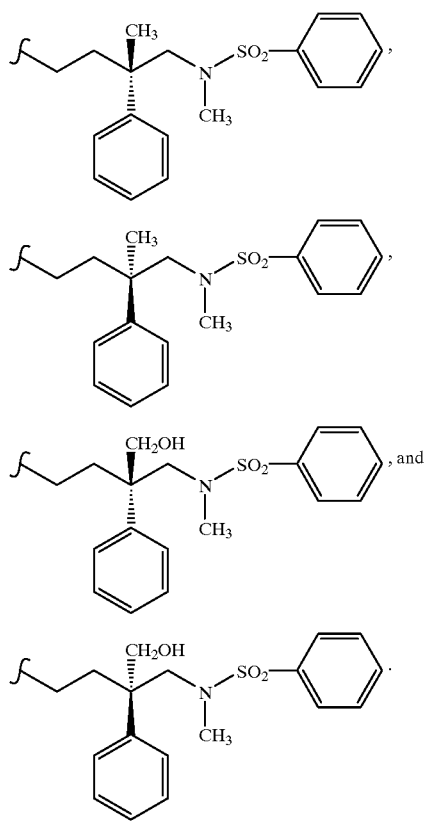

In the present invention it is preferred that $R^2$ is selected from the group consisting of:
(1) hydrogen,
(2) hydroxy,
(3) $C_{1-6}$ alkyl,
(4) —O—$C_{1-6}$ alkyl
(5) phenyl,
(6) —N($CH_3$)—CO—N(H)($CH_3$),
(7) —N(H)—CO—O—$CH_3$, and
(8) —CO—$CH_3$.

In the present invention it is more preferred that $R^2$ is selected from the group consisting of:

(1) hydrogen,
(2) hydroxy, and
(3) phenyl.

In the present invention it is most preferred that $R^2$ is hydrogen.

In the present invention it is preferred that $R^3$ is selected from the group consisting of:
(1) Ar,
(2) —($C_{1-6}$ alkyl)—Ar,
(3) —($C_{1-6}$ alkyl)—O—($C_{1-6}$ alkyl)—Ar, and
(4) —N($R^4$)—CO—O—($C_{1-6}$ alkyl)—Ar, wherein $R^4$ is selected from hydrogen, $C_{1-10}$ linear or branched alkyl, and $C_{0-6}$ alkyl substituted with $C_{3-8}$ cycloalkyl,
(5) —N($R^4$)—CO—O—$R^7$.

In the present invention it is more preferred that $R^3$ is selected from the group consisting of:
(1) Ar,
(2) —($C_{1-6}$ alkyl)—Ar,
(3) —N($R^4$)—CO—O—($C_{1-6}$ alkyl)—Ar, wherein $R^4$ is selected from hydrogen, $C_{1-10}$ linear or branched alkyl, and $C_{0-6}$ alkyl substituted with $C_{3-8}$ cycloalkyl, and
(4) —N($R^4$)—CO—O—$R^7$.

In the present invention it is preferred that Ar is selected from the group consisting of:
(1) phenyl,
(2) pyrazinyl,
(3) pyrazolyl,
(4) pyridyl,
(5) pyrimidyl, and
(6) thienyl,
wherein the Ar is unsubstituted or mono or di-substituted, and substituents are independently selected from:
(a) $C_{1-3}$ alkyl, unsubstituted or substituted with
(1') oxo,
(2') hydroxy,
(3') —$OR^7$,
(4') phenyl, and
(5') trifluoromethyl,
(b) $CONR^6$—($C_{1-2}$ alkyl),
(c) $CO_2H$,
(d) $CO_2$—($C_{1-2}$ alkyl),
(e) $CH_2NR^6$—($C_{1-2}$ alkyl),
(f) $CH_2NH$—C(O)—$C_{1-3}$alkyl,
(h) $CH_2NH$—C(O)$NH_2$,
(i) $CH_2NH$—C(O)$NHC_{1-3}$alkyl,
(j) $CH_2NH$—C(O)N—di$C_{1-3}$ alkyl),
(k) $CH_2NH$-S(O)$_j$—$C_{1-3}$alkyl,
(l) $CH_2$—heteroaryl, with the heteroaryl is selected from the group consisting of:
(1') imidazolyl,
(2') oxazolyl,
(3') pyridyl,
(4') tetrazolyl,
(5') triazolyl, and the heteroaryl is unsubstituted, mono, di or tri-substituted, where the substituents selected from:
(a') hydrogen,
(b') $C_{1-6}$ alkyl, branched or unbranched, unsubstituted or mono or di-substituted, the substituents being selected from hydrogen and hydroxy.

In the present invention it is more preferred that Ar is selected from:

phenyl, mono substituted phenyl or di-substituted phenyl, wherein the substituents are selected from the group consisting of:
(a) $C_{1-3}$ alkyl, unsubstituted or substituted with
   (1') oxo,
   (2') hydroxy, or
   (3') —$OR^6$, wherein $R^6$ is hydrogen or $C_{1-3}$ alkyl,
(b) —$CH_2NR^6$—($C_{1-2}$ alkyl),
(c) —$CH_2NH$—$C(O)$—$C_{1-3}$alkyl,
(d) —$CH_2NH$—$C(O)NH_2$,
(i) —$CH_2NH$—$C(O)NHC_{1-3}$alkyl,
(j) —$CH_2NH$—$C(O)N$—$diC_{1-3}$ alkyl),
(k) —$CH_2NH$—$S(O)_j$—$C_{1-3}$alkyl,
(l) —$CH_2$—heteroaryl, where heteroaryl is selected from the group consisting of:
   (1') imidazolyl,
   (2') oxazolyl,
   (3') pyridyl,
   (4') tetrazolyl,
   (5') triazolyl, and where heteroaryl is unsubstituted, mono, di or tri substituted, where the substituents are independently selected from:
      (a') hydrogen,
      (b') $C_{1-6}$ alkyl, branched or unbranched, unsubstituted or mono or disubstituted, where the substituents are selected from: hydrogen and hydroxy.

In the present invention it is more preferred that $R^3$ is selected from:
(1) phenyl, and
(2) —$N(R^4)$—$CO$—$O$—($C_{1-6}$ alkyl)-phenyl, wherein $R^4$ is selected from hydrogen, $C_{1-10}$ linear or branched alkyl, and $C_{0-6}$ alkyl substituted with $C_{3-8}$ cycloalkyl.

In the present invention it is even more preferred that $R^3$ is:
—$N(R^4)$—$CO$—$O$—($CH_2$)-phenyl, wherein $R^4$ is selected from hydrogen, $C_{1-6}$ linear or branched alkyl, and $CH_2$ substituted with $C_{3-8}$ cycloalkyl.

In the present invention it is still more preferred that $R^3$ is:
—$N(R^4)$—$CO$—$O$—($CH_2$)-phenyl, wherein $R^4$ is selected from hydrogen and $C_{1-6}$ alkyl.

In the present invention it is most preferred that $R^3$ is:
—$N(CH_2CH_3)$—$CO$—$O$—($CH_2$)-phenyl.

In the present invention it is preferred that
m is an integer selected from 0, 1 and 2,
n is an integer selected from 0, 1 and 2, with the proviso that the sum of m+n is 2.

In the present invention it is more preferred that m is 1, and n is 1.

As appreciated by those of skill in the art, halo as used herein are intended to include chloro, fluoro, bromo and iodo. Similarly, $C_{1-6}$, as in $C_{1-6}$alkyl is defined to identify the group as having 1, 2, 3, 4, 5, or 6 carbons, such that $C_{1-6}$alkyl specifically includes methyl, ethyl, propyl, butyl, pentyl, hexyl, and cyclohexyl.

Exemplifying the invention is the use of the compounds disclosed in the Examples and herein.

Preferred compounds of the present invention include the compounds of the formula:

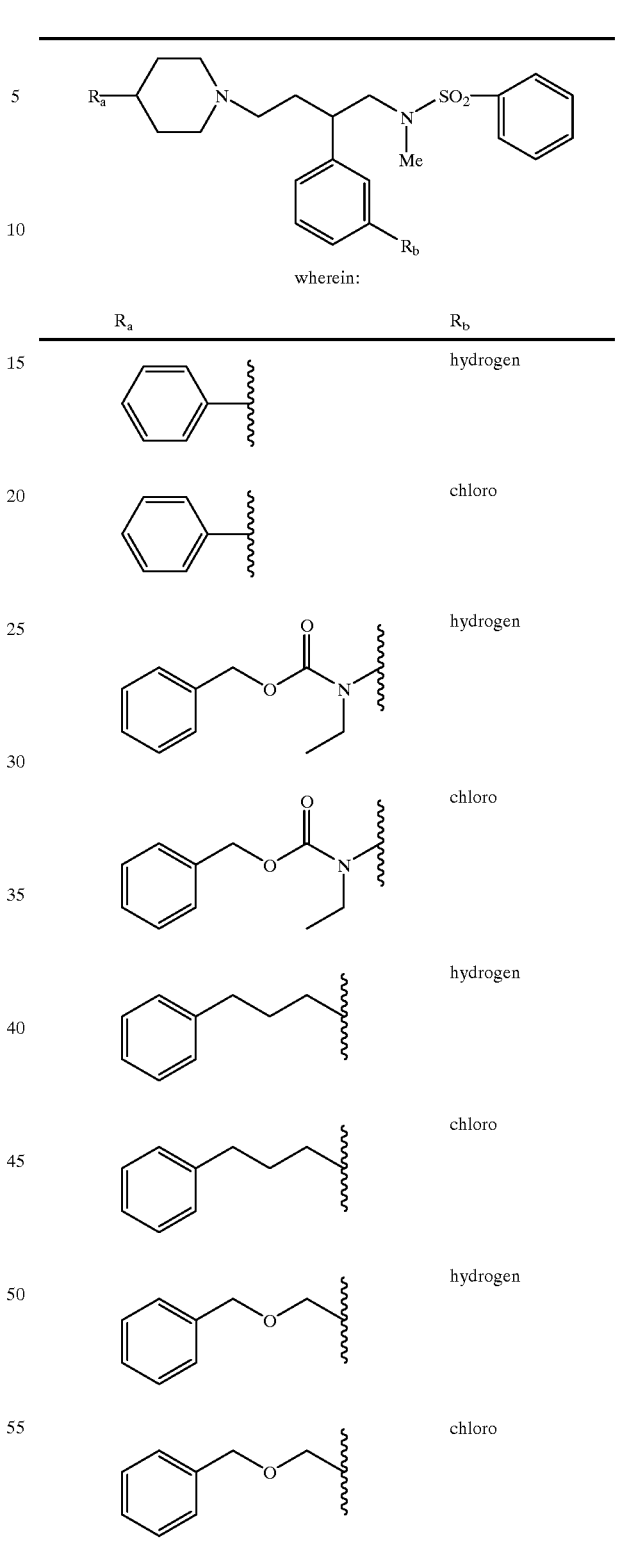

wherein:

| $R_a$ | $R_b$ |
|---|---|
| phenyl | hydrogen |
| phenyl | chloro |
| benzyloxycarbonyl-N-ethyl | hydrogen |
| benzyloxycarbonyl-N-ethyl | chloro |
| phenylpropyl | hydrogen |
| phenylpropyl | chloro |
| benzyloxy | hydrogen |
| benzyloxy | chloro | and pharmaceutically acceptable salts thereof.

Specific compounds within the present invention include a compound which selected from the group consisting of:

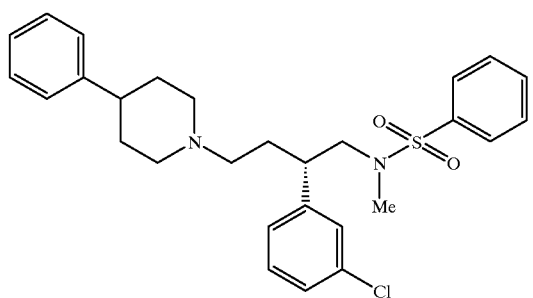
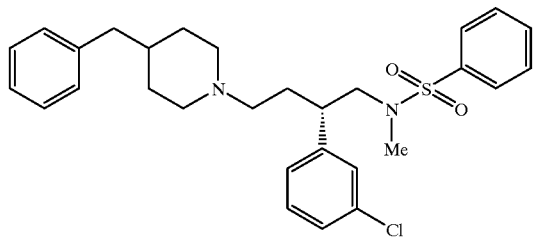
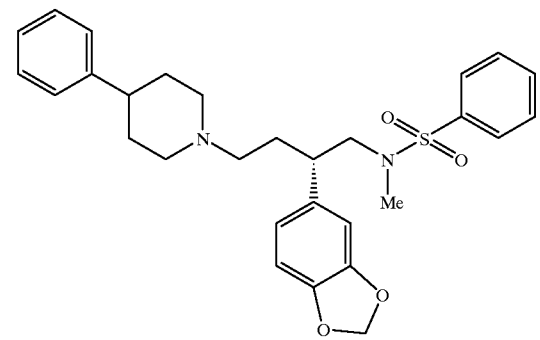
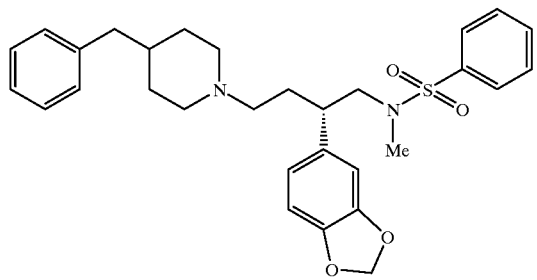
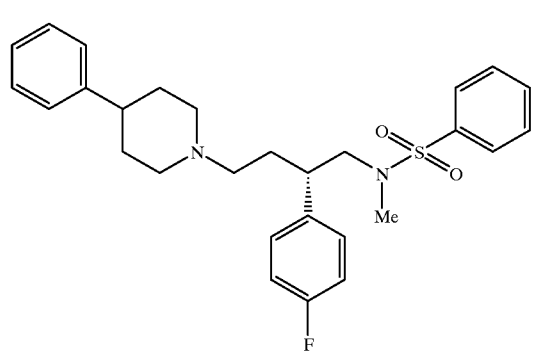
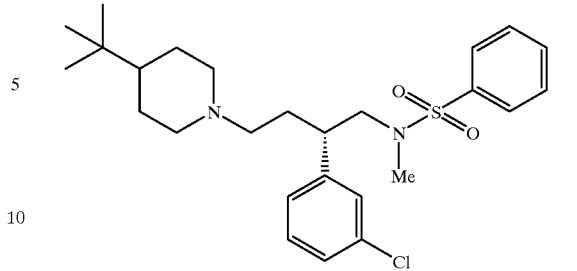
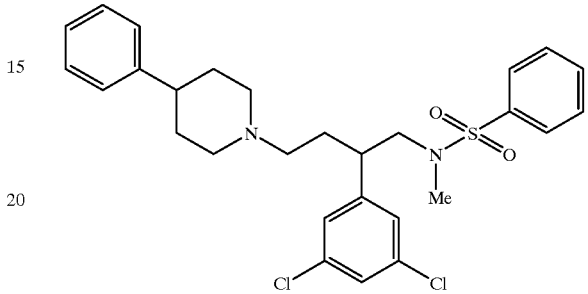
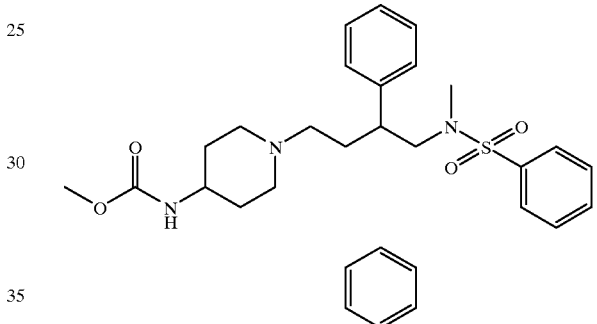
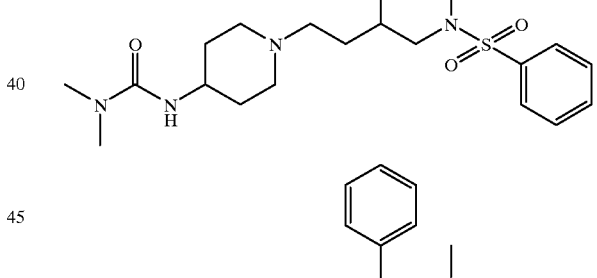
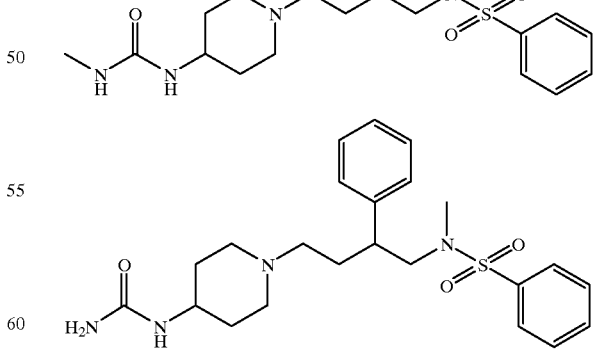

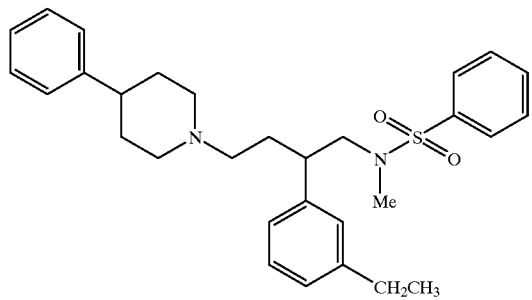
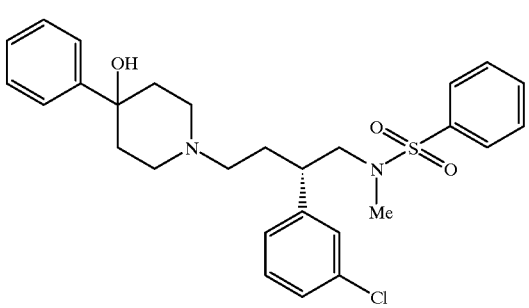
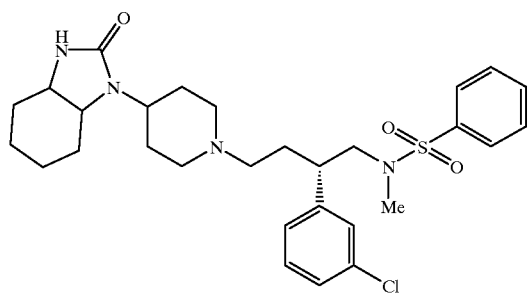
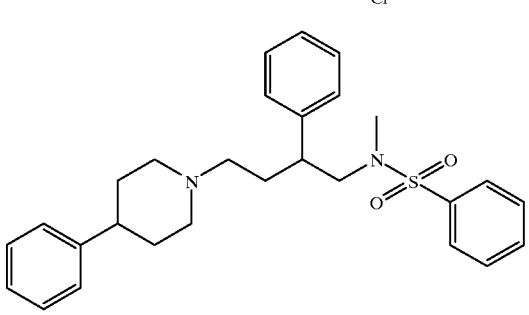
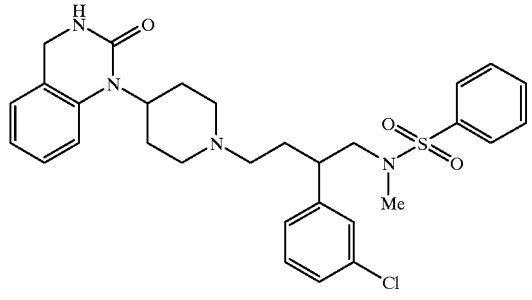
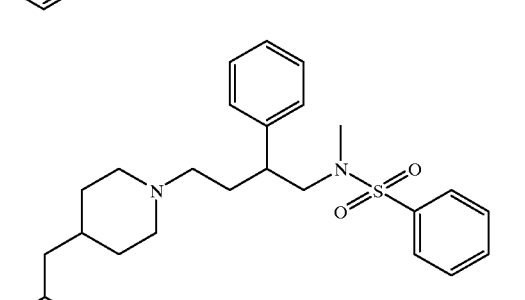
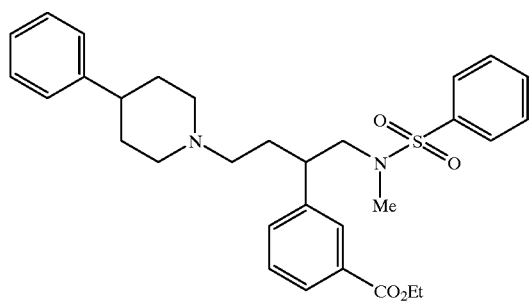
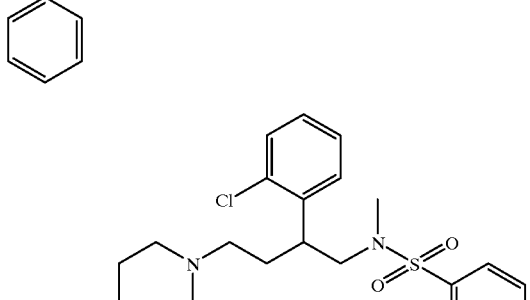
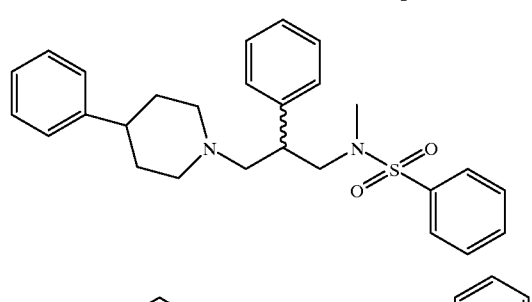
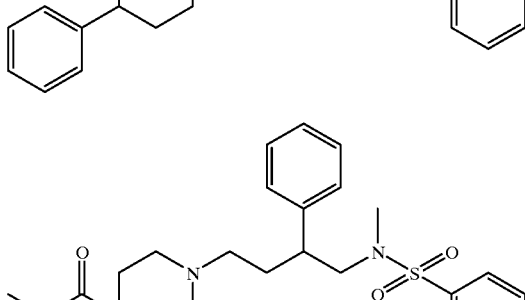
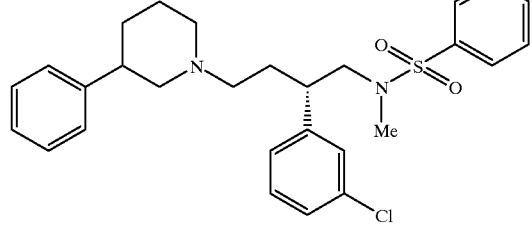
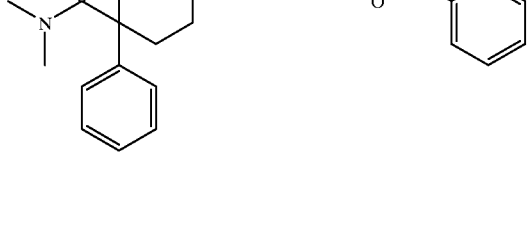

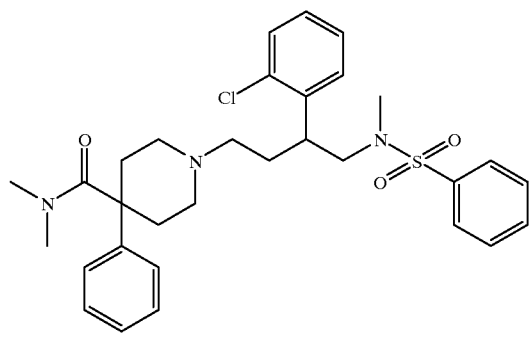
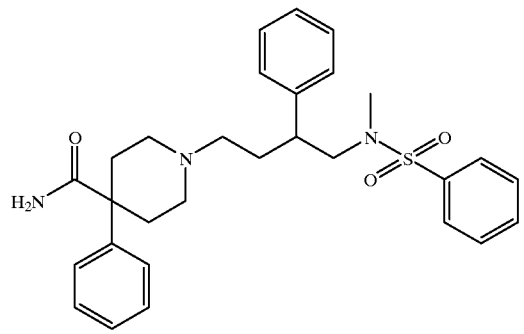
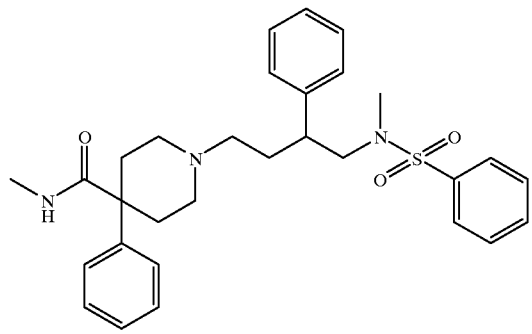
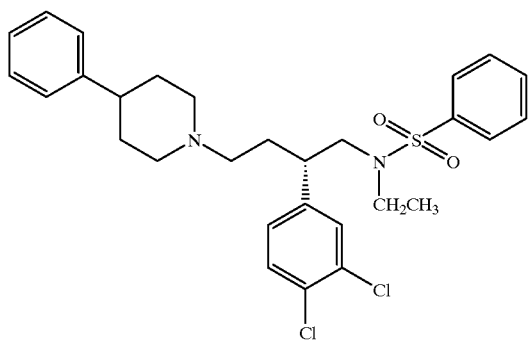
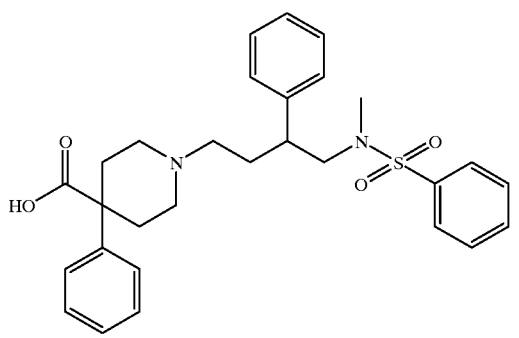
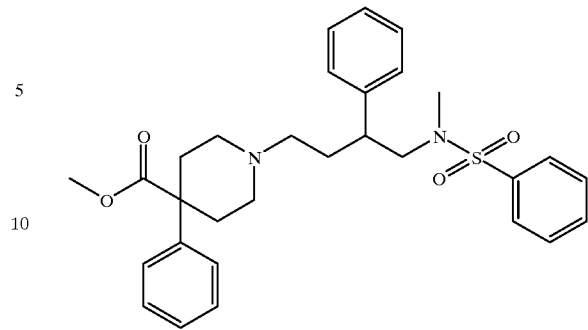
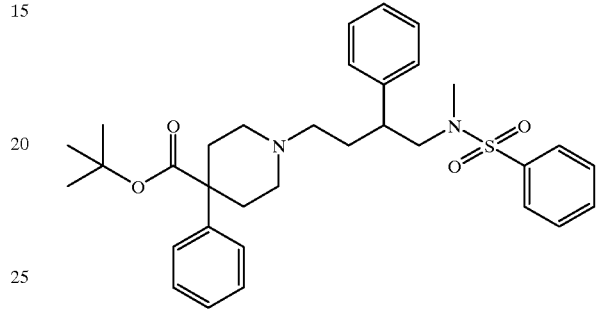
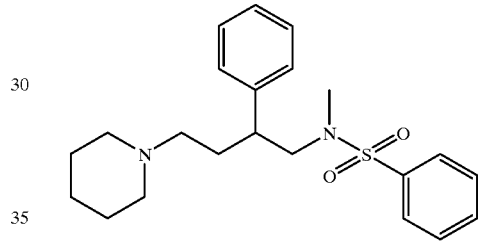
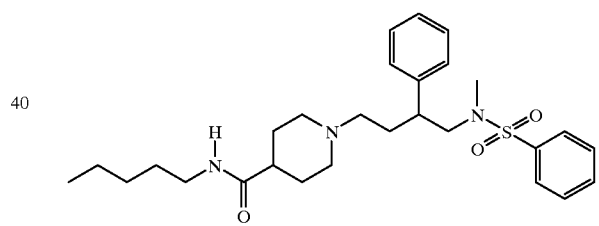
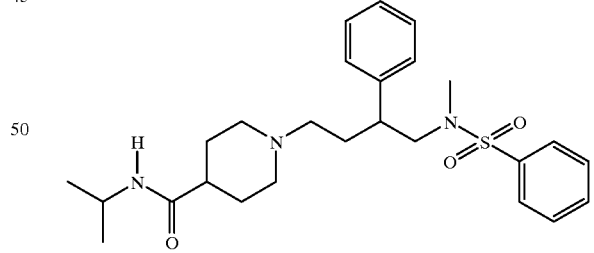
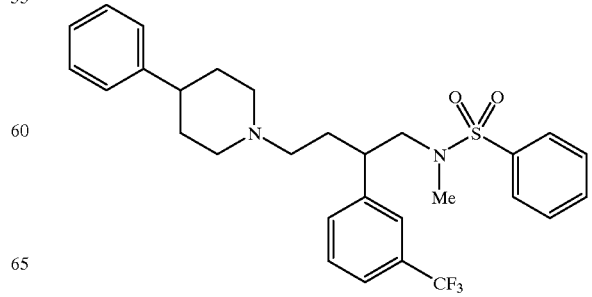

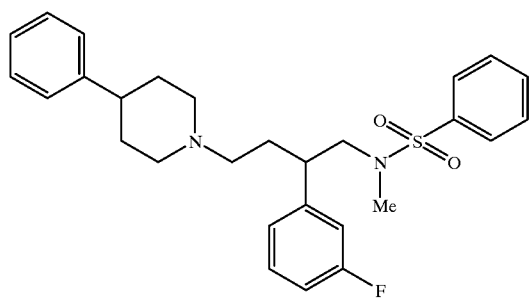
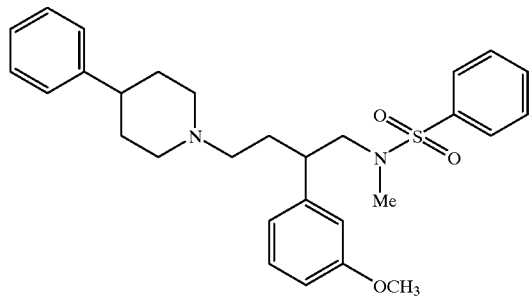
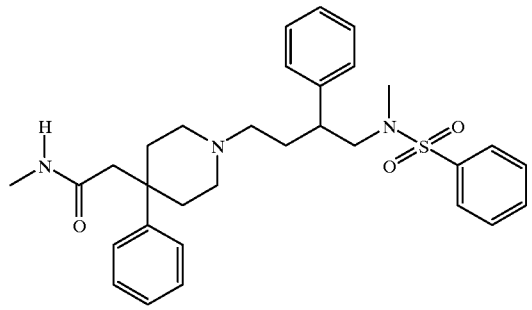
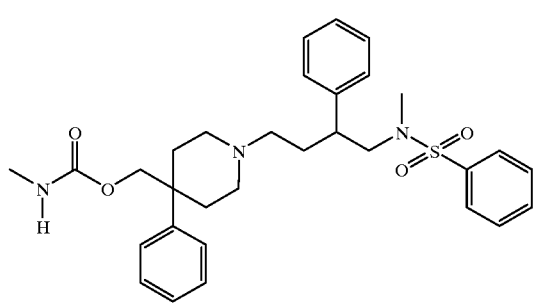
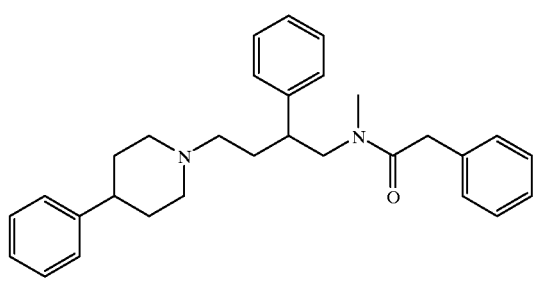
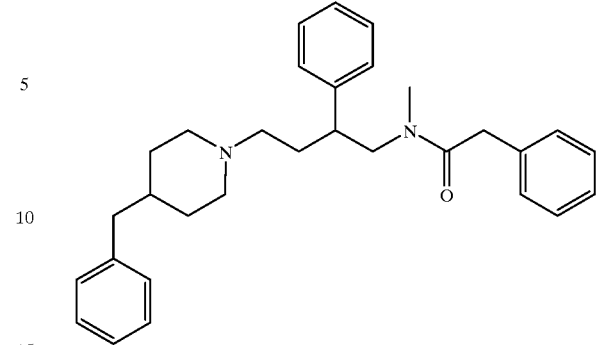
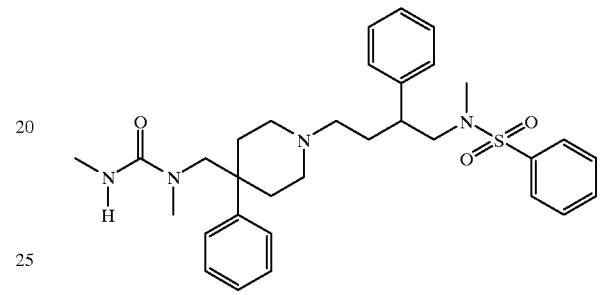
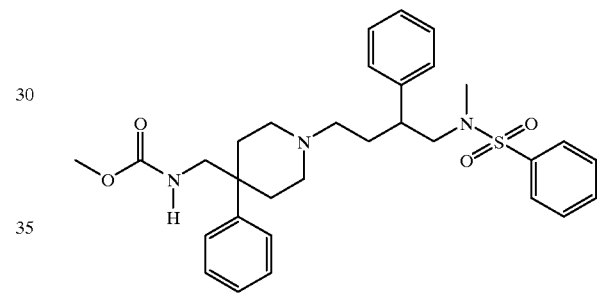
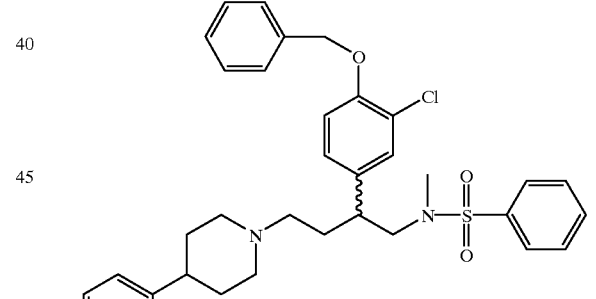
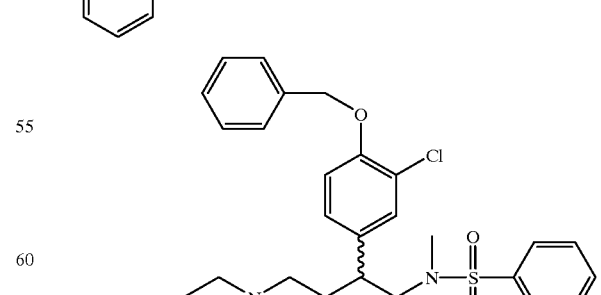
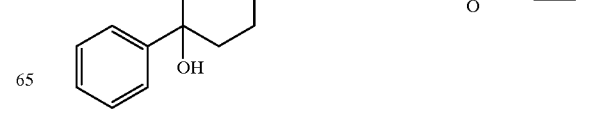

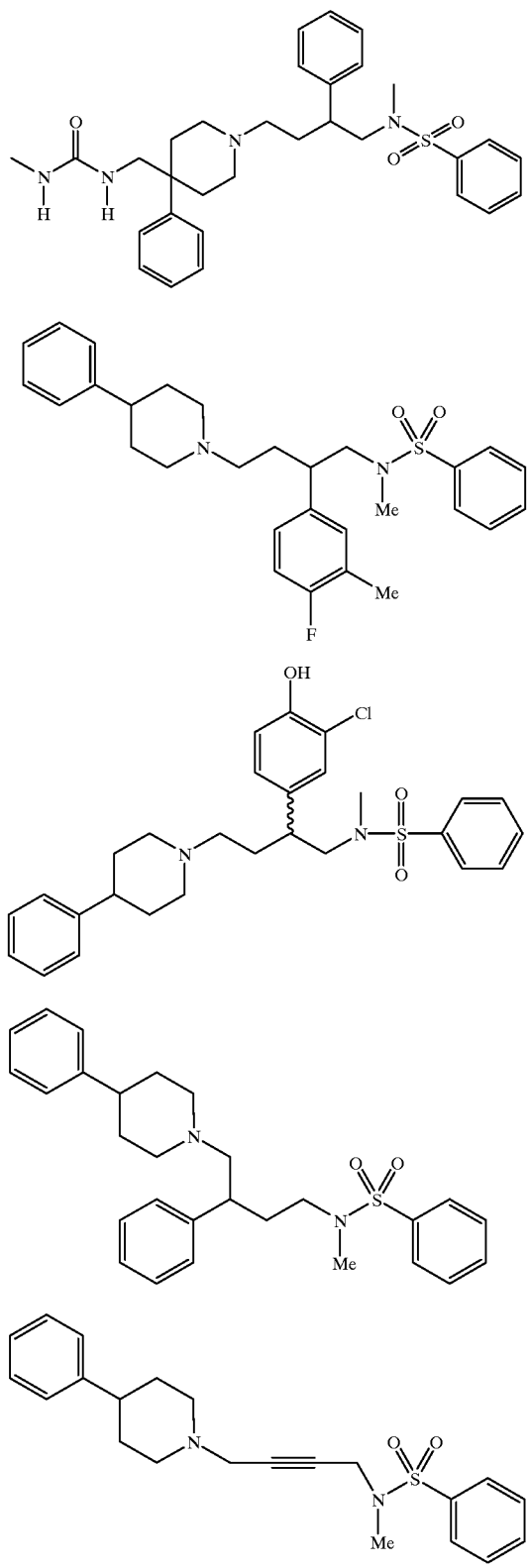
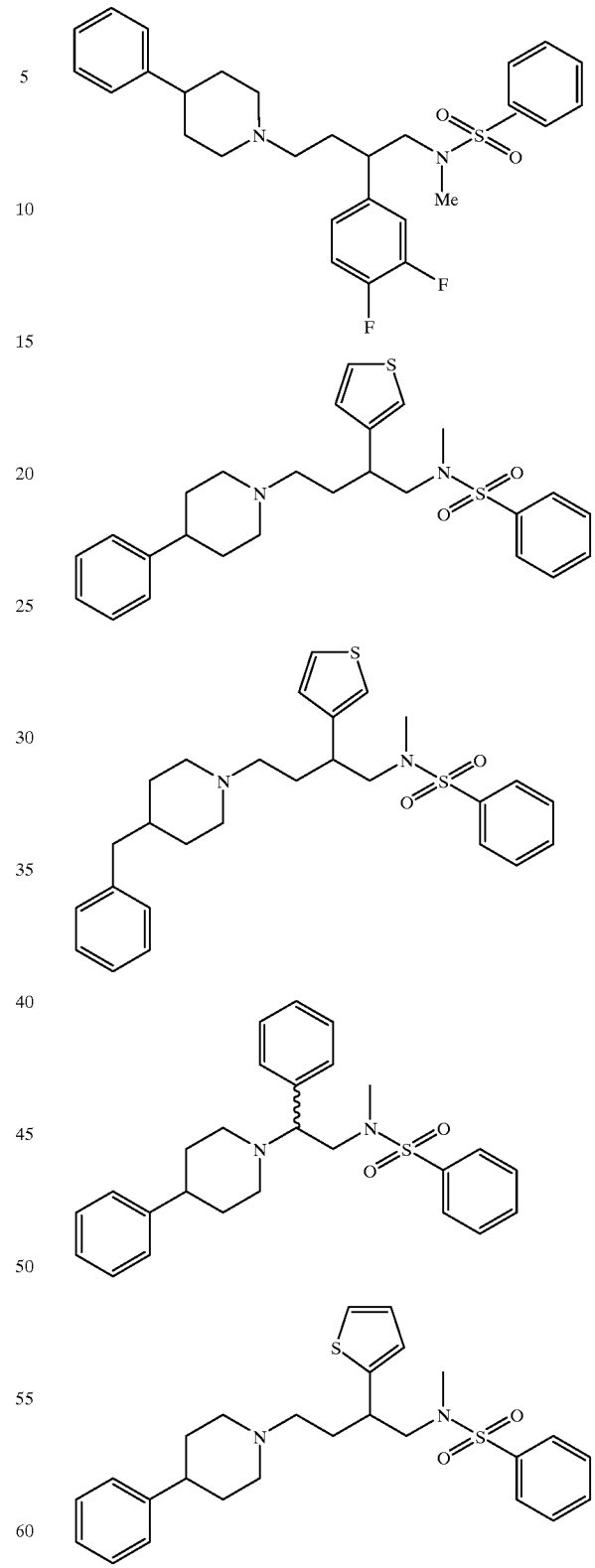

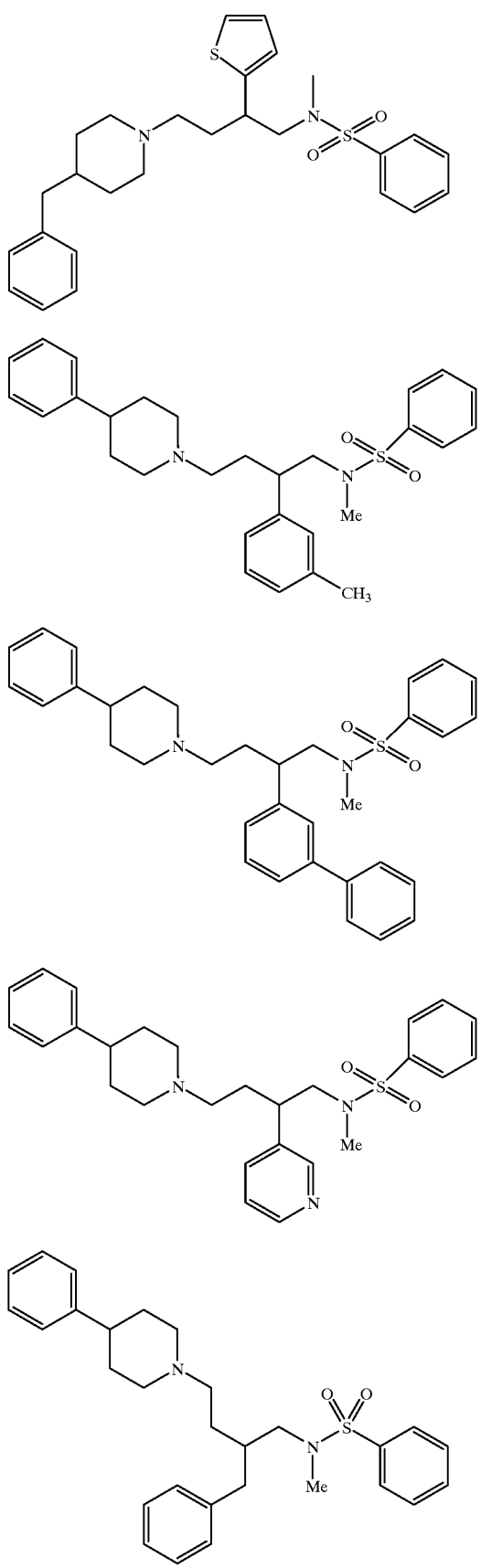
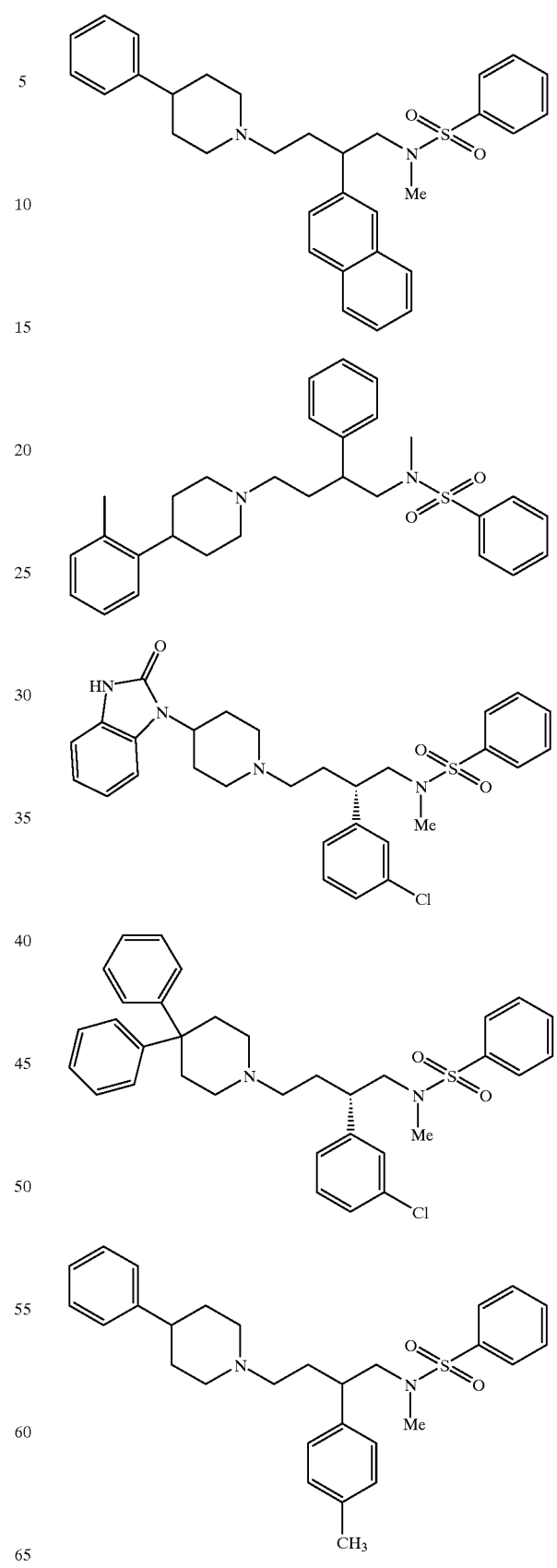

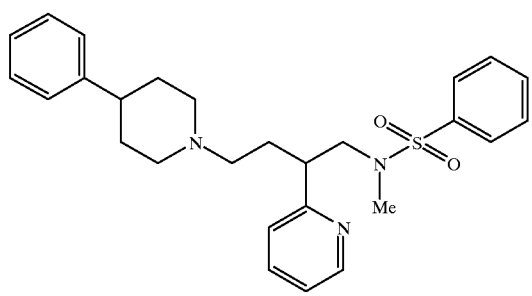
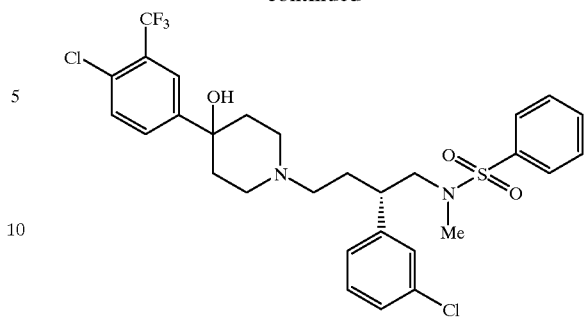
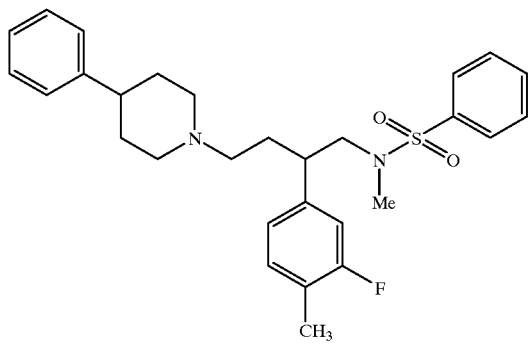
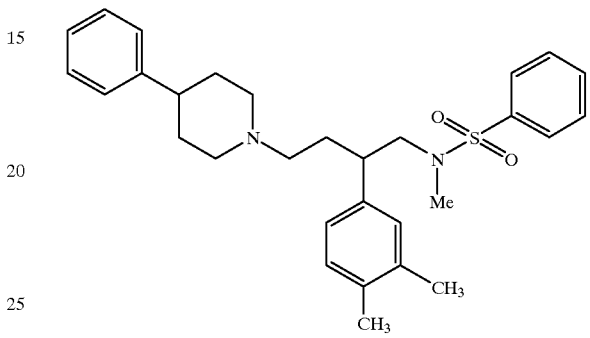
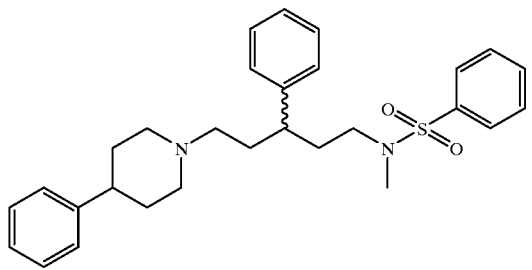
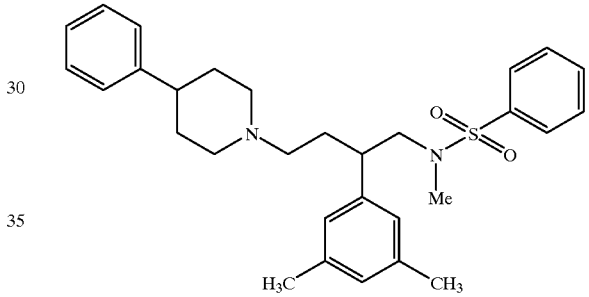
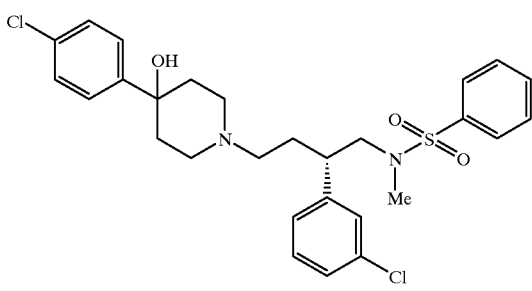
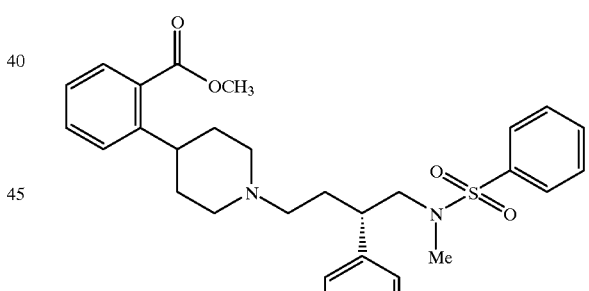
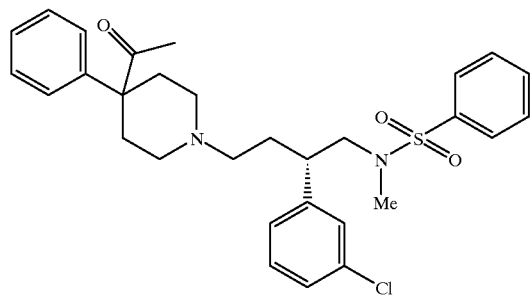
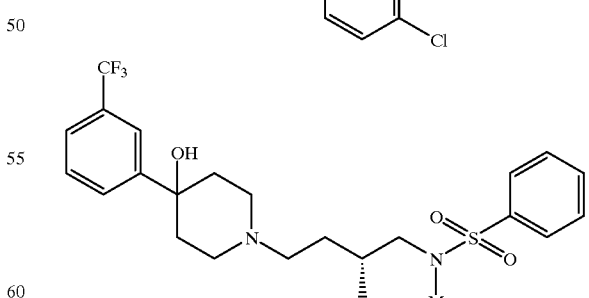

31
-continued
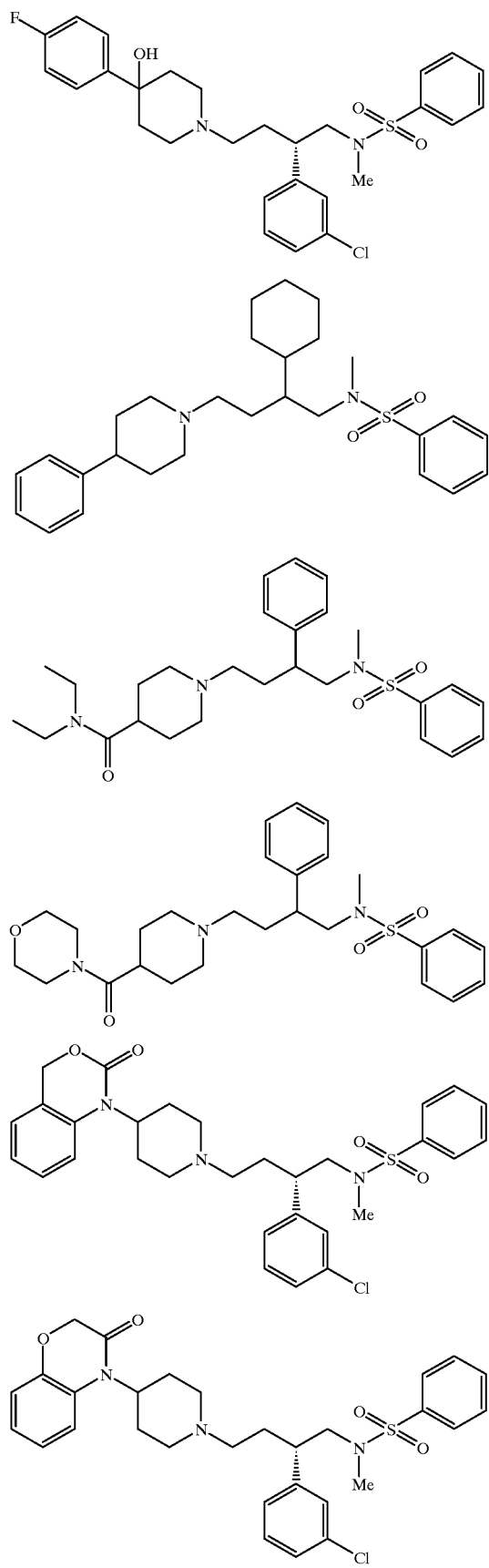
32
-continued
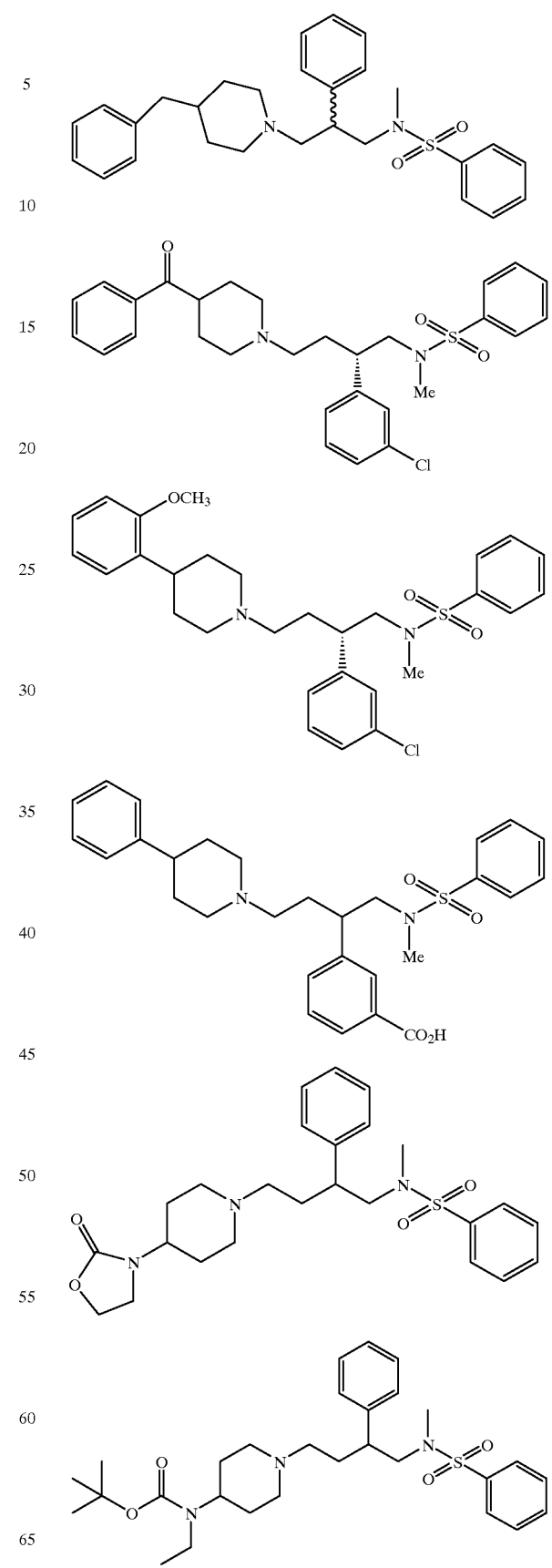

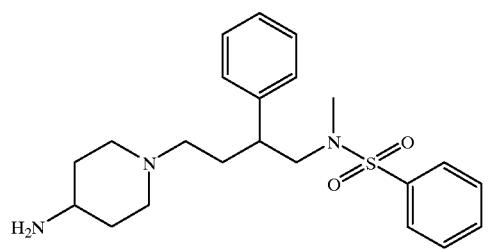
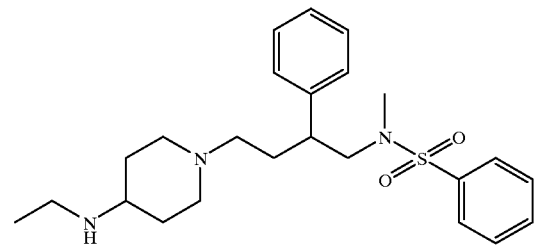
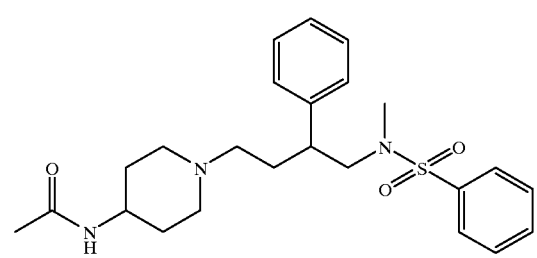
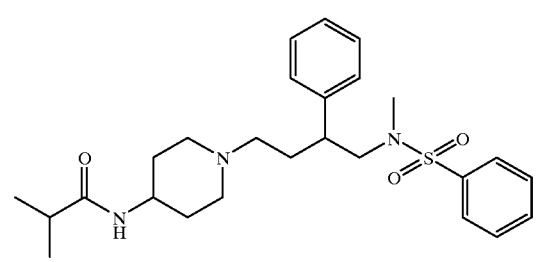
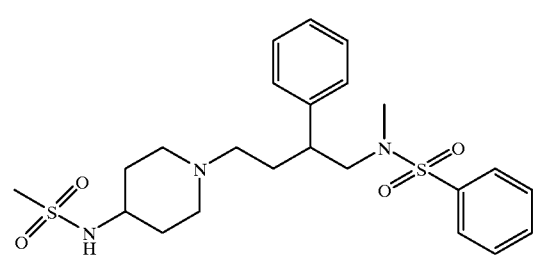
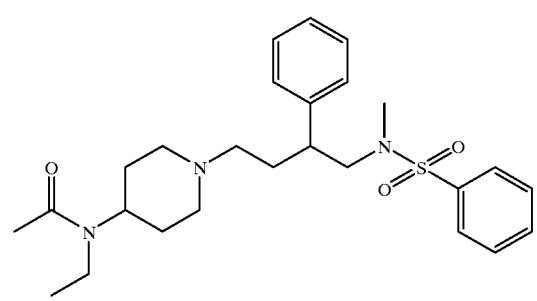
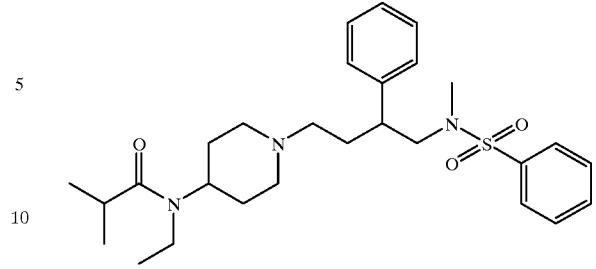
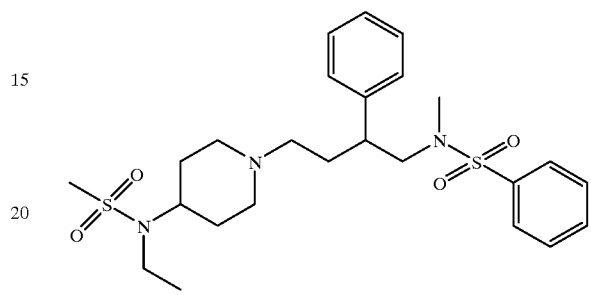
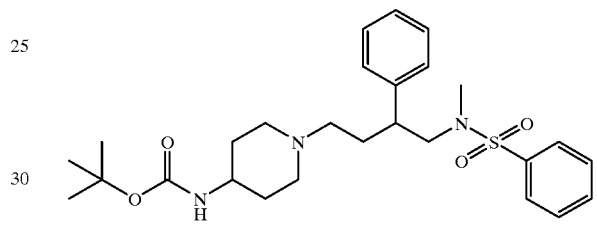
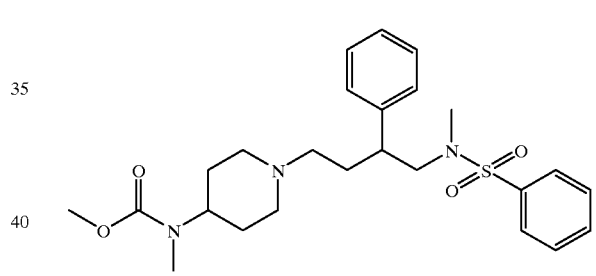
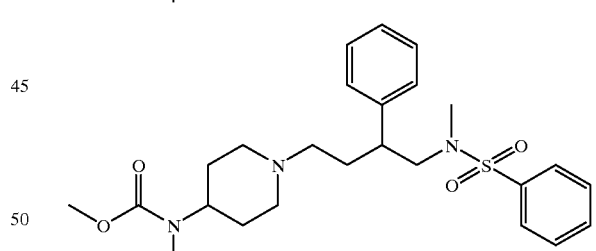
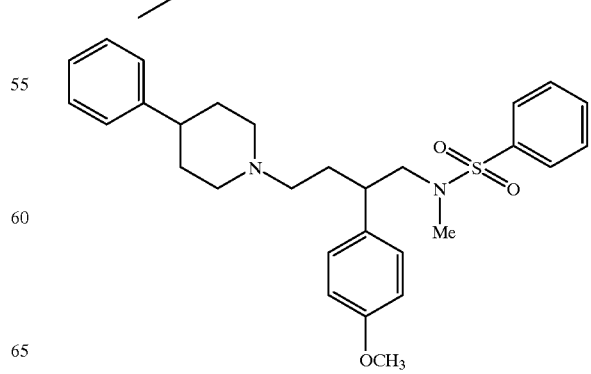

35
-continued
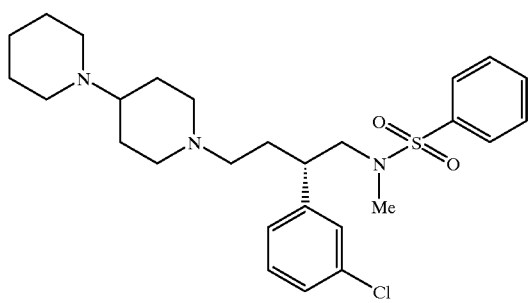
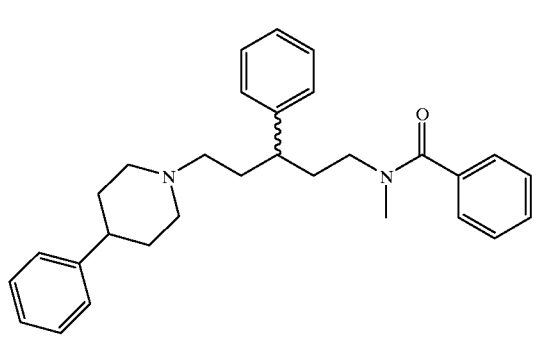
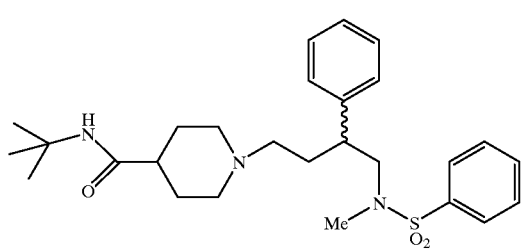
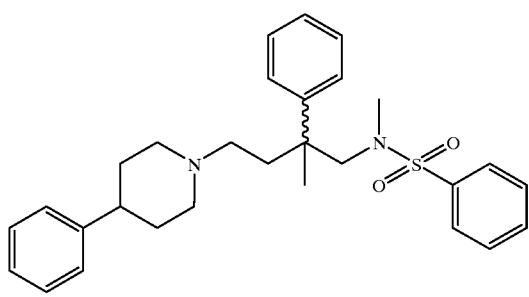
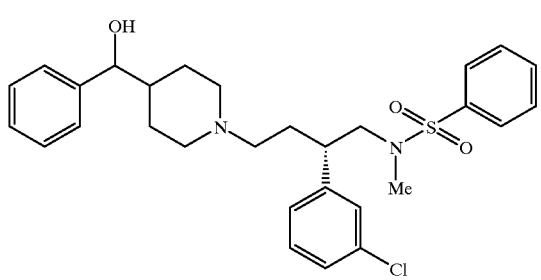
36
-continued
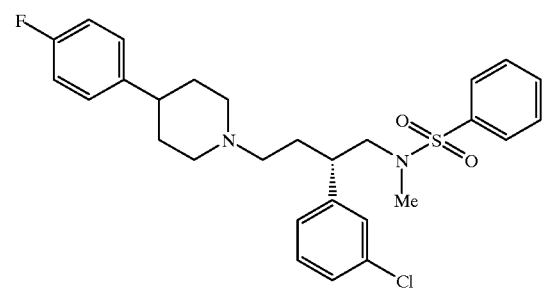
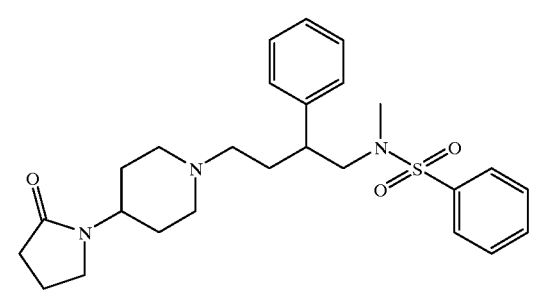
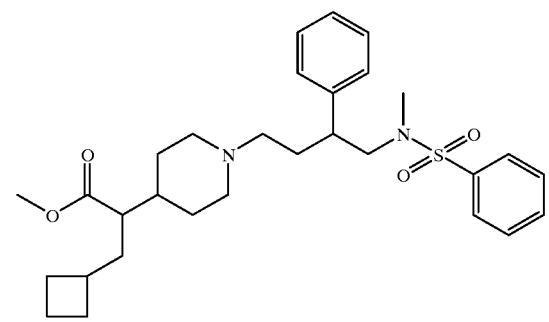
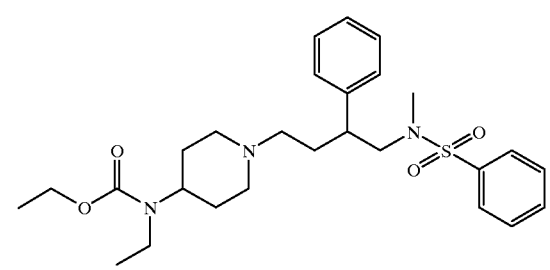
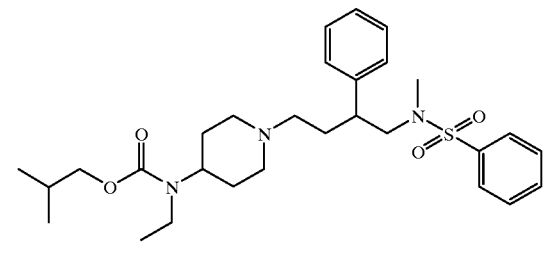

37
-continued
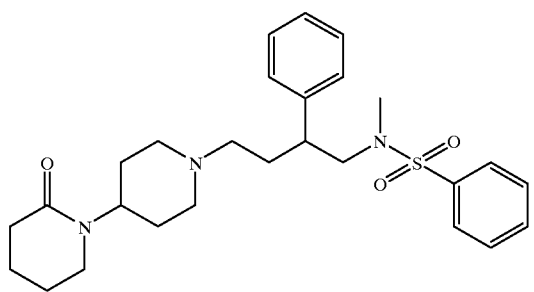
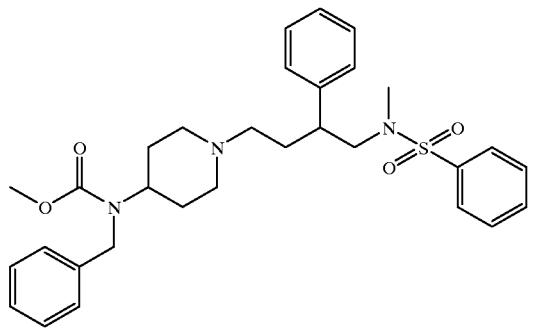
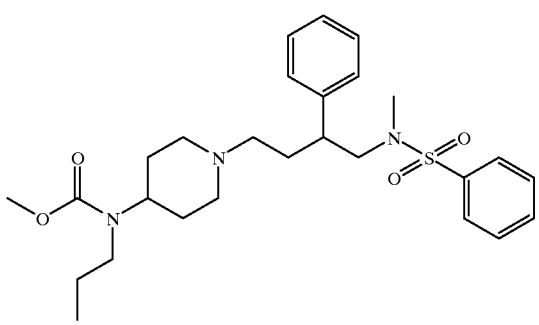
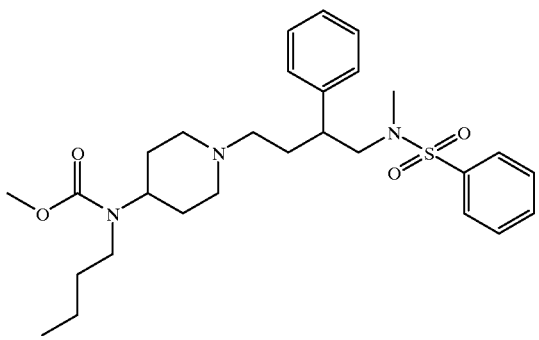
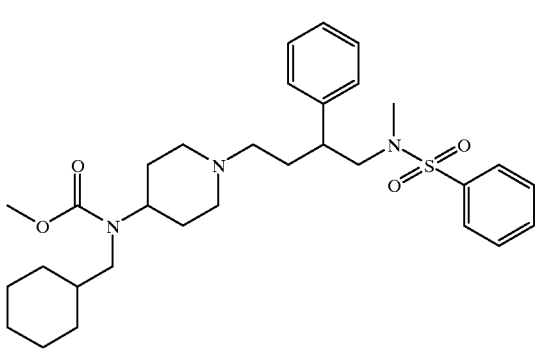
38
-continued
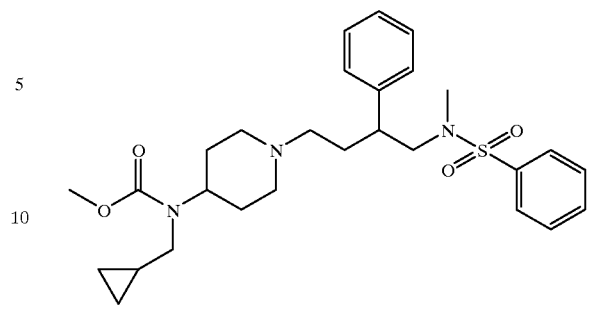
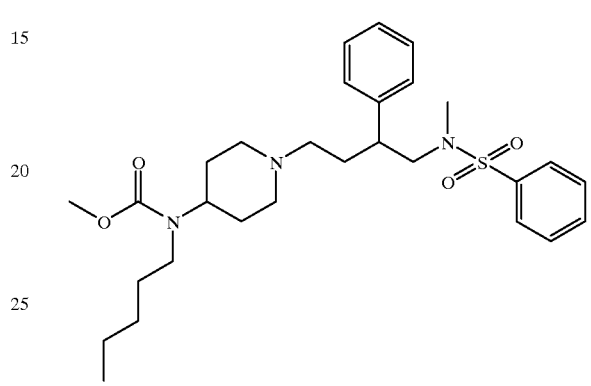
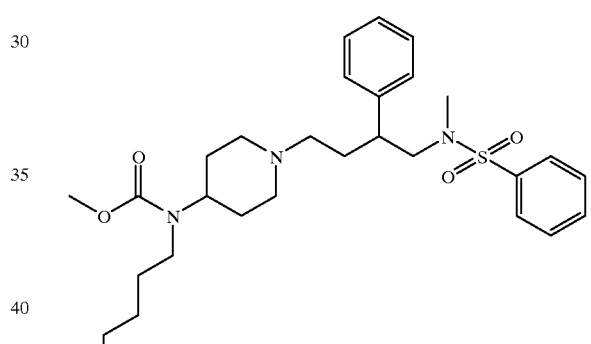
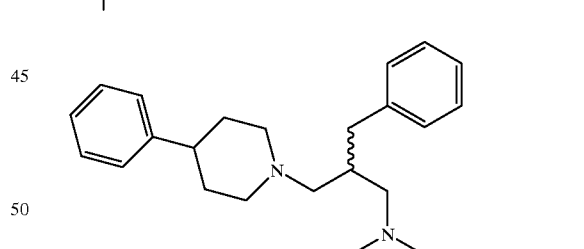
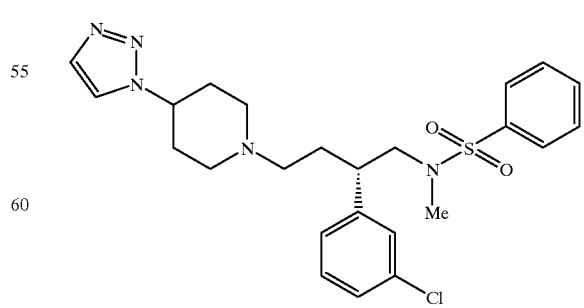

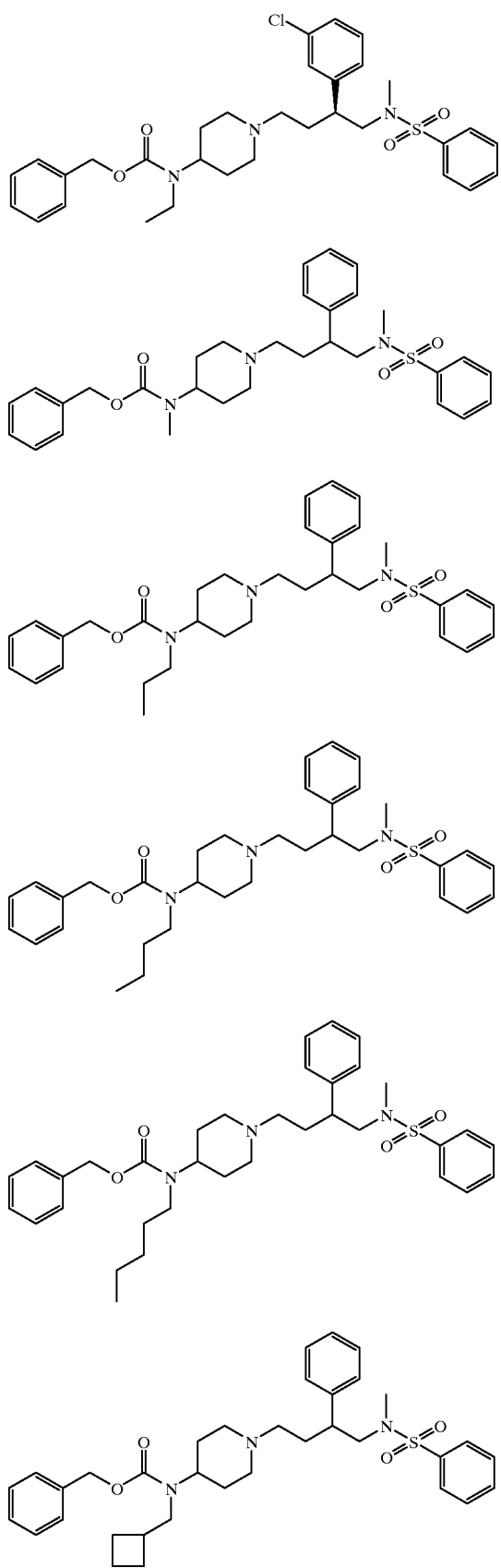
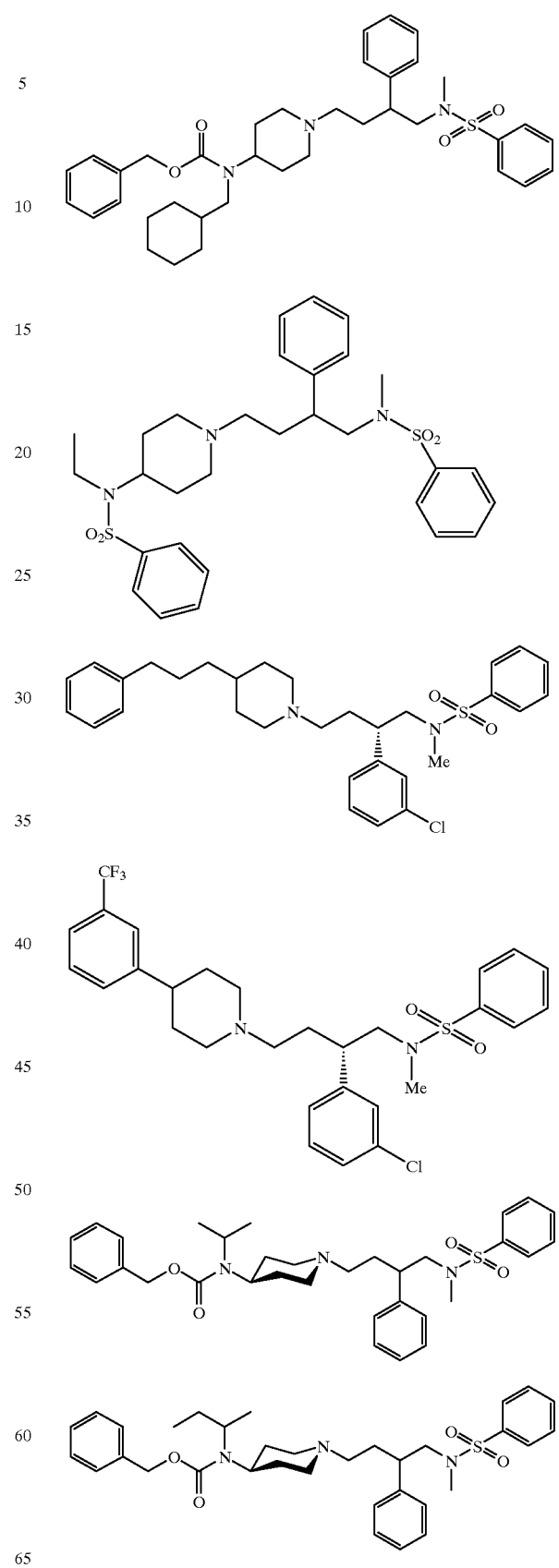

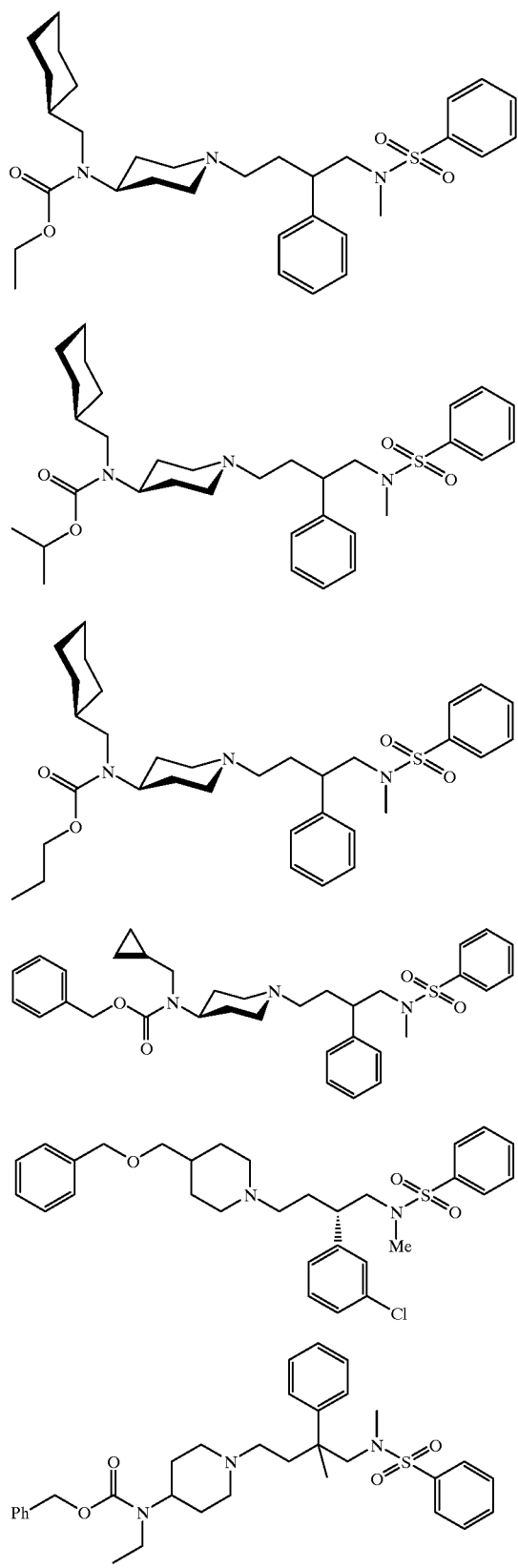
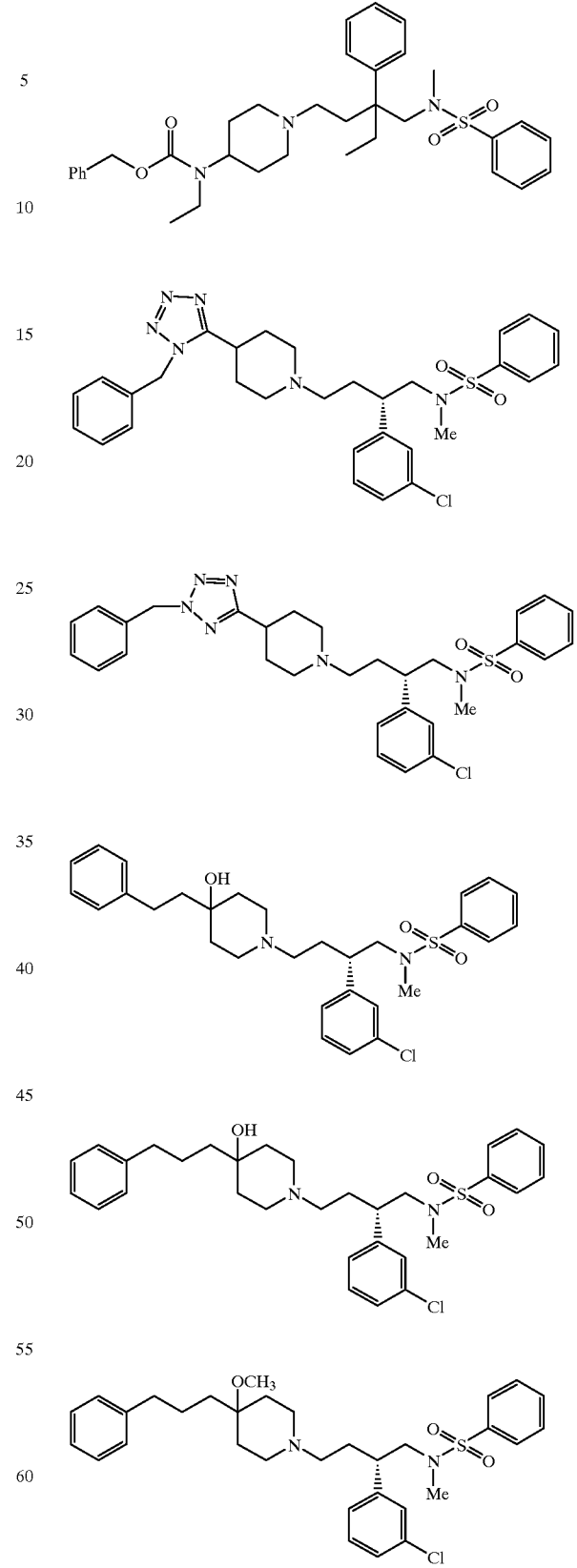

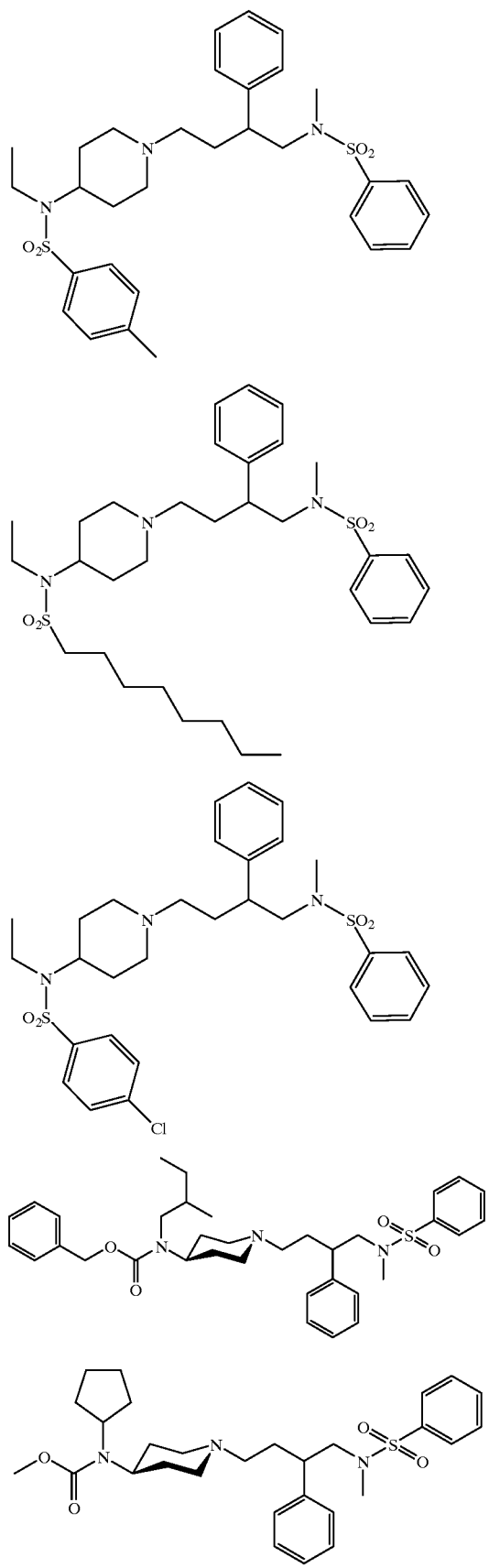
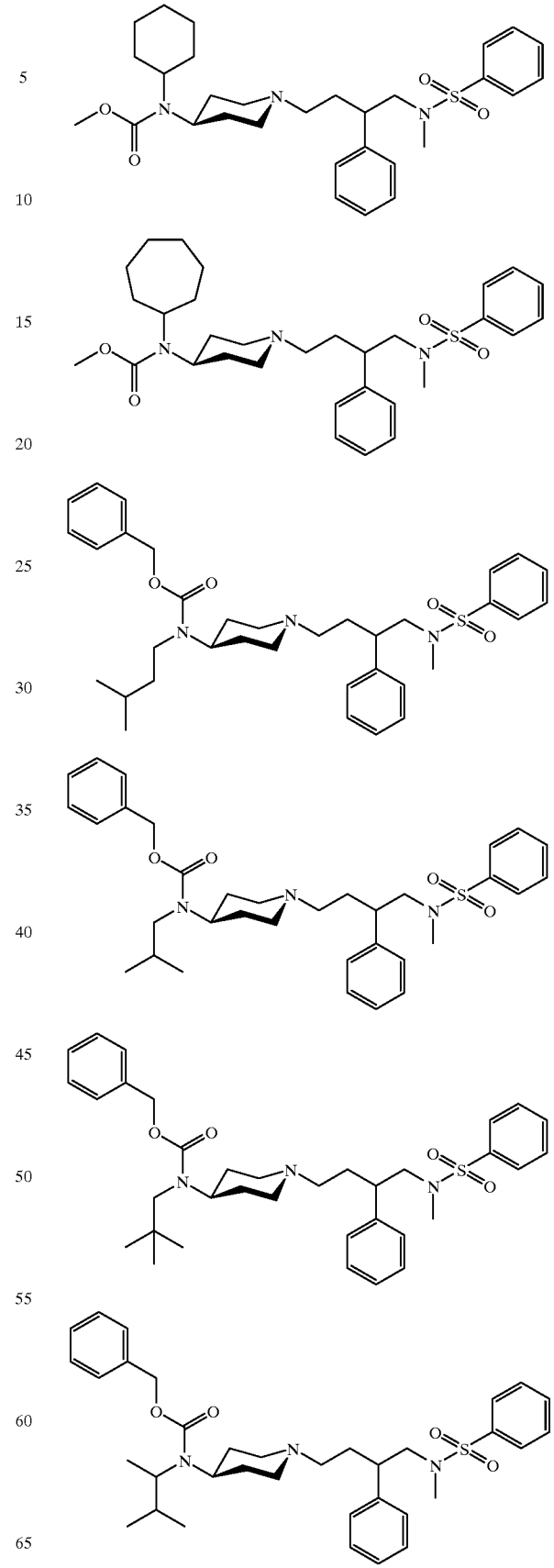

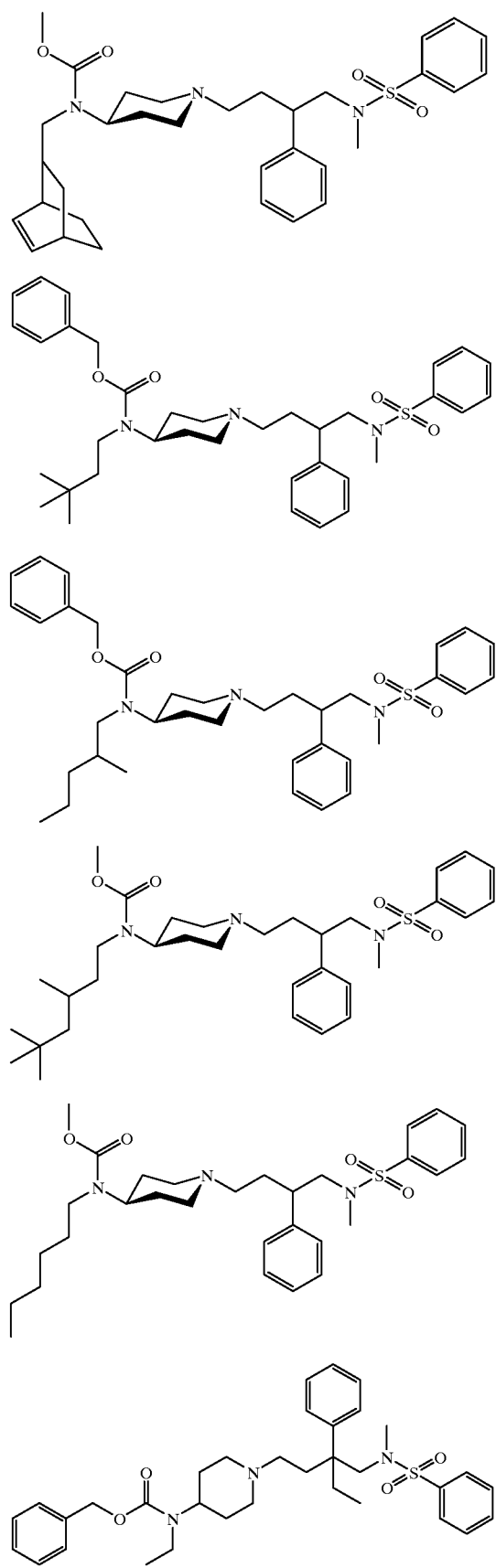
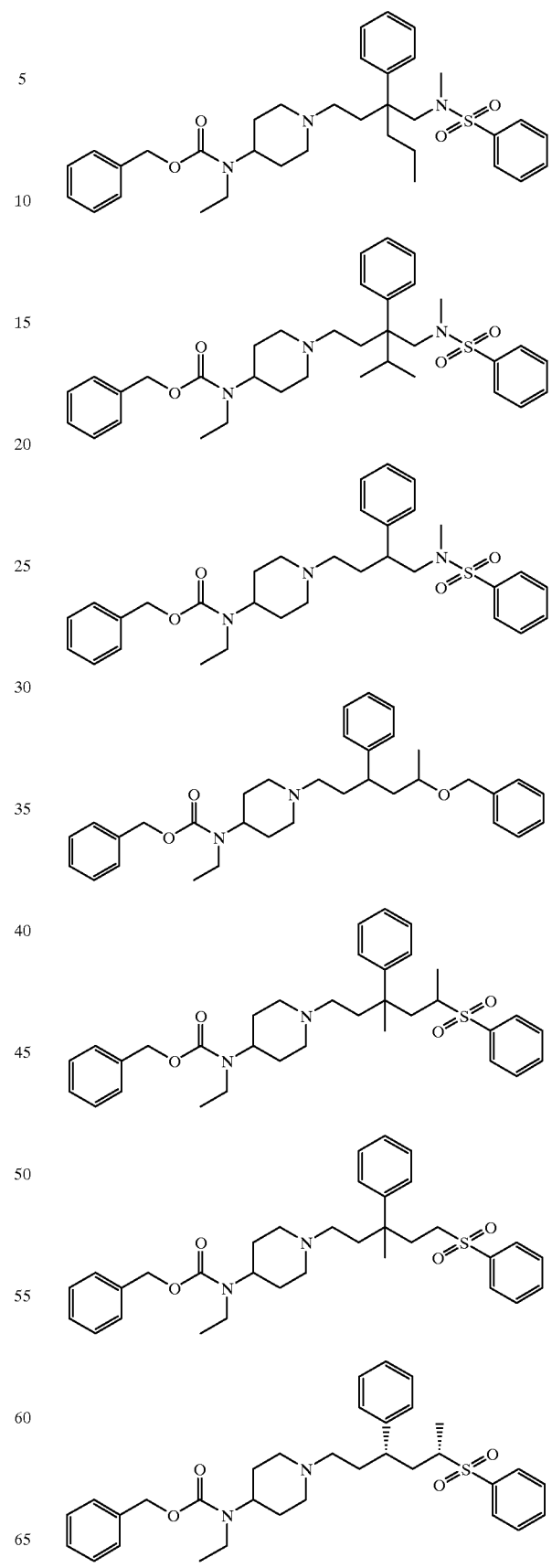

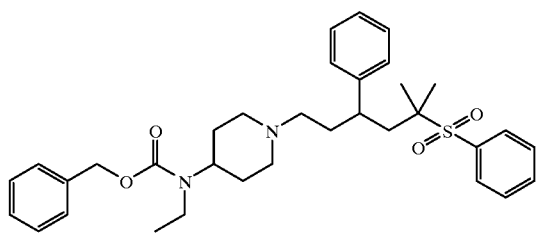
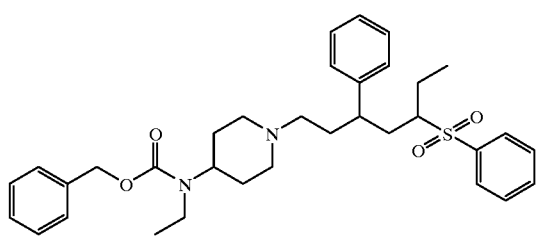
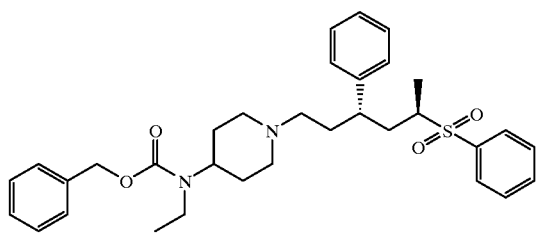
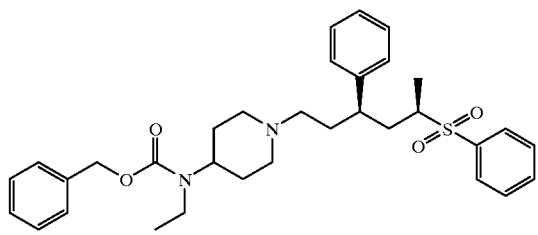
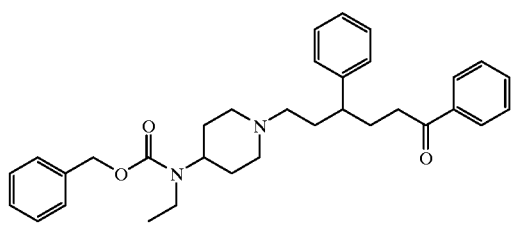
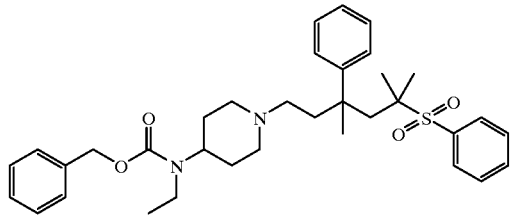
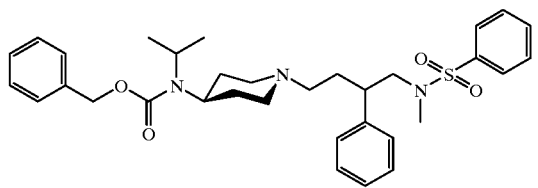
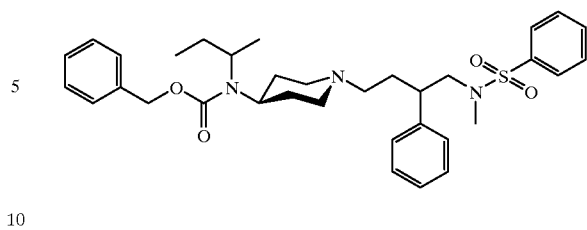
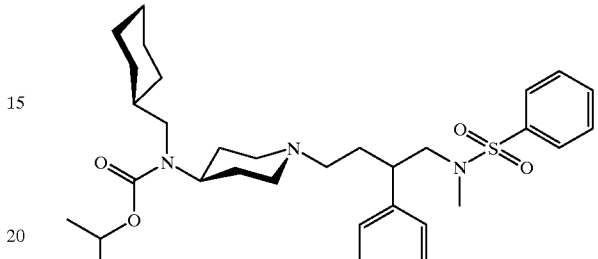
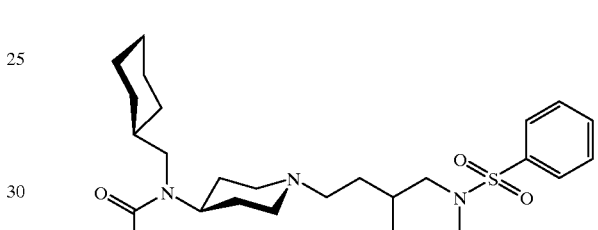
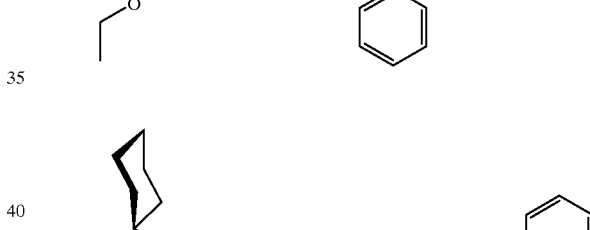
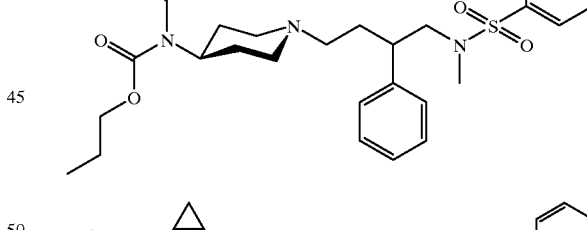
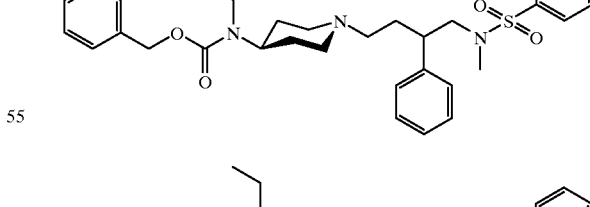
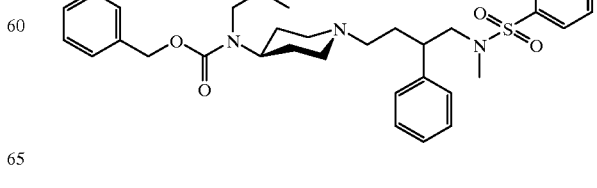

49
-continued
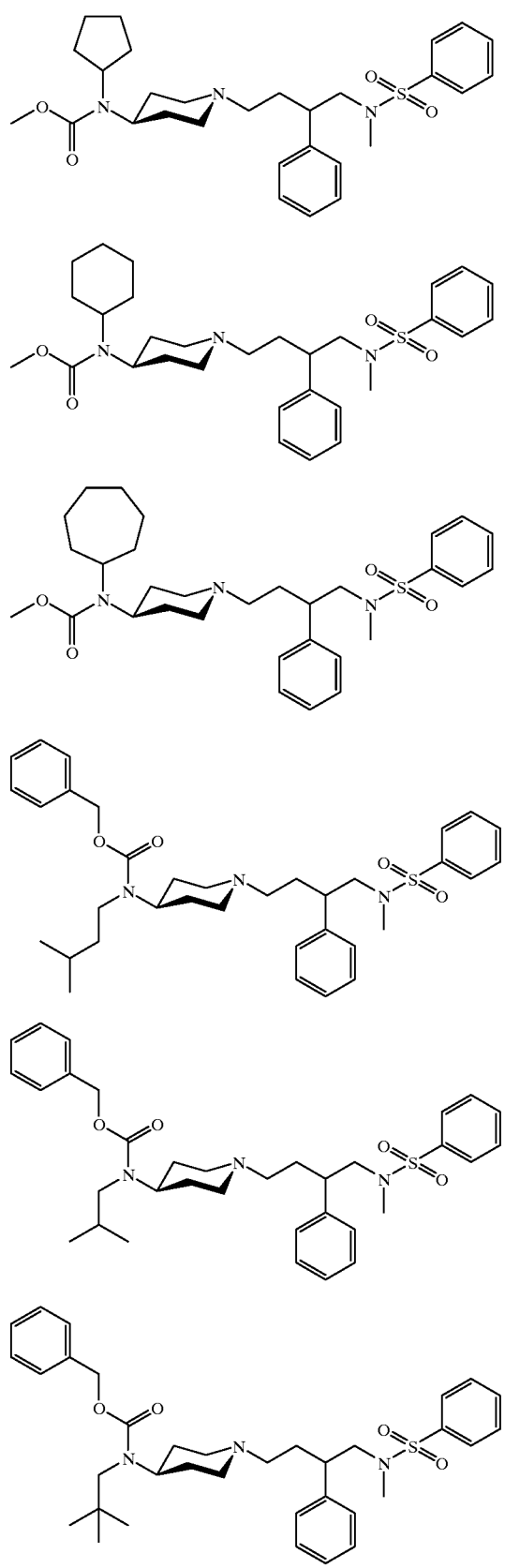
50
-continued
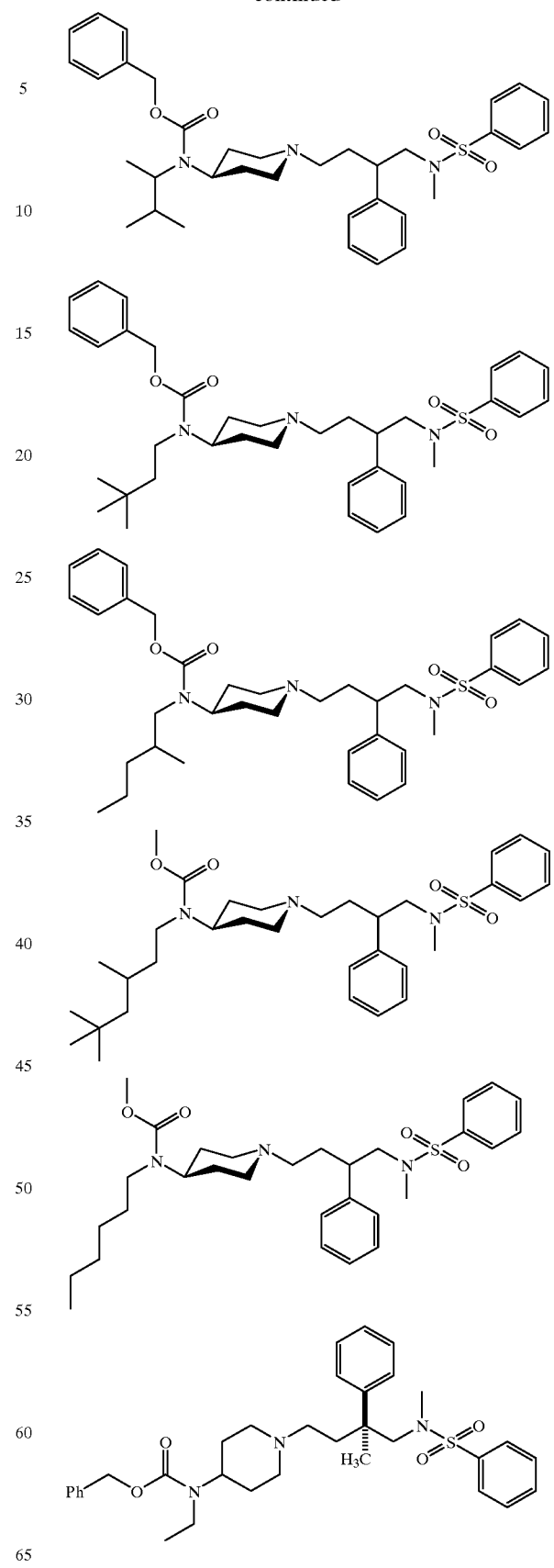

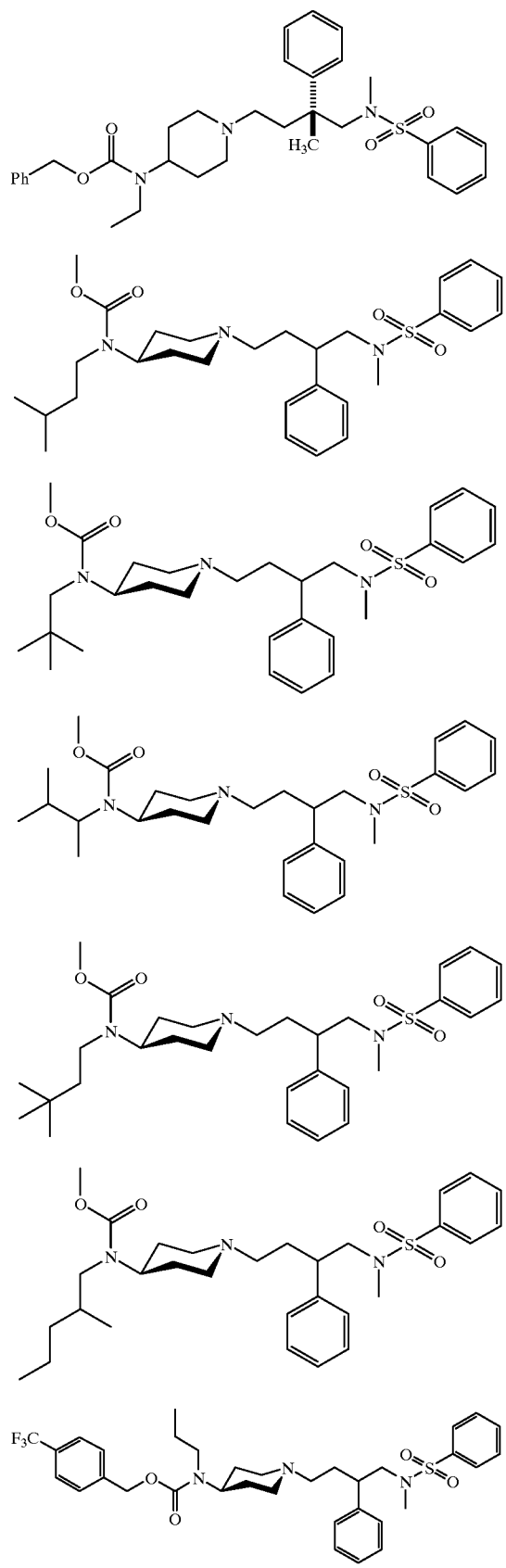
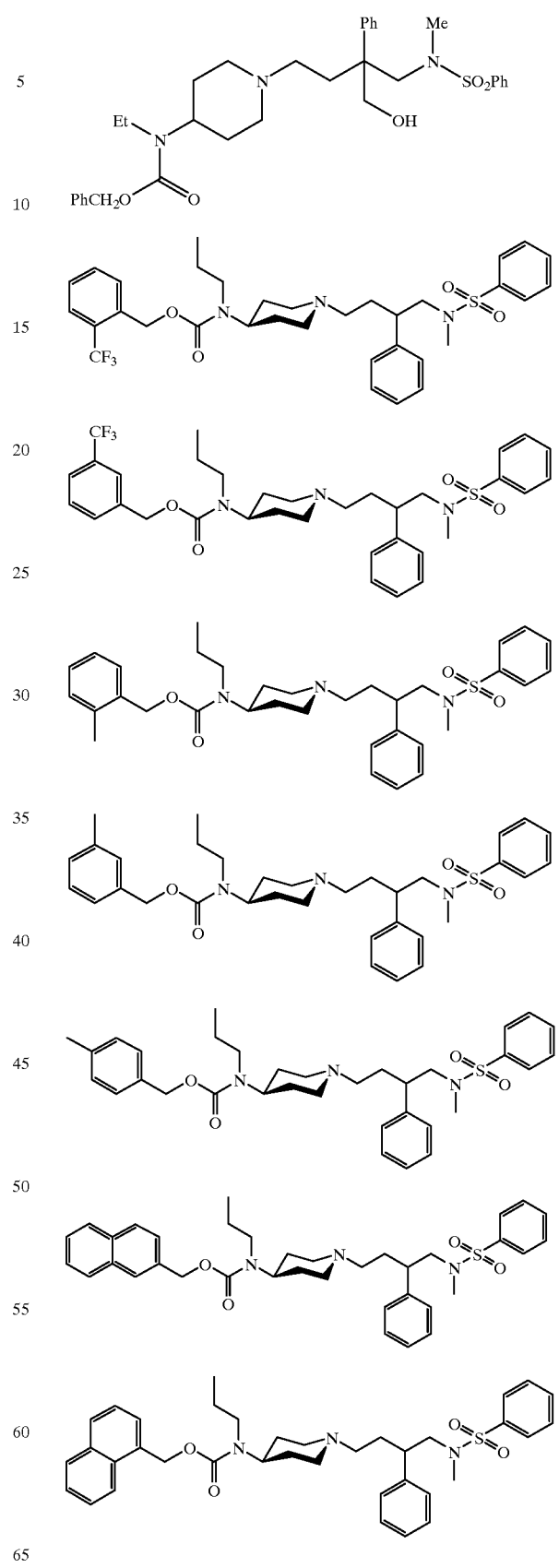

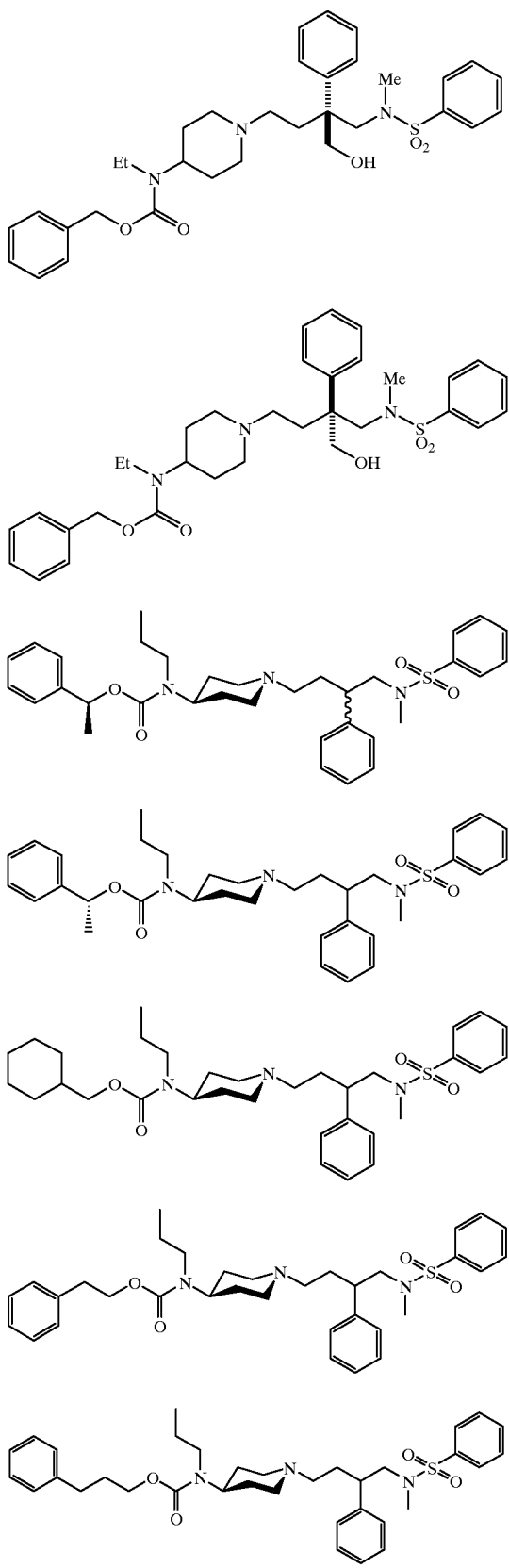
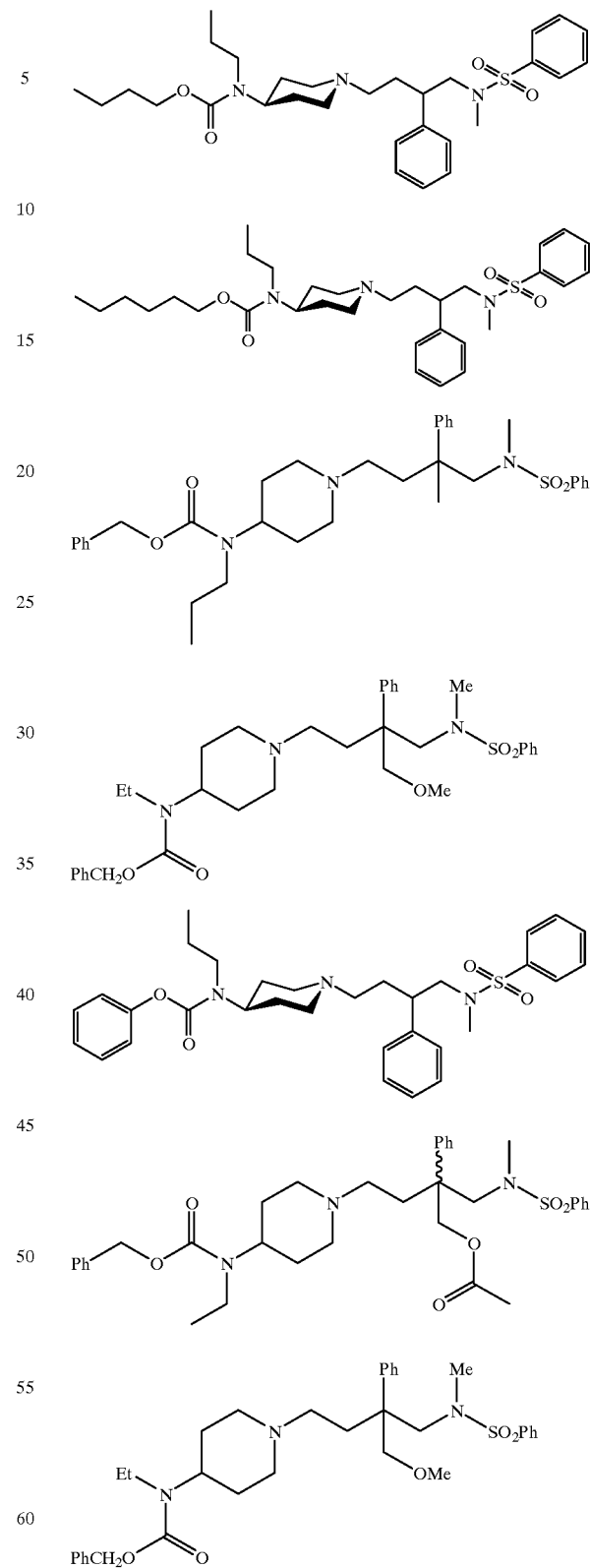

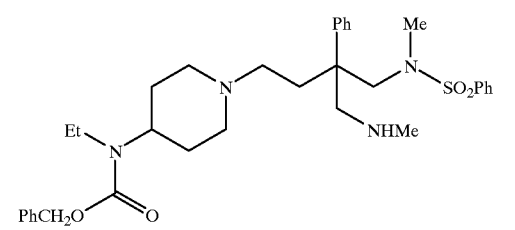
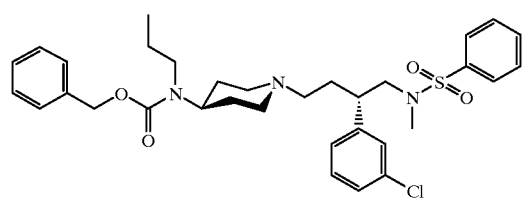
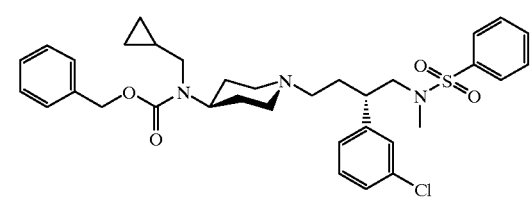
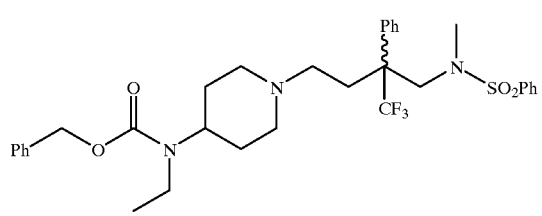
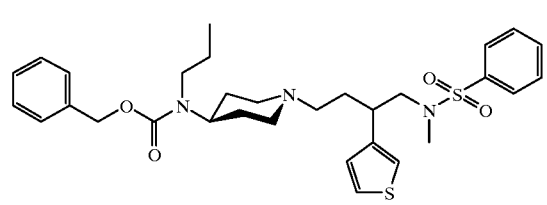
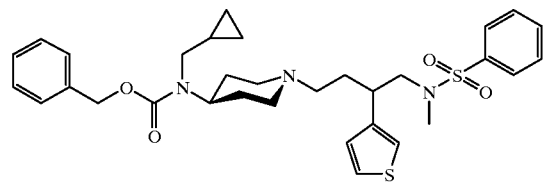
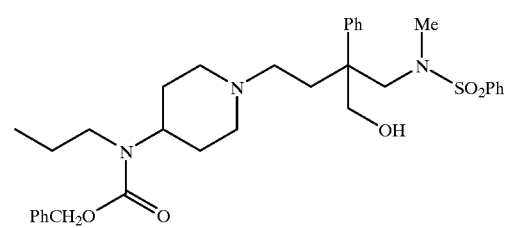
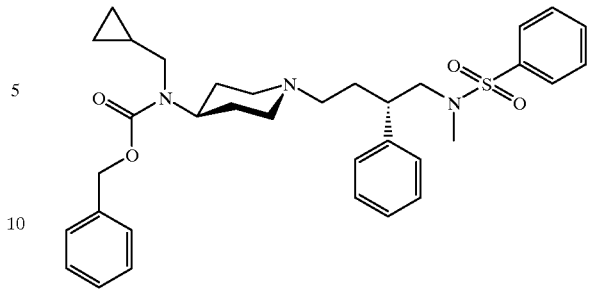
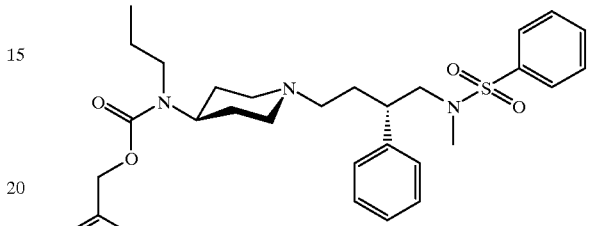
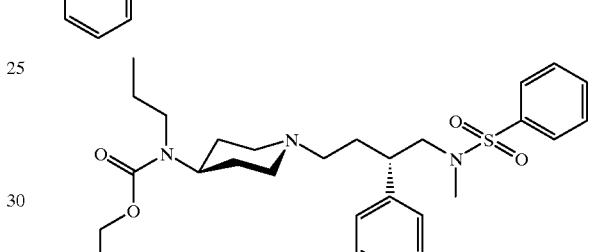
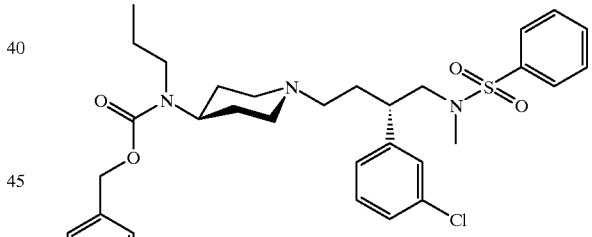
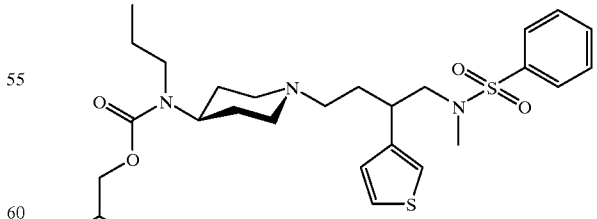

57
-continued
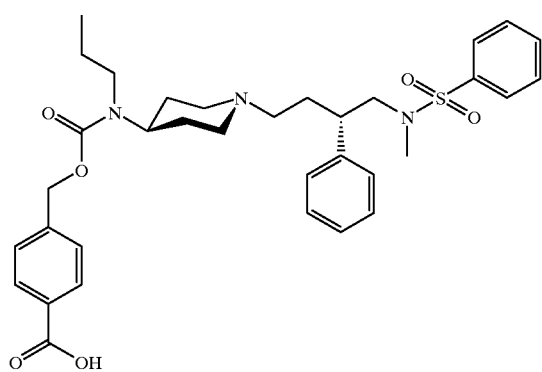
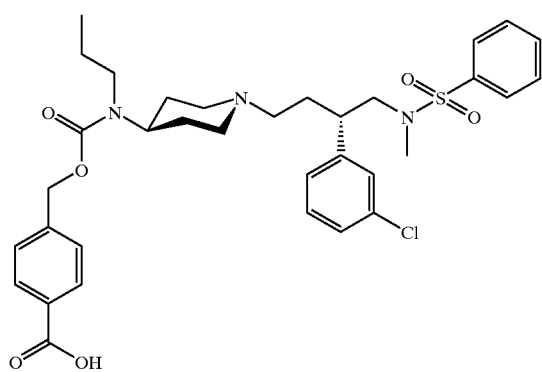
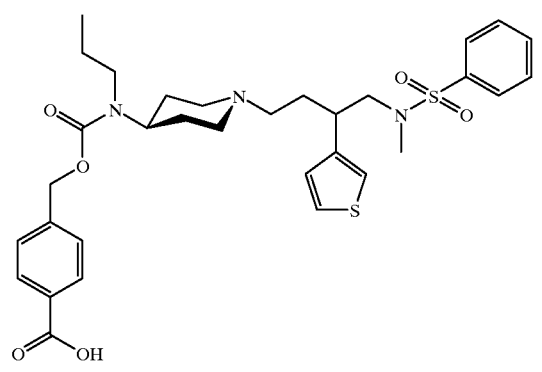
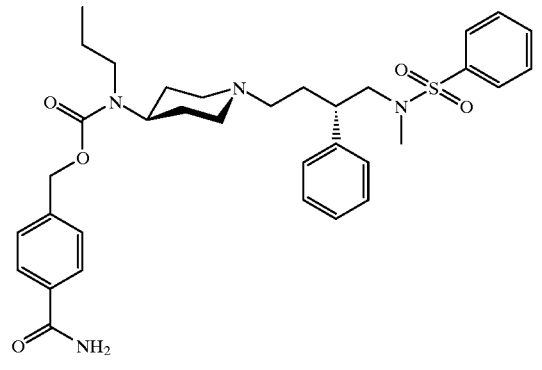
58
-continued
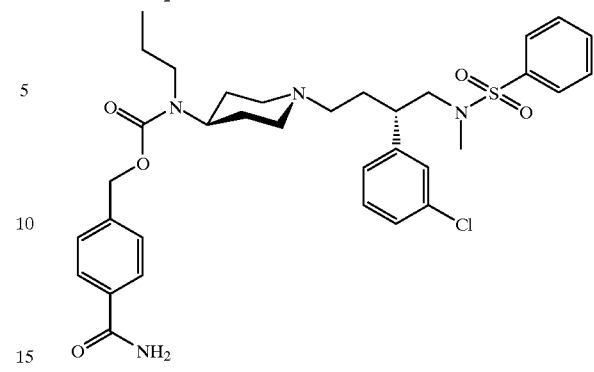
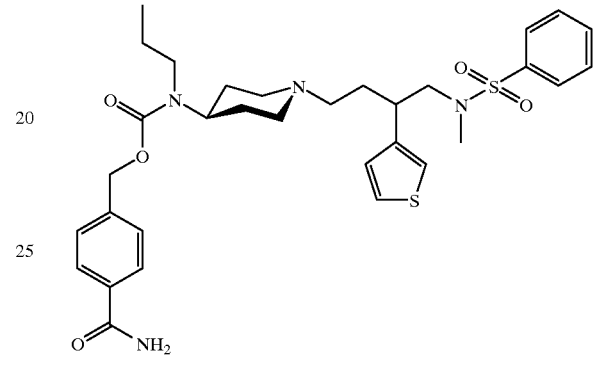
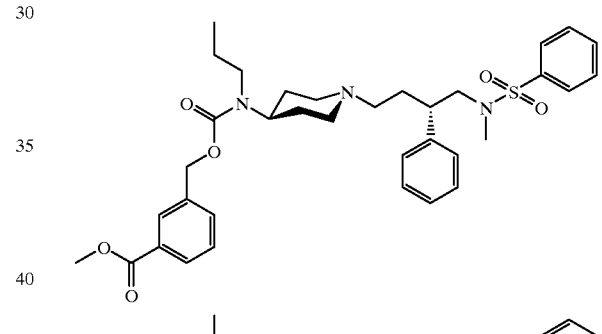
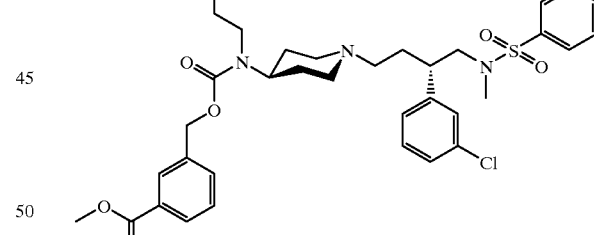
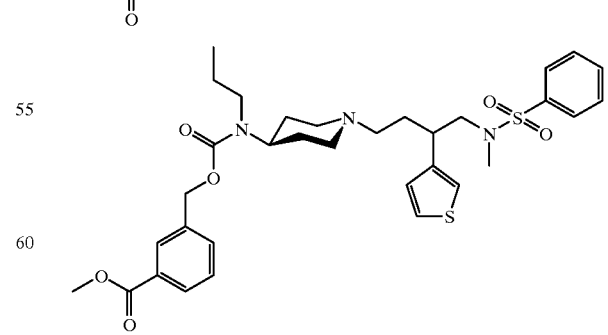

59
-continued
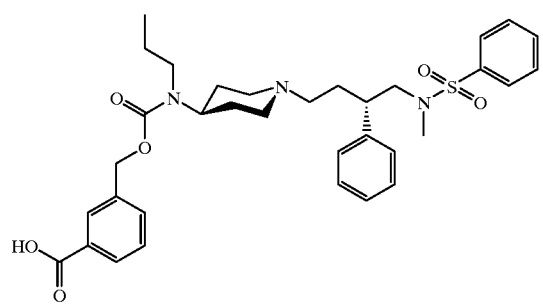
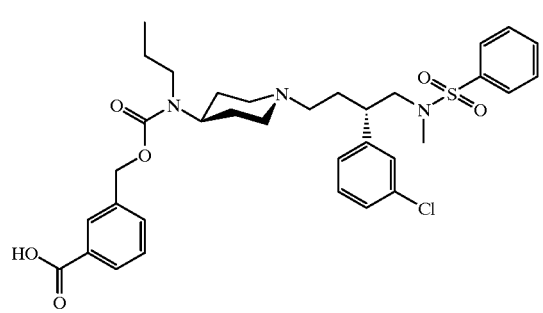
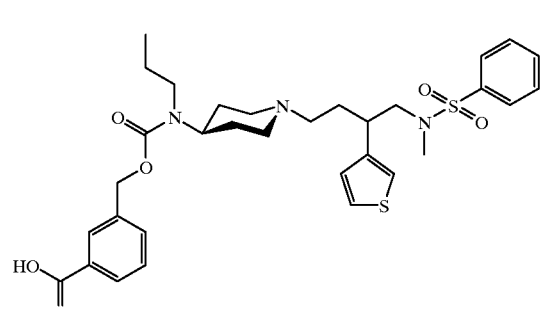
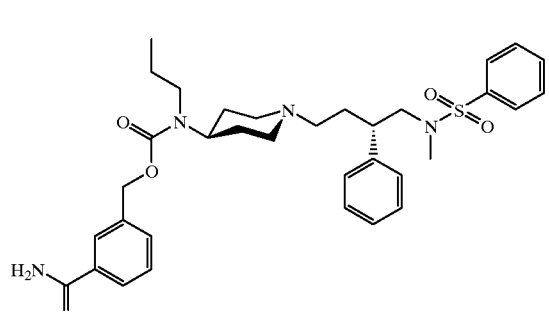
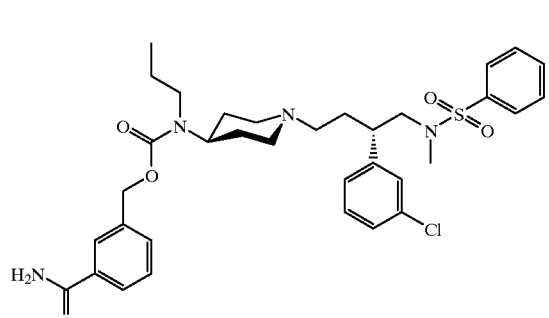
60
-continued
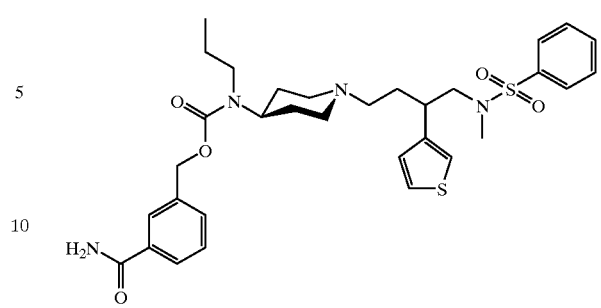
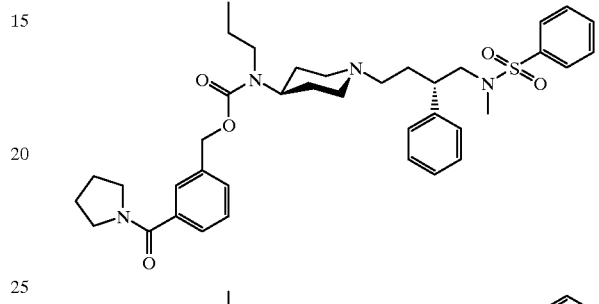
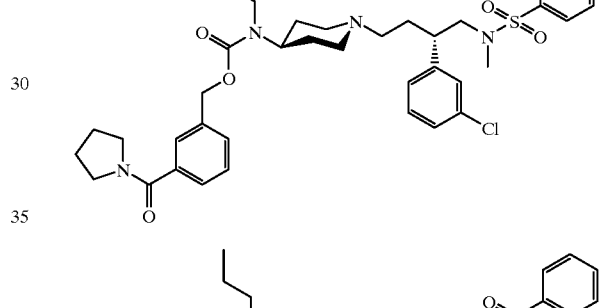
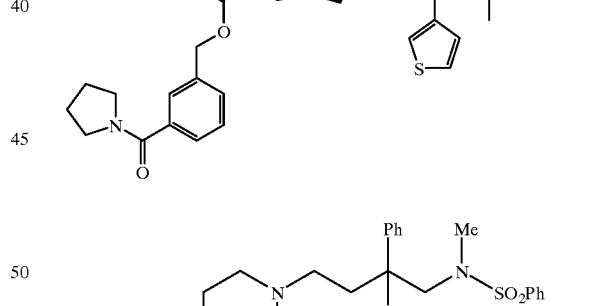
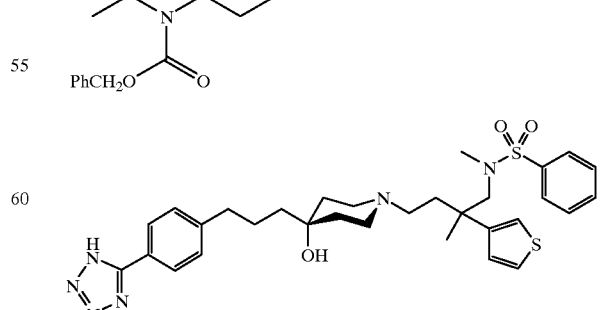

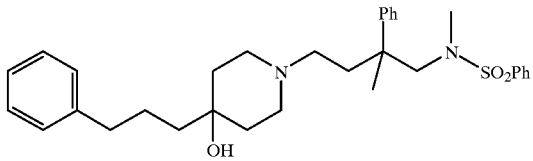

and pharmaceutically acceptable salts thereof.

The subject compounds are useful in a method of modulating chemokine receptor activity in a patient in need of such modulation comprising the administration of an effective amount of the compound.

The present invention is directed to the use of the foregoing spiro-substituted azacycles as modulators of chemokine receptor activity. In particular, these compounds are useful as modulators of the chemokine receptors, including CCR-1, CCR-2, CCR-2A, CCR-2B, CCR-3, CCR-4, CCR-5, CXCR-3, and/or CXCR-4.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.*, 177, 851–856 (1993), and the assay for CCR-2 and/or CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to either the CCR-5 receptor or the CCR-3 receptor in the aforementioned assays, generally with an $IC_{50}$ of less than about 10 $\mu$M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, including asthma and allergic diseases, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors, including CCR-1, CCR-2, CCR-2A, CCR-2B, CCR-3, CCR-4, CCR-5, CXCR-3, and CXCR-4. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-1, CCR-2, CCR-2A, CCR-2B, CCR-3, CCR-4, CCR-5, CXCR-3, and CXCR-4. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a human immunodeficiency virus to a chemokine receptor, such as CCR-5 and/or CXCR-4, of a target cell, which comprises contacting the target cell with an amount of the compound which is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

ANTIVIRALS

| Drug Name | Manufacturer | Indication |
| --- | --- | --- |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in |

-continued

| Drug Name | Manufacturer | Indication |
|---|---|---|
| AD-439 | Tanox Biosystems | combination with AZT<br>HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (−) 6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz, DMP-266 | Dupont-Merck Pharmaceuticals | HIV infection, AIDS, ARC (non-nucleoside reverse transcriptase inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston Tx) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2 (S)-N'-(t-butylcarbo-xamido)-piperazinyl))-pentaneamide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (-) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following (1) indinavir, with efavirenz or (-) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl- pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

Several methods for preparing the compounds of this invention are illustrated in the following Schemes and Examples.

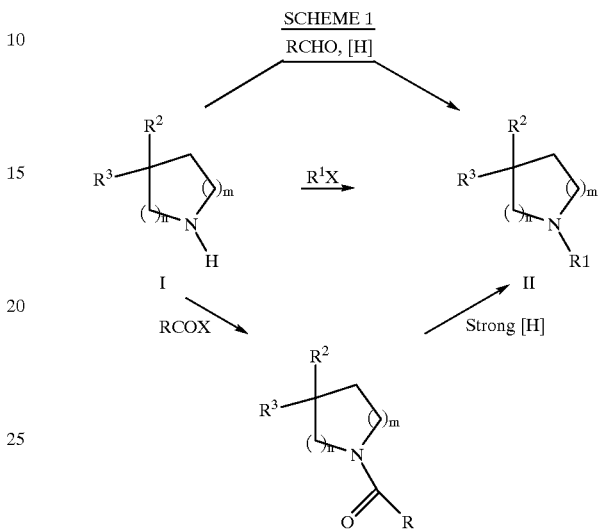

The compounds of the present invention are prepared by alkylating heterocycle I under appropriate conditions to provide compound II (Scheme 1). The required starting materials for preparing heterocycle I are available commercially or can be prepared using the methods given below.

Thus, heterocycle I is combined with the appropriate aldehyde and the intermediate imine or iminium species is reduced to the tertiary amine chemically (e.g. using sodium cyanoborohydride, sodium borohydride, or sodium triacetoxyborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention one preparation of a representative aldehyde is described in Hale, J. J.; Finke, P. E.; MacCoss, M. *Bioorganic & Medicinal Chemistry Letters* 1993,3, 319–322.

In an alternative embodiment of the present invention, heterocycle I can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol converted to either the alkyl halide using methods described in March J. "Advanced Organic Chemistry", 4th ed., John Wiley & Sons, New York, pp. 431–433 (1992), or alkyl sulfonate ester using methods described in March J. "Advanced Organic Chemistry", 4th ed., John Wiley & Sons, New York, p. 498–499 (1992).

In an alternative embodiment of the present invention, I can be acylated to give a tertiary amide; subsequent reduction with a strong reducing agent (e.g. diborane; borane in THF; borane dimethylsulfide, or lithium aluminum hydride)

will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate I. The product amide can in and of itself be a chemokine receptor modulator or can be reduced as noted above to give the tertiary amine.

Optionally, compound II may be further modified in subsequent reactions, as illustrated below.

In an alternative embodiment of the present invention, compounds of interest can be prepared by activating the hydroxyl groups of 1,4-dihydroxy-2-butyne, for example by treatment with triphenyl-phosphine dibromide in acetonitrile, to give 1,4-dibromo-2-butyne (Scheme 2). Displacement of one bromide with the sodium salt of an arylsulfonamide (wherein Rs and Rt are substituents on the phenyl or Ar as defined herein), followed by displacement of the other bromide with a suitable cyclic secondary amine, provides the acetylene derivative III. Palladium-catalysed hydrostannylation preferentially forms the 3-tributylstannyl olefin IV. The minor product from this reaction can also be isolated and carried through the sequence described below.

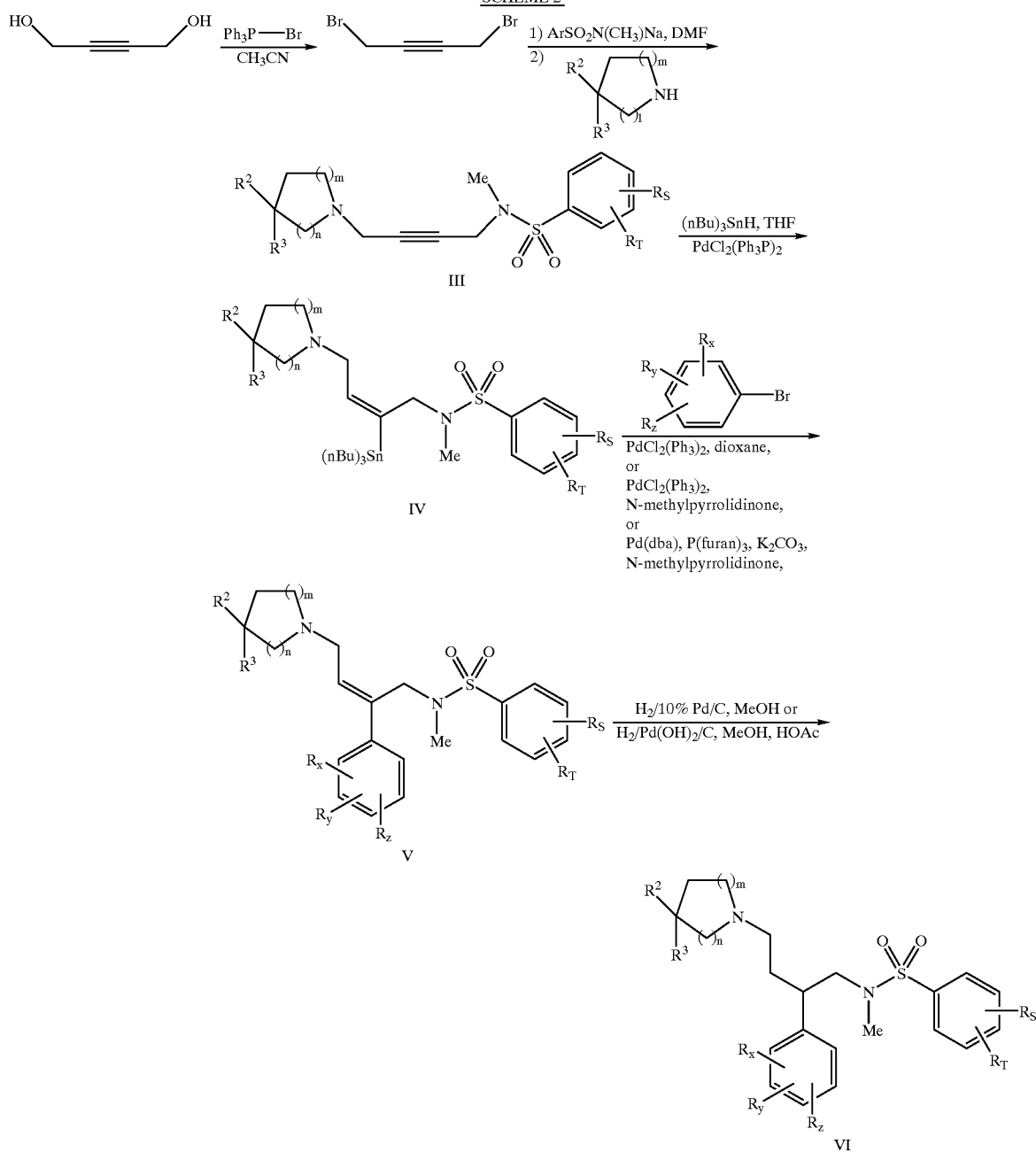

Compound IV can be converted to the corresponding 3-aryl derivative V by treatment with an aryl bromide (wherein Rx, Ry and Rz are substituents on the phenyl or heteroaryl as defined herein) in the presence of a suitable palladium catalyst at or above room temperature. Suitable catalysts include palladium acetate and triphenylphosphine, bis(triphenylphosphine) palladium (II) chloride, or palladium (0) bis(dibenzylidineacetone) in the presence of triphenylphosphine or tri-2-furylphosphine. Suitable solvents include 1,4-dioxane, DMF, and N-methylpyrrolidinone. A base such as potassium carbonate or potassium phosphate may also be employed. Compound V may be employed as a chemokine receptor modulator itself or it can be reduced to saturated derivative VI by standard conditions, for example catalytic hydrogenation with palladium on carbon or with palladium hydroxide in the presence of a mild acid such as acetic acid.

SCHEME 3

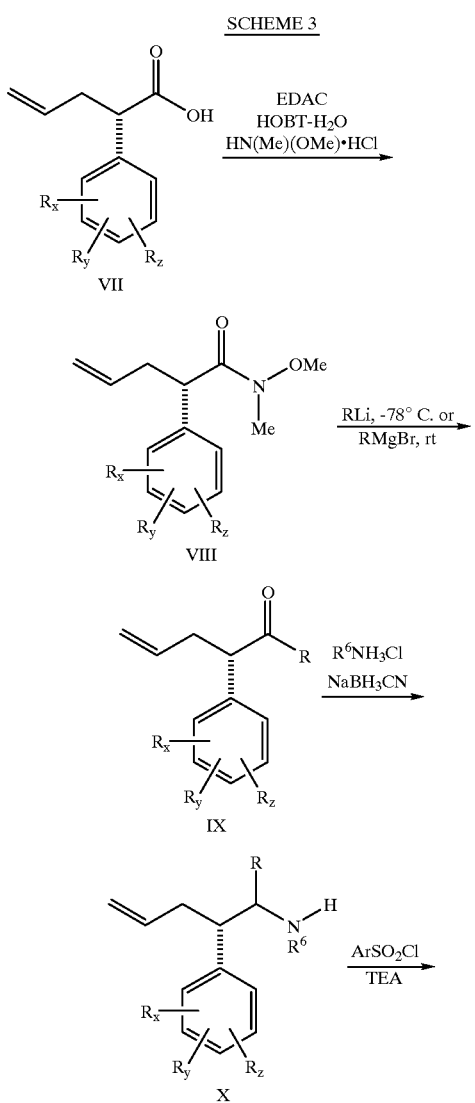

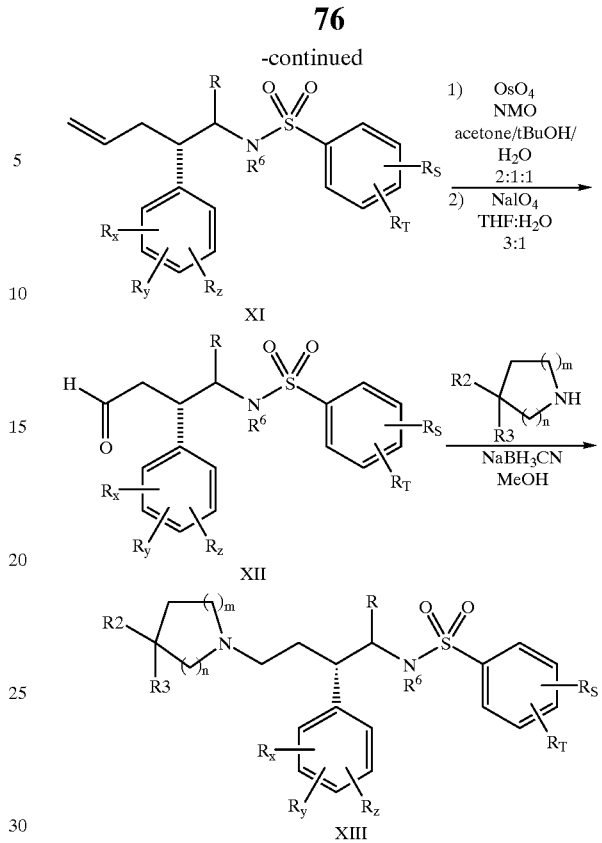

In an alternative embodiment of the present invention, the allyl acid VII (prepared, for example, as described in Hale et al; see above) can be converted into the N-methyl-N-methoxy amide VIII, which is then treated with an alkyl or aryl metal reagent, for example methyllithium or butyllithium, to provide the ketone IX (Scheme 3). The ketone can be converted into an imine which can then be reduced to secondary amine X chemically, (e.g using sodium cyanoborohydride or sodium borohydride), or catalytically (e.g. using hydrogen and palladium on carbon or Raney nickel catalyst). Acylation under standard conditions, for example with an acid chloride, provides the corresponding amide. Alternatively, amine X can be sulfonylated, for example with a alkyl or aryl sulfonyl chloride or an alkyl or aryl sulfonic anhydride, to give (for aryl substituted sulfonylating reagents) sulfonamide XI. The allyl group in XI can be oxidatively cleaved to aldehyde XII with osmium tetroxide followed by sodium periodate or with ozone at low temperature. Reductive amination of aldehyde XII with azacycle I can then be carried out under the conditions described above to give the desired product XIII.

SCHEME 4

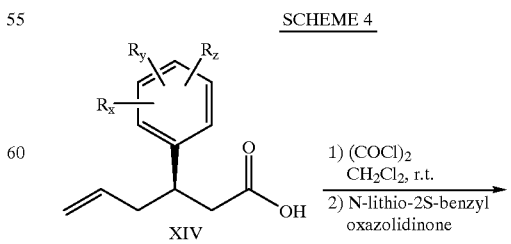

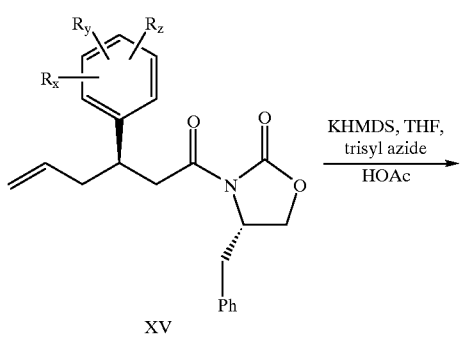

XV

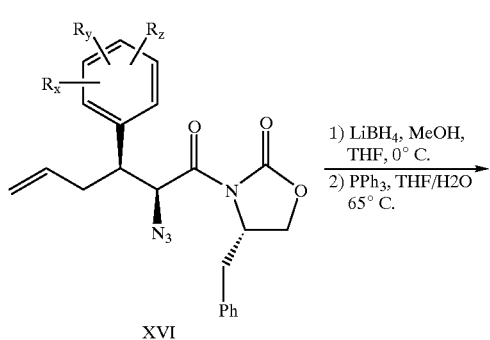

XVI

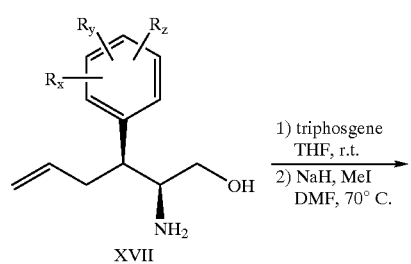

XVII

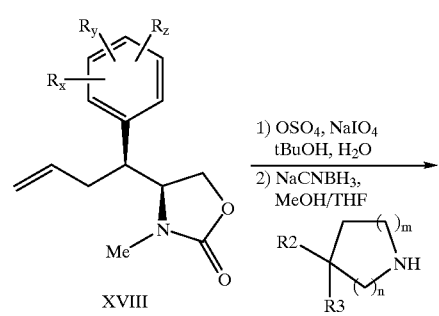

XVIII

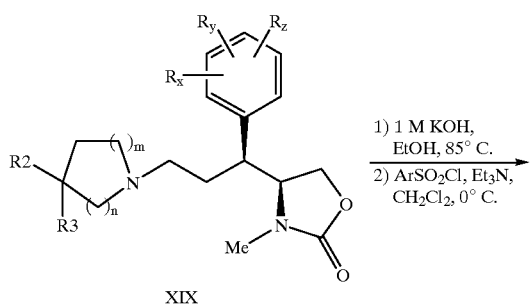

XIX

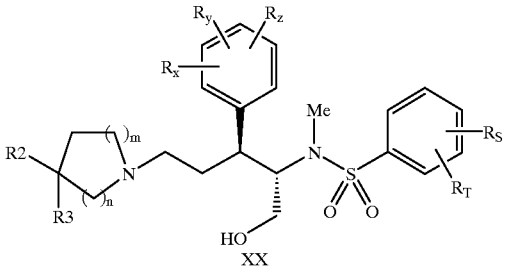

XX

Preparation of hydroxymethyl derivatives of the target compounds is outlined in Scheme 4. The oxazolidinone imide XV is prepared from acid XIV, by formation of the corresponding acid chloride (by treatment with oxalyl chloride or thionyl chloride) and addition of N-lithio 2(S)-benzyl oxazolidinone. The enolate azidation can be accomplished by a variety of methods, such as the procedure of Evans, D. A.; et. al. *J. Am. Chem. Soc.* 1990, 112, 4011–4030. Reduction of the oxazolidinone moiety of XVI can be carried out by a variety of metal hydride reagents (e.g. $LiBH_4/MeOH$, $LiAlH_4$, etc.). The azide is then reduced by treatment with $PPh_3/H_2O$ to provide alcohol XVII. Formation of cyclic carbamate XVIII is accomplished by literature methods; i.e. phosgene, triphosgene or carbonyl diimidazole, followed by N-alkylation with sodium hydride and methyl iodide. The target compounds are prepared by oxidative cleavage of the olefin to the aldehyde followed by reductive amination with an amine salt as described for Scheme 1, to provide XIX. Hydrolysis of the cyclic carbamate under basic conditions (for example, potassium hydroxide in ethanol at elevated temperature) followed by selective amide formation at 0° C. by combining with an acylating agent or a sulfonating agent such as an arylsulfonyl chloride gives the corresponding hydroxyamides or hydroxysulfonamides (i.e. XX).

SCHEME 5

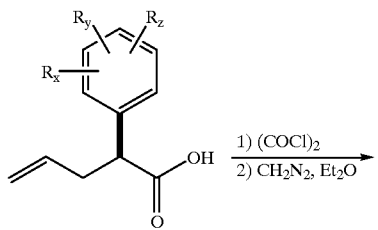

VII

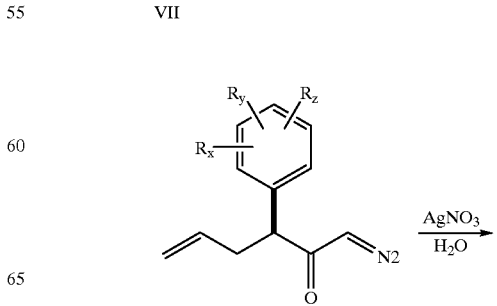

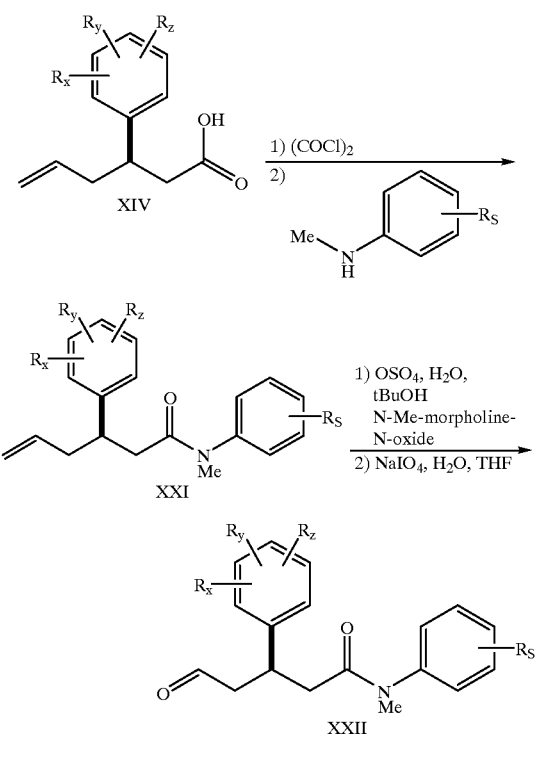

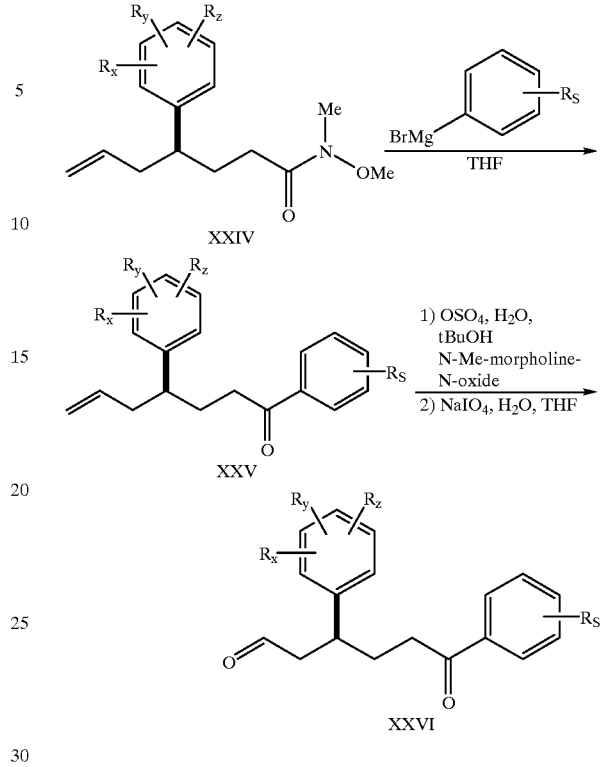

Compounds with alternate arrangements of an amide bond are prepared as shown in Scheme 5. Acid VII can be homologated under Arndt-Eistert conditions to give the chain-extended acid XIV, which can be derivatized under standard acylating conditions with, for example, an aniline derivative, to give the amide XXI. Oxidative cleavage of the olefin with osmium tetroxide or ozone then provides aldehyde XXII as an intermediate suitable for coupling as described earlier.

In addition, ketone derivatives are prepared by an extension of the chemistry given above, as shown in Scheme 6. An Arndt-Eistert chain extension of acid XIV provides heptenoic acid XXIII, which after conversion into N-methoxy-N-methyl amide XXIV, can be reacted with an aryl organometallic reagent, such as an aryl magnesium bromide, to provide ketone XXV. Routine oxidative cleavage then gives the desired aldehyde XXVI, which can be coupled with an appropriate amine as described above.

SCHEME 6

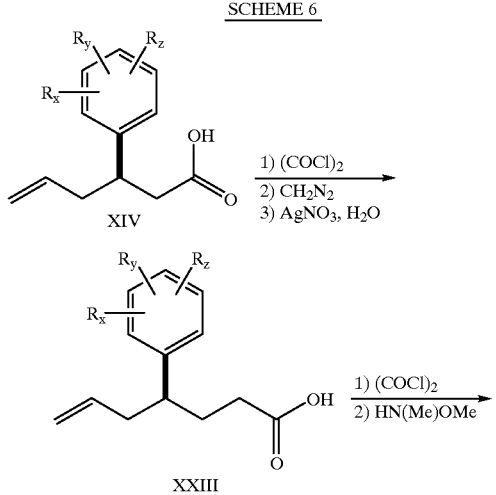

SCHEME 7

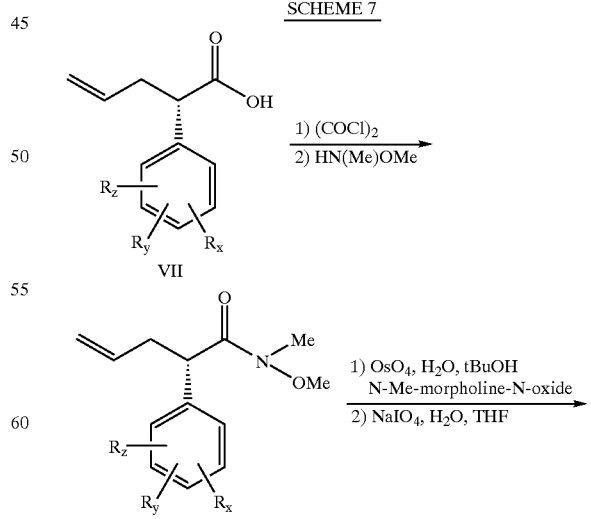

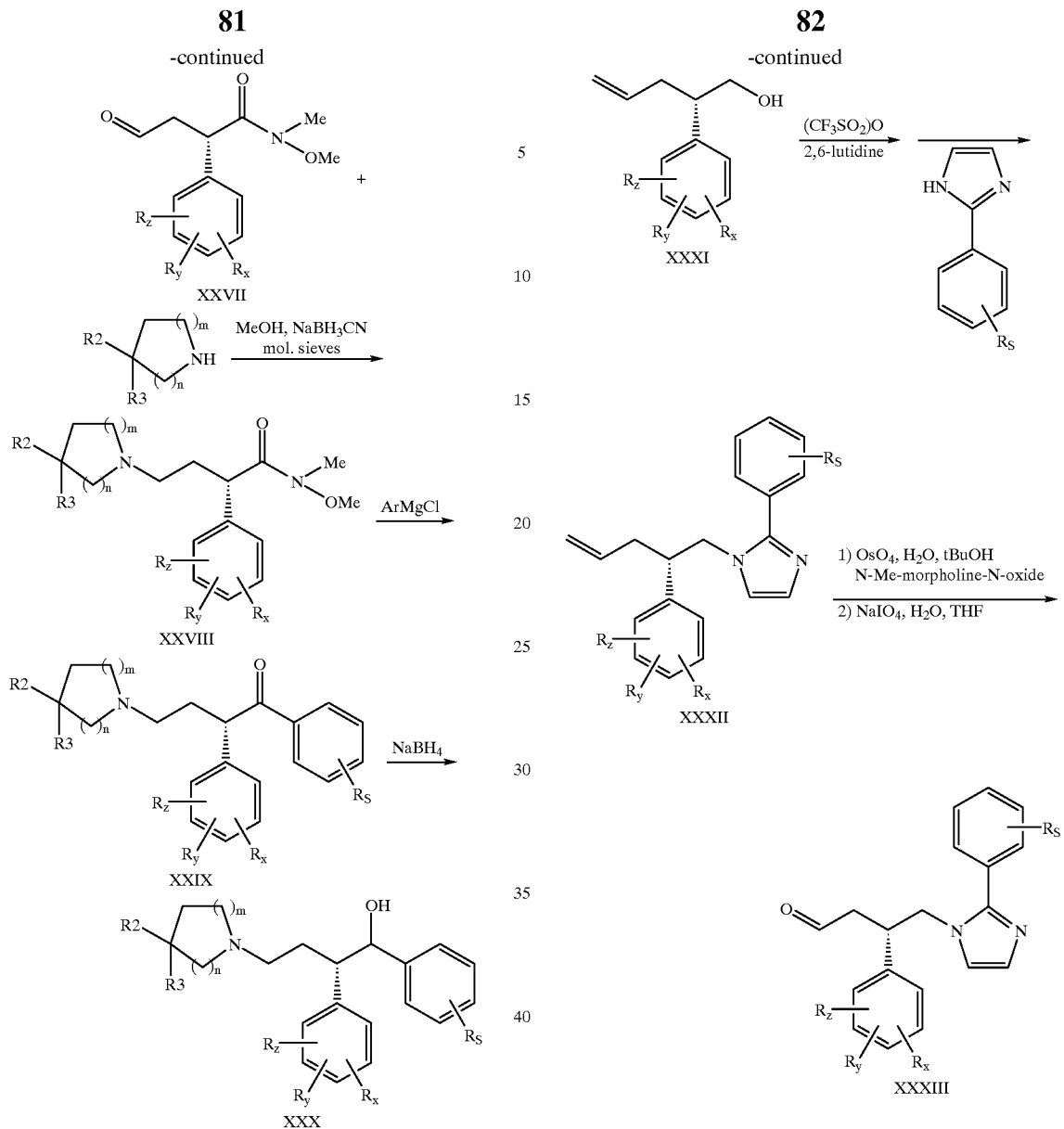

Alcohol containing compounds are prepared according to procedures given in Scheme 7. Formation of the N-methyl-N-methoxy amide of acid VII followed by oxidative cleavage of the olefin provides intermediate aldehyde XXVII. Coupling with an appropriate amine provides amide XXVIII. Addition of an organometallic reagent to compound XXVIII provides illustrated ketone XXIX. Treatment with a hydride reducing agent, such as sodium borohydride, then yields the desired alcohol XXX.

Formation of heterocycle compounds is carried out according to the procedure given in Scheme 8 for substituted imidazoles. Reduction of allyl acid VII with a strong reducing agent such as lithium aluminum hydride provides alcohol XXXI. In situ formation of the trifluoromethanesulfonate ester of the formed alcohol allows for displacement of the triflate with a nucleophile such as 2-phenyl-imidazole, to give imidazole XXXII. Oxidative cleavage under standard conditions provides the aldehyde XXXIII which can then be coupled under the conditions described above to the appropriate amine.

SCHEME 8

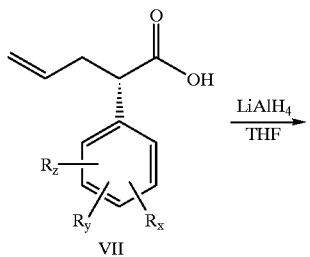

SCHEME 9

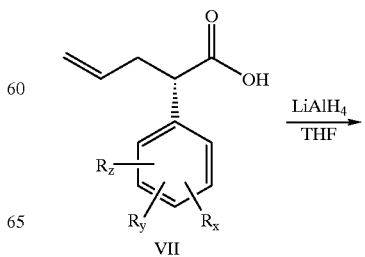

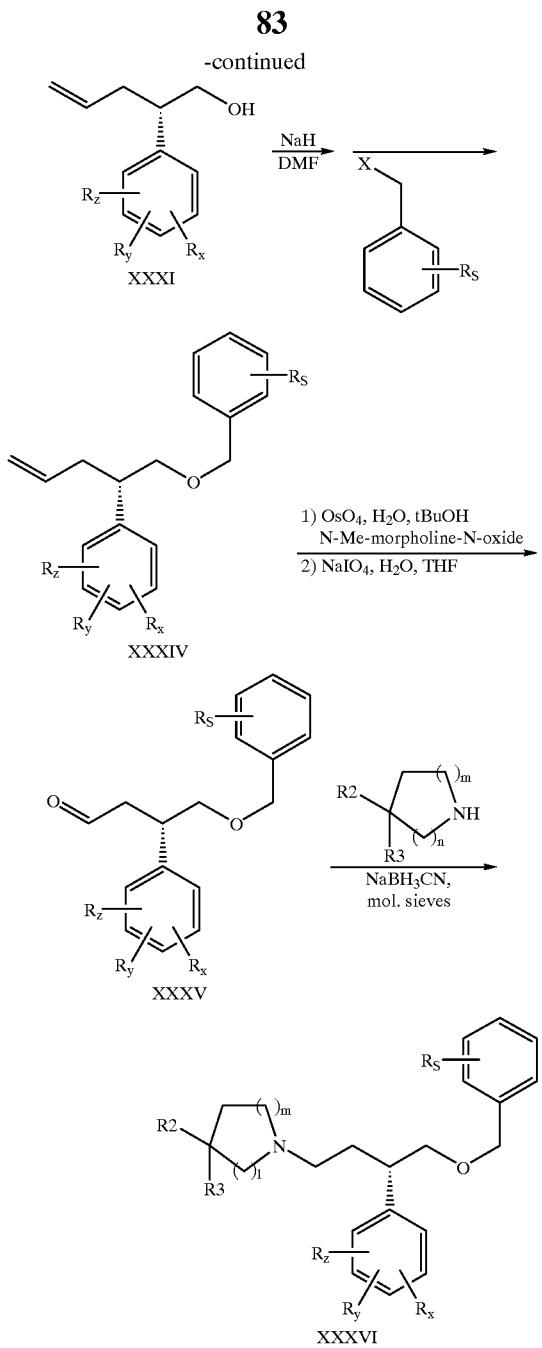

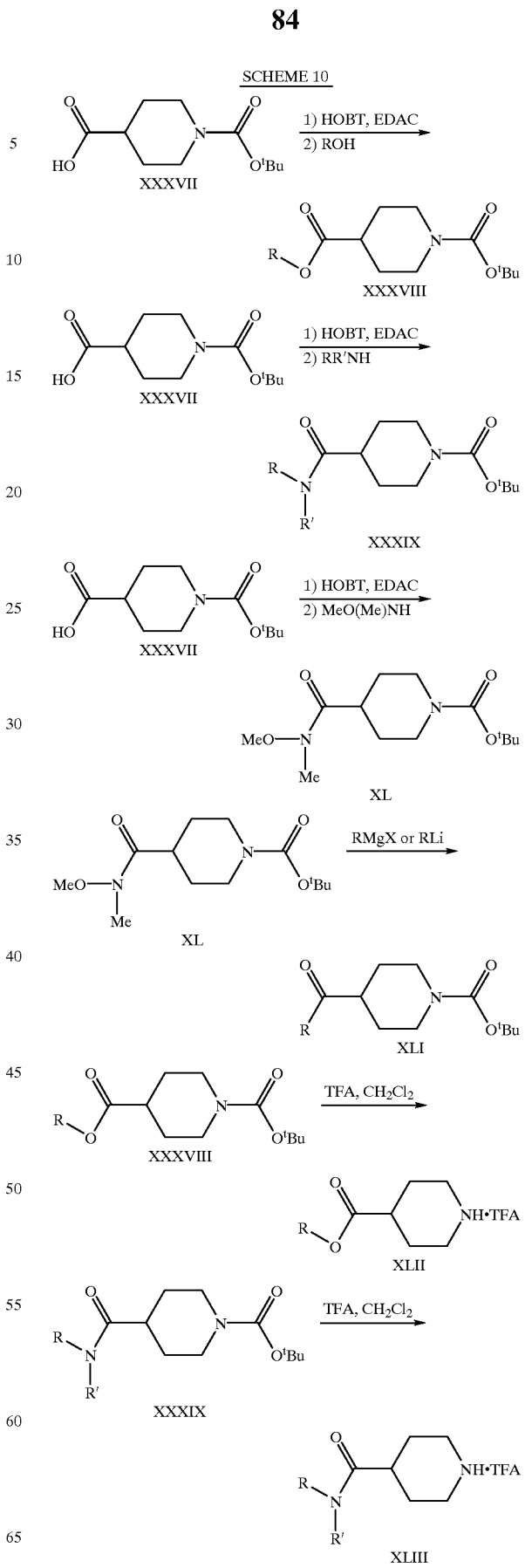

SCHEME 10

Compounds with ether substituents are prepared by the route shown in Scheme 9. Thus, allyl acid VII can be reduced to alcohol XXXI with, for example, lithium aluminum hydride. This alcohol can be alkylated by a Williamson ether synthesis, by deprotonation with a strong base such as sodium hydride or sodium hexamethyldisilazide followed by reaction with a benzyl halide such as benzyl bromide. The resulting ether XXXIV can be processed through the oxidative cleavage steps described earlier to provide aldehyde XXXV. This aldehyde can then be coupled with an appropriate amine under reductive amination conditions to give XXXVI. Alternatively, reduction of XXXV to the corresponding alcohol followed by conversion to the bromide allows for alkylation with an amine to provide XXXVI.

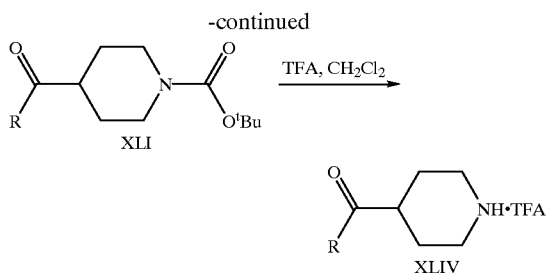

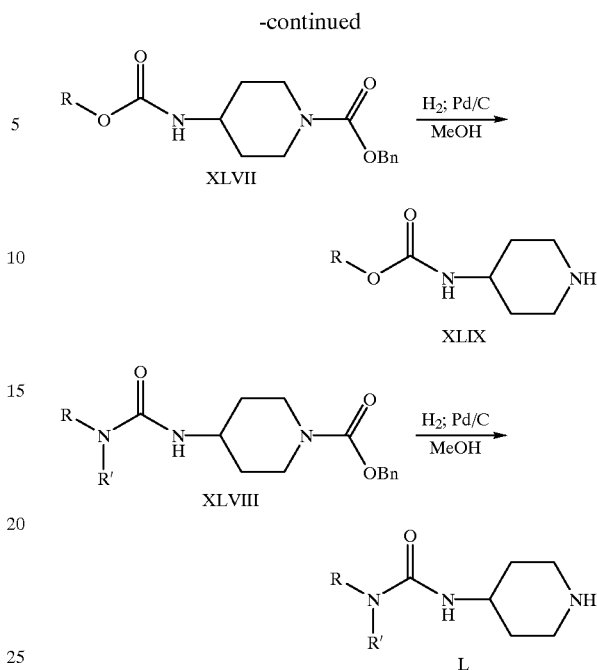

The substituted amines employed in the preceding Schemes can be obtained commercially in many cases or are prepared by a number of procedures. For example, as shown in Scheme 10, compound XXXVII, the N-t-butoxycarbonyl protected form of isonipecotic acid (4-piperidinecarboxylic acid) can be activated under standard conditions, for example with a carbodiimide, and converted into ester XXXVIII or amide XXXIX. Alternatively, acid XXXVII can be converted into the N-methyl-N-methoxy amide, XL, which upon reaction with organomagnesium and organolithium reagents forms the ketone XLI. The Boc group of XXXVIII, XXXIX and XLI can be removed under acidic conditions to provide secondary amines XLII, XLIII and XLIV, respectively.

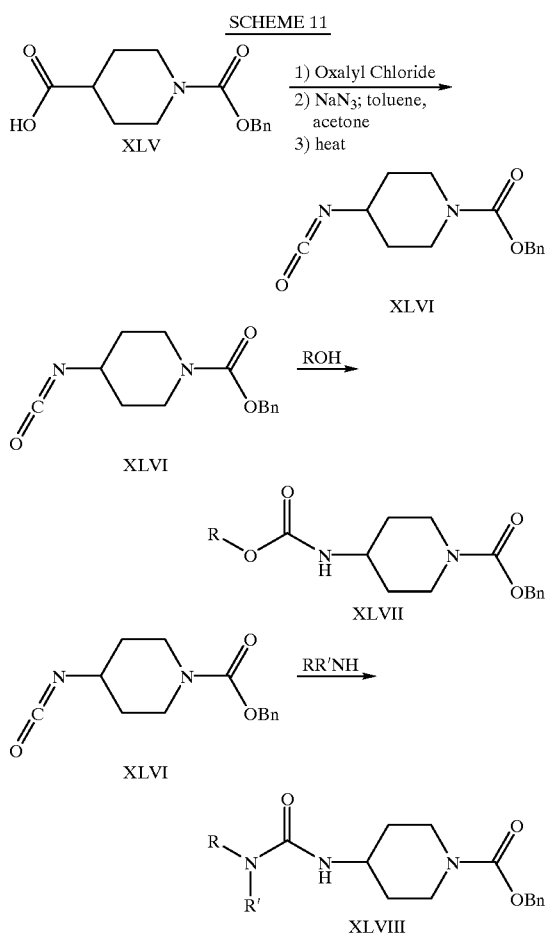

Alternatively, CBZ-protected piperidine XLV can be allowed to react with oxalyl chloride and then sodium azide, to provide the corresponding acyl azide, which can then be thermally rearranged to isocyanate XLVI (Scheme 11). Compound XLVI can be treated with an alcohol ROH or an amine RR'NH to form carbamate XLVII or urea 20003Y XLVIII, respectively, each of which can be deprotected with hydrogen in the presence of palladium on carbon to secondary amines XLIX or L.

-continued

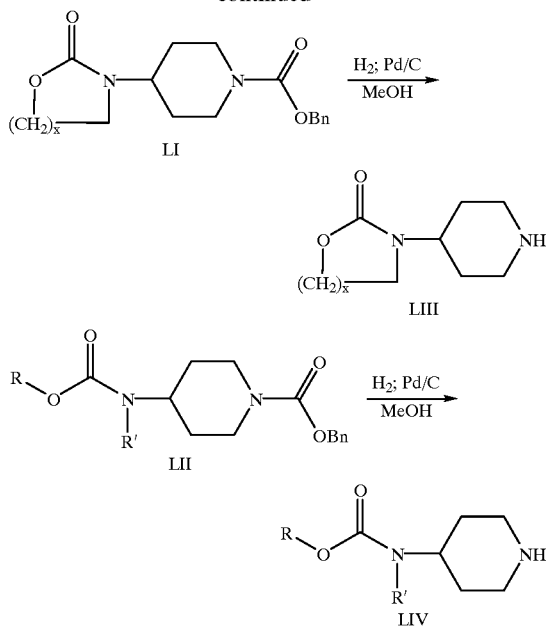

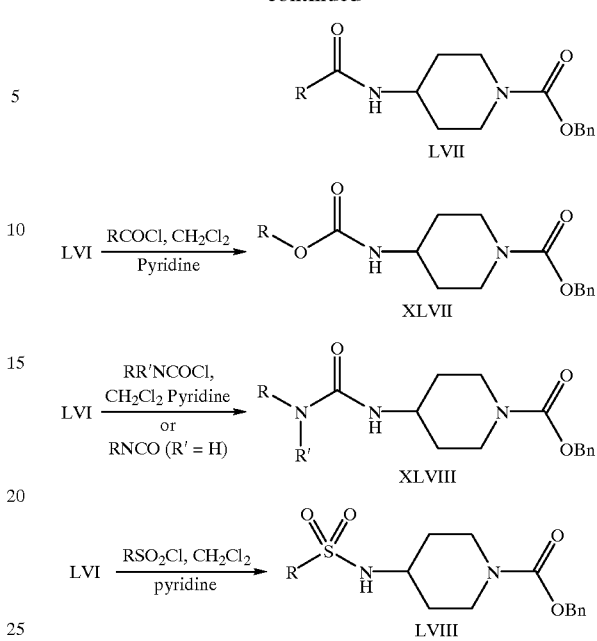

If the carbamate XLVII has R=—(CH₂)ₓCH₂Cl, where x =1–3, then treatment with a suitable base, such as sodium hydride, lithium hexamethyldisilazide or potassium t-butoxide, can induce cyclization to compound LI (Scheme 12). For other R groups, carbamate XLVII can be treated with an alkylating agent R'X, where R'=primary or secondary alkyl or alkyl-cycloalkyl, while X=bromide, iodide, tosylate, mesylate or trifluoromethanesulfonate, in the presence of a suitable base, such as sodium hydride, lithium hexamethyldisilazide or potassium t-butoxide, to give derivative LII. In each case, removal of the CBZ protecting group under standard conditions provides the secondary amines LIII and LIV.

Additional derivatives of a piperidine with nitrogen functionality at C₄ can be carried out as shown in Scheme 13. For example, if the ring nitrogen is protected with a CBZ group, as with isocyanate XLVI, treatment with tert-butyl alcohol in the presence of copper(I) chloride, provides Boc derivative LV. This compound can be selectively deprotected to the free amine LVI. This amine can be acylated with an acid chloride, a chloroformate, an isocyanate, or a carbamyl chloride, to provide compounds LVII, XLVII or XLVIII. Alternatively, amine LVI can be sulfonated with an alkyl or arylsulfonyl chloride, to give sulfonamide LVIII.

SCHEME 13

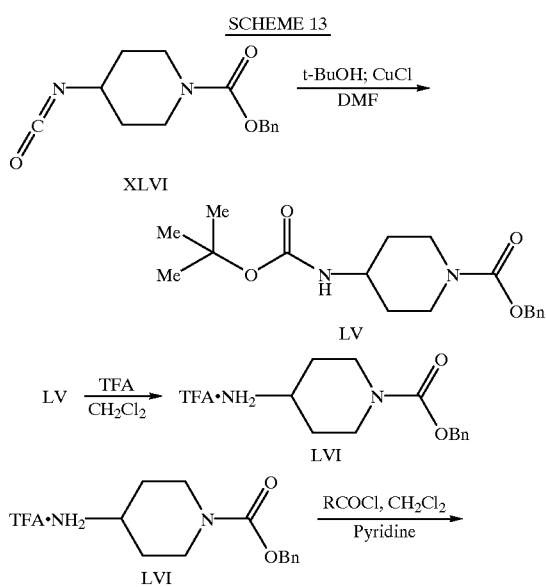

SCHEME 14

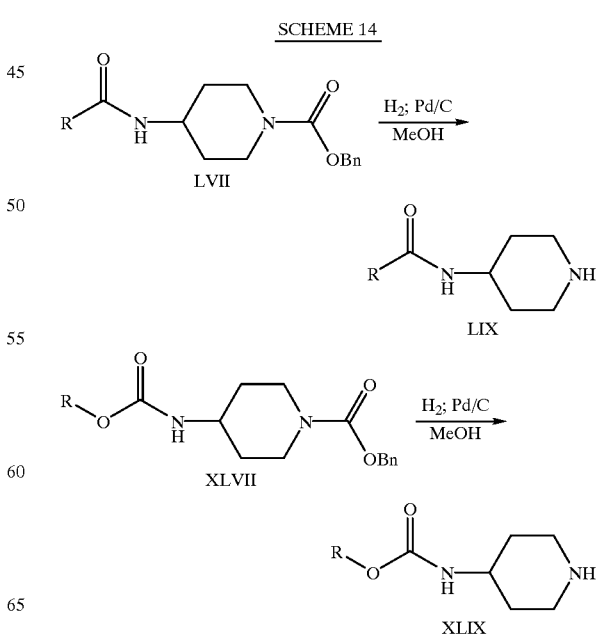

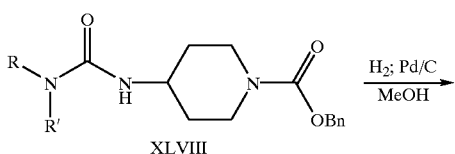

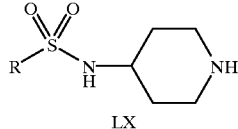

In each case, removal of the CBZ group under reductive conditions gives the desired secondary amines LIX, XLIX, L, and LX (Scheme 14).

SCHEME 15

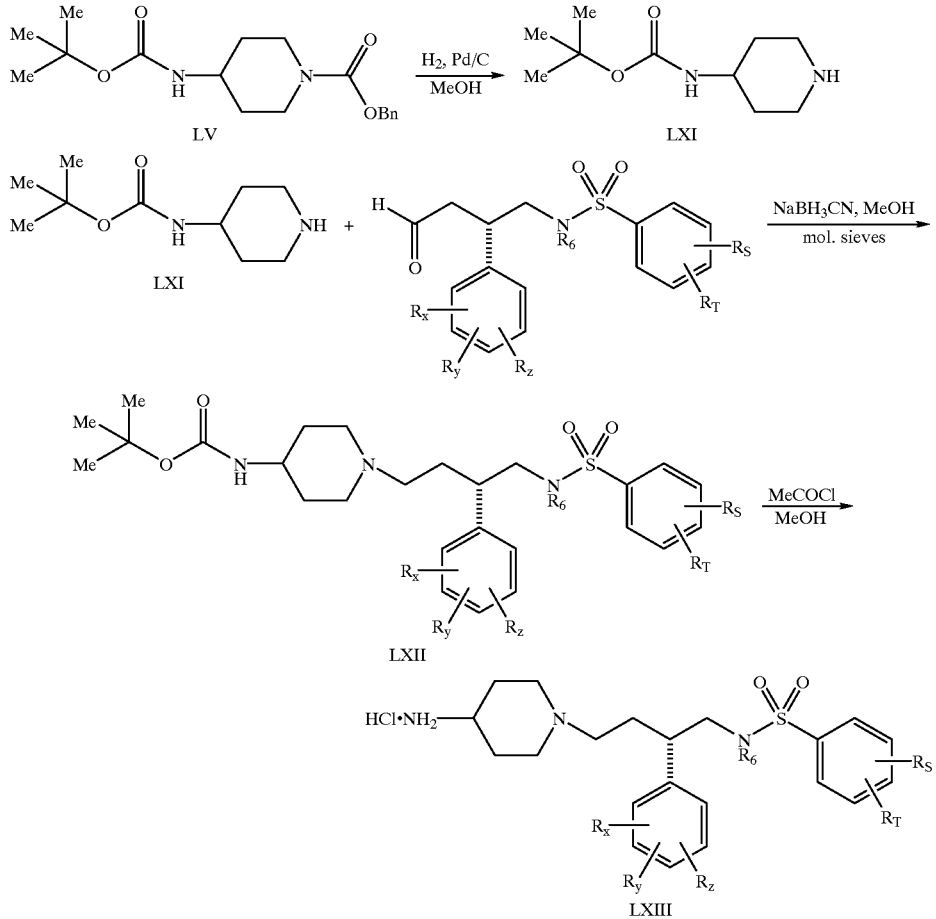

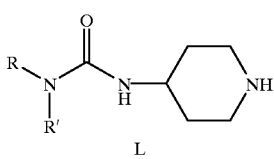

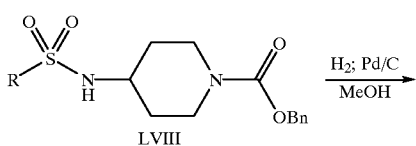

Functionalization of the piperidine can also be carried out after it has been coupled with an N1 substituent. For example, as shown in Scheme 15, reductive deprotection of CBZ derivative LV yields secondary amine LXI. Reductive amination with an appropriate aldehyde fragment (as described above) provides piperidine LXII. Removal of the Boc group under acidic conditions then gives primary amine LXIII. This primary amine can then be functionalized by analogy to the chemistry given in Scheme 13. Compound LXI can also be alkylated as described above in Scheme 12, and then carried through the remaining sequence given in Scheme 15.

SCHEME 16

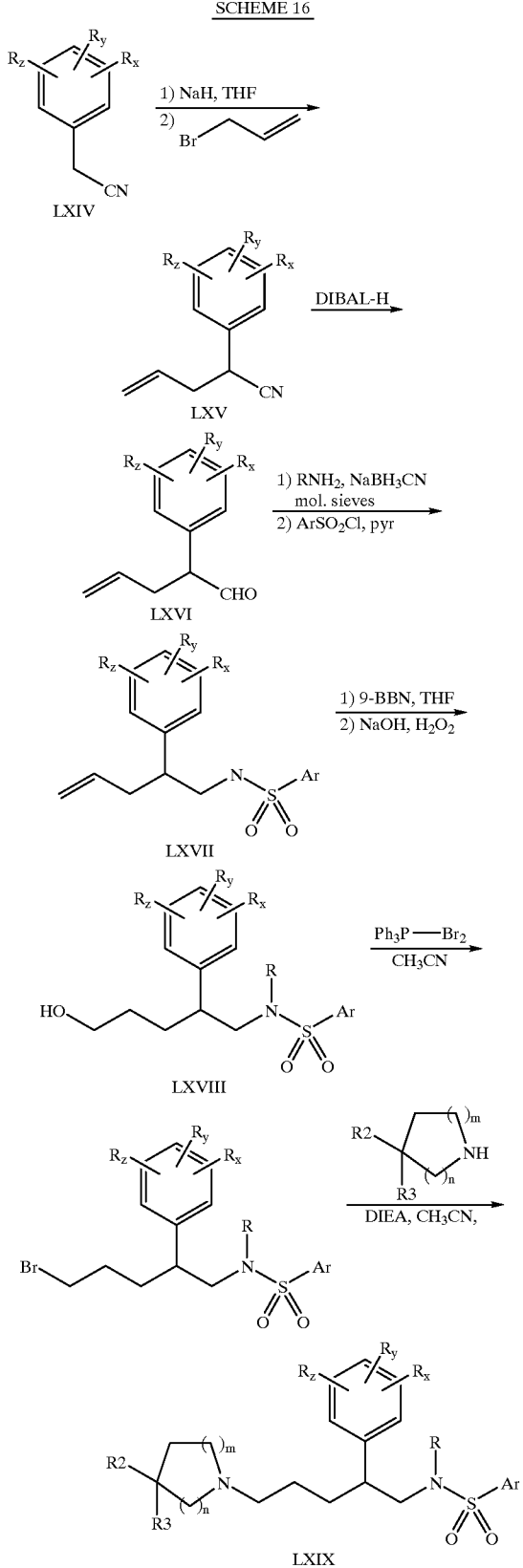

A method of preparing a backbone with an alternate spacing from the one described above is given in Scheme 16.

Deprotonation of a suitable phenylacetonitrile derivative LXIV with sodium hydride followed by addition of allyl bromide provides the allyl nitrile LXV. Reduction to the corresponding aldehyde LXVI is carried out with diisobutylaluminum hydride in THF. Reductive amination with a primary amine followed by sulfonylation then provides sulfonamide LXVII. Selective hydroboration of the terminal position of the olefin, for example with 9-BBN, followed by oxidation with basic hydrogen peroxide, then gives primary alcohol LXVIII. Conversion of this alcohol to the corresponding bromide with triphenylphosphine-dibromide complex followed by alkylation with a cyclic secondary amine then gives the desired product LXIX.

SCHEME 17

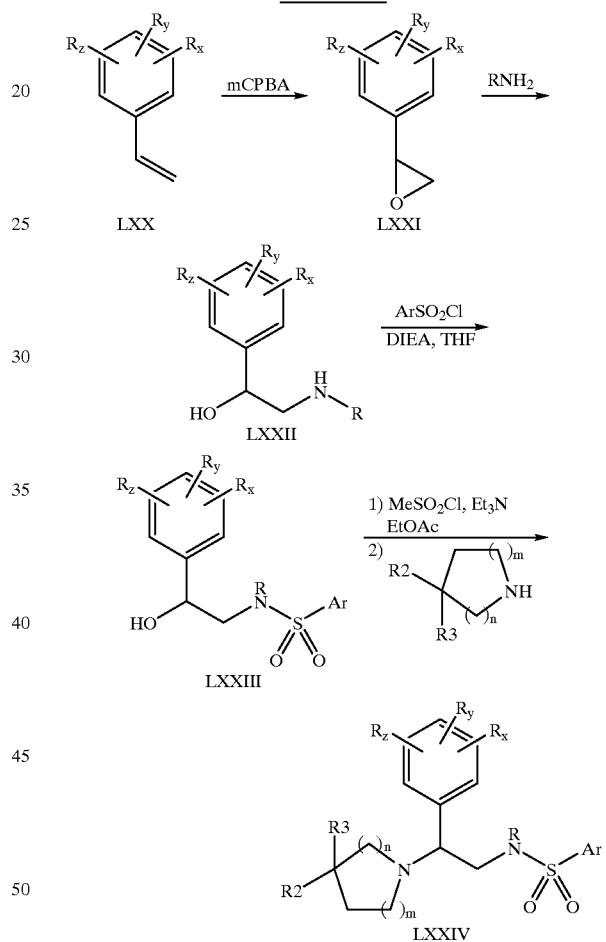

Another backbone variation is prepared according to Scheme 17. Epoxidation of a suitably substituted styrene derivative LXX with an oxidizing agent such as mCPBA provides the epoxide LXXI which is converted to the aminoalcohol LXXII by treatment with a primary amine $RNH_2$. Treatment of LXXII with an acylating agent or a sulfonylating agent under mild conditions (as shown for the conversion to compound LXXIII) produces the corresponding neutral alcohol. Activation of the hydroxy group with, for example, methanesulfonyl chloride, followed by treatment with a secondary cyclic amine yields the aminosulfonamide LXXIV.

SCHEME 18

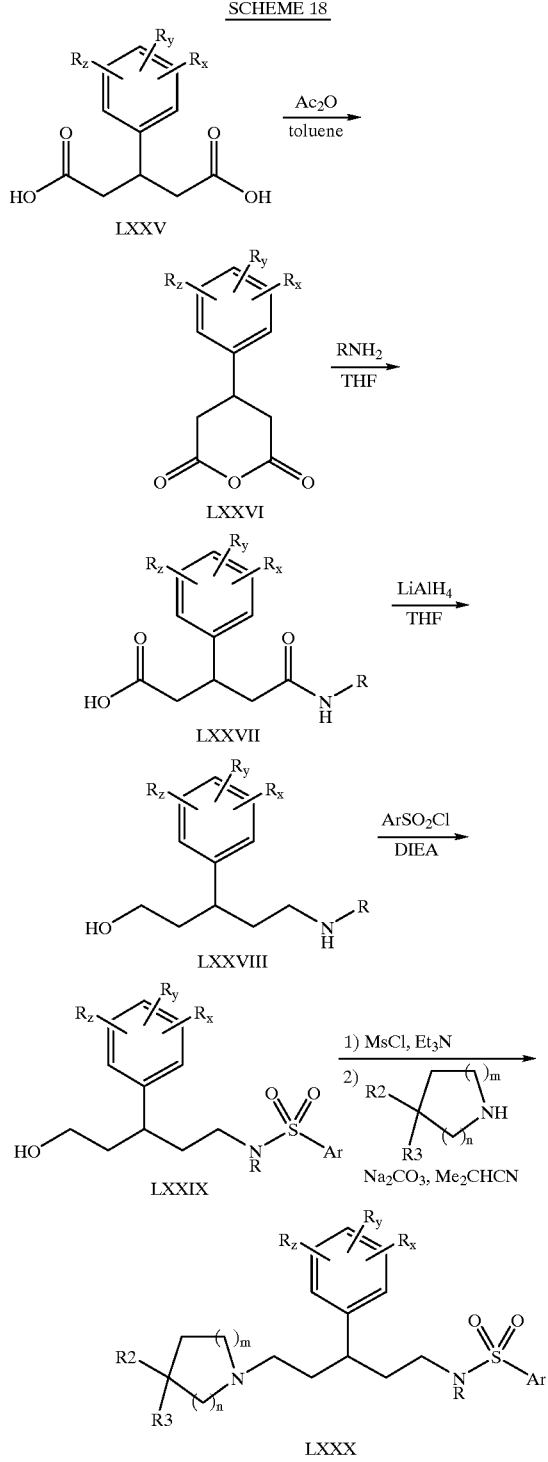

Another backbone variation is prepared according to Scheme 18. Treatment of 3-arylpentane-1,5-dioic acid LXXV with acetic anhydride in toluene provides anhydride LXXVI. Addition of an amine $RNH_2$ yields amidoacid LXXVII, which can be reduced with a strong reducing agent like lithium aluminum hydride to give aminoalcohol LXXVIII. Selective sulfonylation on nitrogen can be accomplished by treatment with a suitable arylsulfonyl chloride, to produce sulfonamide LXXIX. Activation of the hydroxy group with methanesulfonyl chloride in the presence of triethylamine followed by addition of a cyclic secondary amine in isobutyronitrile in the presence of sodium carbonate at elevated temperatures then provides the desired sulfonamidoamine LXXX.

SCHEME 19

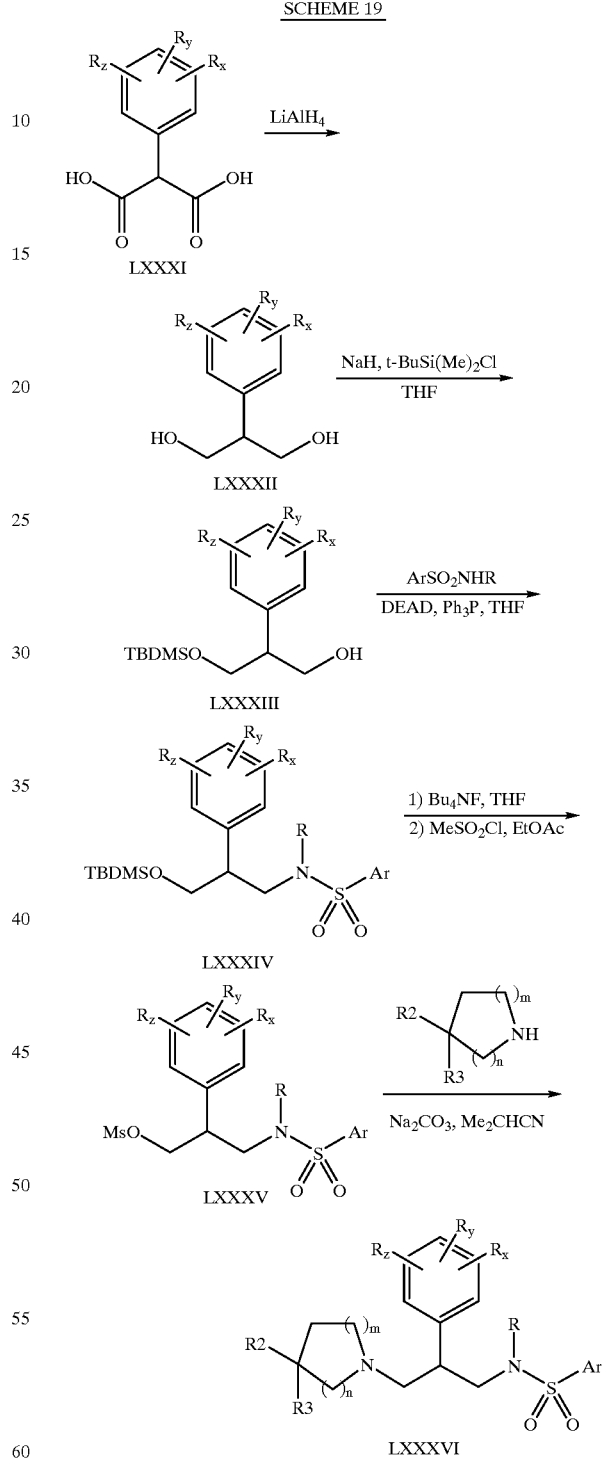

Another backbone variation is prepared according to Scheme 19. Reduction of 2-arylmalonic acid derivative LXXXI with lithium aluminum hydride provides diol LXXXII, which upon treatment with sodium hydride and t-butyldimethylsilyl chloride in THF produces selectively the monosilyl ether LXXXIII. Exposure of this compound to an N-substituted arylsulfonamide in the presence of DEAD and triphenylphosphine in THF provides the sulfonamide LXXXIV. Removal of the silyl group, for example with tetrabutylammonium fluoride in THF, followed by treatment with methanesulfonyl chloride in ethyl acetate, yields the mesylate LXXXV. Treatment of this mesylate with a cyclic secondary amine then provides the desired product LXXXVI.

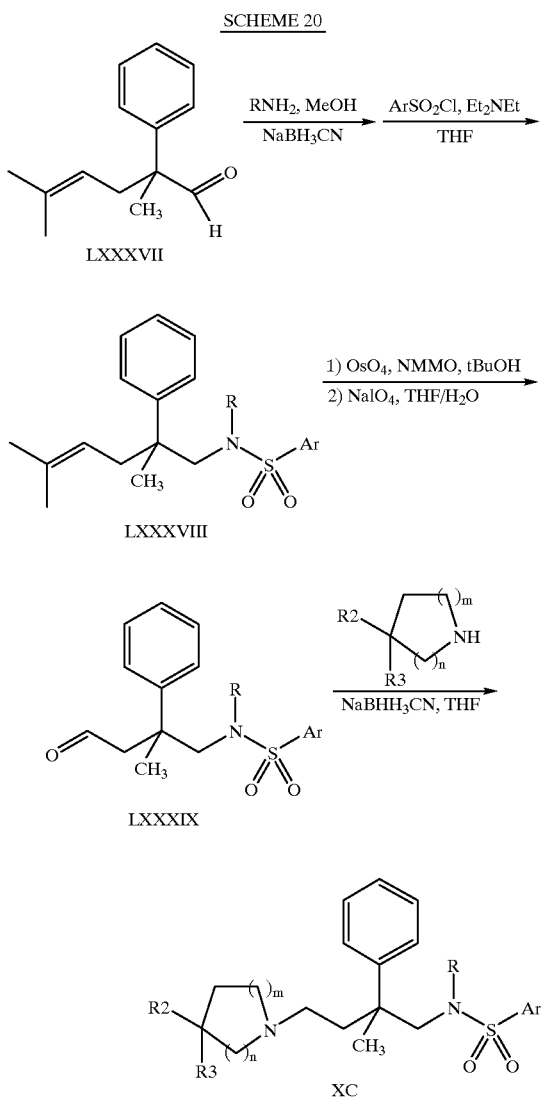

Another backbone variation is prepared according to Scheme 20. Reductive alkylation of the commercially available aldehyde LXXXVII with a suitable primary amine followed by sulfonylation provides sulfonamide LXXXVIII. Treatment of this olefin with osmium tetroxide followed by sodium periodate provides aldehyde LXXXIX. Reductive amination with a cyclic secondary amine then provides the target compound XC.

In some cases the order of carrying out the foregoing reaction schemes may be varied to facilitate the reaction or to avoid unwanted reaction products.

The following examples are provided for the purpose of further illustration only and are not intended to be limitations on the disclosed invention.

EXAMPLE 1

(R,S)-N-[2-Phenyl-4-(4-phenylpiperidin-1-yl)but-1-yl]-N-methylbenzene-sulfonamide Step A: (R,S)-N-(2-Phenylpent-4-en-1-yl)-N-methylbenzene-sulfonamide A solution of 2.0 g (11.4 mmol) of (R,S)-4-phenyl-5-methylamino-1-pentene (prepared as described by J. Hale et al., *Bioorganic and Medicinal Chemistry Letters*, 1993, 3, 319–322) and 6.0 mL (34 mmol) of diisopropylethylamine (DIPEA) in 25 mL of methylene chloride was cooled in an ice/ethanol bath. To this was added 2.2 mL (17 mmol) of benzenesulfonyl chloride and after 5 min the ice bath was removed. After stirring for 16 h, the reaction mixture was diluted with methylene chloride and washed with water containing 20 mL of 2 N HCl. The aqueous layer was reextracted with methylene chloride and the organic layers were washed with brine, combined, dried over sodium sulfate and concentrated in vacuo. The residue was purified by flash column chromatography (FCC) eluting with 5% ethyl acetate/hexanes to afford 3.2 g of the title compound. $^1$H NMR (400 MHz, CDCl$_3$): δ 2.38 (p, J=8, 1H), 2.55 (m, 1H), 2.57 (s, 3H), 2.94 (m, 2H), 3.41 (m, 1H), 4.95 (m, 2H), 5.62 (m, 1H), 7.1–7.3 (m, 5H), 7.45 (m, 2H), 7.52 (m, 1H), 7.69 (dd, J=1.5 and 6, 2H).

Step B: (R,S)-N-(2-Phenyl-4-oxobut-1-yl)-N-methylbenzene-sulfonamide

To a solution of 1.0 g (3.2 mmol) of (R,S)-N-(2-phenylpent-4-en-1-yl)-N-methylbenzenesulfonamide from Step A in 7 mL of acetone, 3.5 mL of t-butanol and 3.5 mL of water was added 413 mg (3.5 mmol) of N-methylmorpholine-N-oxide followed by 0.14 mL of 4% osmium tetroxide in water. The reaction was stirred at rt for 16 h and was then quenched with aqueous sodium bisulfite and concentrated in vacuo. The residue was diluted with water and extracted twice with ether. The ether layers were each washed with brine, combined, dried over sodium sulfate and concentrated in vacuo. The residue was purified by FCC eluting with 5% methanol in methylene chloride to afford the diol intermediate. The above product was taken up in 10 mL of THF and 755 mg (3.5 mmole) of sodium periodate in 3 mL of water was added. The mixture was stirred at rt for 3 h, poured into water and extracted twice with ether. The ether layers were each washed with brine, combined, dried over sodium sulfate and concentrated in vacuo to afford 940 mg of the title compound. 1H NMR (400 MHz, CDCl$_3$): δ 2.62 (s, 3H), 2.75–2.9 (m, 2H), 3.14 (dd, J=6 and 17, 1H), 3.39 (m, 1H), 3.55 (m, 1H), 7.15–7.35 (2 m, 5H), 7.46 (m, 2H), 7.53 (m, 1H), 7.70 (dd, J=1.5 and 7, 2H), 9.78 (d, J=1.2, 1H).

Step C: (R,S)-N-[2-Phenyl-4-(4-phenylpiperidin-1-yl)but-1-yl]-N-methylbenzenesulfonamide hydrochloride salt To a solution of 0.020 g (0.063 mmol) of (R,S)-N-(2-phenyl-4-oxobut-1-yl)-N-methylbenzenesulfonamide from Step B in 1.2 mL of THF were added 31 mg (0.19 mmol) of 4-phenylpiperidine, 3 Å molecular sieves and 0.011 mL of acetic acid. After stirring the mixture for 20 min, 27 mg (0.126 mmol) of sodium triacetoxy-borohydride was added. After 16 h the mixture was filtered through a pad of celite and the reaction flask and the pad were rinsed with water and ethyl acetate. The layers were separated and the aqueous layer was extracted twice more with ethyl acetate. The organic layers were each washed with brine, combined, dried over sodium sulfate and concentrated in vacuo. The residue was purified by prep TLC using 5% methanol in methylene chloride to isolate 25 mg of the free amine of the title compound as an oil. 1H NMR (400 MHz, CDCl$_3$): δ 1.80 (m, 5H), 1.9–2.3 (3 m, 5H), 2.4–2.5 (m, 1H), 2.59 (s, 3H), 2.9–3.1 (m, 4H), 3.35–3.45 (m, 1H), 7.1–7.3 (m, 10H), 7.4–7.5 (m, 2H), 7.5–7.6 (m, 1H), 7.70 (dd, J=1.5 and 7.0, 2H). Mass spectrum (NH$_3$/CI): m/z 463 (M+1, 100%). The hydrochloride salt of the title compound was prepared by dissolving the above oil in ether/methanol and addition of 2–3 equivalents of 1 M ethereal HCl. Evaporation of the volatiles and drying in vacuo afforded 26 mg of the title salt as a white solid after trituration with ether.

The following Examples were prepared following the procedure described in Example 1, Step C but using the appropriate substituted amine in the reductive amination.

EXAMPLE 2

(R,S)-N-[2-Phenyl-4-(4-benzylpiperidin-1-yl)but-1-yl]-N-methylbenzenesulfonamide Mass spectrum (NH$_3$/CI): m/z 477 (M+1, 100%).

EXAMPLE 3

(R,S)-N-[2-Phenyl-4-(4-dimethylaminocarbonyl-4-phenylpiperidin-1-yl)but-1-yl]-N-methylbenzenesulfonamide Mass spectrum (NH$_3$/CI): m/z 534 (M+1, 100%).).

EXAMPLE 4

(R,S)-N- [2-Phenyl-4-(4-aminocarbonyl-4-phenylpiperidin-1-yl)but-1-yl]-N-methylbenzenesulfonamide Mass spectrum (NH$_3$/CI): m/z 506 (M+1), 249 (100%).

EXAMPLE 5

(R,S)-N-[2-Phenyl-4-(4-hydroxymethyl-4-phenylpiperidin-1-yl)but-1-yl]-N-methylbenzenesulfonamide Mass spectrum (NH$_3$/CI): m/z 493 (M+1, 100%).

EXAMPLE 6

(R,S)-N-[2-Phenyl-4-(4-methoxycarbonyl-4-phenylpiperidin-1-yl)but-1-yl]-N-methylbenzenesulfonamide Mass spectrum (NH$_3$/CI): m/z 521 (M+1, 100%).

EXAMPLE 7

(R,S)-N-[2-Phenyl-4-(piperidin-1-yl)but-1-yl]-N-methylbenzenesulfonamide

Mass spectrum (NH$_3$/CI): m/z 387 (M+1, 100%).

EXAMPLE 8

(R,S)-N-[2-Phenyl-4-(4-pentylaminocarbonylpiperidin-1-yl)but-1-yl]-N-methylbenzenesulfonamide Mass spectrum (NH$_3$/CI): m/z 500 (M+1, 100%).

EXAMPLE 9

(R,S)-N-[2-Phenyl-4-(4-isopropylaminocarbonylpiperidin-1-yl)but-1-yl]-N-methylbenzenesulfonamide Mass spectrum (NH$_3$/CI): m/z 472 (M+1, 100%).

EXAMPLE 10

(R,S)-N-[2-Phenyl-4-(4-methylaminocarbonylmethylene-4-phenylpiperidin-1-yl)but-1-yl]-N-methylbenzenesulfonamide Mass spectrum (NH$_3$/CI): m/z 534 (M+1, 100%).

EXAMPLE 11

(R,S)-N-[2-Phenyl-4-(4-methylaminocarbonyl (methylamino)methylene-4-phenylpiperidin-1-yl)but-1-yl]-N-methylbenzenesulfonamide Mass spectrum (ESI): m/z 563 (M+1, 100%).

EXAMPLE 12

(R,S)-N-[2-Phenyl-4-(4-methoxycarbonylaminomethylene-4-phenylpiperidin-1-yl)but-1-yl]-N-methylbenzenesulfonamide Mass spectrum (ESI): m/z 550 (M+1, 100%).

EXAMPLE 13

(R,S)-N-[2-Phenyl-4-(4-methylaminocarbonylaminomethylene-4-phenylpiperidin-1-yl)but-1-yl]-N-methylbenzenesulfonamide Mass spectrum (ESI): m/z 549 (M+1, 100%).

EXAMPLE 14

(R,S)-N-[2-Phenyl-4-(4-(2-methyl)phenylpiperidin-1-yl)but-1-yl]-N-methylbenzenesulfonamide Mass spectrum (NH$_3$/CI): m/z 477 (M+1, 100%).

EXAMPLE 15

(R,S)-N-[2-Phenyl-4-(4-morpholinocarbonylpiperidin-1-yl)but-1-yl]-N-methylbenzenesulfonamide Mass spectrum (NH$_3$/CI): m/z 500 (M+1, 100%).

The following Examples were prepared following the procedure described in Example 1, Step A–C but starting with (R,S)-4-(2-chlorophenyl), (3,5-dichlorophenyl), (2-thienyl), (3-thienyl), or (cyclohexyl)-5-methylamino-1-pentene (prepared as described by J. Hale et al., *Bioorganic and Medicinal Chemistry Letters*, 1993, 3, 319–322) and using the appropriate substituted piperidine in the reductive amination.

EXAMPLE 16

(R,S)-N-[2-(2-Chlorophenyl)-4-(4-phenylpiperidin-1-yl)but-1-yl]-N-methylbenzenesulfonamide Mass spectrum (NH$_3$/CI): m/z 497 (M+1, 100%).

EXAMPLE 17

(R,S)-N-[2-(2-Thienyl)-4-(4-phenylpiperidin-1-yl)but-1-yl]-N-methylbenzenesulfonamide Mass spectrum (ESI): m/z 469 (M+1, 100%).

EXAMPLE 18

(R,S)-N-[2-(3-Thienyl)-4-(4-phenylpiperidin-1-yl)but-1-yl]-N-methylbenzenesulfonamide Mass spectrum (ESI): m/z 469 (M+1, 100%).

EXAMPLE 19

(R,S)-N-[2-(3-Thienyl)-4-(4-benzylpiperidin-1-yl)but-1-yl]-N-methylbenzenesulfonamide Mass spectrum (ESI): m/z 483 (M+1, 100%).

EXAMPLE 20

(R,S)-N-[2-Cyclohexyl-4-(4-phenylpiperidin-1-yl)but-1-yl]-N-methylbenzenesulfonamide Mass spectrum ($NH_3$/CI): m/z 469 (M+1, 100%).

EXAMPLE 21

(R,S)-N-[2-(3,5-Dichlorophenyl)-4-(4-phenylpiperidin-1-yl)but-1-yl]-N-methylbenzenesulfonamide hydrochloride salt Mass spectrum ($NH_3$—CI): m/z 531 (M+1, 100%).

EXAMPLE 22

(R,S)-N-[2-(3-Methylphenyl)-4-(4-phenylpiperidin-1-yl)but-1-yl]-N-methylbenzenesulfonamide Step A: N-[4-(4-Phenylpiperidin-1-yl)but-2-yn-1-yl]-N-methylbenzenesulfonamide To a suspension of triphenylphosphine dibromide at 0° C. (prepared by addition of bromine to 53.5 g (210 mmol) of triphenylphosphine in 200 mL of acetonitrile at 0° C.) was added 8.0 g (93 mmol) of 2-butyne-1,4-diol. The reaction was stirred for 10 min, the ice bath was removed, the mixture was stirred for 2 hr, and then concentrated in vacuo. The residue was triturated with ether and filtered to remove the precipitated triphenylphosphine oxide. The filtrate was washed with water and brine, dried over sodium sulfate and concentrated. The residue of crude dibromide was taken up in 50 mL of DMF under nitrogen and cooled in an ice bath.

A solution of the sodium salt of N-methylbenzenesulfonamide in 50 mL of DMF was prepared at 0° C. under nitrogen by portionwise addition of 3.2 g (80 mmol) of 60% sodium hydride over 0.5 h and then stirred with cooling for 0.5 h. This salt solution was added via canula over 15 min with cooling to the above dibromide solution. After 0.5 h, 18.0 g (110 mmol) of 4-phenylpiperidine was added and the reaction was stirred a further 2 h at rt. The reaction was diluted with water and extracted three times with ether. The ether layers were each washed with a portion of brine, dried over sodium sulfate, combined and concentrated in vacuo. The residue was purified by FCC eluting with 30 to 50% ethyl acetate/hexanes to afford 11.3 g of title compound. 1H NMR (400 MHz, $CDCl_3$): δ 1.65–1.85 (m, 4H), 2.07 (dt, J=3 and 8, 2H), 2.4 (m, 1H), 2.78 (br d, J=11, 2H), 2.84 (s, 3H), 3.09 (t, J=2, 2H), 4.07 (t, J=2, 2H), 7.1–7.3 (2 m, 5H), 7.45–7.6 (m, 3H), 7.82 (dd, J=1.5 and 7, 2H). Mass spectrum ($NH_3$—CI): m/z 383 (M+1, 100%).

Step B: N-[4-(4-Phenylpiperidin-1-yl)-2-tributylstannylbut-2-en-1-yl]-N-methylbenzenesulfonamide and N-[4-(4-Phenylpiperidin-1-yl)-3-tributylstannylbut-2-en-1-yl]-N-methylbenzene-sulfonamide To a solution of 11.0 g (29 mmol) of N-[4-(4-phenylpiperidin-1-yl)but-2-yn-1-yl]-N-methylbenzenesulfonamide from Step A in 75 mL of THF under nitrogen was added 400 mg (0.58 mmol) of dichlorobis(triphenylphosphine)palladium (II) and then 13.7 mL (51 mmol) of tributylstannane was added dropwise via syringe over 0.5 h. After a further 0.5 h, the dark reaction (from precipitated palladium) was concentrated in vacuo. The residue was purified by FCC eluting with 20% ethyl acetate/hexanes to give 2.5 g of the higher $R_{f3}$-stannyl title product. Elution with 30–40% ethyl acetate/hexanes afforded 10.8 g of the lower $R_f$2-stannyl title compound. Further elution with 50–70% ethyl acetate/hexanes afforded 3.5 g of recovered starting material. higher $R_f$ product: $^1$H NMR (400 MHz, $CDCl_3$): δ 0.8–0.9 (m, 6H), 0.87 (t, J=7, 9H), 1.25–1.35 (m, 6H), 1.35–1.5 (m, 6H), 1.6–1.85 (2 m, 4H), 1.94 (dt, J=3 and 8, 2H), 2.43 (m, 1H), 2.69 (s, 3H), 3.01 (br t, $J_{H-Sn}$=25, 2H), 3.78 (d, J=6, 2H), 5.44 (br ttt, J=1.5 and 6, $J_{H-Sn}$=34, 1H), 7.1–7.3 (2 m, 5H), 7.5–7.65 (m, 3H), 7.77 (dd, J=1.5 and 7.0, 2H). Lower $R_f$ product: 1H NMR (400 MHz, $CDCl_3$): δ 0.87 (t, J=7, 9H), 0.95–1.05 (m, 6H), 1.25–1.4 (m, 6H), 1.45–1.6 (m, 6H), 1.7–1.85 (m, 4H), 1.92 (dt, J=3 and 8, 2H), 2.42 (m, 1H), 2.48 (s, 3H), 2.96 (m, 2H), 3.74 (br t, $J_{H-Sn}$=23, 2H), 5.88 (br tt, J=6, $J_{H-Sn}$=32, 1H), 7.1–7.3 (2 m, 5H), 7.5–7.65 (m, 3H), 7.77 (dd, J=1.5 and 7.0, 2H).

Step C: N-[2-(3-Methylphenyl)-4-(4-phenylpiperidin-1-yl)but-2-en-1-yl]-N-methylbenzenesulfonamide To 250 mg (0.37 mmol) of N-[4-(4-phenylpiperidin-1-yl)-2-tributylstannylbut-2-en-1-yl]-N-methylbenzenesulfonamide from Step B in 0.4 mL of N-methylpyrrolidinone under argon was added 77 mg (0.55 mmol) of potassium carbonate, 8 mg (catalytic) of dichlorobis(triphenylphosphine)palladium (II) and 0.067 mL (0.55 mmol) of 3-methylbromobenzene. The mixture was heated at 70° C. for 24 h, cooled, treated with aqueous sodium fluoride for 10 min, and partitioned between water and ether. The water layer was reextracted with ether and each organic layer was washed with brine, dried over sodium sulfate, combined and concentrated in vacuo. The residue was purified by FCC eluting with 25–50% ethyl acetate/hexanes to give 57 mg of product contaminated with stannane biproduct. The product was further purified by prep TLC (50% ethyl acetate/hexanes) to afford 53 mg of title compound. $^1$H NMR (400 MHz, $CDCl_3$): δ 1.7–1.9 (m, 4H), 2.0–2.2 (m, 2H), 2.32 (s, 3H), 2.6–2.6 (m, 1H), 2.50 (s, 3H), 3.05 (m, 2H), 3.20 (m, 2H), 4.12 (s, 2H), 6.11 (br t, J=7, 1H), 7.07 (m, 1H), 7.15–7.35 (m, 8H), 7.52 (m, 2H), 7.60 (m, 1H), 7.74 (dd, J=1.5 and 7, 2H).

Step D: (R,S)-N-[4-(4-Phenylpiperidin-1-yl)-2-(3-methylphenyl)-but-1-yl]-N-methylbenzenesulfonamide A mixture of 46 mg (0.097 mmol) of N-[4-(4-phenylpiperidin-1-yl)-2-(3-methylphenyl)but-2-en-1-yl]-N-methylbenzenesulfonamide from Step C, 12 mg of 20% palladium hydroxide/C (50% water), and 2 drops of acetic acid in 3 mL of methanol was hydrogenated at 40 psi for 24 h. The catalyst was removed by filtration and the filtrate concentrated in vacuo. The residue was purified by prep TLC (50% ethyl acetate/hexanes) to afford 20 mg of title compound. A major biproduct was cleavage of the 4-phenylpiperidine to give N-[2-(3-methylphenyl)but-1-yl]-N-methylbenzenesulfonamide. $^1$H NMR (400 MHz, $CDCl_3$): δ 1.8–2.0 (m, 5H), 2.1–2.3 (m, 3H), 2.32 (s, 3H), 2.38 (m, 1H), 2.51 (m, 2H), 2.61 (s, 3H), 2.88 (m, 2H), 3.21 (m, 2H), 3.32 (dt, J=3 and 9, 1H), 6.96 (br s, 2H), 7.05 (d, J=8, 1H), 7.15–7.3 (m, 6H), 7.46 (m, 2H), 7.54 (m, 1H), 7.70 (dd, J=1.5 and 7, 2H). Mass spectrum ($NH_3$—CI): m/z 477 (M+1, 100%).

The following Examples were prepared following the procedure described in Example 22, Steps C–D but using the appropriate substituted bromobenzene in Step C.

EXAMPLE 23

(R,S)-N-[2-(3-Ethylphenyl)-4-(4-phenylpiperidin-1-yl)but-1-yl]-N-methylbenzenesulfonamide hydrochloride salt Mass spectrum (ESI): m/z 491 (M+1, 100%).

EXAMPLE 24

(R,S)-N-[2-(3-Carboethoxyphenyl)-4-(4-phenylpiperidin-1-yl)but-1-yl]-N-methylbenzenesulfonamide hydrochloride salt Mass spectrum (ESI): m/z 535 (M+1, 100%).

EXAMPLE 25

(R,S)-N-[2-(3-Fluorophenyl)-4-(4-phenylpiperidin-1-yl)but-1-yl]-N-methylbenzenesulfonamide hydrochloride salt Mass spectrum ($NH_3$—CI): m/z 481 (M+1, 100%).

EXAMPLE 26

(R,S)-N-[2-(3-Methoxyphenyl)-4-(4-phenylpiperidin-1-yl)but-1-yl]-N-methylbenzenesulfonamide hydrochloride salt Mass spectrum ($NH_3$—CI): m/z 493 (M+1, 100%).

EXAMPLE 27

(R,S)-N-[2-(3,4-Difluorophenyl)-4-(4-phenylpiperidin-1-yl)but-1-yl]-N-methylbenzenesulfonamide hydrochloride salt Mass spectrum ($NH_3$—CI): m/z 499 (M+1, 100%).

EXAMPLE 28

(R,S)-N-[2-(3-Biphenyl)-4-(4-phenylpiperidin-1-yl)but-1-yl]-N-methylbenzenesulfonamide hydrochloride salt Mass spectrum ($NH_3$—CI): m/z 539 (M+1, 100%).

EXAMPLE 29

(R,S)-N-[2-(3-Pyridyl)-4-(4-phenylpiperidin-1-yl)but-1-yl]-N-methylbenzenesulfonamide hydrochloride salt Mass spectrum ($NH_3$—CI): m/z 464 (M+1, 100%).

EXAMPLE 30

(R,S)-N-[2-(Naphthalen-2-yl)-4-(4-phenylpiperidin-1-yl)but-1-yl]-N-methylbenzenesulfonamide hydrochloride salt Mass spectrum ($NH_3$—CI): m/z 513 (M+1, 100%).

EXAMPLE 31

(R,S)-N-[2-(4-Methylphenyl)-4-(4-phenylpiperidin-1-yl)but-1-yl]-N-methylbenzenesulfonamide hydrochloride salt Mass spectrum ($NH_3$—CI): m/z 553 (M+1, 100%).

EXAMPLE 32

(R,S)-N-[2-(2-Pyridyl)-4-(4-phenylpiperidin-1-yl)but-1-yl]-N-methylbenzenesulfonamide hydrochloride salt Mass spectrum ($NH_3$—CI): m/z 464 (M+1, 100%).

EXAMPLE 33

(R,S)-N-[2-(3-Fluoro-4-methylphenyl)-4-(4-phenylpiperidin-1-yl)but-1-yl]-N-methylbenzenesulfonamide hydrochloride salt Mass spectrum ($NH_3$—CI): m/z 495 (M+1, 100%).

EXAMPLE 34

(R,S)-N-[2-(3,4-Dimethylphenyl)-4-(4-phenylpiperidin-1-yl)but-1-yl]-N-methylbenzenesulfonamide hydrochloride salt Mass spectrum ($NH_3$—CI): m/z 491 (M+1, 100%).

EXAMPLE 35

(R,S)-N-[2-(3,5-Dimethylphenyl)-4-(4-phenylpiperidin-1-yl)but-1-yl]-N-methylbenzenesulfonamide hydrochloride salt Mass spectrum ($NH_3$—CI): m/z 491 (M+1, 100%).

EXAMPLE 36

(R,S)-N-[2-(4-Methoxyphenyl)-4-(4-phenylpiperidin-1-yl)but-1-yl]-N-methylbenzenesulfonamide hydrochloride salt Mass spectrum (ESI): m/z 493 (M+1, 100%).

EXAMPLE 37

(R,S)-N-[2-(3-Trifluoromethylphenyl)-4-(4-phenylpiperidin-1-yl)but-1-yl]-N-methylbenzenesulfonamide hydrochloride salt Mass spectrum (ESI): m/z 531 (M+1, 100%).

EXAMPLE 38

(R,S)-N-[2-(3-Methyl-4-fluorophenyl)-4-(4-phenylpiperidin-1-yl)but-1-yl]-N-methylbenzenesulfonamide hydrochloride salt Mass spectrum (ESI): m/z 495 (M+1, 100%).

EXAMPLE 39

(S)-N-[2-(3-Chlorophenyl)-4-(4-phenylpiperidin-1-yl)but-1-yl]-N-methylbenzenesulfonamide hydrochloride salt Step A: (S)-N-[2-(3-Chlorophenyl)pent-4-en-1-yl]-N-methylbenzenesulfonamide A solution of 2.0 g (9.53 mmol) of (S)-4-(3-chorophenyl)-5-methylamino-1-pentene (prepared as described by J. Hale et al., *Bioorganic and Medicinal Chemistry Letters*, 1993, 3, 319–322) and 5.0 mL (28.6 mmol) of diisopropylethylamine (DIPEA) in 20 mL of methylene chloride was cooled in an ice/ethanol bath. To this was added 1.46 mL (11.4 mmol) of benzenesulfonyl chloride and after 5 min the ice bath was removed. After stirring for 16 h, the reaction mixture was diluted with methylene chloride and washed with water containing 20 mL of 2 N HCl. The aqueous layer was reextracted with methylene chloride and the organic layers were washed with brine, combined, dried over sodium sulfate and concentrated in vacuo. The residue was purified by flash column chromatography (FCC) eluting with 15% ethyl acetate/hexanes to afford 3.44 g of the title compound. 1H NMR (400 MHz, $CDCl_3$): δ 2.38 (p, J=8, 1H), 2.55 (m, 1H), 2.59 (s, 3H), 2.94 (m, 2H), 3.37 (m, 1H), 4.95 (m, 2H), 5.60 (m, 1H), 7.05–7.3 (m, 4H), 7.46 (m, 2H), 7.55 (m, 1H), 7.69 (dd, J=1.5 and 6, 2H).

Step B: (S)-N-[2-(3-Chlorophenyl)-4-oxo-but-1-yl]-N-methylbenzene-sulfonamide

To a solution of 3.33 g (9.53 mmol) of (S)-N-[2-(3-chlorophenyl)pent-4-en-1-yl]-N-methylbenzenesulfonamide from Step A in 16 mL of acetone, 8 mL of t-butanol and 8 mL of water was added 1.22 g (10.4 mmol) of N-methylmorpholine-N-oxide followed by 0.50 mL of 4% osmium tetroxide in water. The reaction was stirred at rt for 16 h and was then quenched with aqueous sodium sulfite and concentrated in vacuo after 20 min. The residue was diluted with water and extracted twice with ethyl acetate. The organic layers were each washed with brine, combined, dried over sodium sulfate and concentrated in vacuo to afford the crude diol intermediate.

The above product was taken up in 30 mL of THF and 2.45 g (11.4 mmole) of sodium periodate in 10 mL of water was added. The mixture was stirred at rt for 2 h, poured into water and extracted twice with ether. The ether layers were each washed with brine, combined, dried over sodium sulfate and concentrated in vacuo. The residue was purified by FCC (20% ethyl acetate/hexanes) to afford 2.57 g of the title compound. 1H NMR (400 MHz, CDCl$_3$): δ 2.63 (s, 3H), 2.75–2.9 (m, 2H), 3.14 (dd, J=6 and 16, 1H), 3.35 (dd, J=10 and 14, 1H), 3.55 (m, 1H), 7.15–7.35 (2 m, 4H), 7.46 (m, 2H), 7.53 (m, 1H), 7.70 (dd, J=1.5 and 7, 2H), 9.78 (s, 1H).

Step C: (S)-N-[2-(3-Chlorophenyl)-4-(4-phenylpiperidin-1-yl)but-1-yl]-N-methylbenzenesulfonamide hydrochloride salt To a solution of 20 mg (0.057 mmol) of (S)-N-[2-(3-chlorophenyl)-4-oxo-but-1-yl]-N-methylbenzenesulfonamide from Step B in 1.0 mL of THF were added 27 mg (0.17 mmol) of 4-phenylpiperidine, 3 Å molecular sieves and 0.010 mL of acetic acid. After stirring the mixture for 20 min, 24 mg (0.113 mmol) of sodium triacetoxyborohydride was added. After 16 h the reaction was quenched with aqueous sodium bicarbonate, the mixture was filtered through a pad of celite and the reaction flask and the pad were rinsed with water and ethyl acetate. The layers were separated and the aqueous layer was extracted twice more with ethyl acetate. The organic layers were each washed with brine, combined, dried over sodium sulfate and concentrated in vacuo. The residue was purified by prep TLC using 2% triethylamine in 5% methanol/ethyl acetate to isolate 20 mg of the free amine of the title compound as an oil. 1H NMR (400 MHz, CDCl$_3$): δ 1.80 (m, 5H), 1.9–2.3 (3 m, 5H), 2.4–2.5 (m, 1H), 2.61 (s, 3H), 2.9–3.1 (m, 4H), 3.35–3.45 (m, 1H), 7.1–7.3 (m, 9H), 7.4–7.5 (m, 2H), 7.5–7.6 (m, 1H), 7.70 (dd, J=1.5 and 7.0, 2H). Mass spectrum (ESI): m/z 497 (M+1, 100%).

The hydrochloride salt of the title compound was prepared by dissolving the above oil in ether/methanol and addition of 2–3 equivalents of 1 M ethereal HCl. Evaporation of the volatiles and drying in vacuo afforded 21 mg of the title salt as a white solid after trituration with ether.

The following Examples were prepared following the procedure described in Example 39, Step C but using the appropriate substituted piperidine in the reductive amination.

EXAMPLE 40

(S)-N-[4-(4-Benzylpiperidin-1-yl)-2-(3-chlorophenyl)but-1-yl]-N-methylbenzenesulfonamide hydrochloride salt Mass spectrum (ESI): m/z 511 (M+1, 100%).

EXAMPLE 41

(S)-N-[4-(4-(3-Phenylprop-1-yl)piperidin-1-yl)-2-(3-chlorophenyl)but-1-yl]-N-methylbenzenesulfonamide hydrochloride salt Mass spectrum (ESI): m/z 539 (M+1, 100%).

EXAMPLE 42

(S)-N-[2-(3-Chlorophenyl)-4-(4-t-butylpiperidin-1-yl)but-1-yl]-N-methylbenzenesulfonamide hydrochloride salt Mass spectrum (NH$_3$—CI): m/z 477 (M+1, 100%).

EXAMPLE 43

(S)-N-[2-(3-Chlorophenyl)-4-(4-(cis-octahydro-2H-benzimidazol-2-on-1-yl)piperidin-1-yl)but-1-yl]-N-methylbenzenesulfonamide hydrochloride salt Mass spectrum (ESI): m/z 559 (M+1, 100%).

EXAMPLE 44

(S)-N-[2-(3-Chlorophenyl)-4-(4-(1,2,3,4-tetrahydro-2H-quinazolin-2-on-1-yl)piperidin-1-yl)but-1-yl]-N-methylbenzenesulfonamide hydrochloride salt Mass spectrum (ESI): m/z 567 (M+1, 100%).

EXAMPLE 45

(S)-N-[2-(3-Chlorophenyl)-4-(3-phenylpiperidin-1-yl)but-1-yl]-N-methylbenzenesulfonamide hydrochloride salt Mass spectrum (ESI): m/z 497 (M+1, 100%).

EXAMPLE 46

(S)-N-[2-(3-Chlorophenyl)-4-(4-hydroxy-4-phenylpiperidin-1-yl)but-1-yl]-N-methylbenzenesulfonamide hydrochloride salt Mass spectrum (NH$_3$—CI): m/z 513 (M+1, 100%).

EXAMPLE 47

(S)-N-[2-(3-Chlorophenyl)-4-(4-(2,3-dihydro-2H-benzimidazol-2-on-1-yl)piperidin-1-yl)but-1-yl]-N-methylbenzenesulfonamide hydrochloride salt Mass spectrum (NH$_3$—CI): m/z 553 (M+1, 100%).

EXAMPLE 48

(S)-N-[2-(3-Chlorophenyl)-4-[4,4-diphenylpiperidin-1-yl] -butyl}-N-methylbenzenesulfonamide hydrochloride salt Mass spectrum (NH$_3$—CI): m/z 573 (M+1, 100%).

EXAMPLE 49

(S)-N-[4- [4-(4-Chlorophenyl)-4-hydroxypiperidin-1-yl]-2-(3-chlorophenyl)-but-1-yl]-N-methylbenzenesulfonamide hydrochloride salt Mass spectrum (NH$_3$—CI): m/z 547 (M+1, 100%).

EXAMPLE 50

(S)-N-[4-(4-Acetyl-4-phenylpiperidin-1-yl)-2-(3-chlorophenyl)but-1-yl]-N-methylbenzenesulfonamide hydrochloride salt Mass spectrum (NH$_3$—CI): m/z 539 (M+1, 100%).

EXAMPLE 51

(S)-N-[4-[4-(4-Chloro-3-trifluoromethylphenyl)-4-hydroxypiperidin-1-yl]-2-(3-chlorophenyl)but-1-yl]-N-methylbenzenesulfonamide hydrochloride salt Mass spectrum (NH$_3$—CI): m/z 614 (M+1, 100%).

EXAMPLE 52

(S)-N-[2-(3-Chlorophenyl)-4-[4-(2-methoxycarbonylphenyl)piperidin-1-yl]-but-1-yl]-N-methylbenzenesulfonamide hydrochloride salt Mass spectrum ($NH_3$—CI): m/z 555 (M+1, 100%).

EXAMPLE 53

(S)-N-[2-(3-Chlorophenyl)-4-[4-hydroxy-4-(3-trifluoromethyl)phenyl-piperidin-1-yl]-but-1-yl]-N-methylbenzenesulfonamide hydrochloride salt Mass spectrum ($NH_3$—CI): m/z 581 (M+1, 100%).

EXAMPLE 54

(S)-N-[2-(3-Chlorophenyl)-4-[4-(4-fluorophenyl)-4-hydroxypiperidin-1-yl]but-1-yl]-N-methylbenzenesulfonamide hydrochloride salt Mass spectrum (ESI): m/z 531 (M+1, 100%).

EXAMPLE 55

(S)-N-[2-(3-Chlorophenyl)-4-[4-(2-oxo-4H-benzo[d][1,3]oxazin-1-yl)piper-idin-1-yl]but-1-yl]-N-methylbenzenesulfonamide hydrochloride salt Mass spectrum ($NH_3$—CI): m/z 568 (M+1, 100%).

EXAMPLE 56

(S)-N-[2-(3-Chlorophenyl)-4-[4-(2-oxo-3H-benzo[d][1,4]oxazin-1-yl)piper-idin-1-yl]but-1-yl]-N-methylbenzenesulfonamide hydrochloride salt Mass spectrum ($NH_3$—CI): m/z 568 (M+1, 100%).

EXAMPLE 57

(S)-N-[4-(4-Benzoylpiperidin-1-yl)-2-(3-chlorophenyl)but-1-yl]-N-methylbenzenesulfonamide hydrochloride salt Mass spectrum ($NH_3$—CI): m/z 525 (M+1, 100%).

EXAMPLE 58

(S)-N-[2-(3-Chlorophenyl)-4-[4-(2-methoxy)phenylpiperidin-1-yl]but-1-yl]-N-methylbenzenesulfonamide hydrochloride salt Mass spectrum (ESI): m/z 527 (M+1, 100%).

EXAMPLE 59

(S)-N-[2-(3-Chlorophenyl)-4-(4-piperidin-1-ylpiperidin-1-yl)but-1-yl]-N-methylbenzenesulfonamide hydrochloride salt Mass spectrum (ESI): m/z 504 (M+1, 100%).

The following Examples were prepared using the procedure described in Example 39 but utilizing the appropriate substituted 4-phenyl pentene derivative (prepared as described by J. Hale et al., *Bioorganic and Medicinal Chemistry Letters*, 1993, 3, 319–322) as the starting material.

EXAMPLE 60

(S)-N-[2-(3,4-Methylenedioxyphenyl)-4-(4-phenylpiperidin-1-yl)but-1-yl]-N-methylbenzenesulfonamide hydrochloride salt Mass spectrum (ESI): m/z 507 (M+1, 100%).

EXAMPLE 61

(S)-N-[2-(4-Fluorophenyl)-4-(4-phenylpiperidin-1-yl)but-1-yl]-N-methylbenzenesulfonamide hydrochloride salt Mass spectrum ($NH_3$—CI): m/z 481 (M+1, 100%).

EXAMPLE 62

(S)-N-[2-(3,4-Dichlorophenyl)-4-(4-phenylpiperidin-1-yl)-but-1-yl]-N-ethylbenzenesulfonamide hydrochloride salt Following essentially the same procedure as described in Example 39 but utilizing (S)-4-(3,4-dichlorophenyl)-5-ethylamino-1-pentene (prepared as described by J. Hale et al., *Bioorganic and Medicinal Chemistry Letters*, 1993, 3, 319–322) as the starting material, the title compound was prepared. $^1$H NMR (400 MHz, $CDCl_3$): δ 0.955 (t, J=8, 3H), 1.5–1.9 (3 m, 5H), 1.9–2.3 (2 m, 5H), 2.4–2.6 (m, 1H), 2.8–3.05 (m, 3H), 3.05–3.2 (m, 3H) 3.44 (dd, J=8 and 13, 1H), 7.03 (br d, J=7, 1H), 7.15–7.4 (m, 7H), 7.45 (t, J=7, 2H), 7.52 (br t, J=7, 1H), 7.70 (dd, J=1.5 and 7, 2H). Mass spectrum ($NH_3$—CI): m/z 545 (M+1, 100%).

EXAMPLE 63

(R,S)-N-[2-Phenyl-4-(4-phenylpiperidin-1-yl)but-1-yl]-N-methylphenyl-acetamide

The title compound was prepared following the procedure described in Example 1, Steps A–C but substituting phenylacetyl chloride in Step A. Mass spectrum ($NH_3$—CI): m/z 441 (M+1, 100%).

EXAMPLE 64

(R,S)-N-[2-Phenyl-4-[4-acetyl(ethylamino)piperidin-1-yl]but-1-yl]-N-methylbenzenesulfonamide Step A: (1-Benzyloxycarbonylpiperidin-4-yl)isocyanate To a solution of 9.72 g (34.8 mmol) of 1-benzyloxycarbonyl-4-carboxypiperidine in 100 mL of methylene chloride was added 2 drops of DMF and then slowly 3.34 mL (38.3 mmol) of oxalyl chloride. The reaction was stirred at rt for 1 h (gas evolution had stopped) and the volatiles were removed in vacuo followed by evaporation of a portion of toluene.

The above residue was taken up in 100 mL of acetone and slowly added to a solution of 5.66 g (87 mmol) of sodium azide in 25 mL of water and 25 mL of acetone while stirred in an ice bath. The reaction was stirred at 0° C. for 1.5 h and then diluted with ice water and extracted twice with 2×150 mL of toluene. The organic layers were each washed with a portion of brine, dried over sodium sulfate, combined and concentrated to about 100 mL in vacuo with a minimum of heating. The remaining solution was slowly heated to 85° C. for 1.5 h and then concentrated to dryness in vacuo to afford about 9.5 g of crude title product which can be used directly in subsequent reactions.

Step B: 1-Benzyloxycarbonyl-4-t-butoxycarbonylaminopiperidine

A solution of 3.2 g (12.3 mmol) of (1-benzyloxycarbonyl-piperidin-4-yl)isocyanate from Step A in 25 mL of DMF was slowly added to a suspension of $CuCl_3$ in 25 mL of DMF and 12 mL of t-butanol. The reaction was stirred for 24 h and then diluted with water and extracted twice with 1:1 ether-:ethyl acetate. The organic layers were each washed with a portion of water and brine, dried over sodium sulfate, combined and concentrated. The residue was purified by FCC eluting with 20% ethyl acetate/hexanes to afford 685 mg of title compound. $^1$H NMR (400 MHz, CDCl$_3$): δ 1.26 (m, 2H), 1.42 (s, 9H), 1.90 (br d, J=12, 2H), 2.90 (br t, 2H), 3.58 (m, 1H), 4.08 (m, 2H), 4.42 (br s, 1H), 5.09 (s, 2H), 7.33 (m, 5H).

Step C: 1-Benzyloxycarbonyl-4-t-butoxycarbonyl (ethylamino)-piperidine

To a solution of 476 mg (1.42 mmol) of 1-benzyloxycarbonyl-4-t-butoxycarbonylaminopiperidine and 0.24 mL (2.8 mmol) of ethyl iodide in 10 mL of DMF was added 85 mg (2.1 mmol) of 60% sodium hydride in mineral oil. The reaction was stirred for 16 h and was then poured into water and extracted three times with ether. The organic layers were each washed with a portion of water and brine, dried over sodium sulfate, combined and concentrated. The residue was purified by FCC eluting with 15% ethyl acetate/hexanes to afford 409 mg of title compound. $^1$H NMR (400 MHz, CDCl$_3$): δ 1.06 (t, J=7, 3H), 1.44 (s, 9H), 1.5–1.7 (2 m, 4H), 2.78 (m, 2H), 3.1 (m, 2H), 4.10 (m, 1H), 4.25 (m, 2H), 5.10 (S, 2H), 7.33 (m, 5H).

Step D: 4-t-Butoxycarbonyl(ethylamino)piperidine

A solution of 400 mg (1.1 mmol) of 1-benzyloxycarbonyl-4-t-butoxycarbonyl(ethylamino) piperidine from Step C in 4 mL of methanol was hydrogenated with 40 mg of 10% Pd/C under a hydrogen balloon for 16 h. The reaction was filtered and concentrated in vacuo to give the title compound which was used directly in the next step.

Step E: (R,S)-N-[2-Phenyl-4-[4-t-butoxycarbonyl (ethylamino)-piperidin-1-yl]but-1-yl]-N-methylbenzenesulfonamide Using essentially the same procedure as Example 1, Step C, 235 mg (1.0 mmol) of 4-t-butoxycarbonyl(ethylamino) piperidine from Step D and 212 mg of (R,S)-N-(2-phenyl-4-oxobut-1-yl)-N-methylbenzenesulfonamide from Example 1, Step B afforded 360 mg of title compound. $^1$H NMR (400 MHz, CDCl$_3$): δ 1.06 (t, J=7, 3H), 1.43 (s, 9H), 1.5–2.2 (5 m, 10H), 2.56 (s, 3H), 2.90 (m, 4H), 3.10 (m, 2H), 3.38 (m, 1H), 3.83 (m, 1H), 7.1–7.3 (m, 5H), 7.45 (m, 2H), 7.54 (m, 1H). Mass spectrum (ESI): m/z 530 (M+1, 100%).

Step F: (R,S)-N-[2-Phenyl-4- [4-(ethylamino)piperidin-1-yl]but-1-yl]-N-methylbenzenesulfonamide hydrochloride salt A solution of 10 mmol of HCl in 10 mL of methanol was prepared by slowly adding 0.70 mL (10 mmol) of acetyl chloride with ice bath cooling. To this was added 251 mg (0.489 mmol) of (R,S)-N-[2-phenyl-4-[4-t-butoxycarbonyl (ethylamino)piperidin-1-yl]but-1-yl]-N-methylbenzenesulfonamide. After stirring at rt for 16 h, the volatiles were removed in vacuo to give the title compound. Mass spectrum (ESI): m/z 430 (M+1, 100%).

Step G: (R,S)-N-[2-Phenyl-4- [4-acetyl(ethylamino) piperidin-1-yl]but-1-yl]-N-methylbenzenesulfonamide hydrochloride salt To a solution of 45 mg (0.089 mmol) of (R,S)-N-[2-phenyl-4-[4-(ethylamino)piperidin-1-yl]but-1-yl]-N-methylbenzenesulfonamide hydrochloride salt in 2 mL of methylene chloride at 0° C. was added 0.067 mL (0.38 mmol) of DIPEA and 0.014 mL (0.19 mmol) of acetyl chloride. The reaction was stirred at rt for 16 h and then was quenched with aqueous sodium carbonate and extracted three times with methylene chloride. The organic layers were each washed with a portion of brine, dried over sodium sulfate, combined and concentrated. The residue was purified by prep TLC eluting with 10% methanol in methylene chloride and converted to the hydrochloride salt to afford 40 mg of title compound. Mass spectrum (ESI): m/z 472 (M+1, 100%).

EXAMPLE 65

(R,S)-N-[2-Phenyl-4-[4-(oxazolidin-2-on-3-yl) piperidin-1-yl]but-1-yl]-N-methylbenzenesulfonamide hydrochloride salt Step A: 1-Benzyloxycarbonyl-4-(oxazolidin-2-on-3-yl) piperidine To a solution of 0.53 g (2.0 mmol) of (1-benzyloxycarbonylpiperidin-4-yl)isocyanate from Example 64, Step A in 10 mL of methylene chloride was added 690 mg (2.0 mmol) of 2-chloroethanol and 5 mg (cat) of DMAP. The reaction was stirred under nitrogen at rt for 24 h and then evaporated to dryness to give the crude 2-chloroethylcarbamate intermediate.

The above residue was taken up in 10 mL of DMF under nitrogen and 197 mg (4.93 mmol) of 60% sodium hydride in mineral oil was added. The reaction was stirred at rt for 1 h and then poured into water containing 3 mL of 2 N hydrochloric acid and extracted twice with ether. The organic layers were each washed with a portion of brine, dried over sodium sulfate, combined and concentrated. The residue was purified by FCC eluting with 70% ethyl acetate/hexanes to afford 533 mg of title compound. $^1$H NMR (400 MHz, CDCl$_3$): δ 1.55 (m, 2H), 1.76 (br d, J=10, 2H), 2.83 (m, 2H), 3.46 (t, J=8, 2H), 3.87 (m, 1H), 4.27 (m, 2H), 4.31 (t, J=8, 2H), 5.10 (s, 2H), 7.35 (m, 5H).

Step B: 4-(Oxazolidin-2-on-3-yl)piperidine

Using essentially the same procedure as in Example 64, Step D, 525 mg (1.72 mmol) of 1-benzyloxycarbonyl-4-(oxazolidin-2-on-3-yl)piperidine from Step A was hydrogenated to afford 250 mg of the title compound.

Step C: (R,S)-N-[2-Phenyl-4-[4-(oxazolidin-2-on-3-yl) piperidin-1-yl]but-1-yl]-N-methylbenzenesulfonamide hydrochloride salt Using essentially the same procedure as in Example 1, Step C, the piperidine derivative from Step B was utilized to reductively alkylate (R,S)-N-(2-phenyl-4-oxobut-1-yl)-N-methylbenzenesulfonamide to provide the title compound. Mass spectrum (ESI): m/z 472 (M+1, 100%).

EXAMPLE 66

(R,S)-N-[2-Phenyl-4-(4-methoxycarbonyl (ethylamino)piperidin-1-yl)but-1-yl]-N-methylbenzenesulfonamide hydrochloride salt Step A: 1-Benzyloxycarbonyl-4-(methoxycarbonylamino) piperidine To a solution of 1.0 g (3.9 mmol) of (1-benzyloxycarbonyl-piperidin-4-yl)isocyanate from Example 64, Step A in 10 mL of methanol was added 5 mg (cat) of DMAP. The reaction was stirred under nitrogen at rt for 24 h and then poured into water containing 2 mL of 2 N hydrochloric acid and was extracted twice with ethyl acetate. The organic layers were each washed with a portion of brine, dried over sodium sulfate, combined and concentrated to give 1.4 g of the crude title compound which can be used directly in subsequent reactions. $^1$H NMR (400 MHz, CDCl$_3$): δ 1.32 (m, 2H), 1.92 (br d, J=10, 4H), 2.91 (v br t, 2H), 3.66 (br s, 3H+1H), 4.10 (m, 2H), 4.58 (br s, 1H), 5.09 (s, 2H), 7.33 (m, 5H).

Step B: 1-Benzyloxycarbonyl-4-[methoxycarbonyl (ethylamino)]-piperidine

To 82 mg (0.28 mmol) of 1-benzyloxycarbonyl-4-(methoxycarbonylamino)piperidine from Step A and 0.045 mL (0.56 mmol) of ethyl iodide in 4 mL of DMF under nitrogen was added 22 mg (0.56 mmol) of 60% sodium hydride in mineral oil. The reaction was stirred at rt for 1 h and was then poured into water containing 1 mL of 2 N hydrochloric acid and extracted twice with ether. The organic layers were each washed with a portion of brine, dried over sodium sulfate, combined and concentrated. The residue was purified by FCC eluting with 50% ethyl acetate/hexanes to afford 87 mg of title compound. 1H NMR (400 MHz, CDCl$_3$): δ 1.07 (t, J=7, 3H), 1.5–1.8 (m, 4H), 2.79 (m, 2H), 3.15 (m, 2H), 3.68 (s, 3H), 4.10 (m, 1H), 4.26 (m, 2H), 5.10 (s, 2H), 7.34 (m, 5H).

Step C: 4-[Methoxycarbonyl(ethylamino)]piperidine

Using essentially the same procedure as in Example 64, Step D, 85 mg (0.27 mmol) of 1-benzyloxycarbonyl-4-[methoxycarbonyl-(ethylamino)]piperidine from Step B was hydrogenated to afford 37 mg of the title compound.

Step D: (R,S)-N-[2-Phenyl-4-(4-methoxycarbonyl(ethylamino)-piperidin-1-yl)but-1-yl]-N-methylbenzenesulfonamide hydrochloride salt Using essentially the same procedure as in Example 1, Step C, the piperidine derivative from Step C was utilized to reductively alkylate (R,S)-N-(2-phenyl-4-oxobut-1-yl)-N-methylbenzenesulfonamide to provide the title compound. Mass spectrum (ESI): m/z 488 (M+1, 100%).

EXAMPLE 67

(R,S)-N-[2-Phenyl-4-(4-dimethylaminocarbonylaminopiperidin-1-yl)but-1-yl]-N-methylbenzenesulfonamide Step A: 1-Benzyloxycarbonyl-4-(dimethylaminocarbonylamino)-piperidine To 0.83 g (3.2 mmol) of (1-benzyloxycarbonylpiperidin-4-yl)isocyanate from Example 64, Step A in 10 mL was added 16 mL (32 mmol) of 2 M dimethylamine in THF. The reaction was stirred under nitrogen at rt for 24 h and then poured into water containing 20 mL of 2 N hydrochloric acid and was extracted twice with ethyl acetate. The organic layers were each washed with a portion of brine, dried over sodium sulfate, combined and concentrated to give 0.95 g of the crude title compound which can be used directly in subsequent reactions. $^1$H NMR (400 MHz, CDCl$_3$): δ 1.25 (m, 2H), 1.95 (br d, J=10, 2H), 2.86 (br s, 6H+2H), 3.79 (m, 1H), 4.0–4.25 (m, 3H), 5.09 (s, 2H), 7.35 (m, 5H).

Step B: 4-(Dimethylaminocarbonylamino)piperidine

Using essentially the same procedure as in Example 64, Step D, 1.4 g (4.6 mmol) of 1-benzyloxycarbonyl-4-(dimethylaminocarbonylamino)piperidine from Step A was hydrogenated to afford 690 mg of the title compound.

Step C: (R,S)-N-[2-Phenyl-4-(4-dimethylaminocarbonylamino-piperidin-1-yl)but-1-yl]-N-methylbenzenesulfonamide Using essentially the same procedure as in Example 1, Step C, the piperidine derivative from Step C was utilized to reductively alkylate (R,S)-N-(2-phenyl-4-oxobut-1-yl)-N-methylbenzenesulfonamide to provide the title compound. Mass spectrum (ESI): m/z 473 (M+1, 100%).

EXAMPLE 68

(R,S)-N-[2-Phenyl-4-(4-benzyloxycarbonyl(prop-1-ylamino)piperidin-1-yl)but-1-yl]-N-methylbenzenesulfonamide hydrochloride salt Step A: 4-Azido-1-t-butoxycarbonylpiperidine To a solution of 45.3 g (172 mmol) of 4-bromo-1-t-butoxycarbonylpiperidine in 750 mL of DMF was added 22.3 g (343 mmol) of sodium azide and 2.5 g (17 mmol) of sodium iodide. The reaction was stirred at rt for 24 h and then at 60° C. for 4 h. The mixture was poured into water containing 20 mL of sodium bicarbonate and extracted twice with 1:1 ether:hexanes. The organic layers were each washed with a portion of water and brine, dried over sodium sulfate, combined and concentrated. The residue was purified by FCC eluting with 5 –10% ethyl acetate/hexanes to afford 39 g of title compound having a trace of elimination biproduct. $^1$H NMR (400 MHz, CDCl$_3$): δ 1.43 (s,9H), 1.52 (m, 2H), 1.85 (m, 2H), 3.07 (m, 2H), 3.55 (m, 1H), 3.78 (m, 2H).

Step B: 4-Amino-1-t-butoxycarbonylpiperidine

A solution of 4.05 g (17.9 mmol) of 4-azido-1-t-butoxycarbonylpiperidine from Step A in 50 mL of methanol was hydrogenated with 350 mg of 10% Pd/C under a hydrogen balloon for 16 h when the reaction was complete by TLC (10% ethyl acetate/hexanes). The catalyst was filtered off and the volatiles removed in vacuo to give 3.5 g of title compound which was used directly in subsequent reactions.

Step C: 4-Benzyloxycarbonylamino-1-t-butoxycarbonylpiperidine

To a solution of 1.2 g (6.0 mmol) 4-amino-1-t-butoxycarbonylpiperidine from Step B in 40 mL of methylene chloride was added 3.15 mL (18 mmol) of DIPEA and 1.03 mL (7.2 mmol) of benzyl chloroformate while cooled in an ice bath. After 0.5 h the reaction was quenched with aqueous sodium carbonate and extracted three times with methylene chloride. The organic layers were each washed with a portion of brine, dried over sodium sulfate, combined and concentrated. The residue was purified by FCC eluting with 25% ethyl acetate/hexanes to afford 1.94 g of title compound. $^1$H NMR (400 MHz, CDCl$_3$): δ 1.26 (m, 2H), 1.42 (s, 9H), 1.90 (br d, J=12, 2H), 2.90 (br t, 2H), 3.58 (m, 1H), 4.08 (m, 2H), 4.42 (br s, 1H), 5.09 (s, 2H), 7.33 (m, 5H).

Step D: 4-Benzyloxycarbonyl(prop-1-ylamino)-1-t-butoxycarbonylpiperidine

To 110 mg (0.32 mmol) 4-benzyloxycarbonylamino-1-t-butoxycarbonylpiperidine from Step C and 0.16 mL (1.6 mmol) of n-propyl iodide in 2 mL of DMF under nitrogen was added 26 mg (0.65 mmol) of 60% sodium hydride in mineral oil. The reaction was stirred at rt for 16 h and was then poured into water and extracted twice with ether. The organic layers were each washed with a portion of brine, dried over sodium sulfate, combined and concentrated. The residue was purified by FCC eluting with 20% ethyl acetate/hexanes to afford 90 mg of title compound.

Step E: 4-Benzyloxycarbonyl(prop-1-ylamino)piperidine hydrochloride salt

To a solution of 2.4 mmol of HCl in 2 mL of methanol (prepared by the addition of 0.17 mL of acetyl chloride at 0° C. and stirring for 10 min) was added 90 mg of 4-benzyloxycarbonyl(prop-1-ylamino)-1-t-butoxycarbonylpiperidine. The mixture was stirred at rt for 16 h at which time the reaction was complete by TLC (20% ethyl acetate/hexanes) and was evaporated to dryness in vacuo to afford 75 mg of the title compound as the hydrochloride salt.

Step F: (R,S)-N-[2-Phenyl-4-(4-benzyloxycarbonyl(prop-1-ylamino)piperidin-1-yl)but-1-yl]-N-methylbenzenesulfonamide hydrochloride salt Using essentially the same procedure as in Example 1, Step C, the piperidine derivative from Step E was utilized to reductively alkylate (R,S)-N-(2-phenyl-4-oxobut-1-yl)-N-methylbenzenesulfonamide to provide the title compound. Mass spectrum (NH$_3$/CI): m/z 578 (M+1, 100%).

The following Examples were prepared following the procedure described in Example 1, Step C but using the appropriate substituted piperidine in the reductive amination step (prepared by analogy to the piperidine derivatives in Examples 64–68).

EXAMPLE 69

(R,S)-N-[2-Phenyl-4-(4-methoxycarbonylaminopiperidin-1-yl)but-1-yl]-N-methylbenzenesulfonamide Mass spectrum (ESI): m/z 460 (M+1, 100%).

EXAMPLE 70

(R,S)-N-[2-Phenyl-4-(4-aminocarbonylaminopiperidin-1-yl)but-1-yl]-N-methylbenzenesulfonamide Mass spectrum (ESI): m/z 445 (M+1, 100%).

EXAMPLE 71

(R,S)-N-[2-Phenyl-4-(4-aminopiperidin-1-yl)but-1-yl]-N-methylbenzene-sulfonamide hydrochloride salt Mass spectrum (ESI): m/z 402 (M+1, 100%).

EXAMPLE 72

(R,S)-N-[2-Phenyl-4-(4-acetylaminopiperidin-1-yl)but-1-yl]-N-methylbenzenesulfonamide hydrochloride salt Mass spectrum (ESI): m/z 444 (M+1, 100%).

EXAMPLE 73

(R,S)-N-[2-Phenyl-4-(4-isopropylcarbonylaminopiperidin-1-yl)but-1-yl]-N-methylbenzenesulfonamide hydrochloride salt Mass spectrum (ESI): m/z 472 (M+1, 100%).

EXAMPLE 74

(R,S)-N-[2-Phenyl-4-(4-methylsulfonylaminopiperidin-1-yl)but-1-yl]-N-methylbenzenesulfonamide hydrochloride salt Mass spectrum (ESI): m/z 480 (M+1, 100%).

EXAMPLE 75

(R,S)-N-[2-Phenyl-4-(4-isopropylcarbonyl(ethylamino)piperidin-1-yl)but-1-yl]-N-methylbenzenesulfonamide hydrochloride salt Mass spectrum (ESI): m/z 500 (M+1, 100%).

EXAMPLE 76

(R,S)-N-[2-Phenyl-4-(4-methylsulfonyl(ethylamino)piperidin-1-yl)but-1-yl]-N-methylbenzenesulfonamide hydrochloride salt Mass spectrum (ESI): m/z 508 (M+1, 100%).

EXAMPLE 77

(R,S)-N-[2-Phenyl-4-(4-t-butoxycarbonylaminopiperidin-1-yl)but-1-yl]-N-methylbenzenesulfonamide hydrochloride salt Mass spectrum (ESI): m/z 502 (M+1, 100%).

EXAMPLE 78

(R,S)-N-[2-Phenyl-4-(4-methoxycarbonyl(methylamino)piperidin-1-yl)but-1-yl]-N-methylbenzenesulfonamide hydrochloride salt Mass spectrum (PB-EI): m/z 474 (M+1), 211 (100%).

EXAMPLE 79

(R,S)-N-[2-Phenyl-4-(4-(pyrrolidin-2-on-1-yl)piperidin-1-yl)but-1-yl]-N-methylbenzenesulfonamide hydrochloride salt Mass spectrum (PB-EI): m/z 470 (M+1), 160 (100%).

EXAMPLE 80

(R,S)-N-[2-Phenyl-4-(4-methoxycarbonyl(cyclobutylmethylamino)-piperidin-1-yl)but-1-yl]-N-methylbenzenesulfonamide hydrochloride salt Mass spectrum (PB-EI): m/z 528 (M+1), 160 (100%).

EXAMPLE 81

(R,S)-N-[2-Phenyl-4-(4-ethoxycarbonyl(ethylamino)piperidin-1-yl)but-1-yl]-N-methylbenzenesulfonamide hydrochloride salt Mass spectrum (PB-EI): m/z 502 (M+1), 160 (100%).

EXAMPLE 82

(R,S)-N-[2-Phenyl-4-(4-isobutyloxycarbonyl(ethylamino)piperidin-1-yl)but-1-yl]-N-methylbenzenesulfonamide hydrochloride salt Mass spectrum (PB-EI): m/z 530 (M+1), 160 (100%).

EXAMPLE 83

(R,S)-N-[2-Phenyl-4-(4-piperidin-2-on-1-ylpiperidin-1-yl)but-1-yl]-N-methylbenzenesulfonamide hydrochloride salt Mass spectrum (ESI): m/z 484 (M+1), 347 (100%).

EXAMPLE 84

(R,S)-N-[2-Phenyl-4-(4-methoxycarbonyl(benzylamino)piperidin-1-yl)but-1-yl]-N-methylbenzenesulfonamide hydrochloride salt Mass spectrum (ESI): m/z 550 (M+1, 100%).

EXAMPLE 85

(R,S)-N-[2-Phenyl-4-(4-methoxycarbonyl(prop-1-ylamino)piperidin-1-yl)but-1-yl]-N-methylbenzenesulfonamide hydrochloride salt Mass spectrum (NH$_3$/CI): m/z 502 (M+1), 118 (100%).

EXAMPLE 86

(R,S)-N-[2-Phenyl-4-(4-methoxycarbonyl(but-1-ylamino)piperidin-1-yl)but-1-yl]-N-methylbenzenesulfonamide hydrochloride salt Mass spectrum (NH$_3$/CI): m/z 516 (M+1), 132 (100%).

EXAMPLE 87

(R,S)-N-[2-Phenyl-4-(4-methoxycarbonyl(cyclohexylmethylamino)-piper-idin-1-yl)but-1-yl]-N-methylbenzenesulfonamide hydrochloride salt Mass spectrum (NH$_3$/CI): m/z 556 (M+1, 100%).

EXAMPLE 88

(R,S)-N-[2-Phenyl-4-(4-methoxycarbonyl(cyclopropylmethylamino)-piper-idin-1-yl)but-1-yl]-N-methylbenzenesulfonamide hydrochloride salt Mass spectrum (NH$_3$/CI): m/z 514 (M+1, 100%).

EXAMPLE 89

(R,S)-N-[2-Phenyl-4-(4-methoxycarbonyl(pent-1-ylamino)piperidin-1-yl)but-1-yl]-N-methylbenzenesulfonamide hydrochloride salt Mass spectrum (NH$_3$/CI): m/z 530 (M+1, 100%).

EXAMPLE 90

(R,S)-N-[2-Phenyl-4-(4-methoxycarbonyl(pent-1-ylamino)piperidin-1-yl)but-1-yl]-N-methylbenzenesulfonamide hydrochloride salt Mass spectrum (NH$_3$/CI): m/z 530 (M+1, 100%).

EXAMPLE 91

(R,S)-N-[2-Phenyl-4-(4-benzyloxycarbonyl (methylamino)piperidin-1-yl)but-1-yl]-N-methylbenzenesulfonamide hydrochloride salt Mass spectrum (NH$_3$/CI): m/z 550 (M+1, 100%).

EXAMPLE 92

(R,S)-N-[2-Phenyl-4-(4-benzyloxycarbonyl (ethylamino)piperidin-1-yl)but-1-yl]-N-methylbenzenesulfonamide hydrochloride salt Mass spectrum (PB-EI): m/z 564 (M+1), 160 (100%).

EXAMPLE 93

(R,S)-N-[2-Phenyl-4-(4-benzyloxycarbonyl(but-1-ylamino)piperidin-1-yl)but-1-yl]-N-methylbenzenesulfonamide hydrochloride salt Mass spectrum (NH$_3$/CI): m/z 592 (M+1, 100%).

EXAMPLE 94

(R,S)-N-[2-Phenyl-4-(4-benzyloxycarbonyl(pent-1-ylamino)piperidin-1-yl)but-1-yl]-N-methylbenzenesulfonamide hydrochloride salt Mass spectrum (NH$_3$/CI): m/z 606 (M+1, 100%).

EXAMPLE 95

(R,S)-N-[2-Phenyl-4-(4-benzyloxycarbonyl (cyclobutylmethylamino)-piper-idin-1-yl)but-1-yl]-N-methylbenzenesulfonamide hydrochloride salt Mass spectrum (NH$_3$/CI): m/z 604 (M+1, 100%).

EXAMPLE 96

(R,S)-N-[2-Phenyl-4-(4-benzyloxycarbonyl (cyclohexylmethylamino)-piper-idin-1-yl)but-1-yl]-N-methylbenzenesulfonamide hydrochloride salt Mass spectrum (NH$_3$/CI): m/z 632 (M+1, 100%).

EXAMPLE 97

(S)-N-[2-(3-Chlorophenyl-4-(4-benzyloxycarbonyl (ethylamino)-piperidin-1-yl)but-1-yl]-N-methylbenzenesulfonamide hydrochloride salt The title compound was prepared using essentially the same procedure as in Example 39, Step C. The piperidine subunit was prepared by analogy to the procedure given in Example 68.

Mass spectrum (NH$_3$/CI): m/z 598 (M+1, 100%).

EXAMPLE 98

(R,S)-N-[3-Phenyl-4-(4-phenylpiperidin-1-yl)but-1-yl]-N-methylbenzenesulfonamide hydrochloride salt Step A: N-[3-Phenyl-4-(4-phenylpiperidin-1-yl)but-2-en-1-yl]-N-methylbenzenesulfonamide To 250 mg (0.37 mmol) of N-[4-(4-phenylpiperidin-1-yl)-3-tributylstannylbut-2-en-1-yl]-N-methylbenzenesulfonamide from Example 21, Step B (isomeric higher R$_f$ product) in 0.5 mL of N-methylpyrrolidinone under argon was added 75 mg (0.55 mmol) of potassium carbonate, 8 mg (2% cat) of dichlorobis (triphenylphosphine)-palladium (II) and 90 mg (0.55 mmol) of bromobenzene. The mixture was heated at 70° C. for 24 h, cooled, treated with aqueous sodium fluoride for 10 min, and partitioned between water and ether. The water layer was reextracted with ether and each organic layer was washed with brine, dried over sodium sulfate, combined and concentrated in vacuo. The residue was purified by FCC eluting with 20–25% ethyl acetate/hexanes to give 120 mg of title product as an oil. $^1$H NMR (400 MHz, CDCl$_3$): δ 1.55–1.6 (m, 2H), 2.75 (br d, J=11, 2H), 2.00 (br dt, J=2 and 14, 2H), 2.42 (m, 1H), 2.78 (s, 3H), 2.93 (br d, J=11, 2H), 3.33 (s, 2H), 4.05 (d, J=6.5, 2H), 5.78 (t, J=6.5, 1H), 7.1–7.4 (3 m, 5H), 7.5–7.65 (m, 3H), 7.84 (dd, J=1.5 and 7, 2H). Mass spectrum (ESI): m/z 461 (M+1, 100%).

Step B: (R,S)-N-[3-Phenyl-4-(4-phenylpiperidin-1-yl)but-1-yl]-N-methylbenzenesulfonamide A mixture of 90 mg (0.20 mmol) of N-[3-phenyl-4-(4-phenylpiperidin-1-yl)but-2-en-1-yl]-N-methylbenzenesulfonamide from Step A, 12 mg of 20% palladium hydroxide/C (50% water), and 2 drops of acetic acid in 3 mL of methanol was hydrogenated at 40 psi for 24 h. The catalyst was removed by filtration and the filtrate concentrated in vacuo. The residue was purified by prep TLC (50% ethyl acetate/hexanes) to afford 20 mg of title compound. A major biproduct was cleavage of the 4-phenylpiperidine to give N-(3-phenylbut-1-yl)-N-methylbenzenesulfonamide. $^1$H NMR (400 MHz, CDCl$_3$): δ 1.5–1.8 (m, 5H), 1.95 (br t, J=11, 1H), 2.1–2.25 (2 m, 2H), 2.45 (m, 2H), 2.57 (m, 1H), 2.6–2.7 (m, 2H), 2.68 (s, 3H), 2.9 (m, 2H), 3.0–3.2 (2 m, 2H), 7.1–7.3 (m, 5H), 7.45 (m, 2H), 7.54 (m, 1H), 7.69 (dd, J=1.5 and 7, 2H). Mass spectrum (ESI): m/z 463 (M+1, 100%).

EXAMPLE 99

(R,S)-N-Methyl-N-[2-methyl-2-phenyl-4-(4-phenylpiperidin-1-yl)but-1-yl]benzenesulfonamide hydrochloride Step A: (R,S)-N-Methyl(2,5-dimethyl-2-phenylhex-4-enyl) amine Methylamine hydrochloride (500 mg, 7.41 mmol), triethylamine (1.00 mL, 725 mg, 7.17 mmol), and 3 Å molecular sieve pellets (1.05 g) were added to a stirred solution of 2,5-dimethyl-2-phenylhex-4-enal 500 mg, 2.47 mmol) in 5.0 mL of methanol at room temperature. After 1 h, the mixture was cooled in an ice bath and acetic acid (0.29 mL, 0.30 g, 5.1 mmol) was added followed by sodium cyanoborohydride (310 mg, 4.93 mmol). The mixture was allowed to slowly come to room temperature and stirred 16 h before being diluted with ethyl acetate (50 mL) and washed with saturated aqueous sodium bicarbonate (30 mL) and saturated aqueous sodium chloride (30 mL). The aqueous layers were extracted with ethyl acetate (30 mL) and the combined organic layers were dried over sodium sulfate, decanted, and evaporated. The residue was purified by flash column chromatography on silica gel, eluting with 5% methanol in ethyl acetate to give 415 mg the title compound. $^1$H NMR (400 MHz, CD30D): δ 1.34 (s, 3H), 1.54 (s, 3H), 1.59 (s, 3H), 2.27 (s, 3H), 2.30 (dd, J=14 and 8, 1H), 2.39 (dd, J=14 and 7.5, 1H), 2.66 (d, J=12, 1H), 2.87 (d, J=12, 1H), 4.88 (t, J=7.5, 1H), 7.18 (t, J=7, 1H), 7.28–7.36 (m, 4H). Mass spectrum (NH$_3$/CI): m/z 218 (M+1, 100%).

Step B: (R,S)-N-Methyl-N-(2,5-dimethyl-2-phenylhex-4-en-1-yl)benzenesulfonamide

Using essentially the same procedure as in Example 1 (Step A), (R,S)-N-methyl(2,5-dimethyl-2-phenylhex-4-enyl)amine from Step A above was allowed to react with benzenesulfonyl chloride in THF to give the title compound as a colorless oil. $^1$H NMR (400 MHz, CDCl$_3$): δ 1.42 (S, 3H), 1.59 (s, 6H), 2.09 (s, 3H), 2.33 (dd, J=15 and 8, 1H), 2.50 (dd, J=15 and 6, 1H), 2.94 (d, J=13, 1H), 3.40 (d, J=13, 1H), 4.83 (bt, J=7, 1H), 7.17, t, J=7, 1H), 7.23–7.33 (m, 4H), 7.48 (t, J=7.5, 2H), 7.55 (t, J=7.5, 1H), 7.72 (d, J=7.5, 2H). Mass spectrum (NH$_3$/CI): m/z 358 (M+1, 100%).

Step C: (R,S)-N-Methyl-N-(2-methyl-2-phenyl-4-oxobut-1-yl)benzenesulfonamide

To a solution of (R,S)-N-methyl-N-(2,5-dimethyl-2-phenylhex-4-en-1-yl)benzenesulfonamide (300 mg, 0.839 mmol) from Step B in 6.0 mL of acetone, 3.0 mL of t-butanol and 1.5 mL of water was added 0.145 mL (118 mg, 0.012 mmol) of 2.5% osmium tetroxide in t-butanol followed by 433 mg (3.70 mmol) of N-methylmorpholine-N-oxide. The reaction was stirred at room temperature for 18 h and was then quenched with 3 g of aqueous sodium bisulfite and concentrated in vacuo. The residue was partitioned between dichloromethane (20 mL) and water (10 mL). The aqueous layer was extracted with dichloromethane (2×20 mL) and the combined organic layers were dried over sodium sulfate, decanted, and evaportated to give the diol intermediate. The above product was dissolved in 9.0 mL of THF and 3.0 mL of water, and treated with 323 mg (1.51 mmol) of sodium periodate. After 2 h, additional sodium periodate (150 mg, 0.70 mmol) was added and the mixture was stirred 1 h longer. Most of the THF was removed in vacuo and the residue was patitioned between ethyl acetate (20 mL) and water (10 mL). The aqueous layer was extracted with ethyl acetate (2×20 mL) and the combined organic layers were dried (sodium sulfate), decanted, and evaporated. The residue was re-dissolved in 9.0 mL of THF and 3.0 mL of water, and sodium periodate (450 mg, 2.1 mmol) was added in three equal portions at 1.5 h intervals. The mixture was stirred for 1.5 h after the addition of the last portion, and then worked up as before. Flash column chromatography on silica gel, eluting with 20% ethyl acetate in hexane gave 210 mg of the title compound as a colorless syrup. $^1$H NMR (400 MHz, CDCl$_3$): δ 1.64 (s, 3H), 2.21 (s, 3H), 2.78 (dd, J=16 and 2.5, 1H), 3.15 (d, J=13, 1H), 3.19 (dd, J=16 and 2.5, 1H), 3.23 (d, J=13, 1H), 7.23–7.28 (m, 1H), 7.32–7.40 (m, 4H), 7.52 (t, J=7.5, 2H), 7.59 (t, J=7.5, 1H), 7.74 (d, J=7.5, 2H), 9.62 (t, J=2.5, 1H). Mass spectrum (ESI): m/z 332 (M+1, 100%).

Step D: (R,S)-N-Methyl-N-[2-methyl-2-phenyl-4-(4-phenyl-piperidin-1-yl)but-1-yl]benzenesulfonamide hydrochloride Using essentially the same procedure as in Example 1 (Step C), (R,S)-N-methyl-N-(2-methyl-2-phenyl-4-oxobut-1-yl)benzene-sulfonamide from Step C above was allowed to react with 4-phenyl-piperidine to give the free amine of the title compound as a colorless film. $^1$H NMR (400 MHz, CD30D): δ 1.50 (s, 3H), 1.70–1.93 (m, 5H), 2.06–2.23 (m, 3H), 2.11 (s, 3H), 2.29 (td, J=12 and 4, 1H), 2.40–2.59 (m, 2H), 3.03 (d, J=14, 1H), 3.03–3.15 (m, 2H), 3.41 (d, J=14, 1H), 7.15 (t, J=7, 1H), 7.19–7.29 (m, 5H), 7.34 (t, J=7.5, 2H), 7.42 (d, J=8, 2H), 7.57 (t, J=7.5, 2H), 7.64 (t, J=7.5, 1H), 7.76 (d, J=8, 2H). Mass spectrum (ESI): m/z 477 (M+1, 100%). The hydrochloride salt of the title compound was prepared by dissolving the free base in ethanol and adding 1.5 equivalents of aqueous 2 N HCl. Evaporation of the solvent gave the title salt as a white solid.

EXAMPLE 100

(R,S)-N-[4-(4-Benzyloxycarbonyl(ethylamino) piperidin-1-yl)-2-methyl-2-phenylbut-1-yl]-N-methylbenzenesulfonamide hydrochloride Using essentially the same procedure as in Example 1 (Step C), (R,S)-N-methyl-N-(2-methyl-2-phenyl-4-oxobut-1-yl)benzene-sulfonamide (from Example 99, Step B) was allowed to react with 4-benzyloxycarbonyl(ethylamino) piperidine (prepared by analogy to Example 68) to give the free amine of the title compound as a colorless film. $^1$H NMR (400 MHz, CD30D): δ 1.11 (t, J=7, 3H), 1.47 (s, 3H), 1.60–1.70 (m, 2H), 1.72–1.86 (m, 3H), 1.91–2.06 (m, 3H), 2.10 (s, 3H), 2.20 (td, J=12 and 3, 1H), 2.28–2.38 (m, 1H), 2.90–3.02 (m, 2H), 3.00 (d, J=14, 1H), 3.24 (t, J=7, 2H), 3.99 (d, J=14, 1H), 3.78–3.90 (b, 1H), 5.11 (s, 2H), 7.21 (t, J=7, 1H), 7.27–7.42 (m, 9H), 7.56 (t, J=7, 2H), 7.63 (t, J=7.5, 1H), 7.75 (d, J=7.5, 2H). Mass spectrum (NH$_3$/CI): m/z 578 (M+1, 100%). The hydrochloride salt of the title compound was prepared by dissolving the free base in ethanol and adding 1.5 equivalents of aqueous 2 N HCl. Evaporation of the solvent gave the title salt as a clear glass.

EXAMPLE 101

(R,S)-N-[4-(4-Benzyloxycarbonyl(ethylamino) piperidin-1-yl)-2-ethyl-2-phenylbut-1-yl]-N-methylbenzenesulfonamide hydrochloride Step A: (R,S)-2-Ethyl-2-phenylpent-4-enenitrile A solution of 2-phenylpent-4-enenitrile (500 mg, 3.18 mmol) in THF (6.5 mL) was stirred in an ice bath and 1.5 M lithium diisopropylamide monotetrahydrofuran complex in cyclohexane (2.16 mL, 3.23 mmol) was added. After 10 min, the ice bath was removed and the solution was stirred at room temperature for 1 h. The solution was cooled in a dry ice/isopropanol bath and iodoethane (0.280 mL, 546 mg, 3.50 mmol) was added. The reaction was allowed to warm to −20° C. over 30 min, and was then stirred 2 h at room temperature. The mixture was partitioned between ethyl acetate (50 mL) and saturated aqueous ammonium chloride (30 mL). The organic layer was washed with saturated aqueous sodium chloride (30 mL), dried over sodium sulfate, decanted, and evaporated. The residue was purified by flash column chromatography on silica gel, eluting with 5% ether in hexane to give the title compound as 537 mg of yellow oil. $^1$H NMR (400 MHz, CDCl$_3$): δ 0.93 (t, J=7.5, 3H), 1.94 (dq, J=14 and 7, 1H), 2.08 (dq, J=14 and 7, 1H), 2.68 (d, J=7, 2H), 5.12 (d, J=10, 1H), 5.13 (d, J=16, 1H), 5.65 (ddt, J=16, 10, and 7, 1H), 7.28–7.35 (m, 1H), 7.35–7.42 (m, 4H).

Step B: (R,S)-2-Ethyl-2-phenylpent-4-enal

A solution of 500 mg (2.70 mmol) of (R,S)-2-ethyl-2-phenylpent-4-enenitrile from Step A in 2.0 mL of ether was cooled in an ice bath and 1.5 M diisobutylaluminum hydride in toluene (2.65 mL, 3.97 mmol) was added. The solution was stirred for 2 h at 0° C., then quenched by the addition of 15 mL of 2 N aqueous HCl and stirred for 1 h. The mixture was extracted with ether (2×50 mL). The combined organic layers were washed with saturated aqueous sodium bicarbonate (50 mL) and saturated aqueous sodium chloride (50 mL), dried over sodium sulfate, decanted, and evaporated to give 410 mg of the title compound. $^1$H NMR (400 MHz, CDCl$_3$): δ 0.80 (t, J=7.5, 3H), 1.94–2.05 (m, 2H), 2.67 (dd, J=14 and 7, 1H), 2.74 (dd, J=14 and 7, 1H), 5.03 (d, J=10, 1H), 5.07 (d, J=16, 1H), 5.53 (ddt, J=16, 10, and 7, 1H), 7.22 (d, J=8, 2H), 7.29 (t, J=8, 1H), 7.39 (t, J=8, 2H).

Step C: (R,S)-N-Methyl(2-ethyl-2-phenylpent-4-enyl)amine

Using essentially the same procedure as in Example 99 (Step A), the crude (R,S)-2-ethyl-2-phenylpent-4-enal from Step B above gave the title compound as an amber liquid. $^1$H NMR (400 MHz, CD$_3$OD): δ 0.69 (t, J=7.5, 3H), 1.74 (q, J=7.5, 2H), 2.27 (s, 3H), 2.48 (dd, J=14 and 7, 1H), 2.56 (dd, J=14 and 7, 1H), 2.77 (s, 2H), 5.00 (dm, J=10, 1H), 5.07 dm, J=16, 1H), 5.61 (ddt, J=16, 10, and 7, 1H), 7.16–7.22 (m, 1H), 7.30–7.37 (m, 4H). Mass spectrum (ESI): m/z 204 (M+1, 100%).

Step D: (R,S)-N-(2-Ethyl-2-phenylpent-4-enyl)-N-methylbenzene-sulfonamide

Using essentially the same procedure as in Example 1 (Step A), (R,S)-N-methyl(2-ethyl-2-phenylpent-4-enyl) amine from Step A above was allowed to react with benzenesulfonyl chloride in THF to give the title compound as an amber syrup. $^1$H NMR (400 MHz, CDCl$_3$): δ 0.82 (t, J=7.5, 3H), 1.85 (q, J=7.5, 2H), 1.94 (s, 3H), 2.59 (dd, J=14 and 7, 1H), 2.73 (dd, J=14 and 7, 1H), 3.08 (d, J=14, 1H), 3.25 (d, J=14, 1H), 5.10 (dm, J=10, 1H), 5.16 (bd, J=16, 1H), 5.89 (ddt, J=16, 10, and 7, 1H), 7.20 (d, J=7, 1H), 7.27–7.36 (m, 4H), 7.51 (t, J=7, 2H), 7.58 (t, J=7, 1H), 7.73 (d,J=7,2H). Mass spectrum (ESI): m/z 344 (M+1, 33%), 361 (M+NH$_3$+1, 100%).

Step E: (R,S)-N-(2-Ethyl-2-phenyl-4-oxobut-1-yl)-N-methyl-benzenesulfonamide

Using essentially the same procedure as in Example 1 (Step B), (R,S)-N-(2-ethyl-2-phenylpent-4-enyl)-N-methylbenzenesulfonamide from Step D above was oxidized to give the title compound as a syrup. $^1$H NMR (400 MHz, CDCl$_3$): δ 0.79 (t, J=7.5, 3H), 1.92–2.07 (m, 2H), 2.06 (s, 3H), 2.94 (d, J=14, 1H), 2.96 (dd, J=17 and 3, 1H), 3.22 (bd, J=17, 1H), 3.65 (d, J=14, 1H), 7.22–7.38 (m, 5H), 7.53 (t, J=7, 2H), 7.60 (t, J=7, 1H), 7.74 (d, J=7, 2H), 9.92 (dd, J=3 and 2, 1H). Mass spectrum (ESI): m/z 346 (M+1, 85%), 363 (M+NH$_3$+1, 100%).

Step F: (R,S)-N-[4-(4-Benzyloxycarbonyl(ethylamino) piperidin-1-yl)-2-ethyl-2-phenylbut-1-yl]-N-methylbenzenesulfonamide hydrochloride Using essentially the same procedure as in Example 1 (Step C), (R,S)-N-(2-ethyl-2-phenyl-4-oxobut-1-yl)-N-methylbenzene-sulfonamide from Step E above was allowed to react with 4-benzyloxycarbonyl(ethylamino)piperidine (prepared by analogy to Example 68) to give the free amine of the title compound as a colorless film. $^1$H NMR (400 MHz, CD3OD): δ 0.87 (t, J=7, 3H), 1.12 (t, J=7, 3H), 1.63–2.24 (m, 11H), 1.89 (s, 3H), 2.50–2.60 (m, 1H), 3.04 (bd, J=10, 1H), 3.11 (bd, J=10, 1H), 3.16 (d, J=14, 1H), 3.22 (d, J=14, 1H), 3.26 (q, J=7, 2H), 3.82–3.96 (b, 1H), 5.12 (s, 2H), 7.20 (t, J=7, 1H), 7.28–7.42 (m, 4H), 7.58 (t, J=7, 2H), 7.65 (t, J=7, 1H), 7.74 (d, J=7, 2H). Mass spectrum (ESI): m/z 592 (M+1, 100%). The hydrochloride salt of the title compound was prepared by dissolving the free base in ethanol and adding 1.5 equivalents of aq. 2 N HCl. Evaporation of the solvent gave the title salt as a white glass.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

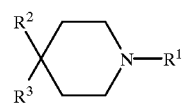

wherein:
R$^1$ is selected from a group consisting of:
C$_3$, C$_4$, C$_5$, C$_6$, C$_7$, or C$_8$ linear or branched alkyl, which is unsubstituted or mono, di or tri-substituted, where the substituents are independently selected from:
(a) hydroxy,
(b) Cl or F,
(c) phenyl,
(d) mono, di or tri-substituted phenyl, where the substituents are independently selected from:
(1') phenyl
(2') hydroxy,
(3') C$_{1-3}$alkyl,
(4') cyano,
(5') halogen, and
(6') trifluoromethyl,
(e) C$_{1-6}$ alkyl, unsubstituted or substituted with hydroxy,
(f) —NR$^6$CO—R$^7$, wherein R$^6$ is hydrogen or C$_{1-3}$ alkyl, unsubstituted or substituted with C$_{5-8}$ cycloaklyl, and R$^7$ is C$_{1-6}$ alkyl, benzyl or phenyl which is unsubstituted or substituted with halo, CF$_3$, C$_{1-3}$alkyl, or C$_{1-3}$alkoxy,
(g) —COR$^6$,
(h) —OR$^6$,
(i) —NR$^6$S(O)$_j$-heteroaryl, wherein heteroaryl is selected from the group consisting of:
(1') benzimidazolyl,
(2') benzofuranyl,
(3') benzoxazolyl,
(4') furanyl,
(5') imidazolyl,
(6') indolyl,
(7') isooxazolyl,
(8') isothiazolyl,
(9') oxadiazolyl,
(10') oxazolyl,
(11') pyrazinyl,
(12') pyrazolyl,
(13') pyridyl,
(14') pyrimidyl, (15') pyirolyl
(16') quinolyl,
(17') tetrazolyl,
(18') thiadiazolyl,
(19') thiazolyl,
(20') thienyl, and
(21') triazolyl,
wherein the heteroaryl is unsubstituted or mono di or tri-substituted, where the substituents are independently selected from:
(a') phenyl,
(b') hydroxy,
(c') oxo,
(d') cyano,
(e') halogen, and
(f) trifluoromethyl,
with the proviso that $R^1$ bears at least one substituent which is selected from:
—$NR^6S(O)_j$—$R^7$ and —$NR^6S(O)_j$-heteroaryl, and when an additional substituent on $R^1$ is dichlorophenyl $R^2$ is hydrogen;
$R^2$ is selected from the group consisting of:
(1) hydrogen,
(2) hydroxy,
(3) $C_{1-6}$ alkyl,
(4) —O—$C_{1-6}$ alkyl,
(5) phenyl,
(6) —$N(CH_3)$—CO—$N(H)(CH_3)$,
(7) —N(H)—CO—O—$CH_3$, and
(8) —CO—$CH_3$;
$R^3$ is selected from the group consisting of:
(1) Ar,
(2) —($C_{1-6}$ alkyl)—Ar,
(3) —($C_{1-6}$ alkyl)—O—($C_{1-6}$ alkyl)—Ar, and
(4) —$N(R^4)$—CO—O—($C_{1-6}$ alkyl)—Ar, wherein $R^4$ is selected from hydrogen, $C_{1-10}$ linear or branched alkyl, and $C_{0-6}$ alkyl substituted with $C_{3-8}$ cycloalkyl,
(5) —$N(R^4)$—CO—O—$R^7$;
Ar is selected from the group consisting of:
(1) phenyl,
(2) pyrazinyl,
(3) pyrazolyl,
(4) pyridyl,
(5) pyrimidyl, and
(6) thienyl,
wherein the Ar is unsubstituted or mono or di-substituted, and the substituents are independently selected from:
(a) $C_{1-3}$ alkyl, unsubstituted or substituted with
(1') oxo,
(2') hydroxy,
(3') —$OR^7$,
(4') phenyl, and
(5') trifluoromethyl,
(b) halogen,
(c) —$OC_{1-6}$ alkyl
(d) trifluoromethyl,
(e) —$NO_2$,
(f) $CONR^6$—($C_{1-2}$ alkyl),
(g) $CO_2H$,
(h) $CO_2$—($C_{1-2}$ alkyl),
(i) $CH_2NR^6$—($C_{1-2}$ alkyl),
(j) $CH_2NH$—C(O)—$C_{1-3}$alkyl,
(k) $CH_2NH$—C(O)$NH_2$,
(l) $CH_2NH$—C(O)$NHC_{1-3}$alkyl,
(m) $CH_2NH$—C(O)N—di$C_{1-3}$ alkyl),
(n) $CH_2NH$—S(O)$_j$—$C_{1-3}$alkyl,
(o) $CH_2$-heteroaryl, with the heteroaryl is selected from the group consisting of:
(1') imidazolyl,
(2') oxazolyl,
(3') pyridyl,
(4') tetrazolyl,
(5') triazolyl,
and the heteroaryl is unsubstituted, mono, di or tri-substituted, where the substituents selected from:
(a') hydrogen,
(b') $C_{1-6}$ alkyl, branched or unbranched, unsubstituted or mono or di-substituted, the substituents being selected from hydrogen and hydroxy;
and pharmaceutically acceptable salts thereof.

2. The compound of claim 1 wherein:
$R^1$ is selected from the group consisting of:
$C_4$, $C_5$, or $C_6$ linear alkyl, which is substituted, where the substituents are independently selected from:
(a) phenyl,
(b) mono, di or tri-substituted phenyl, where the substituents are independently selected from:
(1') hydroxy,
(2') methyl or ethyl,
(3') Cl or F, and
(4') trifluoromethyl,
(c) $C_{1-6}$ alkyl, unsubstituted or substituted with hydroxy,
(d) —$NR^6CO$—$R^7$, wherein $R^6$ is methyl, unsubstituted or substituted with cyclohexyl, and $R^7$ is phenyl which is unsubstituted or substituted with Cl, F, $CF_3$, $C_{1-3}$alkyl or $C_{1-3}$alkoxy, and
(e) —$NR^6S(O)_j$—$R^7$, where j is 1 or 2.

3. The compound of claim 1 wherein:
$R^1$ is $C_4$ linear alkyl, which is substituted, where the substituents are independently selected from:
(a) phenyl,
(b) mono, di or tri-substituted phenyl, where the substituents are independently selected from:
(1') hydroxy,
(2') methyl or ethyl,
(3') Cl or F, and
(4') trifluoromethyl,
(c) $C_{1-6}$ alkyl, unsubstituted or substituted with hydroxy, and
(d) —$NR^6S(O)_j$—$R^7$, where $R^6$ is methyl, unsubstituted or substituted with cyclohexyl, and $R^7$ is phenyl which is unsubstituted or substituted with Cl, F, $CF_3$, $C_{1-3}$alkyl or $C_{1-3}$alkoxy, and j is 1 or 2.

4. The compound of claim 1 wherein:
$R^1$ is selected from the group consisting of:

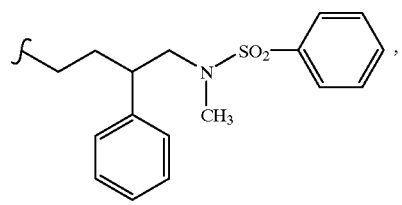

121

-continued

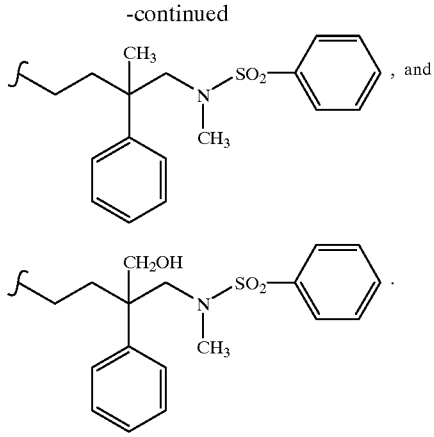

5. The compound of claim 1 wherein:
R$^1$ is selected from the group consisting of:

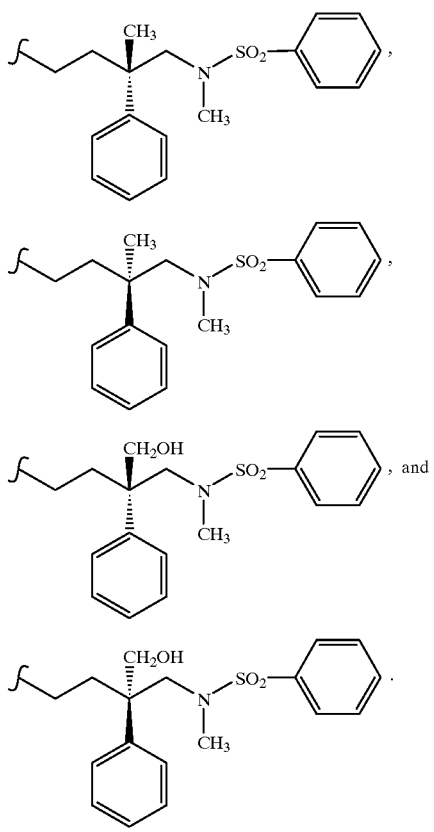

6. The compound of claim 1 wherein:
R$^2$ is selected from the group consisting of:
(1) hydrogen,
(2) hydroxy, and
(3) phenyl.
7. The compound of claim 1 wherein:
R$^2$ is hydrogen.
8. The compound of claim 1 wherein:
R$^3$ is selected from:

122

(1) Ar,
(2) —N(R$^4$)—CO—O—(C$_{1-6}$ alkyl)—Ar, wherein R$^4$ is selected from hydrogen, C$_{1-10}$ linear or branched alkyl, and C$_{0-6}$ alkyl substituted with C$_{3-8}$ cycloalkyl.
9. The compound of claim 1 wherein:
R$^3$ is —N(R$^4$)—CO—O—(C$_{1-6}$ alkyl)—Ar, wherein R$^4$ is selected from hydrogen, C$_{1-10}$ linear or branched alkyl, and C$_{0-6}$ alkyl substituted with C$_{3-8}$ cycloalkyl.
10. The compound of claim 1 wherein:
R$^3$ is selected from:
(1) phenyl, and
(2) —N(R$^4$)—CO—O—(C$_{1-6}$ alkyl)-phenyl, wherein R$^4$ is selected from hydrogen, C$_{1-10}$ linear or branched alkyl, and C$_{0-6}$ alkyl substituted with C$_{3-8}$ cycloalkyl.
11. The compound of claim 1 wherein:
R$^3$ is:
—N(R$^4$)—CO—O—(CH$_2$)-phenyl, wherein R$^4$ is selected from hydrogen, C$_{1-6}$ linear or branched alkyl, and CH$_2$ substituted with C$_{3-8}$ cycloalkyl.
12. The compound of claim 1 wherein:
R$^3$ is:
—N(R$^4$)—CO—O—(CH$_2$)-phenyl, wherein R$^4$ is selected from hydrogen and C$_{1-6}$ alkyl.
13. A compound which is selected from the group consisting of:

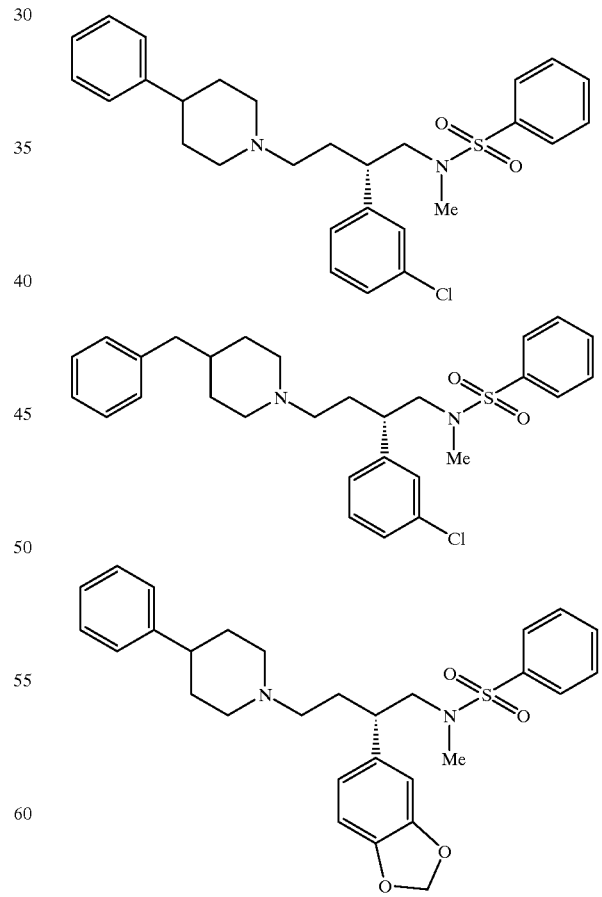

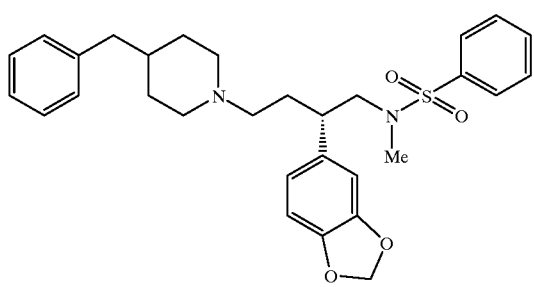
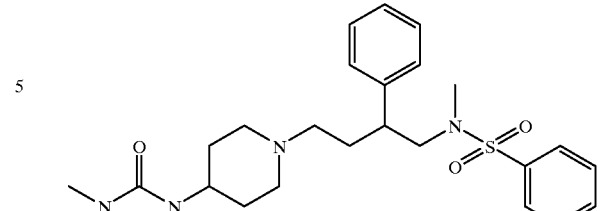
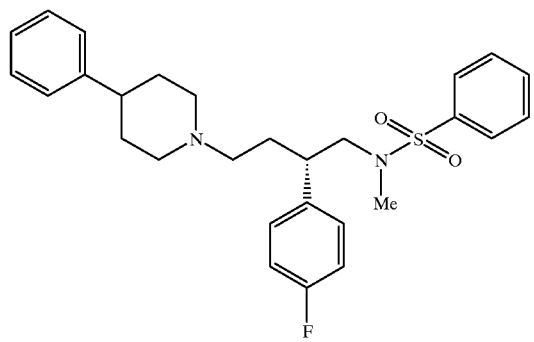
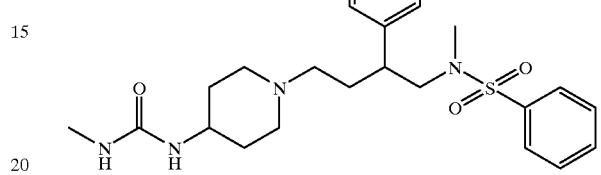
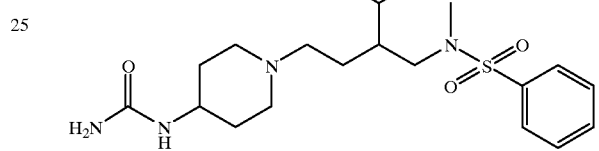
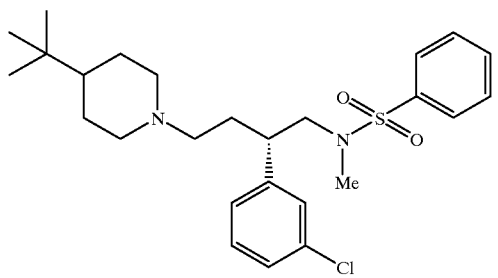
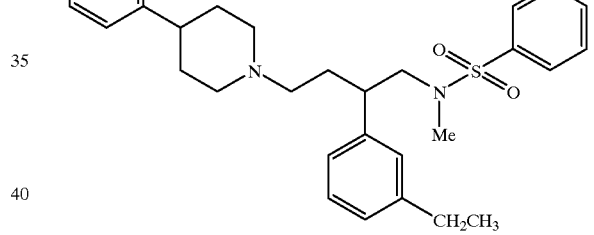
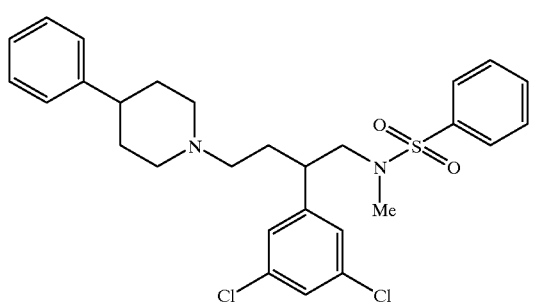
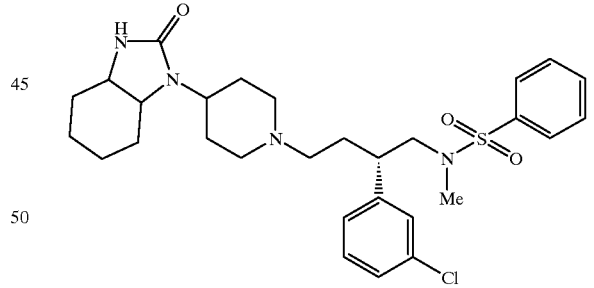
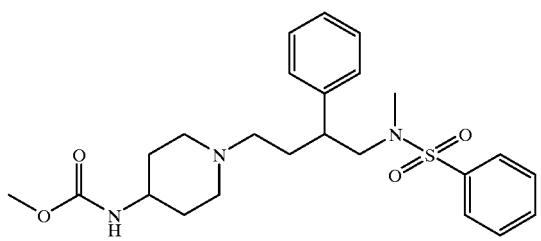
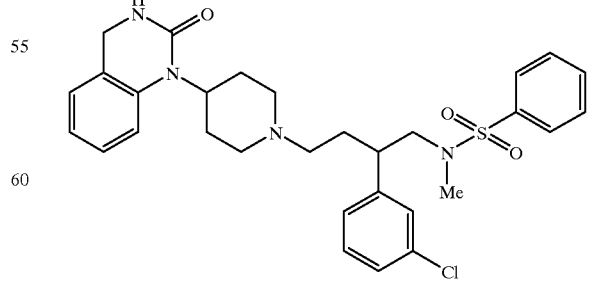

125
-continued
126
-continued
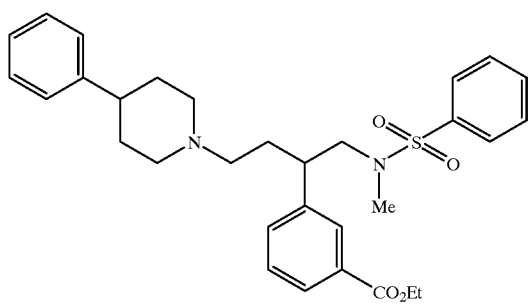
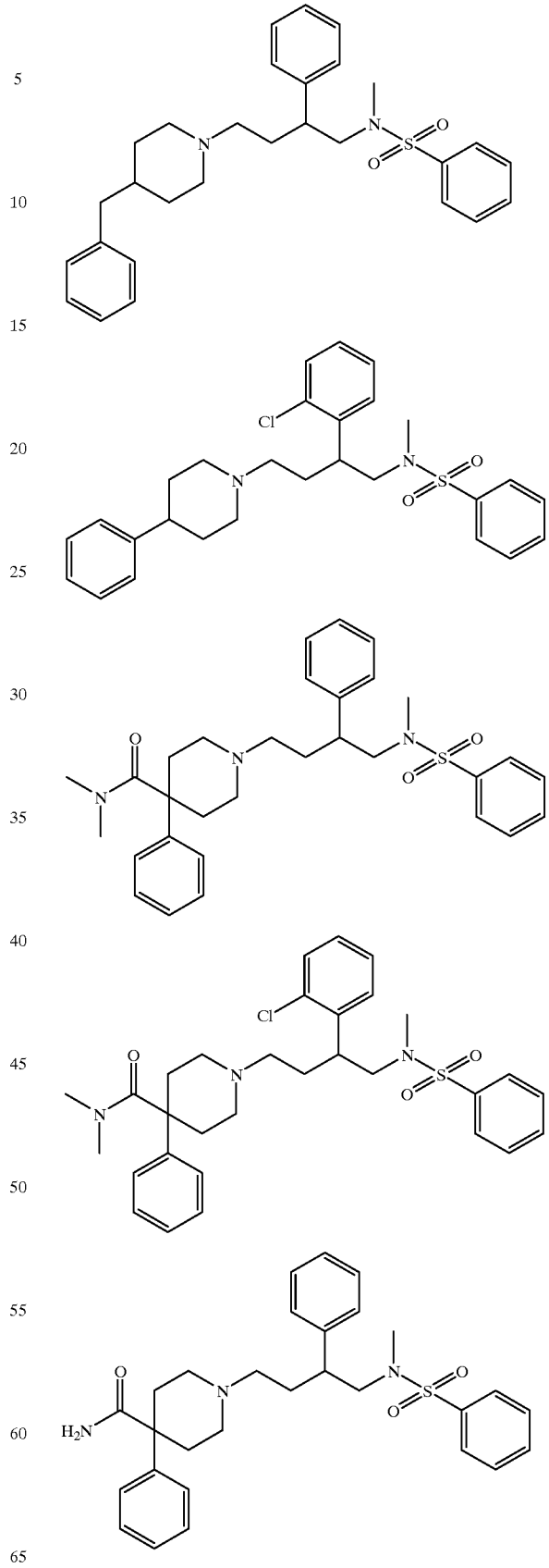

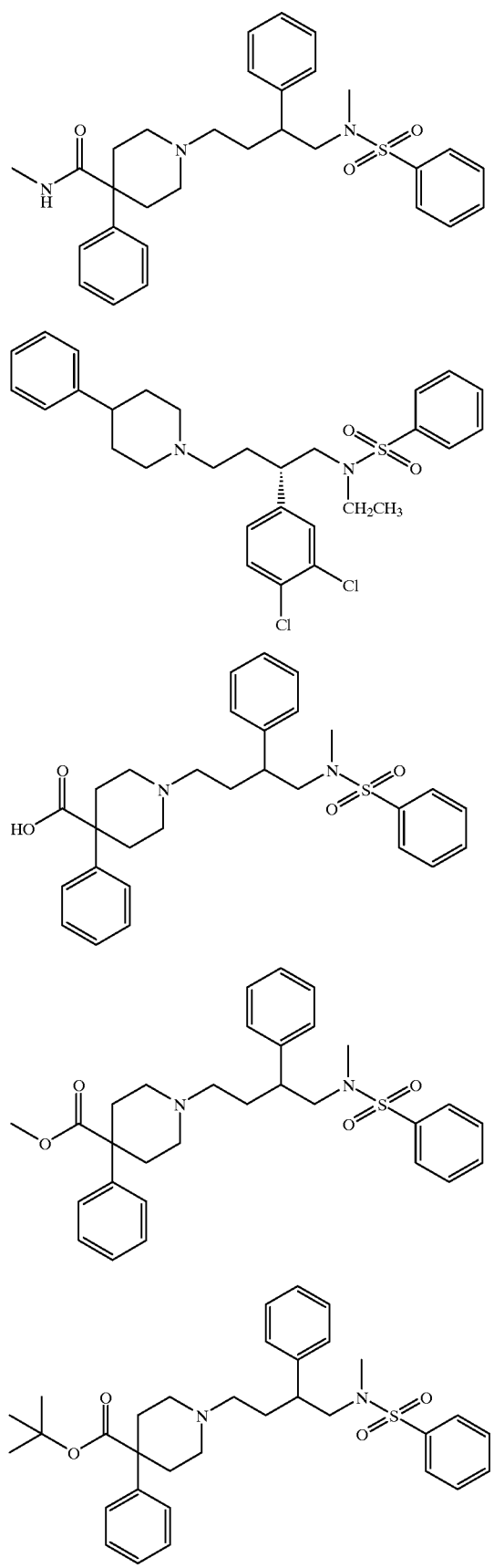
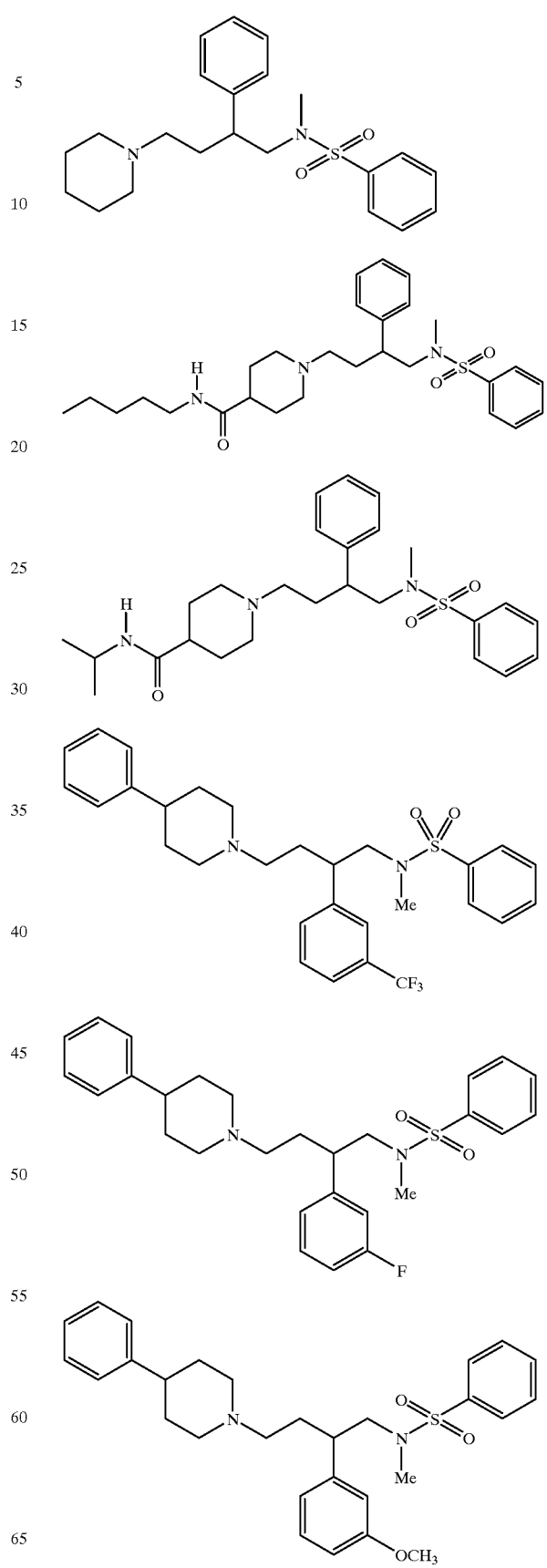

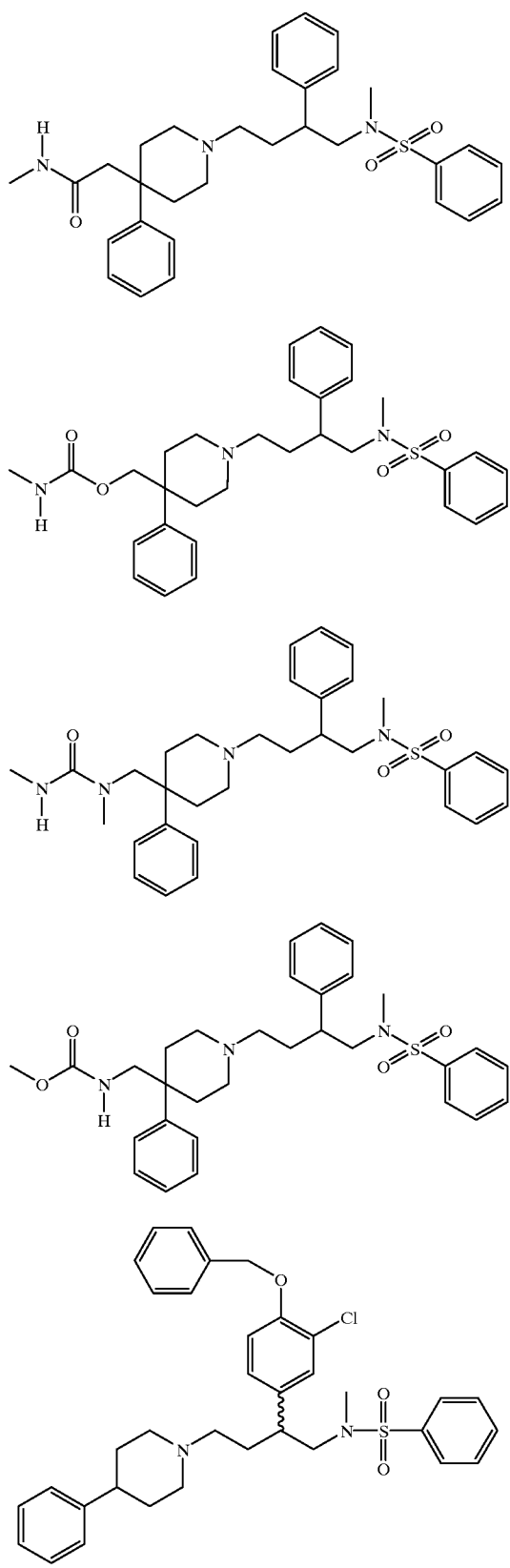
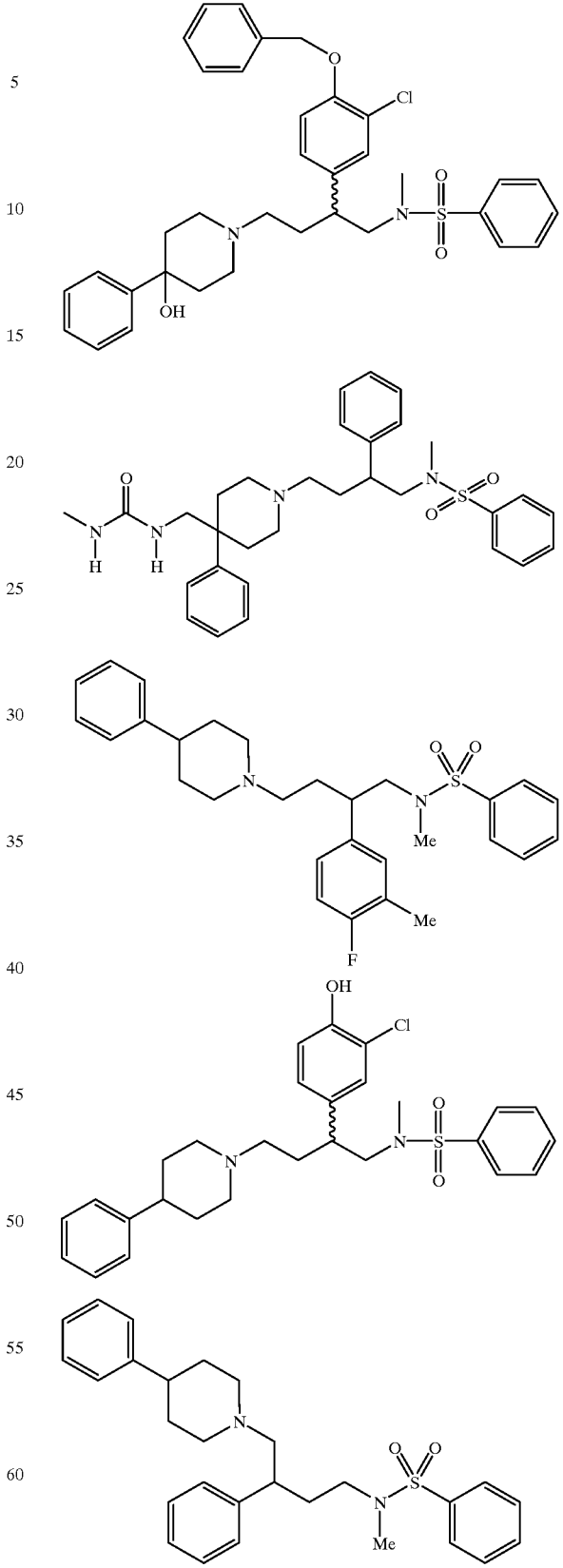

131
-continued
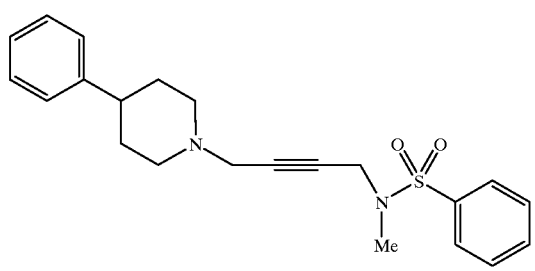
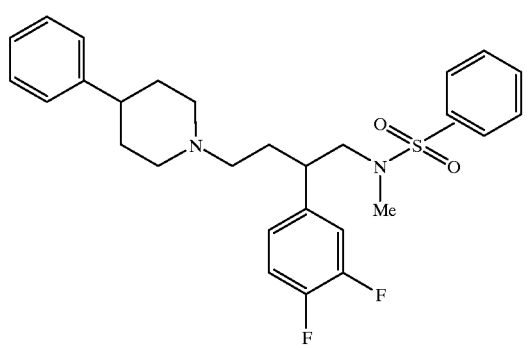
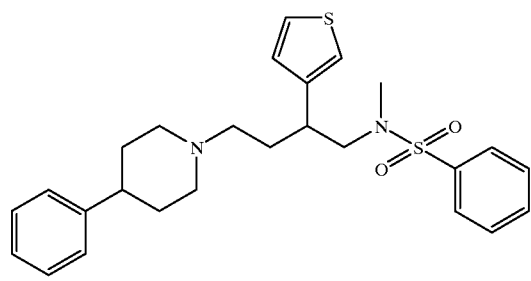
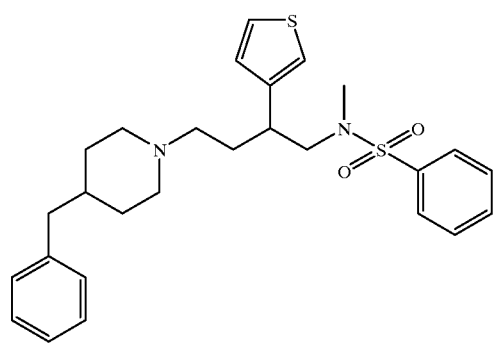
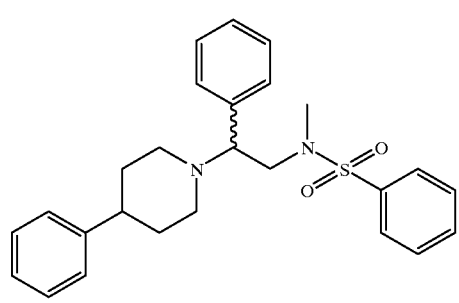
132
-continued
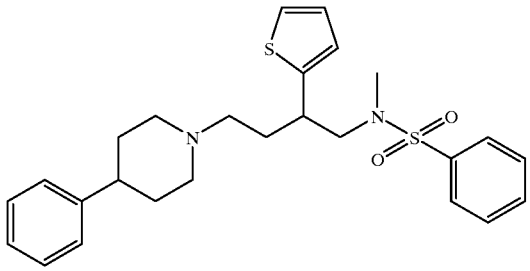
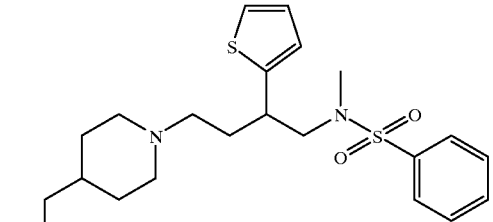
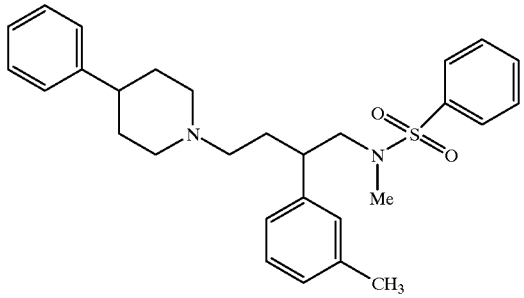
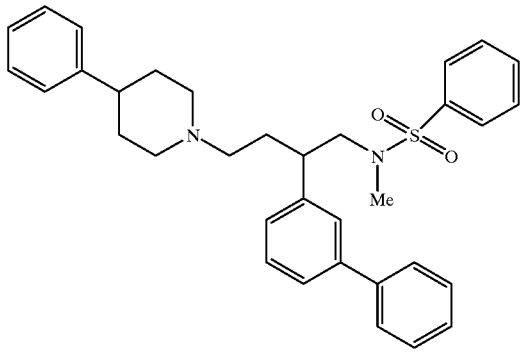
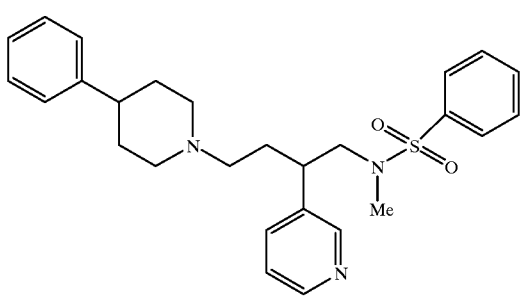

133
-continued
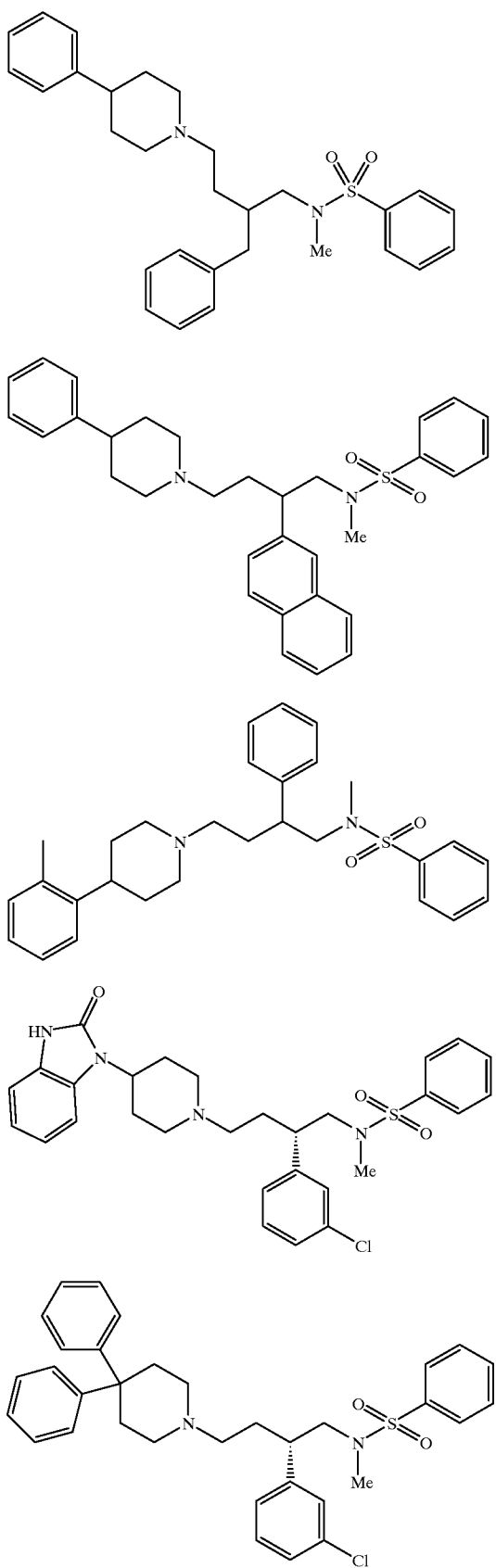
134
-continued
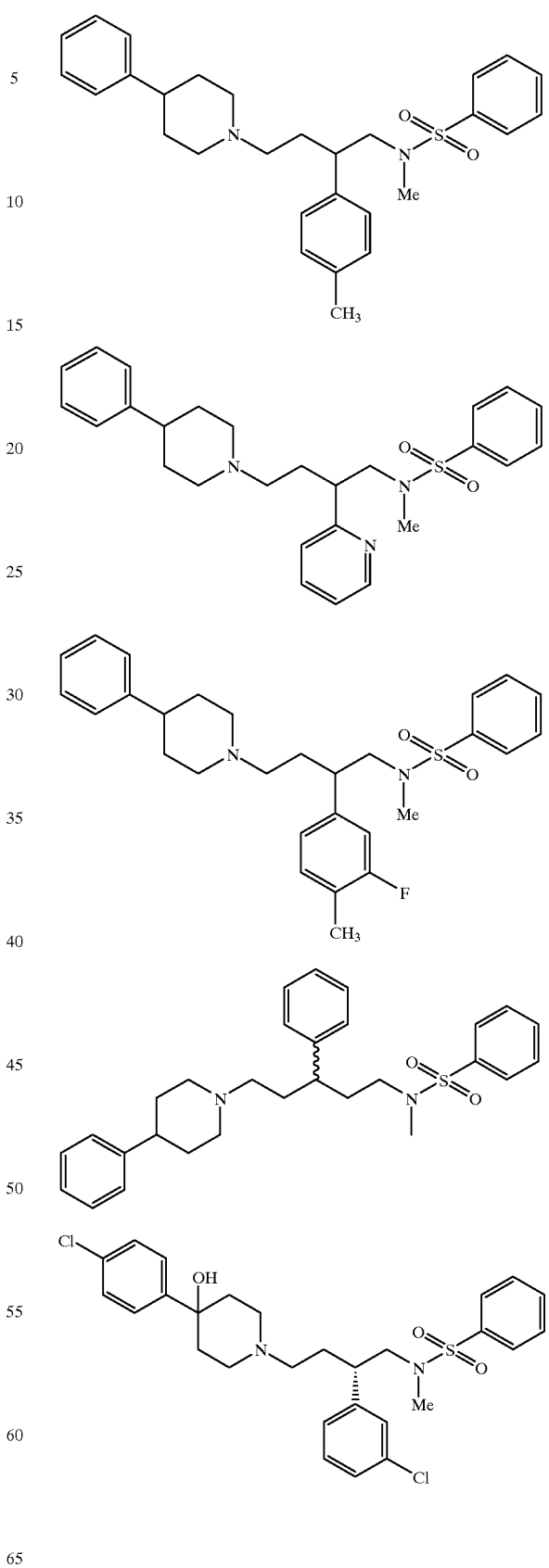

135
-continued
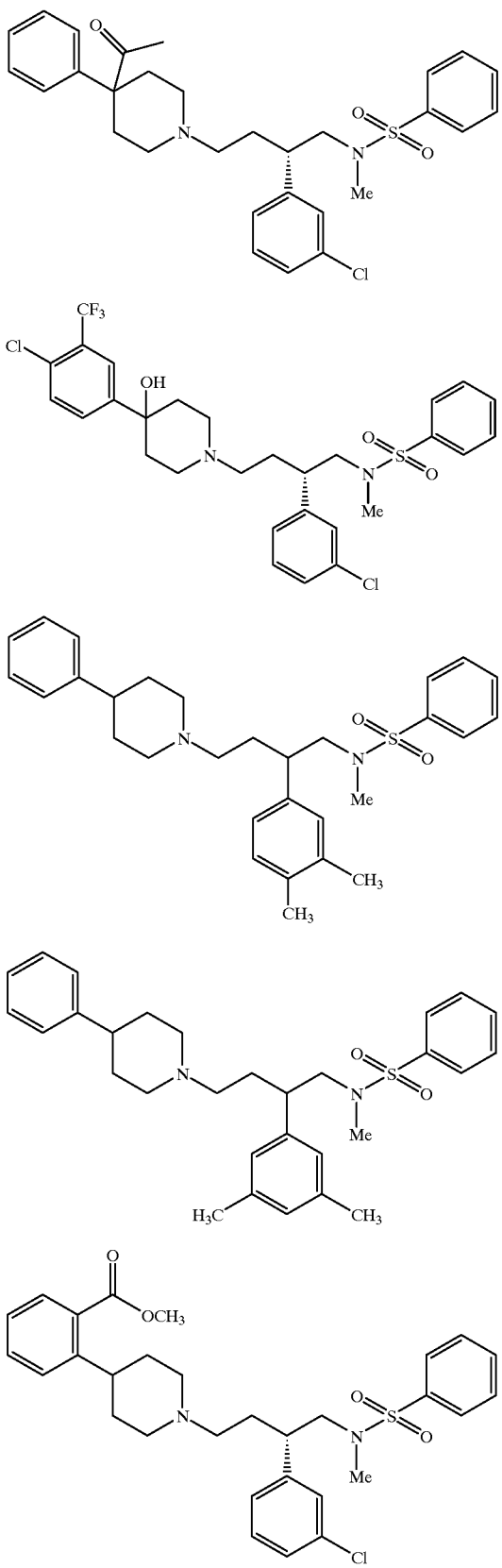
136
-continued
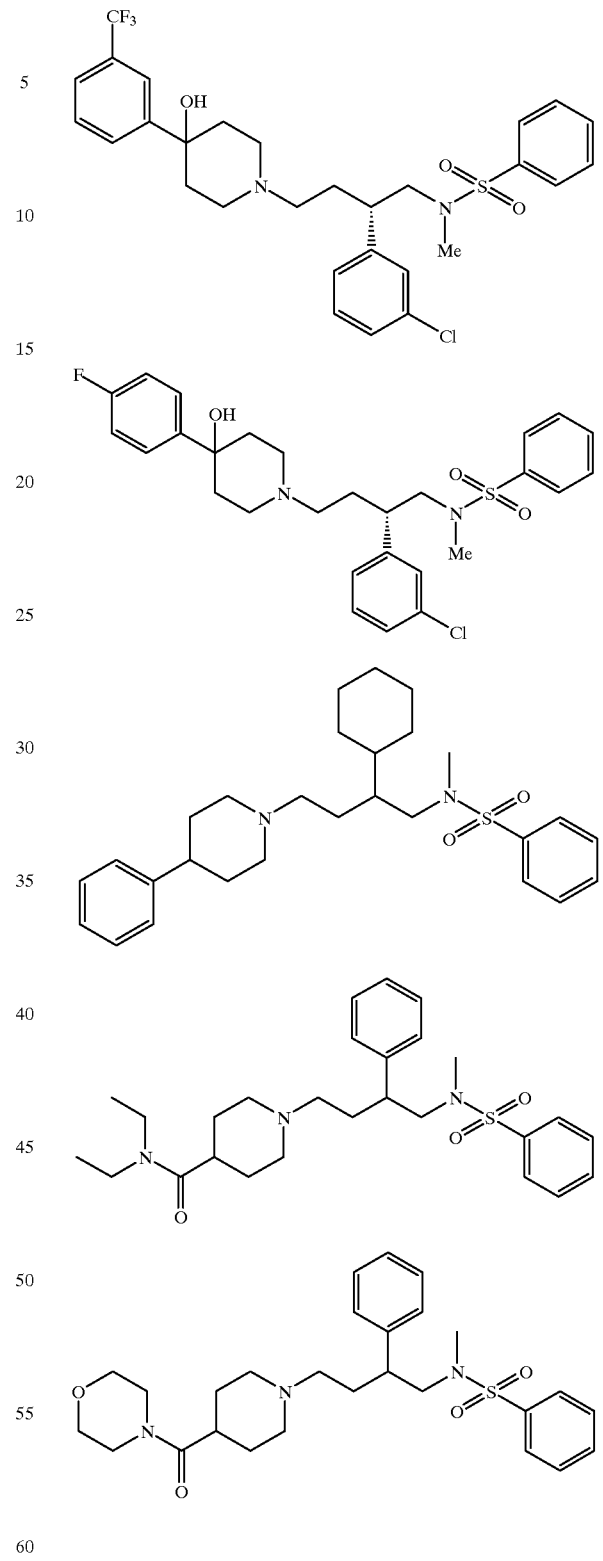

137
-continued
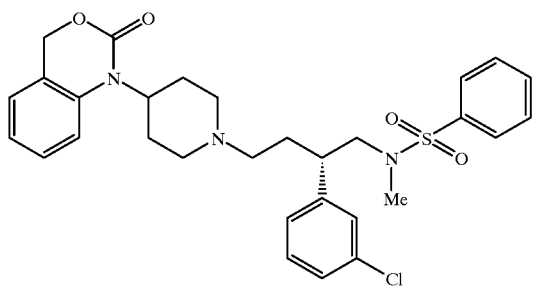
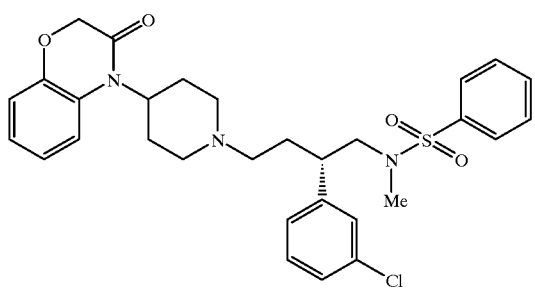
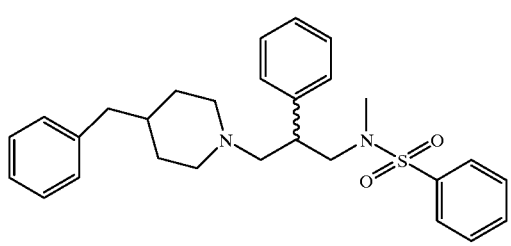
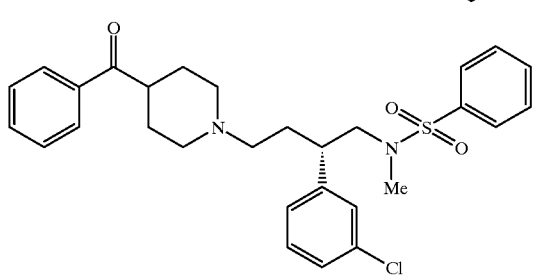
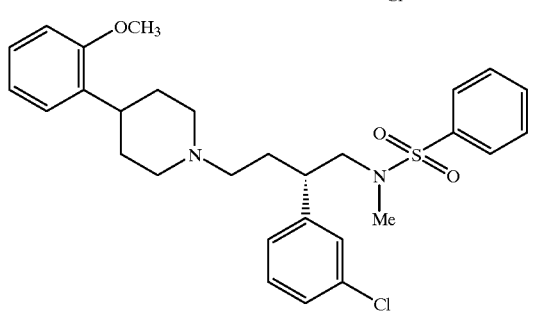
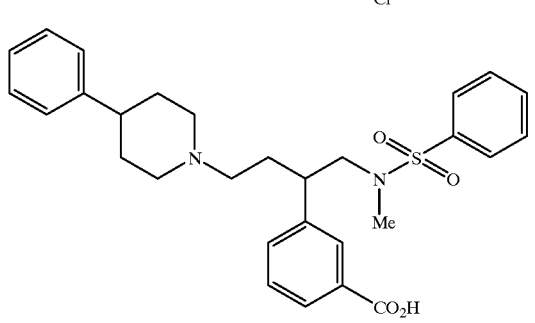
138
-continued
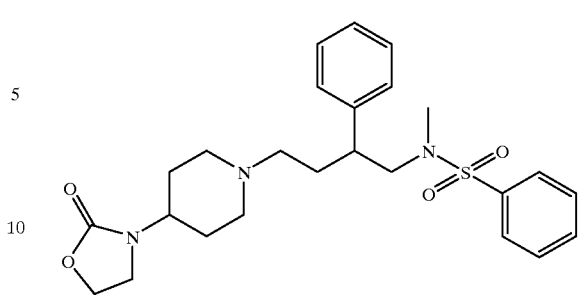
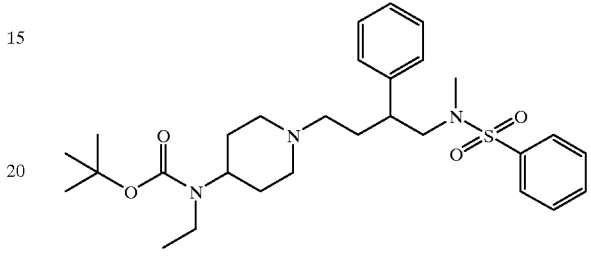
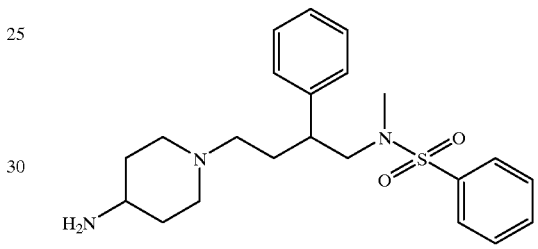
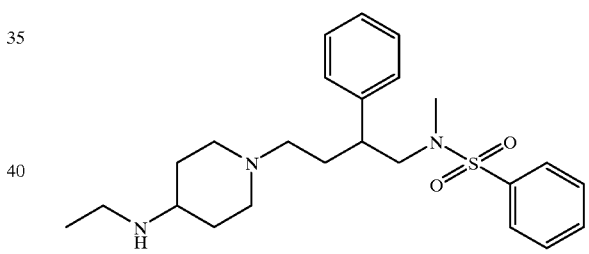
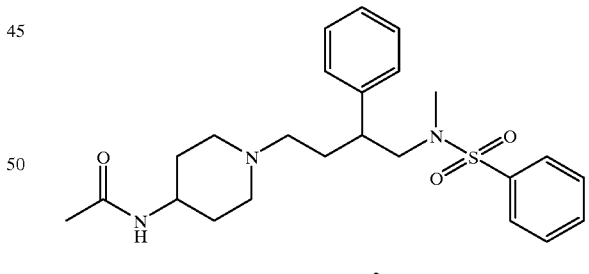
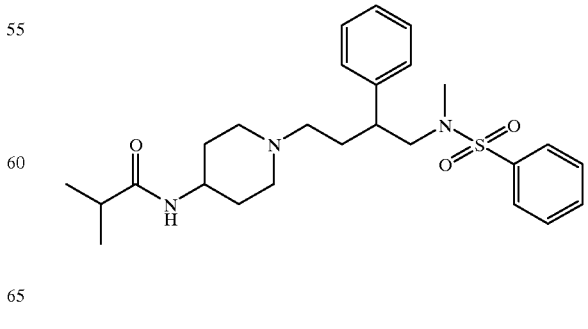

139
-continued
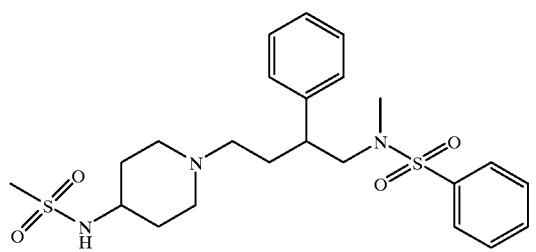
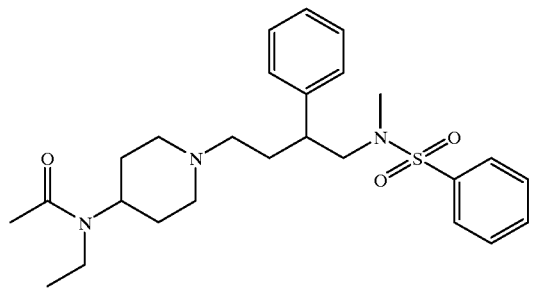
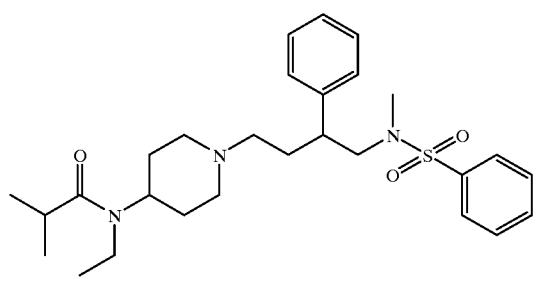
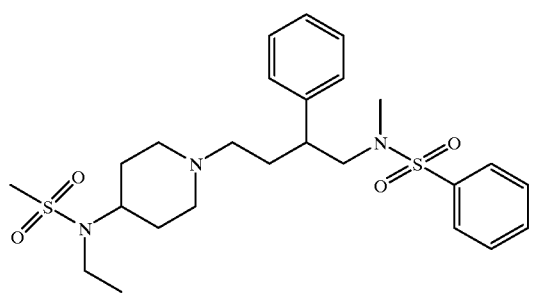
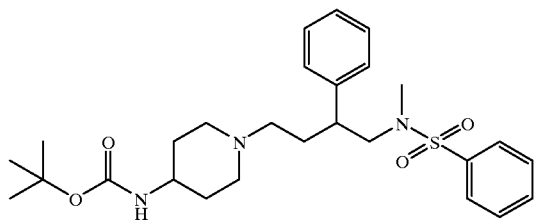
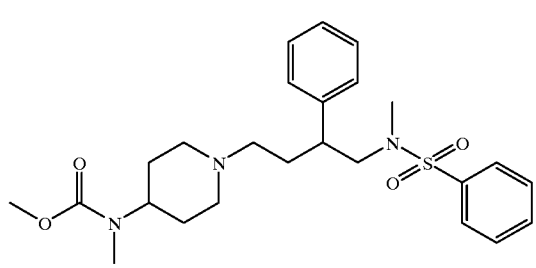
140
-continued
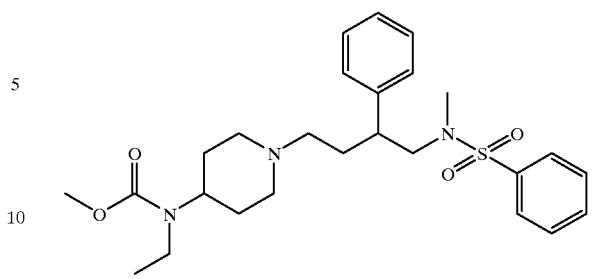
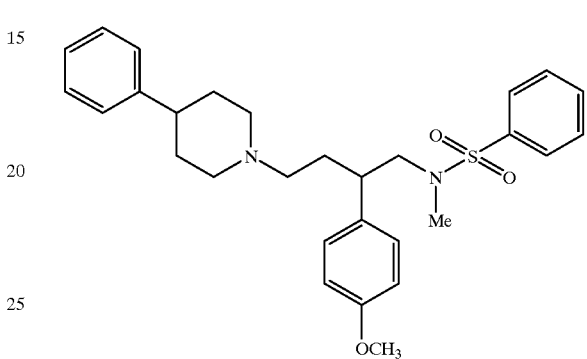
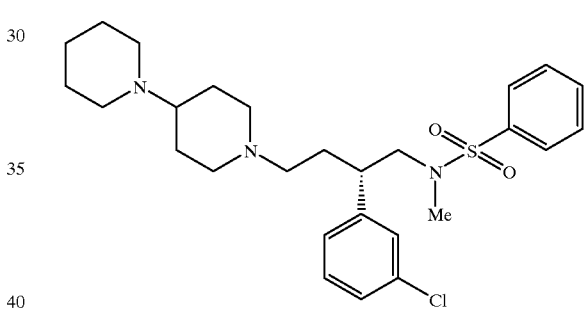
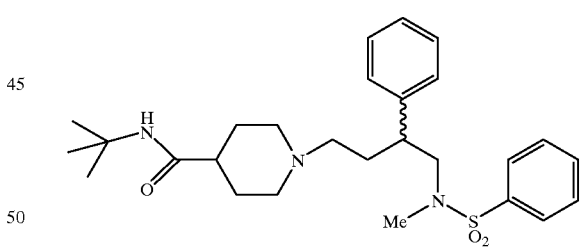
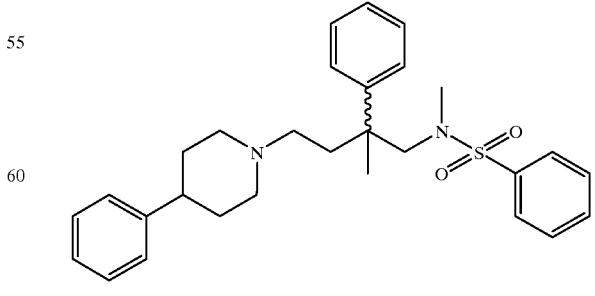

141
-continued
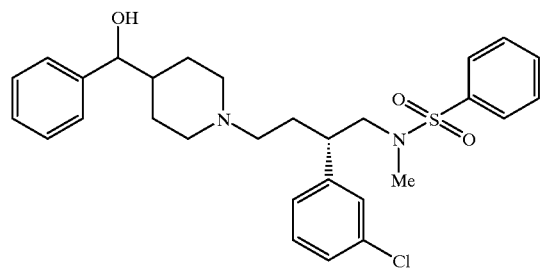
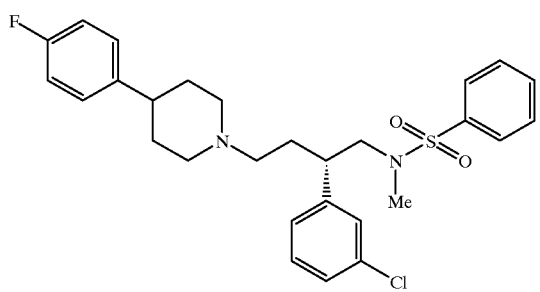
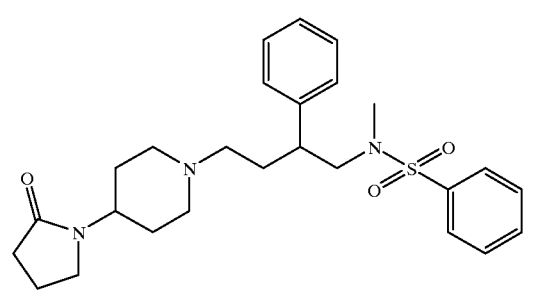
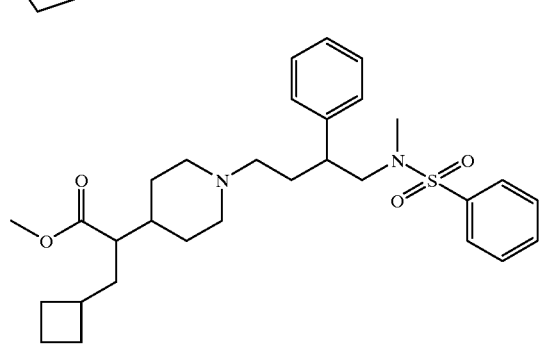
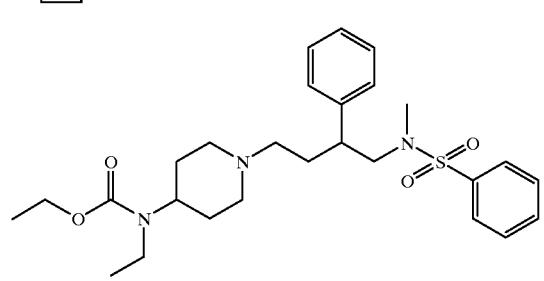
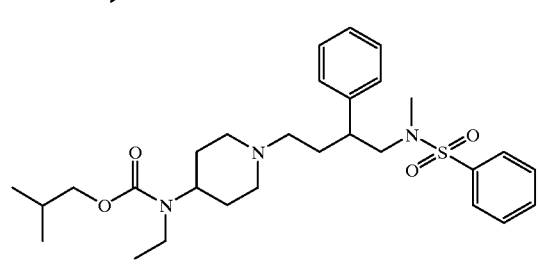
142
-continued
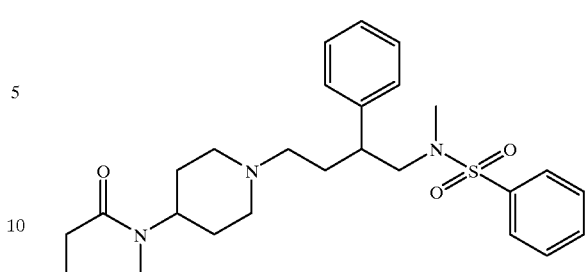
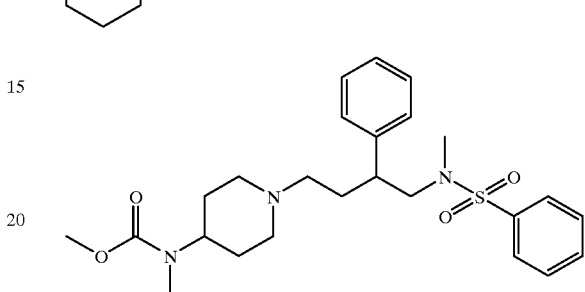
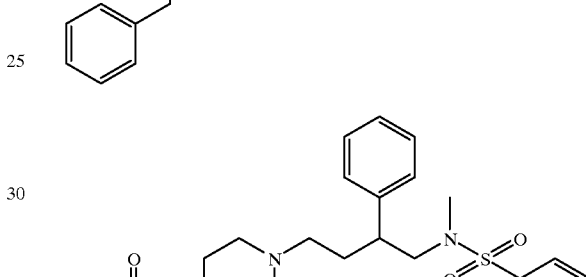
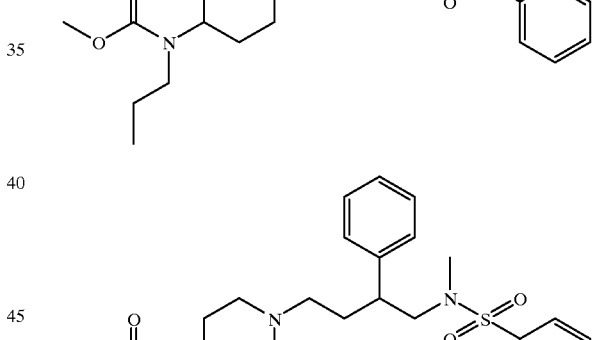
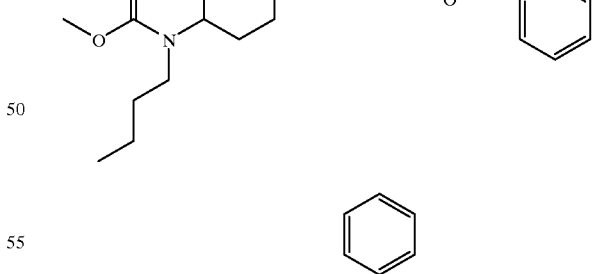
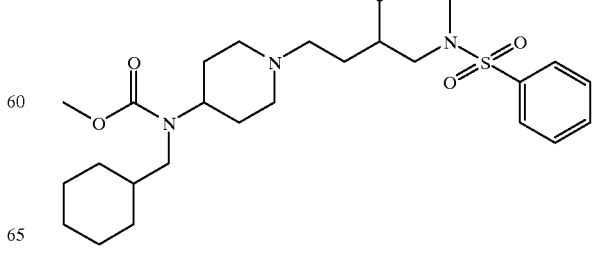

143
-continued
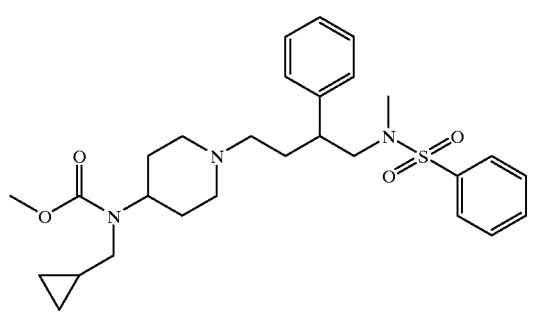
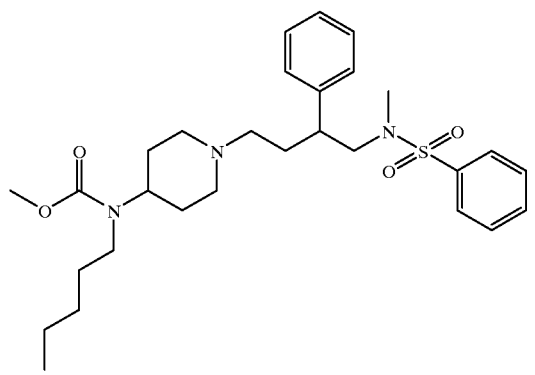
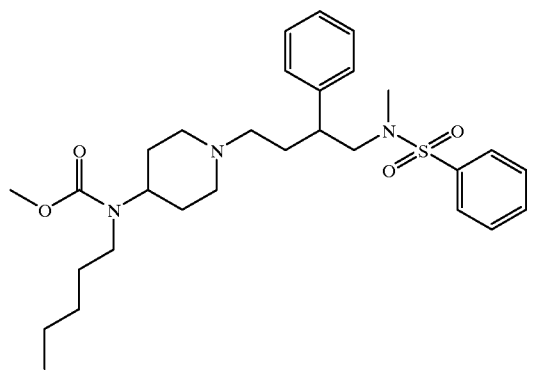
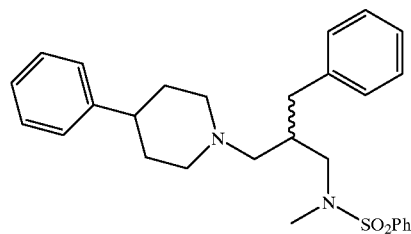
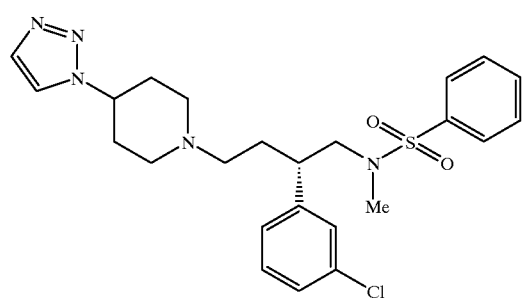
144
-continued
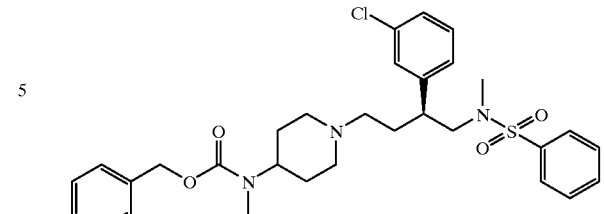
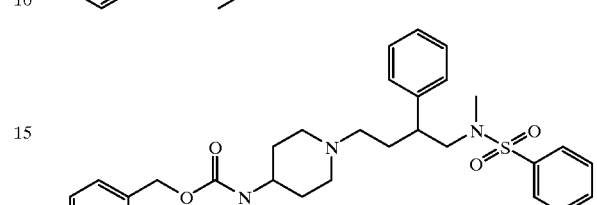
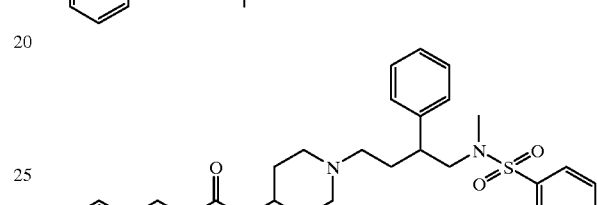
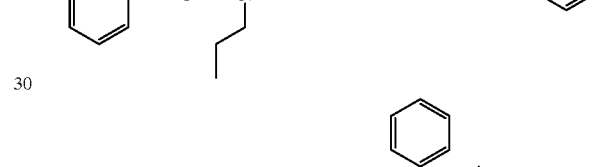
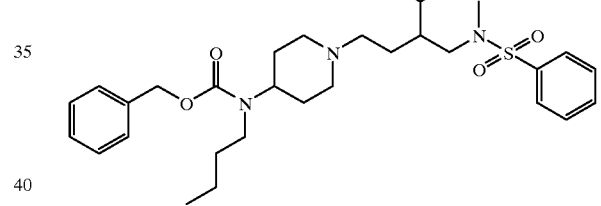
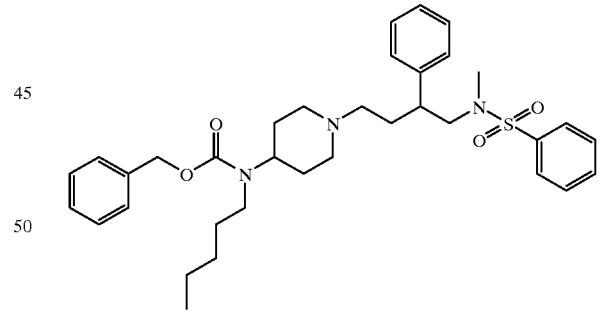
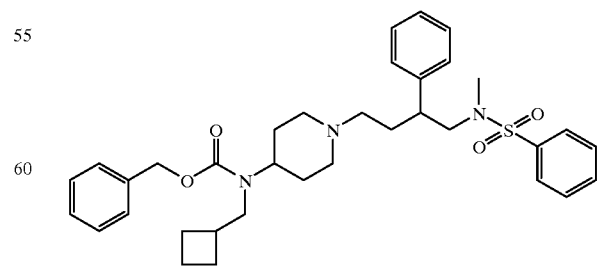

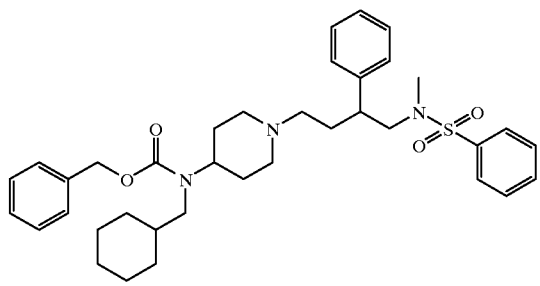
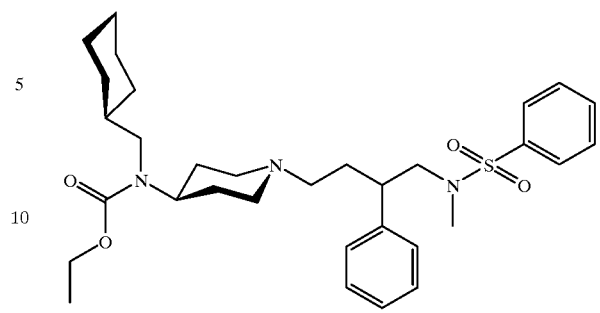
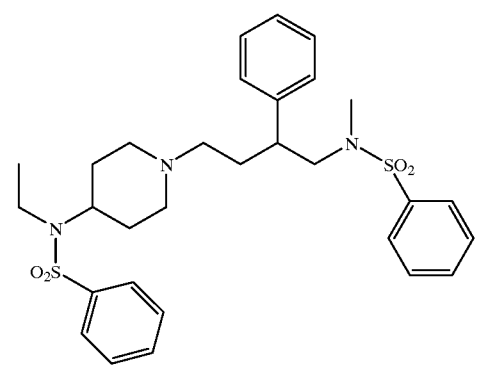
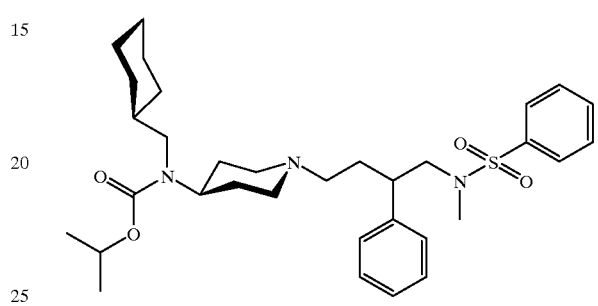
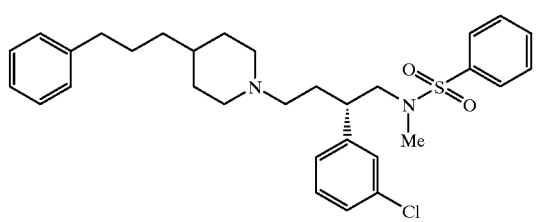
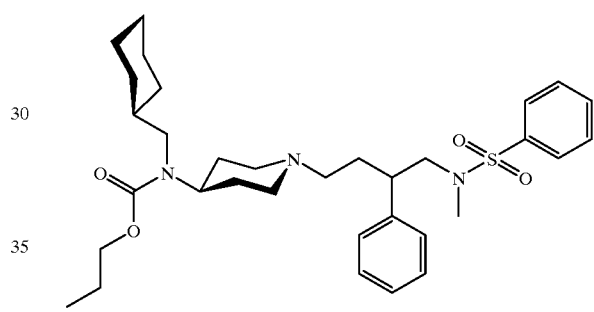
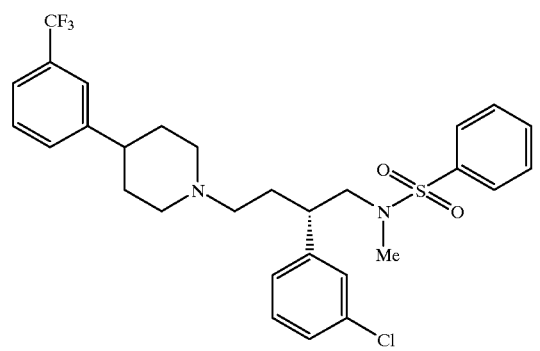
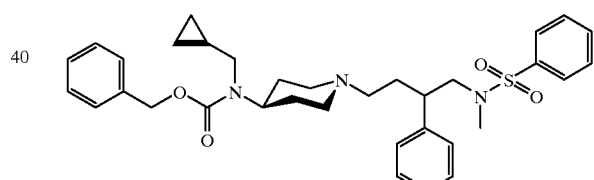
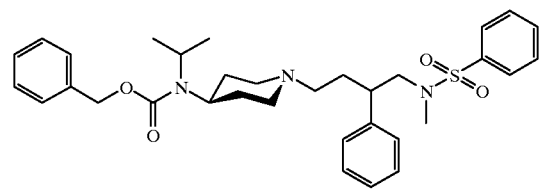
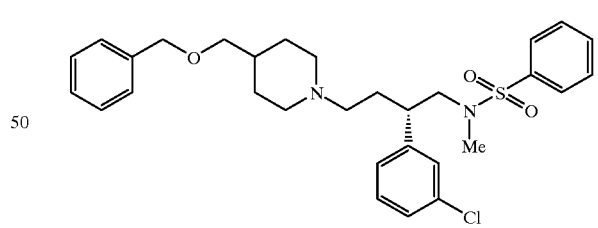
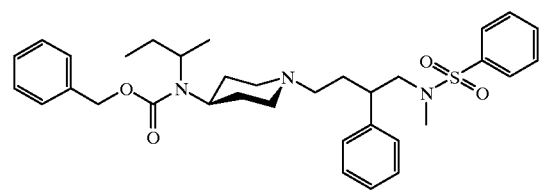
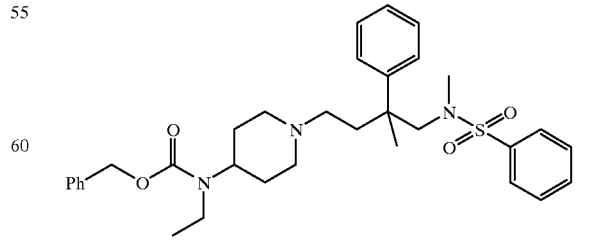

147
-continued
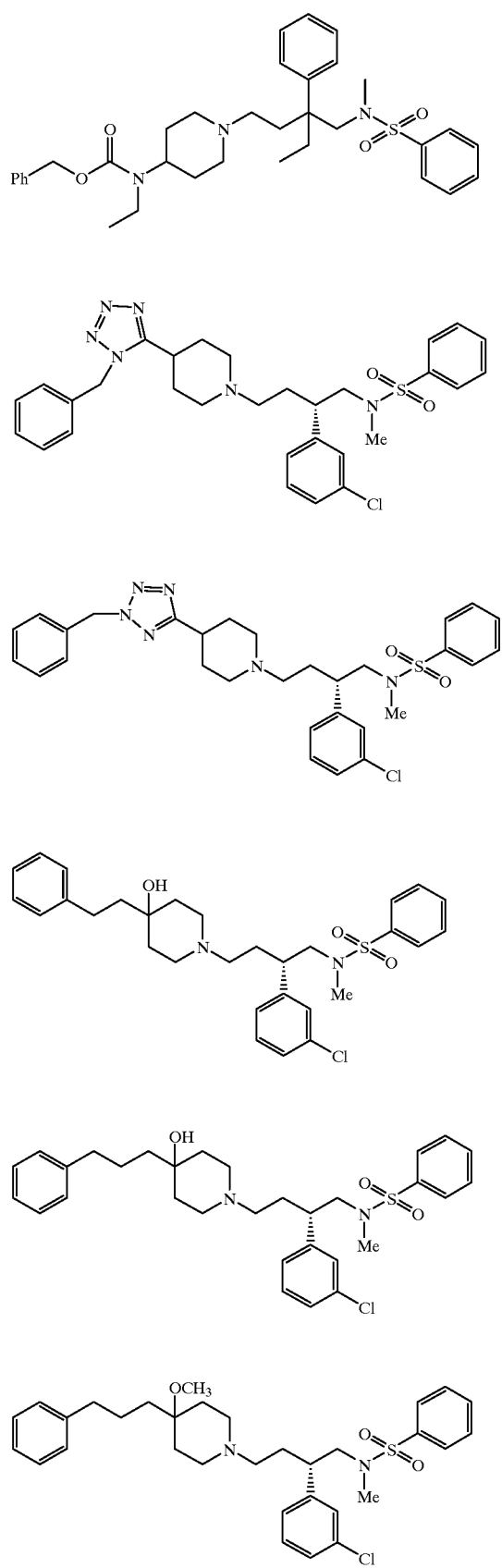
148
-continued
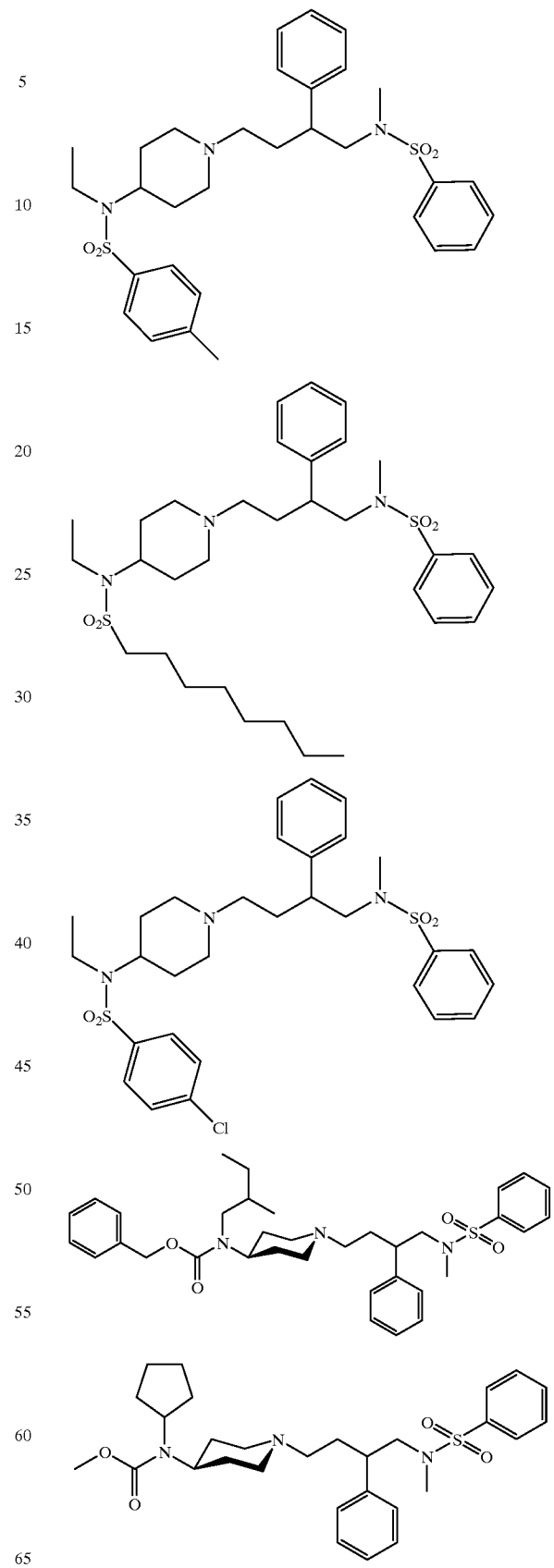

149
-continued
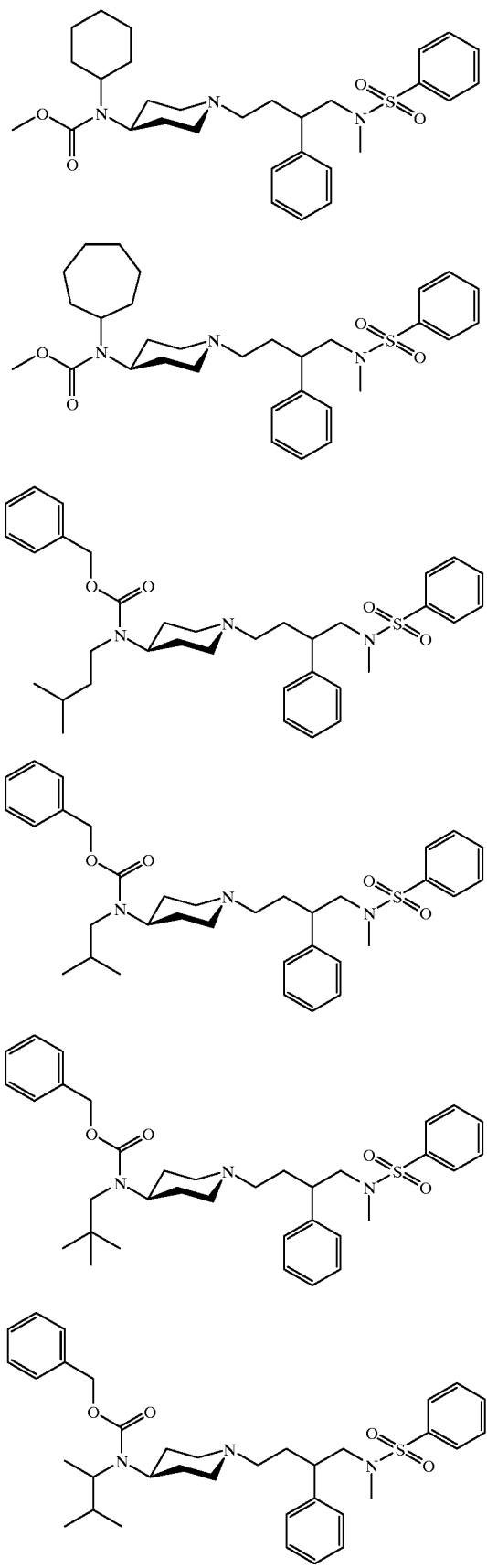
150
-continued
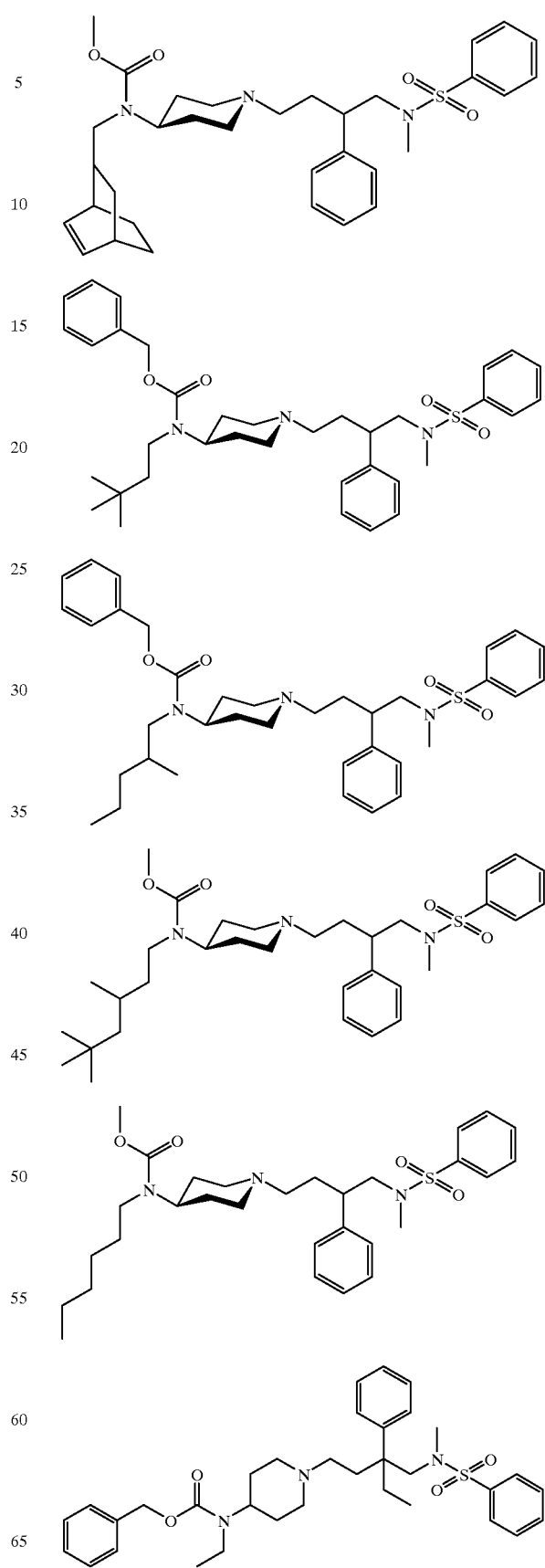

151
-continued
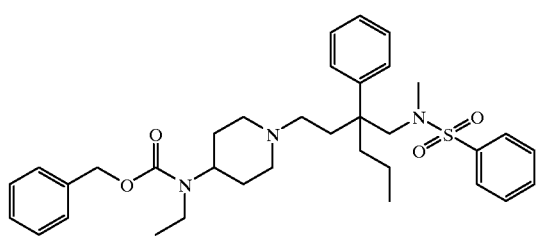
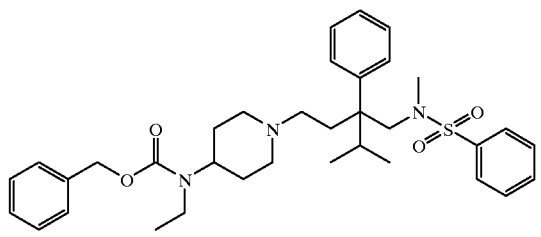
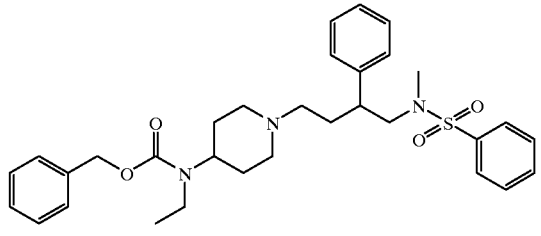
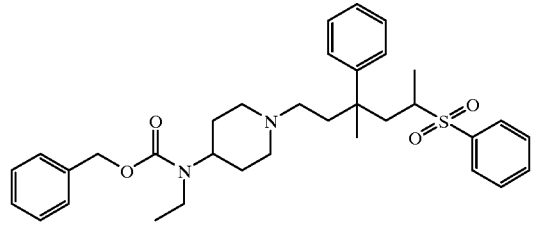
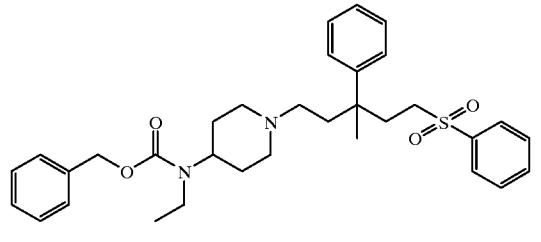
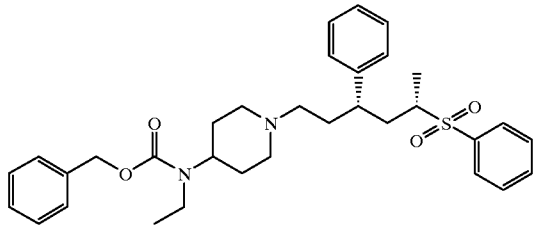
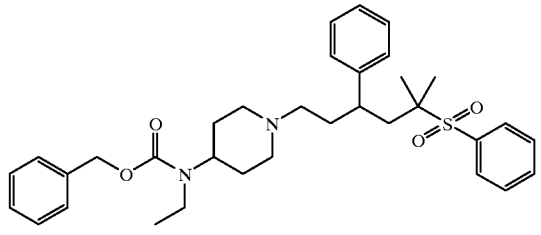
152
-continued
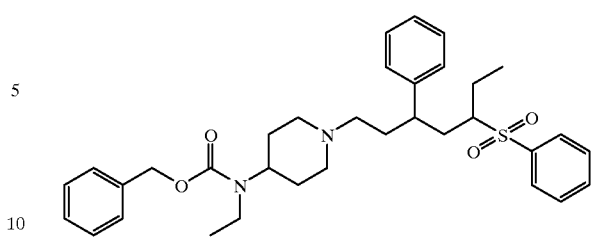
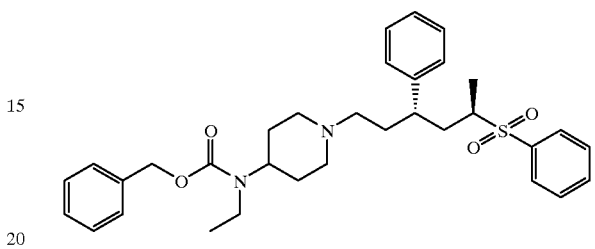
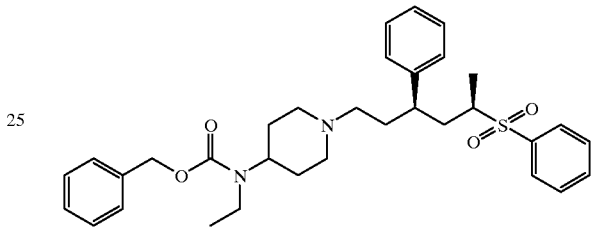
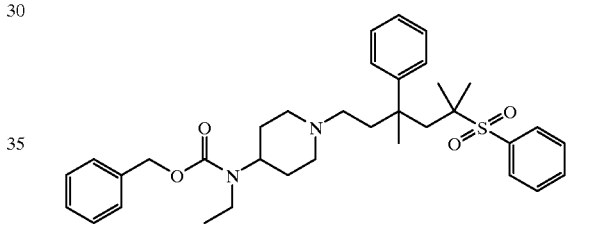
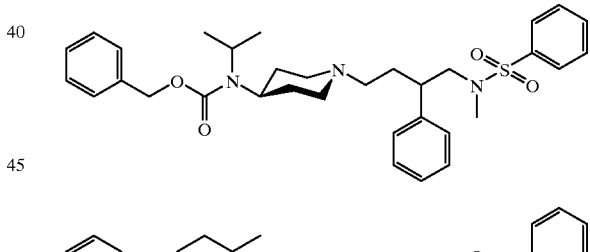
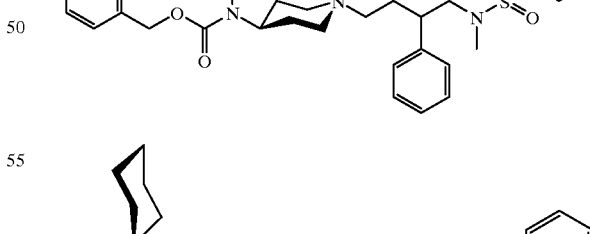
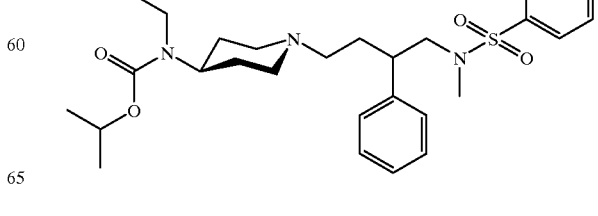

153
-continued
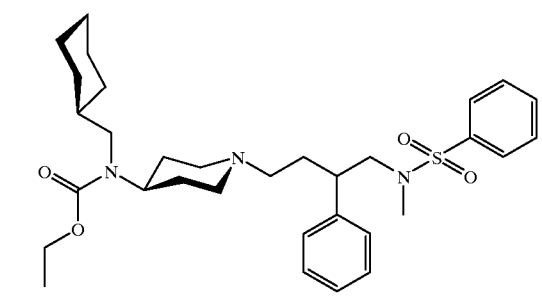
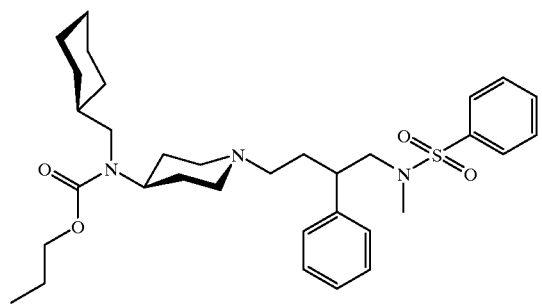
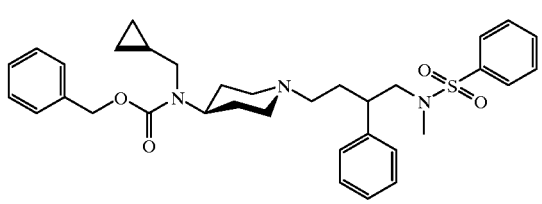
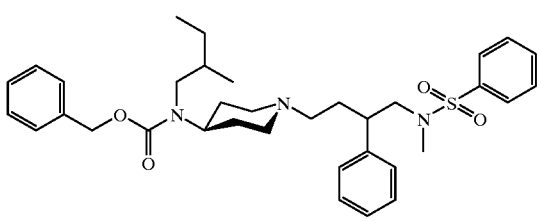
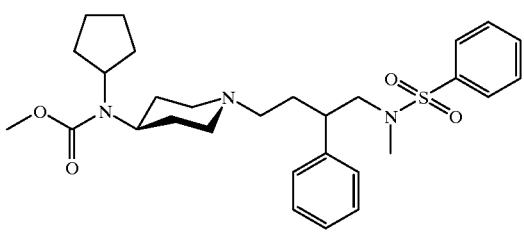
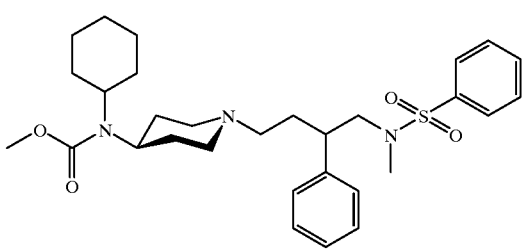
154
-continued
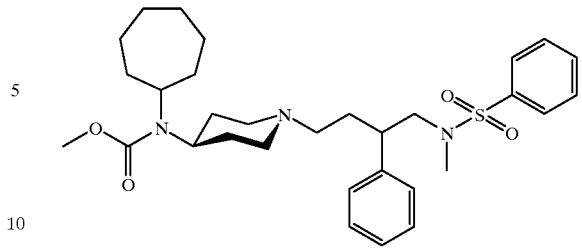
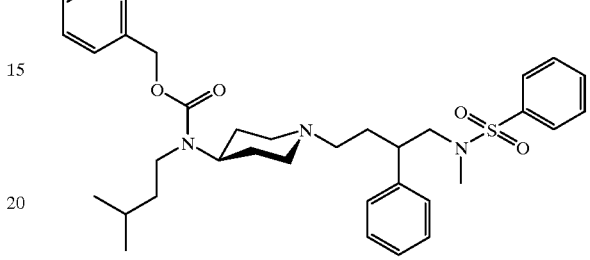
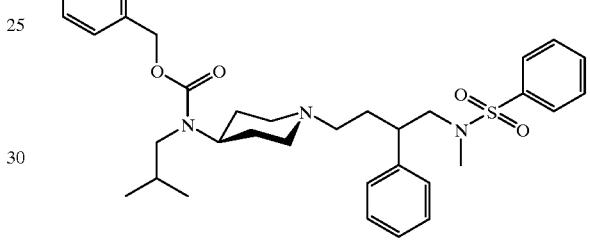
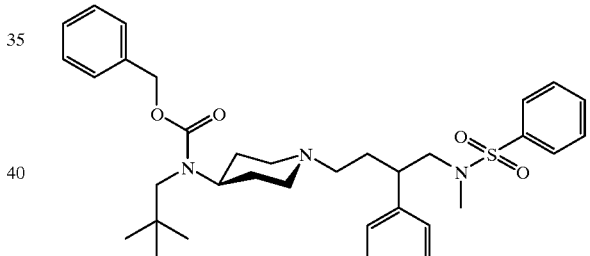
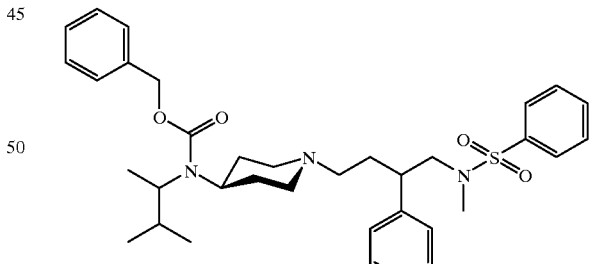
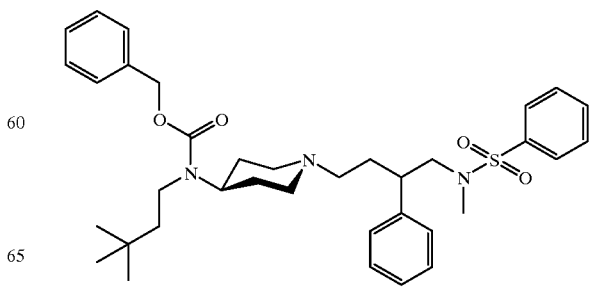

155
-continued
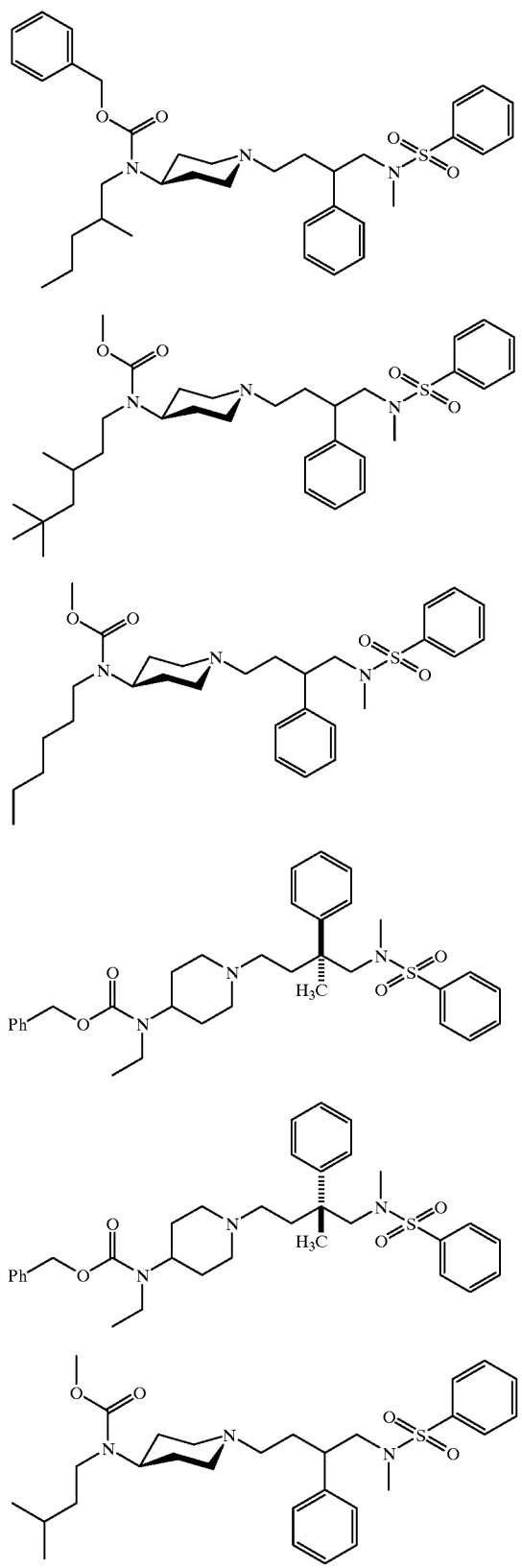
156
-continued
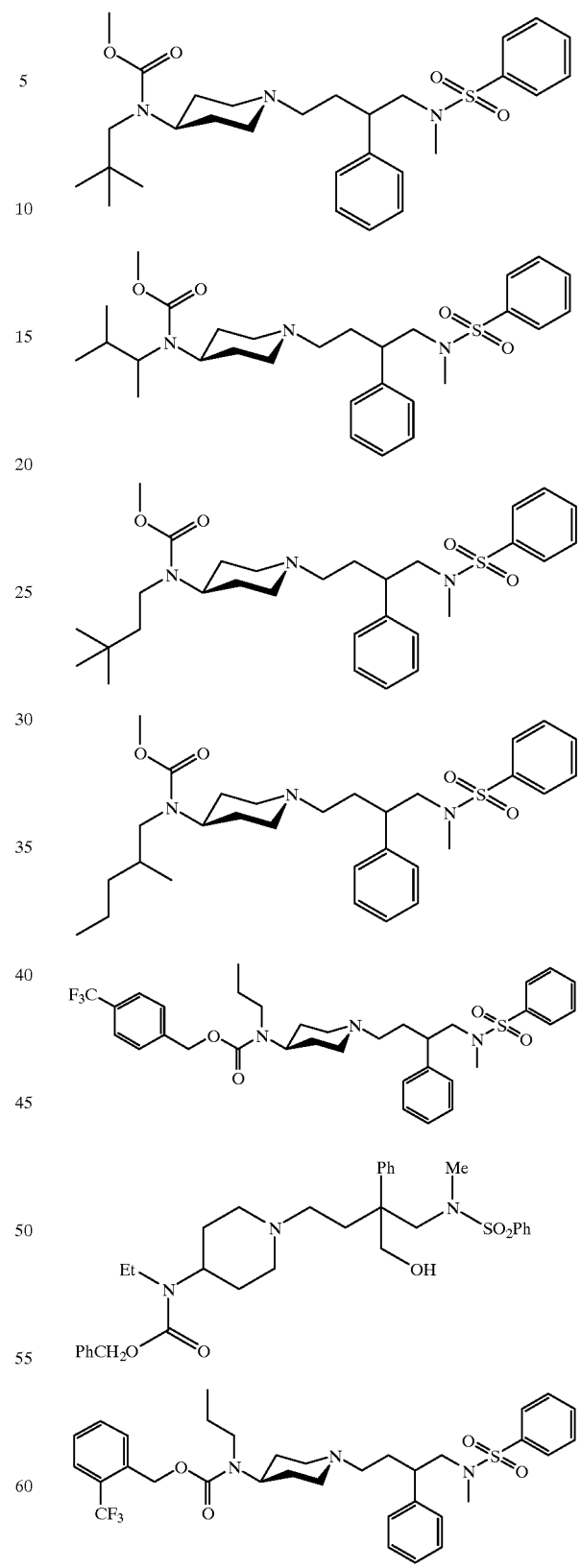

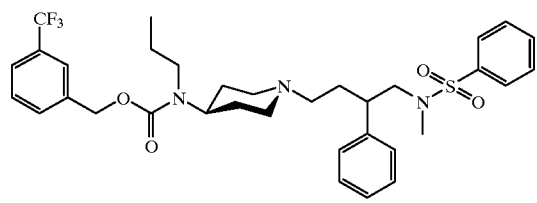
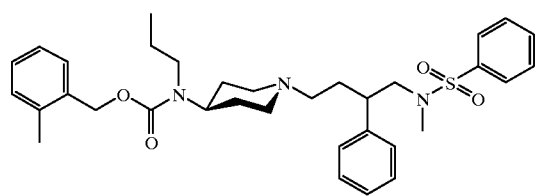
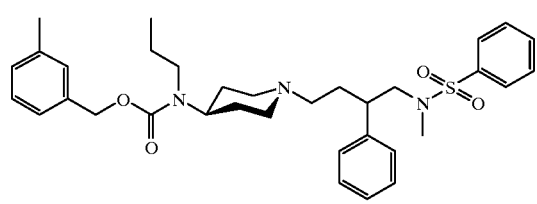
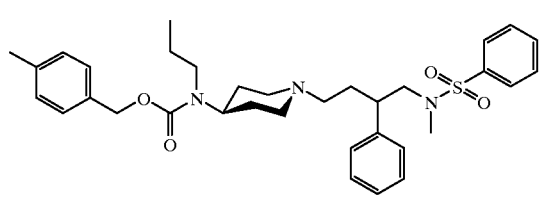
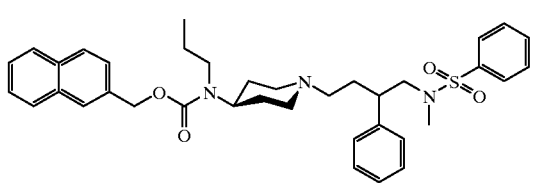
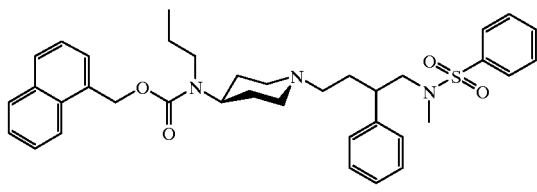
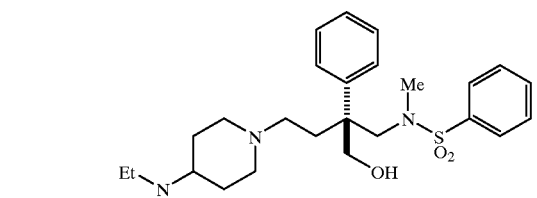
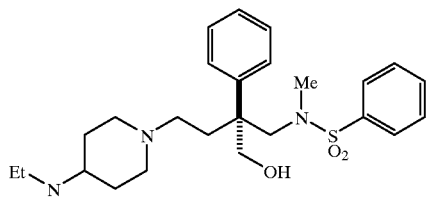
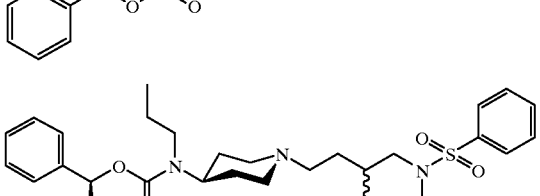
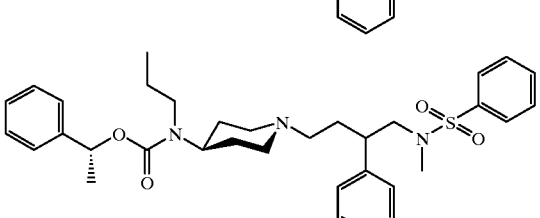
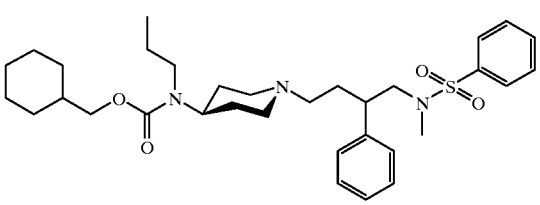
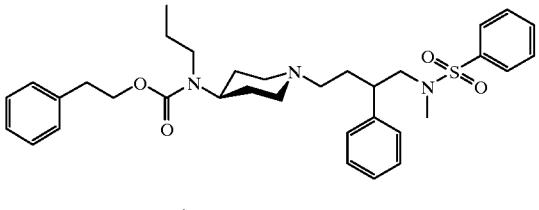
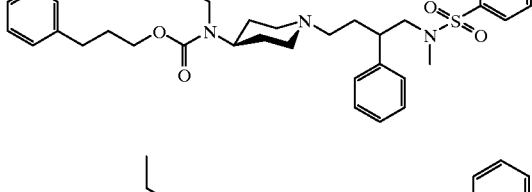
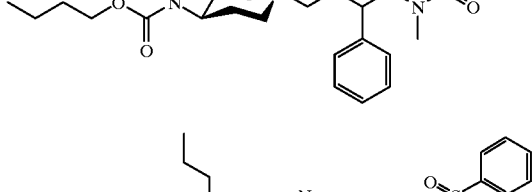
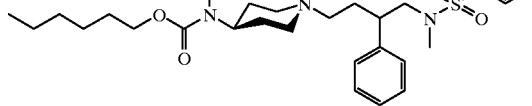

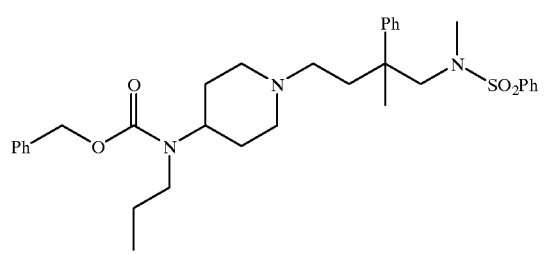
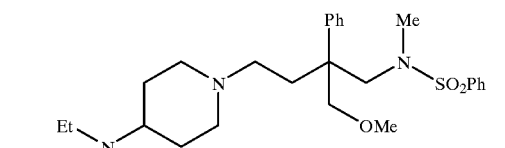
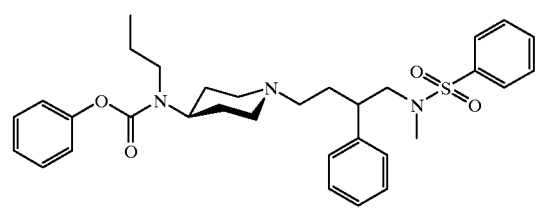
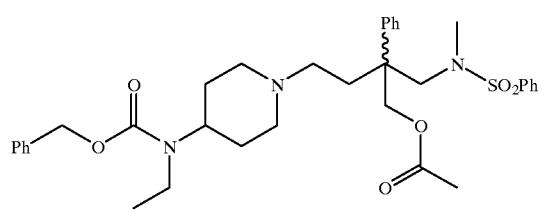
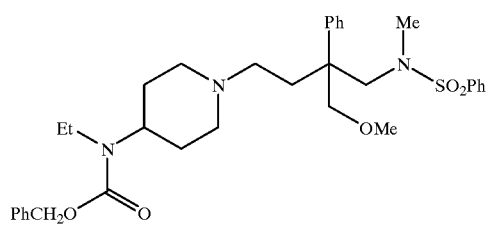
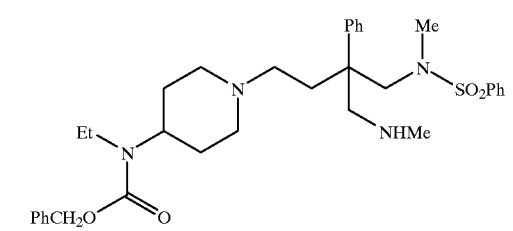
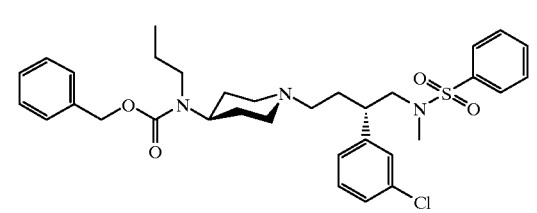
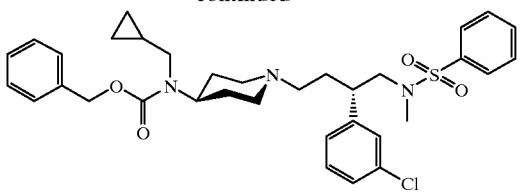
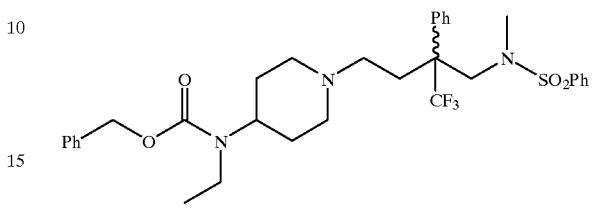
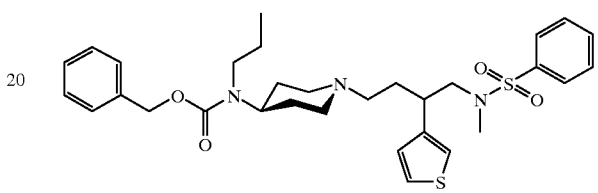
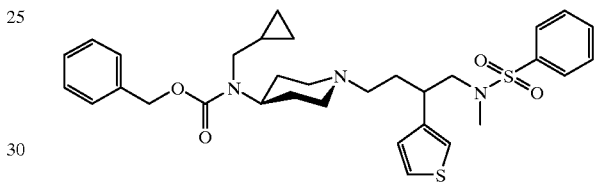
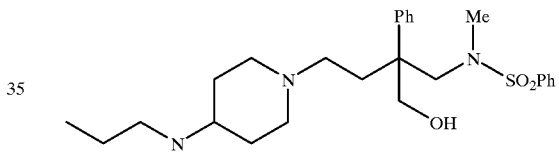
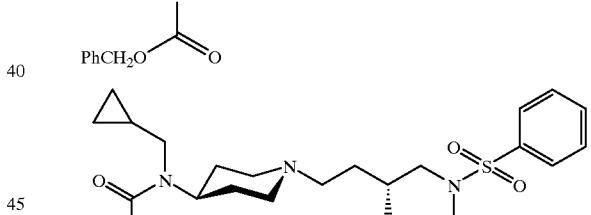
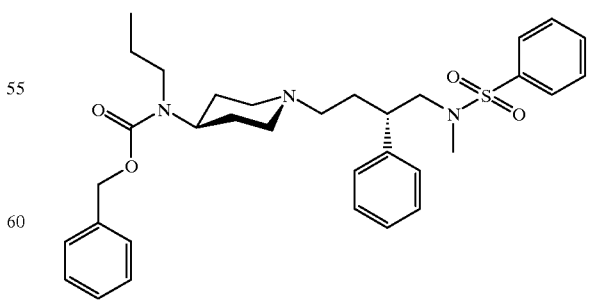

161
-continued
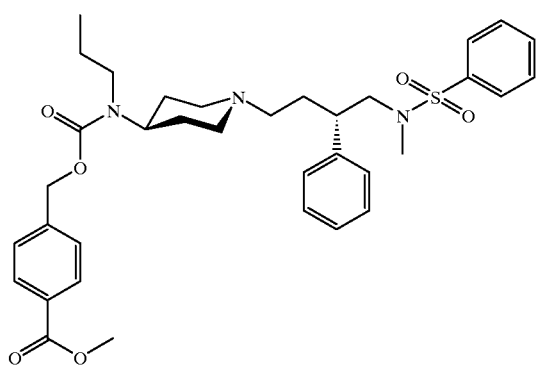
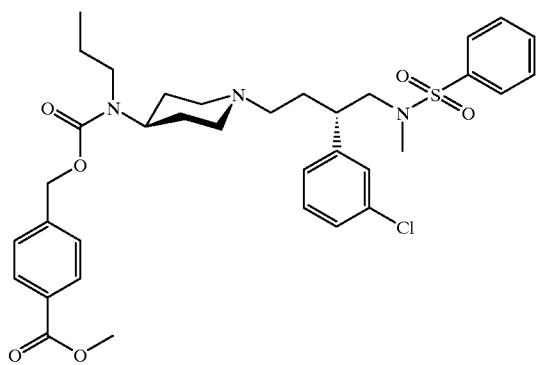
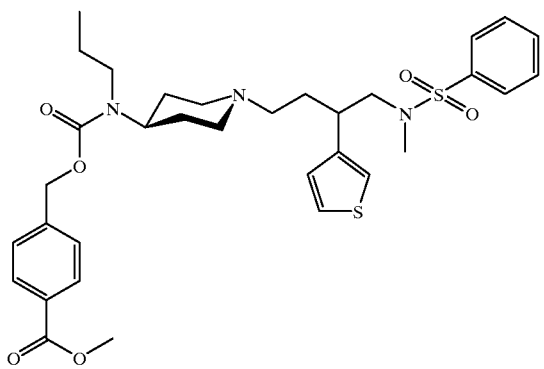
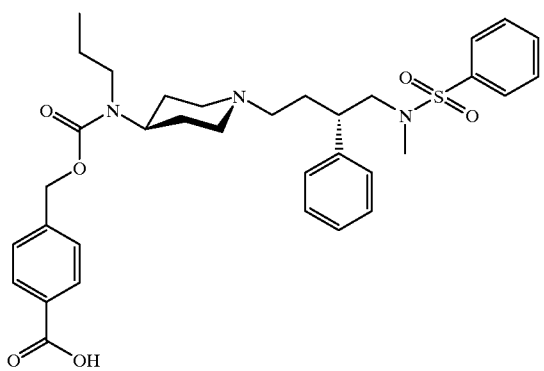
162
-continued
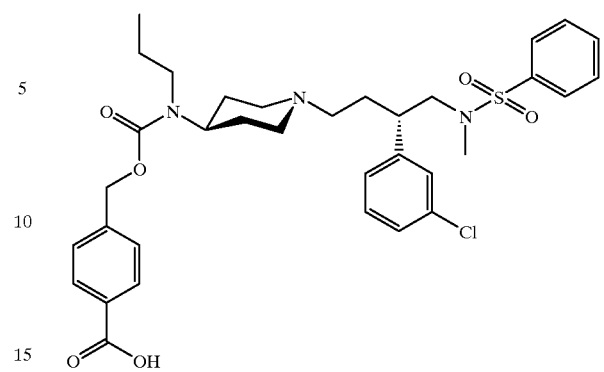
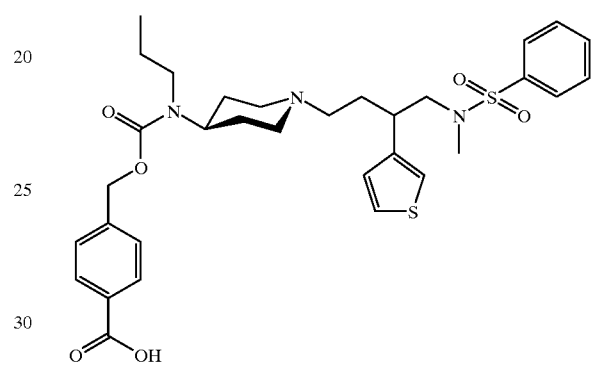
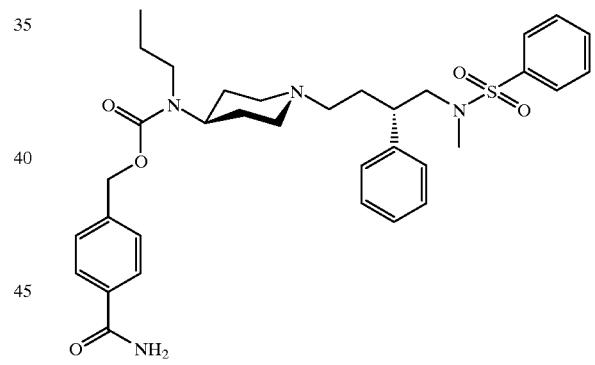
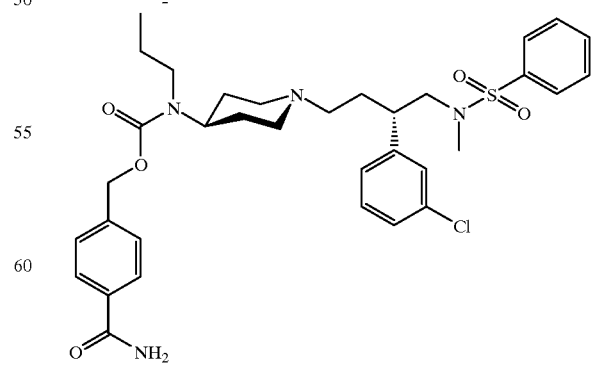

163
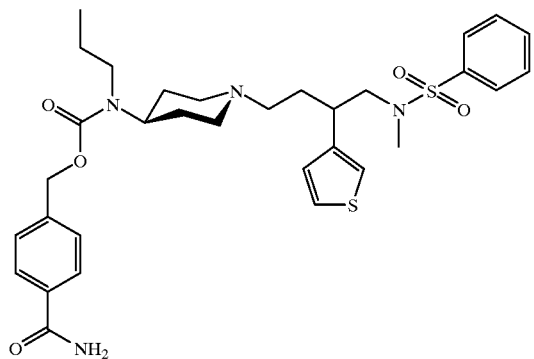
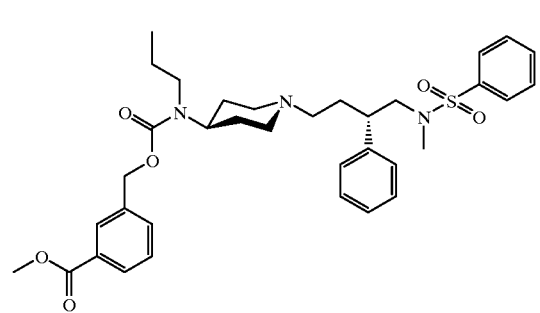
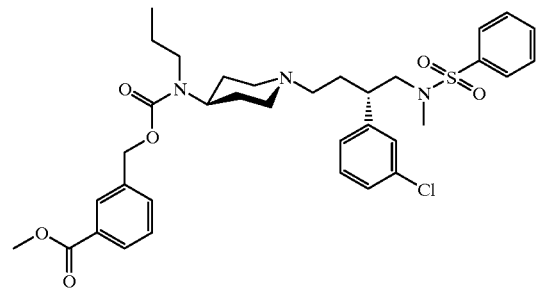
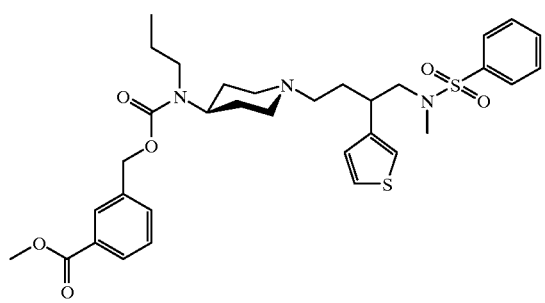
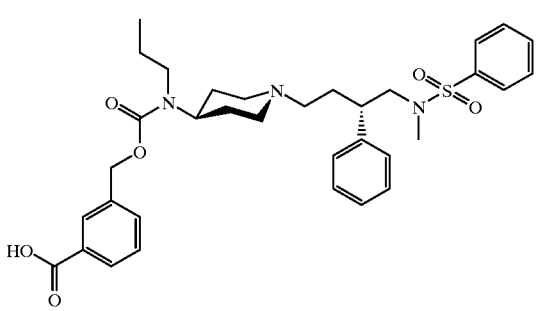
164
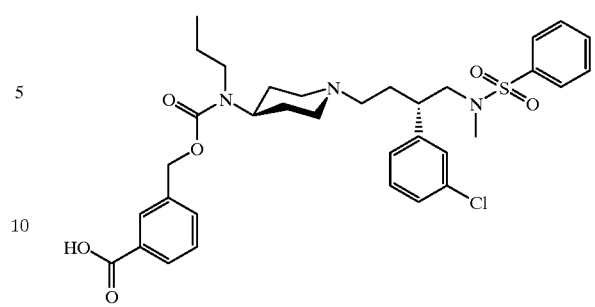
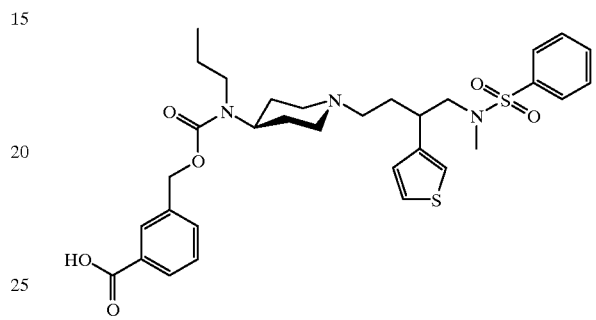
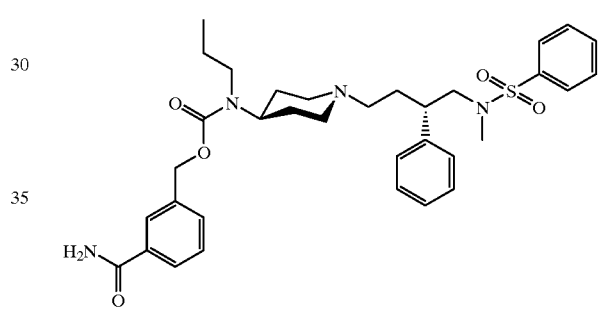
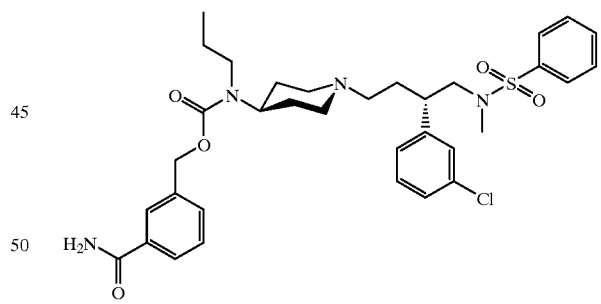
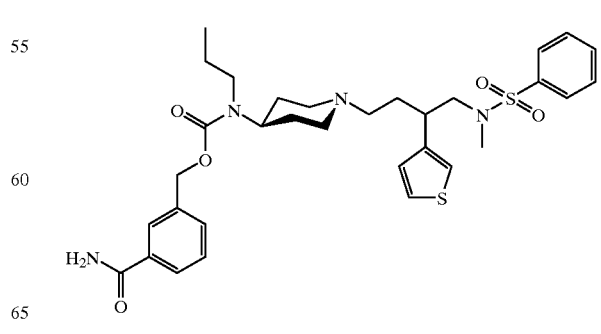

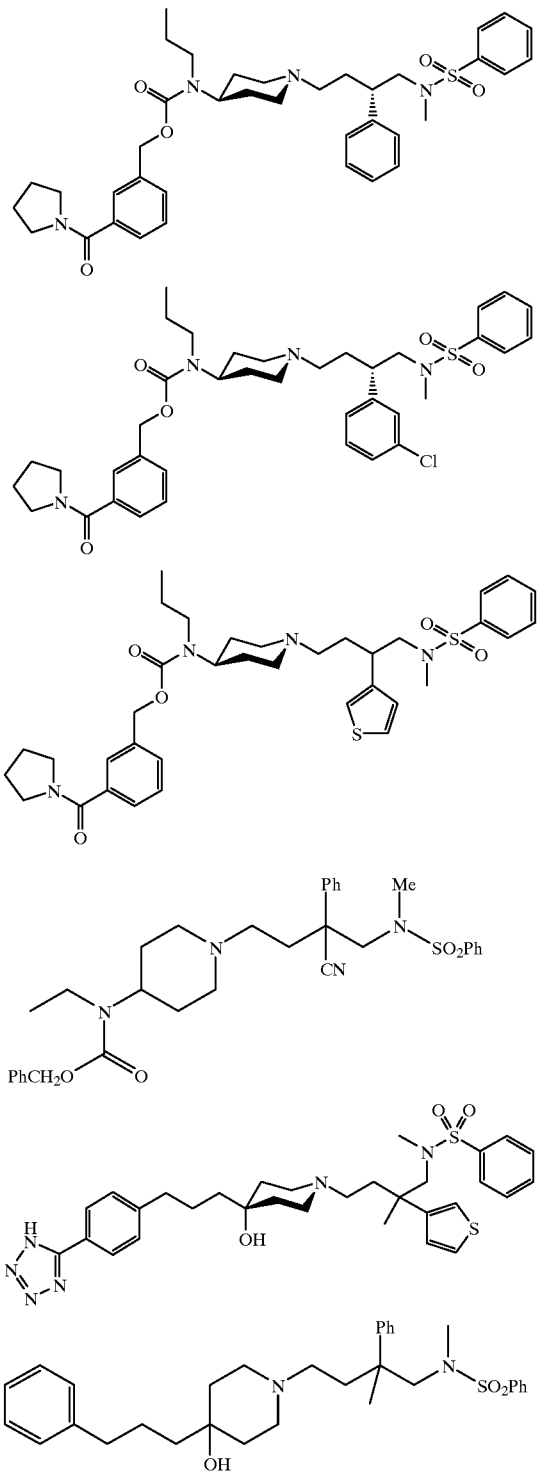

and pharmaceutically acceptable salts thereof.

14. A compound which is selected from the group consisting of:

(R,S)-N-[2-Phenyl-4-(4-phenylpiperidin-1-yl)but-1-yl]-N-methylbenzene-sulfonamide;

(R,S)-N-[2-Phenyl-4-(4-benzylpiperidin-1-yl)but-1-yl]-N-methylbenzene-sulfonamide;

(R,S)-N-[2-Phenyl-4-(4-dimethylaminocarbonyl-4-phenylpiperidin-1-yl)but-1-yl]-N-methylbenzenesulfonamide;

(R,S)-N-[2-Phenyl-4-(4-aminocarbonyl-4-phenylpiperidin-1-yl)but-1-yl]-N-methylbenzenesulfonamide;

(R,S)-N-[2-Phenyl-4-(4-hydroxymethyl-4-phenylpiperidin-1-yl)but-1-yl]-N-methylbenzenesulfonamide;

(R,S)-N-[2-Phenyl-4-(4-methoxycarbonyl-4-phenylpiperidin-1-yl)but-1-yl]-N-methylbenzenesulfonamide;

(R,S)-N-[2-Phenyl-4-(piperidin-1-yl)but-1-yl]-N-methylbenzene-sulfonamide;

(R,S)-N-[2-Phenyl-4-(4-pentylaminocarbonylpiperidin-1-yl)but-1-yl]-N-methylbenzenesulfonamide;

(R,S)-N-[2-Phenyl-4-(4-isopropylaminocarbonylpiperidin-1-yl)but-1-yl]-N-methylbenzenesulfonamide;

(R,S)-N-[2-Phenyl-4-(4-methylaminocarbonylmethylene-4-phenyl-piperidin-1-yl)but-1-yl]-N-methylbenzenesulfonamide;

(R,S)-N-[2-Phenyl-4-(4-methylaminocarbonyl(methylamino)methylene-4-phenylpiperidin-1-yl)but-1-yl]-N-methylbenzenesulfonamide;

(R,S)-N-[2-Phenyl-4-(4-methoxycarbonylaminomethylene-4-phenylpiperidin-1-yl)but-1-yl]-N-methylbenzenesulfonamide;

(R,S)-N-[2-Phenyl-4-(4-methylaminocarbonylaminomethylene-4-phenylpiperidin-1-yl)but-1-yl]-N-methylbenzenesulfonamide;

(R,S)-N-[2-Phenyl-4-(4-(2-methyl)phenylpiperidin-1-yl)but-1-yl]-N-methylbenzenesulfonamide;

(R,S)-N-[2-Phenyl-4-(4-morpholinocarbonylpiperidin-1-yl)but-1-yl]-N-methylbenzenesulfonamide;

(R,S)-N-[2-(2-Chlorophenyl)-4-(4-phenylpiperidin-1-yl)but-1-yl]-N-methylbenzenesulfonamide;

(R,S)-N-[2-(2-Thienyl)-4-(4-phenylpiperidin-1-yl)but-1-yl]-N-methylbenzenesulfonamide;

(R,S)-N-[2-(3-Thienyl)-4-(4-phenylpiperidin-1-yl)but-1-yl]-N-methylbenzenesulfonamide;

(R,S)-N-[2-(3-Thienyl)-4-(4-benzylpiperidin-1-yl)but-1-yl]-N-methyl-benzenesulfonamide;

(R,S)-N-[2-Cyclohexyl-4-(4-phenylpiperidin-1-yl)but-1-yl]-N-methyl-benzenesulfonamide;

(R,S)-N-[2-(3,5-Dichlorophenyl)-4-(4-phenylpiperidin-1-yl)but-1-yl]-N-methylbenzenesulfonamide;

(R,S)-N-[2-(3-Methylphenyl)-4-(4-phenylpiperidin-1-yl)but-1-yl]-N-methyl-benzenesulfonamide;

(R,S)-N-[2-(3-Ethylphenyl)-4-(4-phenylpiperidin-1-yl)but-1-yl]-N-methyl-benzenesulfonamide;

(R,S)-N-[2-(3-Carboethoxyphenyl)-4-(4-phenylpiperidin-1-yl)but-1-yl]-N-methylbenzenesulfonamide;

(R,S)-N-[2-(3-Fluorophenyl)-4-(4-phenylpiperidin-1-yl)but-1-yl]-N-methylbenzenesulfonamide;

(R,S)-N-[2-(3-Methoxyphenyl)-4-(4-phenylpiperidin-1-yl)but-1-yl]-N-methylbenzenesulfonamide;

(R,S)-N-[2-(3,4-Difluorophenyl)-4-(4-phenylpiperidin-1-yl)but-1-yl]-N-methylbenzenesulfonamide;

(R,S)-N-[2-(3-Biphenyl)-4-(4-phenylpiperidin-1-yl)but-1-yl]-N-methylbenzenesulfonamide;

(R,S)-N-[2-(3-Pyridyl)-4-(4-phenylpiperidin-1-yl)but-1-yl]-N-methylbenzenesulfonamide;

(R,S)-N-[2-(Naphthalen-2-yl)-4-(4-phenylpiperidin-1-yl)but-1-yl]-N-methylbenzenesulfonamide;

(R,S)-N-[2-(4-Methylphenyl)-4-(4-phenylpiperidin-1-yl)but-1-yl]-N-methylbenzenesulfonamide;

(R,S)-N-[2-(2-Pyridyl)-4-(4-phenylpiperidin-1-yl)but-1-yl]-N-methylbenzenesulfonamide;

(R,S)-N-[2-(3-Fluoro-4-methylphenyl)-4-(4-phenylpiperidin-1-yl)but-1-yl]-N-methylbenzenesulfonamide;

(R,S)-N-[2-(3,4-Dimethylphenyl)-4-(4-phenylpiperidin-1-yl)but-1-yl]-N-methylbenzenesulfonamide;

(R,S)-N-[2-(3,5-Dimethylphenyl)-4-(4-phenylpiperidin-1-yl)but-1-yl]-N-methylbenzenesulfonamide;

(R,S)-N-[2-(4-Methoxyphenyl)-4-(4-phenylpiperidin-1-yl)but-1-yl]-N-methylbenzenesulfonamide;

(R,S)-N-[2-(3-Trifluoromethylphenyl)-4-(4-phenylpiperidin-1-yl)but-1-yl]-N-methylbenzenesulfonamide;

(R,S)-N-[2-(3-Methyl-4-fluorophenyl)-4-(4-phenylpiperidin-1-yl)but-1-yl]-N-methylbenzenesulfonamide;

(S)-N-[2-(3-Chlorophenyl)-4-(4-phenylpiperidin-1-yl)but-1-yl]-N-methylbenzenesulfonamide;

(S)-N-[4-(4-Benzylpiperidin-1-yl)-2-(3-chlorophenyl)but-1-yl]-N-methylbenzenesulfonamide;

(S)-N-[4-(4-(3-Phenylprop-1-yl)piperidin-1-yl)-2-(3-chlorophenyl)but-1-yl]-N-methylbenzenesulfonamide;

(S)-N-[2-(3-Chlorophenyl)-4-(4-t-butylpiperidin-1-yl)but-1-yl]-N-methylbenzenesulfonamide;

(S)-N-[2-(3-Chlorophenyl)-4-(4-(cis-octahydro-2H-benzimidazol-2-on-1-yl)piperidin-1-yl)but-1-yl]-N-methylbenzenesulfonamide;

(S)-N-[2-(3-Chlorophenyl)-4-(4-(1,2,3,4-tetrahydro-2H-quinazolin-2-on-1-yl)piperidin-1-yl)but-1-yl]-N-methylbenzenesulfonamide;

(S)-N-[2-(3-Chlorophenyl)-4-(3-phenylpiperidin-1-yl)but-1-yl]-N-methylbenzenesulfonamide;

(S)-N-[2-(3-Chlorophenyl)-4-(4-hydroxy-4-phenylpiperidin-1-yl)but-1-yl]-N-methylbenzenesulfonamide;

(S)-N-[2-(3-Chlorophenyl)-4-(4-(2,3-dihydro-2H-benzimidazol-2-on-1-yl)piperidin-1-yl)but-1-yl]-N-methylbenzenesulfonamide;

(S)-N-[2-(3-Chlorophenyl)-4-[4,4-diphenylpiperidin-1-yl]-butyl]-N-methylbenzenesulfonamide;

(S)-N-[4-[4-(4-Chlorophenyl)-4-hydroxypiperidin-1-yl]-2-(3-chlorophenyl)-but-1-yl]-N-methylbenzenesulfonamide;

(S)-N-[4-(4-Acetyl-4-phenylpiperidin-1-yl)-2-(3-chlorophenyl)but-1-yl]-N-methylbenzenesulfonamide;

(S)-N-[4- [4-(4-Chloro-3-trifluoromethylphenyl)-4-hydroxypiperidin-1-yl] -2-(3-chlorophenyl)but-1-yl]-N-methylbenzenesulfonamide;

(S)-N-[2-(3-Chlorophenyl)-4- [4-(2-methoxycarbonylphenyl)piperidin-1-yl] -but-1-yl]-N-methylbenzenesulfonamide;

(S)-N-[2-(3-Chlorophenyl)-4- [4-hydroxy-4-(3-trifluoromethyl)phenyl-piperidin-1-yl]-but-1-yl]-N-methylbenzenesulfonamide;

(S)-N-[2-(3-Chlorophenyl)-4-[4-(4-fluorophenyl)-4-hydroxypiperidin-1-yl]but-1-yl]-N-methylbenzenesulfonamide;

(S)-N-[2-(3-Chlorophenyl)-4-[4-(2-oxo-4H-benzo [d][1,3] oxazin-1-yl)piper-idin-1-yl]but-1-yl]-N-methylbenzenesulfonamide;

(S)-N-[2-(3-Chlorophenyl)-4-[4-(2-oxo-3H-benzo[d][1,4]oxazin-1-yl)piper-idin-1-yl]but-1-yl]-N-methylbenzenesulfonamide;

(S)-N-[4-(4-Benzoylpiperidin-1-yl)-2-(3-chlorophenyl)but-1-yl]-N-methylbenzenesulfonamide;

(S)-N-[2-(3-Chlorophenyl)-4-[4-(2-methoxy)phenylpiperidin-1-yl]but-1-yl]-N-methylbenzenesulfonamide;

(S)-N-[2-(3-Chlorophenyl)-4-(4-piperidin-1-ylpiperidin-1-yl)but-1-yl]-N-5 methylbenzenesulfonamide;

(S)-N-[2-(3,4-Methylenedioxyphenyl)-4-(4-phenylpiperidin-1-yl)but-1-yl]-N-methylbenzenesulfonamide;

(S)-N-[2-(4-Fluorophenyl)-4-(4-phenylpiperidin-1-yl)but-1-yl]-N-methylbenzenesulfonamide;

(S)-N-[2-(3,4-Dichlorophenyl)-4-(4-phenylpiperidin-1-yl)-but-1-yl]-N-ethylbenzenesulfonamide;

(R,S)-N-[2-Phenyl-4-[4-acetyl(ethylamino)piperidin-1-yl]but-1-yl]-N-methylbenzenesulfonamide;

(R,S)-N-[2-Phenyl-4-[4-(oxazolidin-2-on-3-yl)piperidin-1-yl]but-1-yl]-N-methylbenzenesulfonamide;

(R,S)-N-[2-Phenyl-4-(4-methoxycarbonyl(ethylamino)piperidin-1-yl)but-1-yl]-N-methylbenzenesulfonamide;

(R,S)-N-[2-Phenyl-4-(4-dimethylaminocarbonylaminopiperidin-1-yl)but-1-yl]-N-methylbenzenesulfonamide;

(R,S)-N-[2-Phenyl-4-(4-benzyloxycarbonyl(prop-1-ylamino)piperidin-1-yl)but-1-yl]-N-methylbenzenesulfonamide;

(R,S)-N-[2-Phenyl-4-(4-methoxycarbonylaminopiperidin-1-yl)but-1-yl]-N-methylbenzenesulfonamide;

(R,S)-N-[2-Phenyl-4-(4-aminocarbonylaminopiperidin-1-yl)but-1-yl]-N-methylbenzenesulfonamide;

(R,S)-N-[2-Phenyl-4-(4-aminopiperidin-1-yl)but-1-yl]-N-methylbenzene-sulfonamide;

(R,S)-N-[2-Phenyl-4-(4-acetylaminopiperidin-1-yl)but-1-yl]-N-methylbenzenesulfonamide;

(R,S)-N-[2-Phenyl-4-(4-isopropylcarbonylaminopiperidin-1-yl)but-1-yl]-N-methylbenzenesulfonamide;

(R,S)-N-[2-Phenyl-4-(4-methylsulfonylaminopiperidin-1-yl)but-1-yl]-N-methylbenzenesulfonamide;

(R,S)-N-[2-Phenyl-4-(4-isopropylcarbonyl(ethylamino)piperidin-1-yl)but-1-yl]-N-methylbenzenesulfonamide;

(R,S)-N-[2-Phenyl-4-(4-methylsulfonyl(ethylamino)piperidin-1-yl)but-1-yl]-N-methylbenzenesulfonamide;

(R,S)-N-[2-Phenyl-4-(4-t-butoxycarbonylaminopiperidin-1-yl)but-1-yl]-N-methylbenzenesulfonamide;

(R,S)-N-[2-Phenyl-4-(4-methoxycarbonyl(methylamino)piperidin-1-yl)but-1-yl]-N-methylbenzenesulfonamide;

(R,S)-N-[2-Phenyl-4-(4-(pyrrolidin-2-on-1-yl)piperidin-1-yl)but-1-yl]-N-methylbenzenesulfonamide;

(R,S)-N-[2-Phenyl-4-(4-methoxycarbonyl(cyclobutylmethylamino)-piperidin-1-yl)but-1-yl]-N-methylbenzenesulfonamide;

(R,S)-N-[2-Phenyl-4-(4-ethoxycarbonyl(ethylamino)piperidin-1-yl)but-1-yl]-N-methylbenzenesulfonamide;

(R,S)-N-[2-Phenyl-4-(4-isobutyloxycarbonyl (ethylamino)piperidin-1-yl)but-1-yl]-N-methylbenzenesulfonamide;

(R,S)-N-[2-Phenyl-4-(4-piperidin-2-on-1-ylpiperidin-1-yl)but-1-yl]-N-methylbenzenesulfonamide;

(R,S)-N-[2-Phenyl-4-(4-methoxycarbonyl(benzylamino) piperidin-1-yl)but-1-yl]-N-methylbenzenesulfonamide;

(R,S)-N-[2-Phenyl-4-(4-methoxycarbonyl(prop-1-ylamino)piperidin-1-yl)but-1-yl]-N-methylbenzenesulfonamide;

(R,S)-N-[2-Phenyl-4-(4-methoxycarbonyl(but-1-ylamino)piperidin-1-yl)but-1-yl]-N-methylbenzenesulfonamide;

(R,S)-N-[2-Phenyl-4-(4-methoxycarbonyl (cyclohexylmethylamino)-piperidin-1-yl)but-1-yl]-N-methylbenzenesulfonamide;

(R,S)-N-[2-Phenyl-4-(4-methoxycarbonyl (cyclopropylmethylamino)-piperidin-1-yl)but-1-yl]-N-methylbenzenesulfonamide;

(R,S)-N-[2-Phenyl-4-(4-methoxycarbonyl(pent-1-ylamino)piperidin-1-yl)but-1-yl]-N-methylbenzenesulfonamide;

(R,S)-N-[2-Phenyl-4-(4-benzyloxycarbonyl (methylamino)piperidin-1-yl)but-1-yl]-N-methylbenzenesulfonamide;

(R,S)-N-[2-Phenyl-4-(4-benzyloxycarbonyl(ethylamino) piperidin-1-yl)but-1-yl]-N-methylbenzenesulfonamide;

(R,S)-N-[2-Phenyl-4-(4-benzyloxycarbonyl(but-1-ylamino)piperidin-1-yl)but-1-yl]-N-methylbenzenesulfonamide;

(R,S)-N-[2-Phenyl-4-(4-benzyloxycarbonyl(pent-1-ylamino)piperidin-1-yl)but-1-yl]-N-methylbenzenesulfonamide;

(R,S)-N-[2-Phenyl-4-(4-benzyloxycarbonyl (cyclobutylmethylamino)-piperidin-1-yl)but-1-yl]-N-methylbenzenesulfonamide;

(R,S)-N-[2-Phenyl-4-(4-benzyloxycarbonyl (cyclohexylmethylamino)-piperidin-1-yl)but-1-yl]-N-methylbenzenesulfonamide;

(S)-N-[2-(3-Chlorophenyl-4-(4-benzyloxycarbonyl (ethylamino)-piperidin-1-yl)but-1-yl]-N-methylbenzenesulfonamide;

(R,S)-N-[3-Phenyl-4-(4-phenylpiperidin-1-yl)but-1-yl]-N-methylbenzenesulfonamide;

(R,S)-N-Methyl-N-[2-methyl-2-phenyl-4-(4-phenylpiperidin-1-yl)but-1-yl]benzenesulfonamide;

(R,S)-N-[4-(4-Benzyloxycarbonyl(ethylamino)piperidin-1-yl)-2-methyl-2-phenylbut-1-yl]-N-methylbenzenesulfonamide; and (R,S)-N-[4-(4-Benzyloxycarbonyl(ethylamino)piperidin-1-yl)-2-ethyl-2-phenylbut-1-yl]-N-methylbenzenesulfonamide;

and pharmaceutically acceptable salts thereof.

15. A pharmaceutical composition which comprises an inert carrier and a therapeutically effective amount of compound of claim 1.

16. A method for blocking the entry of HIV into target cells of a patient comprising administering to the patient in need thereof the compound of claim 1 in an amount effective to block HIV from binding to surface receptors of the target cells.

17. The method of claim 16 wherein blocking the entry of HIV into target cells prevents infection of the patient by HIV.

18. The method of claim 16 wherein blocking the entry of HIV into target cells prevents infectious spread of HIV in the patient.

19. The method of claim 16 wherein blocking the entry of HIV into target cells delays the onset of AIDS in the patient.

20. The method of claim 16 wherein blocking the entry of HIV into target cells treats the pathological conditions of AIDS in the patient.

* * * * *